US011834686B2

(12) United States Patent
Fauser et al.

(10) Patent No.: US 11,834,686 B2
(45) Date of Patent: Dec. 5, 2023

(54) ENGINEERED TARGET SPECIFIC BASE EDITORS

(71) Applicant: Sangamo Therapeutics, Inc., Richmond, CA (US)

(72) Inventors: Friedrich Fauser, Richmond, CA (US); Jeffrey C. Miller, Richmond, CA (US); Edward Rebar, Richmond, CA (US)

(73) Assignee: Sangamo Therapeutics, Inc., Brisbane, CA (US)

( * ) Notice: Subject to any disclaimer, the term of this patent is extended or adjusted under 35 U.S.C. 154(b) by 611 days.

(21) Appl. No.: 16/545,363

(22) Filed: Aug. 20, 2019

(65) Prior Publication Data

US 2020/0063114 A1 Feb. 27, 2020

Related U.S. Application Data

(60) Provisional application No. 62/867,565, filed on Jun. 27, 2019, provisional application No. 62/817,153, filed on Mar. 12, 2019, provisional application No. 62/753,696, filed on Oct. 31, 2018, provisional application No. 62/721,903, filed on Aug. 23, 2018.

(51) Int. Cl.
| | | |
|---|---|---|
| C12N 9/22 | (2006.01) | |
| C12N 9/78 | (2006.01) | |
| C12N 15/11 | (2006.01) | |
| C12N 15/63 | (2006.01) | |

(52) U.S. Cl.
CPC .............. *C12N 9/22* (2013.01); *C12N 9/78* (2013.01); *C12N 15/11* (2013.01); *C12N 15/63* (2013.01); *C12Y 305/04001* (2013.01); *C12Y 305/04002* (2013.01); *C12N 2310/20* (2017.05); *C12N 2310/3181* (2013.01); *C12N 2310/323* (2013.01); *C12N 2310/3231* (2013.01); *C12N 2800/80* (2013.01)

(58) Field of Classification Search
None
See application file for complete search history.

(56) References Cited

U.S. PATENT DOCUMENTS

| | | | |
|---|---|---|---|
| 5,436,150 A | 7/1995 | Chandrasegaran | |
| 5,789,538 A | 8/1998 | Rebar et al. | |
| 5,925,523 A | 7/1999 | Dove et al. | |
| 5,928,638 A | 7/1999 | Uchida et al. | |
| 6,007,988 A | 12/1999 | Choo et al. | |
| 6,013,453 A | 1/2000 | Choo et al. | |
| 6,140,081 A | 10/2000 | Barbas | |
| 6,140,466 A | 10/2000 | Barbas, III et al. | |
| 6,200,759 B1 | 3/2001 | Dove et al. | |
| 6,242,568 B1 | 6/2001 | Barbas, III et al. | |
| 6,410,248 B1 | 6/2002 | Greisman et al. | |
| 6,453,242 B1 | 9/2002 | Eisenberg et al. | |
| 6,479,626 B1 | 11/2002 | Kim et al. | |
| 6,503,717 B2 | 1/2003 | Case et al. | |
| 6,534,261 B1 | 3/2003 | Cox, III et al. | |
| 6,599,692 B1 | 7/2003 | Case et al. | |
| 6,607,882 B1 | 8/2003 | Cox, III et al. | |
| 6,689,558 B2 | 2/2004 | Case | |
| 6,794,136 B1 | 9/2004 | Eisenberg et al. | |
| 6,824,978 B1 | 11/2004 | Cox, III et al. | |
| 6,903,185 B2 | 6/2005 | Kim et al. | |
| 6,933,113 B2 | 8/2005 | Case et al. | |
| 6,979,539 B2 | 12/2005 | Cox, III et al. | |
| 7,013,219 B2 | 3/2006 | Case et al. | |
| 7,030,215 B2 | 4/2006 | Liu et al. | |
| 7,067,317 B2 | 6/2006 | Rebar et al. | |
| 7,070,934 B2 | 7/2006 | Cox, III et al. | |
| 7,153,949 B2 | 12/2006 | Kim et al. | |
| 7,163,824 B2 | 1/2007 | Cox, III et al. | |
| 7,217,509 B2 | 5/2007 | Wolffe et al. | |
| 7,253,273 B2 | 8/2007 | Collingwood | |
| 7,262,054 B2 | 8/2007 | Jamieson et al. | |
| 7,361,635 B2 | 4/2008 | Miller et al. | |
| 7,785,792 B2 | 8/2010 | Wolffe et al. | |
| 7,888,121 B2 | 2/2011 | Urnov et al. | |
| 7,914,796 B2 | 3/2011 | Miller et al. | |
| 7,923,542 B2 | 4/2011 | Wolffe et al. | |
| 7,951,925 B2 | 5/2011 | Ando et al. | |
| 7,972,854 B2 | 7/2011 | Miller et al. | |
| 8,034,598 B2 | 10/2011 | Miller | |
| 8,071,370 B2 | 12/2011 | Wolffe et al. | |
| 8,110,379 B2 | 2/2012 | DeKelver et al. | |
| 8,409,861 B2 | 4/2013 | Guschin et al. | |
| 8,563,314 B2 | 10/2013 | Gregory et al. | |

(Continued)

FOREIGN PATENT DOCUMENTS

| | | |
|---|---|---|
| GB | 2338237 A | 12/1999 |
| WO | WO 1995/19431 A1 | 7/1995 |

(Continued)

OTHER PUBLICATIONS

Anders, et al., "Structural Basis of Pam-Dependent Target Dna Recognition By the CAS9 Endonuclease," *Nature* 513(7519):569-573 (2014).
Argast, et al., "I-Ppoi and I-Crei Homing Site Sequence Degeneracy Determined By Random Mutagenesis and Sequential in Vitro Enrichment," *J. Mol. Biol.* 280(3):345-353 (1998).
Arnould, et al., "Engineering of Large Nos. of Highly Specific Homing Endonucleases That Induce Recombination On Novel Dna Targets," *J. Mol. Biol.* 355(3):443-458 (2006).
Bahal, et al., "Single-Stranded Ipnas for in Vivo Site-Specific Genome Editing Via Watson-Crick Recognition," (2014) *Curr Gene Ther.* 14(5):331-342.
Beerli, et al., "Engineering Polydactyl Zinc-Finger Transcription Factors," *Nature Biotechnology* 20:135-141 (2002).
Beurdeley, et al., "Compact Designer Talens for Efficient Genome Engineering," *Nat Comm* 4(1762): 1-8, doi: 10.1038/ncomms2782 (2013).

(Continued)

*Primary Examiner* — Suzanne M Noakes
(74) *Attorney, Agent, or Firm* — Steptoe & Johnson LLP; Z. Ying Li; Debashree Chatterjee

(57) ABSTRACT

Described herein are DNA-editing complexes, particularly DNA-editing complexes that specifically alter a single base pair in target DNA sequence as well as methods of making and using these DNA-editing complexes.

8 Claims, 15 Drawing Sheets

Specification includes a Sequence Listing.

(56) References Cited

U.S. PATENT DOCUMENTS

| | | |
|---|---|---|
| 8,586,526 B2 | 11/2013 | Gregory et al. |
| 8,597,912 B2 | 12/2013 | Collingwood et al. |
| 8,623,618 B2 | 1/2014 | Doyon et al. |
| 8,697,359 B1 | 4/2014 | Zhang |
| 8,703,489 B2 | 4/2014 | Wang |
| 8,771,945 B1 | 7/2014 | Zhang |
| 8,772,453 B2 | 7/2014 | Paschon et al. |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,945,868 B2 | 2/2015 | Collingwood et al. |
| 8,956,828 B2 | 2/2015 | Bonini et al. |
| 8,962,281 B2 | 2/2015 | Doyon et al. |
| 8,999,641 B2 | 4/2015 | Zhang et al. |
| 9,005,973 B2 | 4/2015 | Cost et al. |
| 9,045,763 B2 | 6/2015 | DeKelver et al. |
| 9,163,245 B2 | 10/2015 | Paschon et al. |
| 9,200,266 B2 | 12/2015 | Wang |
| 9,255,250 B2 | 2/2016 | Gregory et al. |
| 9,394,531 B2 | 7/2016 | Miller |
| 9,522,936 B2 | 12/2016 | Miller et al. |
| 9,567,604 B2 | 2/2017 | Joung et al. |
| 9,631,186 B2 | 4/2017 | Wang |
| 9,770,489 B2 | 9/2017 | Angel et al. |
| 9,840,713 B2 | 12/2017 | Zhang |
| 9,873,894 B2 | 1/2018 | Conway et al. |
| 9,982,245 B2 | 5/2018 | Miller |
| 10,000,772 B2 | 6/2018 | Doudna et al. |
| 10,113,207 B2 | 10/2018 | Wang |
| 10,655,123 B2 | 5/2020 | Nishida et al. |
| 11,220,693 B2 | 1/2022 | Nishida et al. |
| 2003/0232410 A1 | 12/2003 | Liljedahl et al. |
| 2005/0026157 A1 | 2/2005 | Baltimore et al. |
| 2005/0064474 A1 | 3/2005 | Urnov et al. |
| 2005/0208489 A1 | 9/2005 | Carroll et al. |
| 2005/0267061 A1 | 12/2005 | Martin |
| 2006/0063231 A1 | 3/2006 | Li et al. |
| 2006/0188987 A1 | 8/2006 | Guschin et al. |
| 2007/0218528 A1 | 9/2007 | Miller |
| 2008/0131962 A1 | 6/2008 | Miller |
| 2008/0159996 A1 | 7/2008 | Ando et al. |
| 2009/0068164 A1 | 3/2009 | Segal et al. |
| 2010/0047805 A1 | 2/2010 | Wang |
| 2010/0218264 A1 | 8/2010 | Cui et al. |
| 2011/0145940 A1 | 6/2011 | Voytas et al. |
| 2011/0201055 A1 | 8/2011 | Doyon et al. |
| 2011/0265198 A1 | 10/2011 | Gregory et al. |
| 2011/0301073 A1 | 12/2011 | Gregory et al. |
| 2012/0017290 A1 | 1/2012 | Cui et al. |
| 2012/0040398 A1 | 2/2012 | Miller |
| 2012/0060230 A1 | 3/2012 | Collingwood et al. |
| 2013/0122591 A1 | 5/2013 | Cost et al. |
| 2013/0137104 A1 | 5/2013 | Cost et al. |
| 2013/0177960 A1 | 7/2013 | Rebar |
| 2013/0177983 A1 | 7/2013 | Rebar |
| 2015/0056705 A1 | 2/2015 | Conway et al. |
| 2015/0159172 A1 | 6/2015 | Miller et al. |
| 2016/0177278 A1 | 6/2016 | Wolfe et al. |
| 2017/0073670 A1 | 3/2017 | Nishida et al. |
| 2017/0198268 A1 | 7/2017 | Jacobson et al. |
| 2017/0218349 A1 | 8/2017 | Miller et al. |
| 2017/0349913 A1 | 12/2017 | Chen |
| 2018/0087072 A1 | 3/2018 | Miller et al. |
| 2018/0179503 A1 | 6/2018 | Maianti et al. |
| 2020/0140842 A1* | 5/2020 | Joung ............... C12N 15/10 |
| 2020/0172895 A1* | 6/2020 | Joung ............... C12N 15/90 |
| 2020/0063114 A1 | 7/2020 | Fauser et al. |

FOREIGN PATENT DOCUMENTS

| | | |
|---|---|---|
| WO | WO 1996/06166 A1 | 2/1996 |
| WO | WO 1998/37186 A1 | 8/1998 |
| WO | WO 1998/53057 A1 | 11/1998 |
| WO | WO 1998/53058 A1 | 11/1998 |
| WO | WO 1998/53059 A1 | 11/1998 |
| WO | WO 1998/53060 A1 | 11/1998 |
| WO | WO 1998/54311 A1 | 12/1998 |
| WO | WO 2000/27878 A1 | 5/2000 |
| WO | WO 2001/60970 A2 | 8/2001 |
| WO | WO 2001/88197 A2 | 11/2001 |
| WO | WO 2002/016536 A1 | 2/2002 |
| WO | WO 2002/099084 A2 | 12/2002 |
| WO | WO 2003/016496 A2 | 2/2003 |
| WO | 2007/128982 A2 | 11/2007 |
| WO | WO 2010/079430 A1 | 7/2010 |
| WO | 2011/139349 | 11/2011 |
| WO | WO 2016/183298 A2 | 11/2016 |
| WO | 2017/070633 A2 | 4/2017 |
| WO | WO 2017/079673 A1 | 5/2017 |
| WO | WO 2017/106528 A2 | 6/2017 |
| WO | 2017/209809 A1 | 12/2017 |
| WO | 2018/039438 A1 | 3/2018 |
| WO | WO 2018/049073 A1 | 3/2018 |
| WO | 2018/119243 A1 | 6/2018 |
| WO | 2018/119359 A1 | 6/2018 |
| WO | WO 2018/119354 A1 | 6/2018 |
| WO | 2018/218166 A1 | 11/2018 |
| WO | 2018/218206 A1 | 11/2018 |
| WO | 2020/041249 A1 | 2/2020 |
| WO | 2021/155065 A1 | 8/2021 |
| WO | 2022/155265 | 7/2022 |

OTHER PUBLICATIONS

Bijsterbosch, et al., "BIS-Cholesteryl-Conjugated Phosphorothioate Oligodeoxynucleotides are Highly Selectively Taken Up By the Liver," *J. Pharmacol. Exp. Ther.* 302(2):619-626 (2002).

Bijsterbosch, et al., "Modulation of Plasma Protein Binding and In Vivo Liver Cell Uptake of Phosphorothioate Oligodeoxynucleotides By Cholesterol Conjugation," *Nucleic Acids Res.* 28(14):2717-2725 (2000).

Boch, et al., "Breaking the Code of DNA Binding Specificity of Tal-Type III Effectors," *Science* 326:1509-1512 (2009).

Boehmer, et al., "Herpes Simplex Virus Type 1 ICP8: Helix-Destabilizing Properties," *J Virol* 67(2): 711-715 (1993).

Boissel, et al., "Megatals: A Rare-Cleaving Nuclease Architecture for Therapeutic Genome Engineering," *Nucleic Acids Research* 42(4):2591-2601, doi: 10.1093/nar/gkt1224 (2013).

Bolukbasi, et al., "DNA-Binding-Domain Fusions Enhance the Targeting Range and Precision of CAS9," *Nat Methods* 12(12): 1150-1156 (2015).

Bonas, et al., "Genetic and Structural Characterization of the Avirulence Gene AVRBS3 From Xanthomonas Campestris PV. Vesicatoria," *Mol Gen Genet* 218:127-136 (1989).

Brendza, et al., "Autoinhibition of *Escherichia coli* Rep Monomer Helicase Activity By Its 2B Subdomain," *PNAS* 102(29): 10076-70081 (2005).

Brosh, Jr., "DNA Helicases Involved in DNA Repair and Their Roles in Cancer," *Nat Rev Canc* 13(8):542-558 (2013).

Burstein, et al., "New Crispr-Cas Systems From Uncultivated Microbes," *Nature* 542(7640):237-241 (2017).

Byrne, et al., "Leveraging Jak-Stat Regulation in Myelofibrosis to Improve Outcomes With Allogeneic Hematopoietic Stem-Cell Transplant," *Ther Avd Hematol* 9(9):251-259 (2018).

Cebrian-Serrano, et al., "Crispr-Cas Orthologues and Variants: Optimizing the Repertoire, Specificity and Delivery of Genome Engineering Tools," *Mamm Genome* 28(7):247-261 (2017).

Chames, et al., "In Vivo Selection of Engineered Homing Endonucleases Using Double-Strand Break Induced Homologous Recombination," *Nucleic Acids Res* 33(20):e178 (2005).

Chatterjee, et al., "Minimal Pam Specificity of a Highly Similar SPCAS9 Ortholog," *Sci Adv* 4(10):eaau0766. doi: 10.1126/sciadv.aau0766 (2018).

(56) References Cited

OTHER PUBLICATIONS

Cho, et al., "Analysis of Off-Target Effects of CRISPR/CAS-Derived RNA-Guided Endonucleases and Nickases," *Genome Res.* 24(1): 132-141 (2014).
Choo, et al., "Advances in Zinc Finger Engineering," *Current Opinion in Structural Biology* 10:411-416 (2000).
Cox, et al., "RNA Editing With CRISPR-CAS13," *Science* 358(6366):1019-1027 (2017).
Darbinian, et al., "Helix-Destabilizing Properties of the Human Single-Stranded DNA- and RNA-Binding Protein Puralpha," *J Cell Biochem* 80(4):589-95 (2001).
Dusa, et al., "Substitution of Pseudokinase Domain Residue VAL-617 By Large Non-Polar Amino Acids Causes Activation of JAK2," *J Biol Chem* 283(19):12941-12948 (2008).
Eid, et al., "Crispr Base Editors: Genome Editing Without Double-Stranded Breaks," *Biochem J* 475(11):1955-1964 (2018).
Fagerlund, et al., "THE Cpf1 CRISPR-Cas Protein Expands Genome-Editing Tools," *Genome Biology* 16:251 (2015).
Fregonese, et al., "Hereditary Alpha-1-Antitrypsin Deficiency and Its Clinical Consequences," *Orphanet J Rare Dis* 3:16 (2008).
Frick, et al., "Understanding Helicases as a Means of Virus Control," *Curr Pharm Des* 12(11):1315-1338 (2006).
Gao, et al., "Engineered CPF1 Variants With Altered Pam Specificities," *Nature Biotechnology* 35(8):789-792 (2017).
Gaudelli, et al., "Programmable base editing of A•T to G•C in genomic DNA without DNA cleavage," *Nature* 551(7681):464-471 (2017).
Geny, et al., "Next-Generation Bis-Locked Nucleic Acids With Stacking Linker and 2'-Glycylamino-LNA Show Enhanced DNA Invasion Into Supercoiled Duplexes," *Nucleic Acid Res.* 44(5):2007-2019 (2016).
Gimble, et al., "Substrate Recognition and Induced DNA Distortion By the PL-SCEL Endonuclease, An Enzyme Generated By Protein Splicing," *J. Mol. Biol.* 263(2):163-180 (1996).
Grunewald, et al., "Transcriptome-Wide Off-Target RNA Editing Induced By CRISPR-Guided DNA Base Editors," *Nature* 569(7756):433-437 (2019).
Guillinger, et al., "Fusion of Catalytically Inactive CAS9 To Fokl Nuclease Improves the Specificity of Genome Modification," *Nature Biotech.* 32(6):577-582 (2014).
Guo, et al., "Directed Evolution of an Enhanced and Highly Efficient Fokl Cleavage Domain for Zinc Finger Nucleases," *J. Mol. Biol.* 400(1):96-107 doi.10.1016/j.jmb.2010.04.060 (2010).
Haapaniemi, et al., "CRISPR-CAS9 Genome Editing Induces A PS3-Mediated DNA Damage Response," *Nat Med* 24(7):927-930 (2018).
Haft, et al., "A Guild of 45 CRISPR-Associated (CAS) Protein Families and Multiple CRISPR/CAS Subtypes Exist in Prokaryotic Genomes," *PLoS Computational Biology* 11(6)e60:474-483 (2005).
Heuer, et al., "Repeat Domain Diversity of AVRBS3-Like Genes in Ralstonia Solanacearum Strains and Association with Host Preferences in the Field," *Applied and Environmental Microbiology* 73(13):4379-4384 (2007).
Hu, et al., "Evolved CAS9 Variants With Broad PAM Compatibility and High DNA Specificity," *Nature* 556(7699):57-63 (2018).
Ihry, et al., "P53 Inhibits CRISPR-CAS9 Engineering in Human Pluripotent Stem Cells," *Nat Med* 24(7):939-946 (2018).
Isalan et al., "A Rapid, Generally Applicable Method to Engineer Zinc Fingers Illustrated by Targeting the HIV-1 Promoter," *Nature Biotechnology* 19(7):656-660 (2001).
James, et al., "A Unique Clonal JAK2 Mutation Leading to Constitutive Signalling Causes Polycythaemia Vera," *Nature* 434(7037):1144-1148 (2005).
Jansen, et al., "Identification of Genes that are Associated With DNA Repeats in Prokaryotes," *Molecular Microbiology* 43(6)1:1565-1575 (2002).
Jia, et al., "Role of Human DNA2 (HDNA2) as a Potential Target for Cancer and Other Diseases: A Systematic Review," *DNA Repair (Amst)*. 59:9-19 (2017).

Jiang, et al., "CRISPR-CAS9 Structures and Mechanisms," *Annual Review of Biophysics* 46:505-529 (2017).
Jin, et al., "Cytosine, but Not Adenine, Base Editors Induce Genome-Wide Off-Target Mutations in Rice," *Science* 364(6437):292-295 (2019).
Jinek, et al., "A Programmable Dual-RNA-Guided DNA Endonuclease in Adaptive Bacterial Immunity," *Science* 337:816-821 (2012).
Kay, et al., "A Bacterial Effector Acts as a Plant Transcription Factor and Induces a Cell Size Regulator," *Science* 318:648-651 (2007).
Kim, et al., "Genome-Wide Target Specificity of CRISPR RNA-Guided Adenine Base Editors," *Nat Biotechnol* 37(4):430-435 (2019).
Kim, et al., "Highly Efficient Rna-Guided Genome Editing in Human Cells Via Delivery of Purified CAS9 Ribonucleoproteins," *Genome Res* 24(6):1012 (2014).
Kim, et al., "Hybrid Restriction Enzymes: Zinc Finger Fusions to Foki Cleavage Domain," *Proc Nat'l Acad Sci USA* 93(3):1156-1160 (1996).
Kim, et al., "Increasing the Genome-Targeting Scope and Precision of Base Editing With Engineered CAS9-Cytidine Deaminase Fusions," *Nat Biotechnol* 35(4):371-376 (2017).
Kim, et al., "Structural and Kinetic Characterization of *Escherichia coli* Tada, the Wobble-Specific TRNA Deaminase," *Biochemistry* 45(20):6407-6416 (2006).
Kleinstiver, et al., "High-Fidelity CRISPR-CAS9 Variants With Undetectable Genome-Wide Off-Targets," *Nature* 529(7587):490-495 (2016).
Koblan, et al., "Improving Cytidine and Adenine Base Editors By Expression Optimization and Ancestral Reconstruction," *Nat Biotechnol.* 36(9):843-846 (2018).
Kohwi-Shigematsu, et al., "Exposure of DNA Bases Induced By the Interaction of DNA and Calf Thymus DNA Helix-Destabilizing Protein," *Proc Natl Acad Sci USA* 75(10):4689-93 (1978).
Komor, et al., "Improved Base Excision Repair Inhibition and Bacteriophage MU GAM Protein Yields C:G-To-T:A Base Editors With Higher Efficiency and Product Purity," *Science Advances* 3(8):eaao4774 (2017).
Komor, et al., "Programmable Editing of a Target Base in Genomic Dna Without Double-Stranded DNA Cleavage," *Nature* 533(7603):420-424 (2016).
Kosicki, et al., "Repair of Double-Strand Breaks Induced By CRISPR-CAS9 Leads To Large Deletions and Complex Rearrangements," *Nat Biotechnol* 36(8):765-771 (2018).
Kuscu, et al., "CRISPR-CAS9-AID Base Editor is a Powerful Gain-of-Function Screening Tool," *Nat Methods* 13(12):983-984 (2016).
Ma, et al., "Rational Design of MINI-CAS9 for Transcriptional Activation," *ACS Synth Biol* 7(4):978-985 (2018).
Makarova, et al., "A DNA Repair System Specific for Thermophilic Archaea and Bacteria Predicted By Genomic Context Anlysis," *Nucleic Acids Research* 30(2):482-496 (2002).
Makarova, et al., "A Putative RNA-Interference-Based Immune System in Prokaryotes: Computational Analysis of the Predicted Enzymatic Machinery, Functional Analogies With Eukaryotic RNAI, and Hypothetical Mechanisms of Action," *Biology Direct* 1(7):1-26 (2006).
Manoharan, "Oligonucleotide Conjugates as Potential Antisense Drugs With Improved Uptake, Biodistribution, Targeted Delivery, and Mechanism of Action," *Antisense Nucleic Acid Drug Dev* 12(2):103-28 (2002).
Manoharan, "RNA interference and chemically Modified Small Interfering RNAS," *Curr Opin Chem Biol.* 8(6):570-9 (2004).
Mapp, et al., "Activation of Gene Expression By Small Molecule Transcription Factors," *Proc. Natl. Acad. Sci. USA* 97(8):3930-3935 (2000).
McCaffery, er al., "CRISPR-CAS9 D10A Nickase Target-Specific Fluorescent Labeling of Double Strand DNA for Whole Genome Mapping and Structural Variation Analysis," *Nucleic Acids Res.* 44(2):e11 doi:10.1093/nar/gkv878. (2016).
Miller, et al., "An Improved Zinc-Finger Nuclease Architecture for Highly Specific Genome Editing," *Nat Biotechnol* 25(7):778-784 (2007).

(56) References Cited

OTHER PUBLICATIONS

Miller, et al., "Enhancing Gene Editing Specificity By Attenuating DNA Cleavage Kinetics," *Nature Biotechnology* 37(8):945-952 (2019).
Mo, er al., "Human RECQL4 Helicase Plays Multifaceted Roles in the Genomic Stability of Normal and Cancer cells," *Cancer Lett.* 413:1-10 (2018).
Moreno, et al., "Development of BIS-Locked nucleic acid (BISLNA) Oligonucleotides for Efficient Invasion of Supercoiled Duplex DNA," *Nucleic Acid Res.* 41(5):3257-3273 (2013).
Moscou, et al., "A simplE CIPHER Governs DNA Recognition By TAL effectors," *Science* 326:1501 (2009).
Nielsen, et al., "Sequence-Selective Recognition of DNA By Strand Displacement With a Thymine-Substituted Polyamide," *Science* 254(5037):1497-1500 (1991).
Nishimasu, et al., "Engineered CRISPR-CAS9 Nuclease With Expanded Targeting Space," *Science* 361(6408):1259-1262 (2018).
Olovnikov, et al., "Bacterial Argonaute Samples the Transcriptome to Identify Foreign DNA," *Molecular Cell* 51:594-605 (2013).
Pabo, et al., "Design and Selection of Novel CYS2-HIS2 Zinc Finger Proteins," *Ann. Rev. Biochem.* 70:313-340 (2001).
Paschon, et al., "Diversifying the Structure of Zinc Finger Nucleases for High-Precision Genome Editing," *Nat Commun.* 10(1):1133 (2019).
Pellestor, et al., "The Peptide Nucleic Acids (PNAS), Powerful Tools for Molecular Genetics and Cytogenetics," *European J. Human Genetics* 12(9):694-700 (2004).
Perez, et al., "Establishment of HIV-1 Resistance in CD4+ T Cells By Genome Editing Using Zinc-Finger Nucleases," *Nature Biotechnology* 26(7):808-816 (2008).
Quijano, et al., "Therapeutic peptide nucleic acids: Principles, Limitations, and Opportunities," *Yale J. Biol and Med.* 90(4):583-698 (2017).
Rahman, et al., "2',4'-BNA(NC): A Novel Bridged Nucleic Acid Analogue With Excellent Hybridizing and Nuclease Resistance Profiles," *Nucleosides Nucleotides Nucleic Acids* 26(10-12):1625-1628 (2007).
Ran, et al., "IN Vivo Genome Editing Using *Staphylococcus aureus* CAS9," *Nature* 520:186 (2015).
Schleifman, et al., "Targeted Disruption of the CCR5 Gene in Human Hematopoietic Stem Cells Stimulated By Peptide Nucleic Acids," *Chem Biol.* 18(9):1189-1198 (2011).
Schornack, et al., "Gene-For-Gene-Mediated Recognition of Nuclear-targeted AVRBS3-Like Bacterial Effector Proteins," *Journal of Plant Physiology* 163(3)):256-272 (2006).
Segal, et al., "Custom DNA-Binding Proteins Come of Age: Polydactyl Zinc-Finger Proteins," *Current Opinion Biotechnology* 12:632-637 (2001).
Shadrick, et al., "Discovering New Medicines Targeting Helicases: Challenges and Recent Progress," *J. Biomol Screen* 18(7):761-781 (2013).
Sheng, et al., "Structure-Based Cleavage Mechanism of Thermus Thermophilus Argonaute DNA Guide Strand-Mediated DNA Target Cleavage," *Proc. Natl. Acad. Sci. U.S.A.* 111(2):652-657 (2014).
Shin, et al., "Antibody Targeting Intracellular Oncogenic RAS Mutants Exerts Anti-Tumour Effects After Systemic Administration," *Nat Comm* 8: 15090, doi: 10.1038/ncomms15646 (2017).
Siksnys, et al., "Rewiring CAS9 to Target New PAM Sequences," *Mol Cell* 61(6):793-794 (2016).
Swarts, et al., "CRISPR Interference Directs Strand Specific Spacer Acquisition," *Plos One* 7(4):e35888 (2012).
Swarts, et al., "DNA-Guided DNA Interference By a Prokaryotic Argonaute," *Nature* 507(7491):258-261 (2014).
Troung, et al., "Development of an Intein-Mediated SPLIT-CAS9 System for Gene Therapy," *Nucl Acid Res* 43(13):6450-8 (2015).
Turunen, et al., "The Significant Other: Splicing By the Minor Spliceosome," *Wiley Interdiscip Rev RNA* 4(1):61-76 (2013).
Urnov, et al., "Highly Efficient Endogenous Human Gene Correction Using Designed Zinc-Finger Nucleases," *Nature* 435(7042):646-651 (2005).
Vogel, "A Bacterial Seek-and-Destroy System for Foreign DNA," *Science* 344(6187):972-973 (2014).
Yang, et al., "APOBEC: From Mutator to Editor," *J Genet Genomics* 44(9):423-437 (2017).
Yang, et al., "Engineering and Optimising Deaminase Fusions for Genome Editing," *Nat Commun* 7:13330, doi 10.1038/ncomms13330 (2016).
Yin, et al., "Therapeutic Genome Editing By Combined Viral and Non-Viral Delivery of CRISPR System Components In Vivo," *Nat Biotechnol* 34(3):328-333 (2016).
Yuan, et al., "Crystal Structure of *A. aeolicus* Argonaute, a Site-Specific DNA-Guided Endoribonuclease, Provides Insights Into RISC-Mediated mRNA Cleavage," *Molecular Cell* 19:405-419 (2005).
Zetsche, et al., "A Split-CAS9 Architecture for Inducible Genome Editing and Transcription Modulation," *Nat Biotechnol* 33(2):139-142 (2015).
Zhao, et al., "Identification of an Acquired JAK2 Mutation in Polycythemia Vera," *J. Biol Chem* 280(24):22788-22792 (2005).
Zuo, et al., "Cytosine Base Editor Generates Substantial Off-Target Single-Nucleotide Variants in Mouse Embryos," *Science* 364(6437):289-292 (2019).
Malzahn, et al., "Plant Genome Editing with TALEN and CRISPR," *Cell & Bioscience* (2017) 7(21):1-18.
Warejoncas, et al., "Precision Gene Editing Technology and Applications in Nephrology," *Nature Reviews* (2018) 14(11):663-77.
Ribeiro, et al., "Protein Engineering Strategies to Expand CRISPR-Cas9 Applications," *International Journal of Genomics* (2018) 2018:1-12.
Zhang, et al., "Myoediting: Toward Prevention of Muscular Dystrophy by Therapeutic Genome Editing," *Physiological Reviews* (2018) 98(3):1205-40.
Gee, et al., "Cellular Reprogramming, Genome Editing, and Alternative CRISPR Cas9 Technologies for Precise Gene Therapy of Duchenne Muscular Dystrophy," *Stem Cells International* (2017) 2017:1-11.
Mok et al., "A Bacterial Cytidine Deaminase Toxin Enables CRISPR-free Mitochondrial Base Editing", *Nature* (2020) 583:631-37.
Mok et al., "A Bacterial Cytidine Deaminase Toxin Enables CRISPR-free Mitochondrial Base Editing", *Nature* (Supplemental Information).
Remacle et al., "New Mode of DNA Binding of Multi-zinc Finger Transcription Factors: DeltaEF1 Family Members Bind with two Hands to two Target Sites," *EMBO J.* (1999) 18(18):5073-84.
Shekhawat et al., "Split-protein Systems: Beyond Binary Protein-Protein Interactions", *Current Opinion in Chemical Biology* (2011) 15(6):789-97.

\* cited by examiner

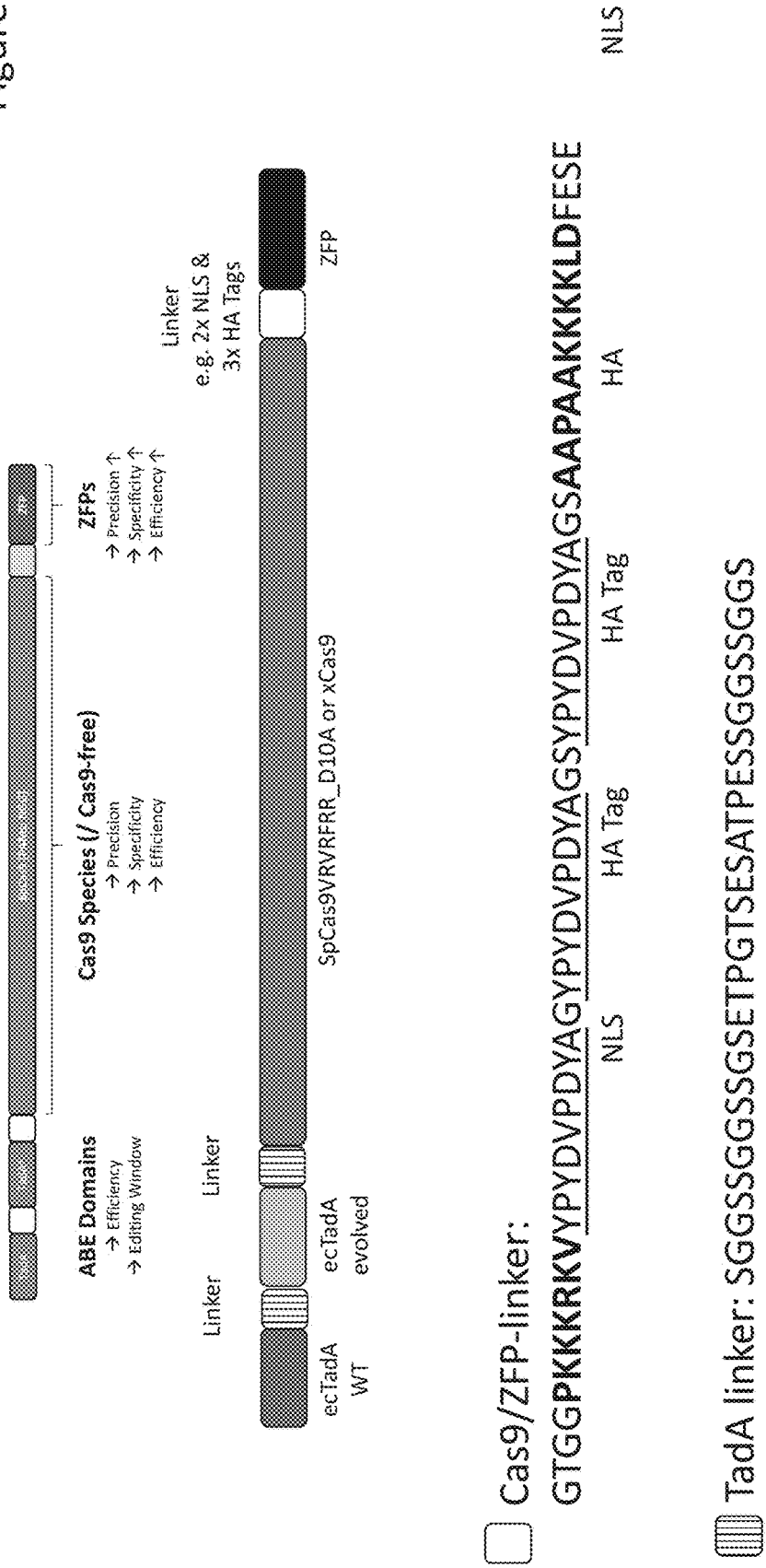

| | V617 (V617F) | | |
|---|---|---|---|
| | G (>T) | T | C | T |
| ABEmax-Cas9NG_AAT_PAM | NA | 0.59 | NA | 6.78 |
| ABEmax-Cas9NG_ZFP_2_AAT_PAM | NA | 0.50 | NA | 6.94 |
| ABEmax-Cas9NG_ZFP_4_AAT_PAM | NA | 0.71 | NA | 8.65 |
| ABEmax-Cas9NG_ZFP_6_AAT_PAM | NA | 1.29 | NA | 13.11 |
| ABEmax-Cas9NG_ZFP_7_AAT_PAM | NA | 1.14 | NA | 10.94 |
| ABEmax-Cas9NG_TAA_PAM | NA | 0.25 | NA | 0.06 |
| ABEmax-Cas9NG_ZFP_2_TAA_PAM | NA | 1.30 | NA | 0.24 |
| ABEmax-Cas9NG_ZFP_4_TAA_PAM | NA | 1.19 | NA | 0.16 |
| ABEmax-Cas9NG_ZFP_6_TAA_PAM | NA | 0.93 | NA | 0.18 |
| ABEmax-Cas9NG_ZFP_7_TAA_PAM | NA | 0.69 | NA | 0.09 |
| ABEmax-Cas9NG_AAA_PAM | NA | 0.17 | NA | 0.10 |
| ABEmax-Cas9NG_ZFP_2_AAA_PAM | NA | 0.17 | NA | 0.15 |
| ABEmax-Cas9NG_ZFP_4_AAA_PAM | NA | 0.17 | NA | 0.09 |
| ABEmax-Cas9NG_ZFP_6_AAA_PAM | NA | 0.21 | NA | 0.15 |
| ABEmax-Cas9NG_ZFP_7_AAA_PAM | NA | 0.16 | NA | 0.17 |

(T column values, leftmost: 0.54, 0.27, 0.26, 0.67, 0.52, 0.43, 5.48, 4.18, 3.06, 2.11, 2.76, 4.65, 6.90, 4.76, 4.58)

800 ng

| | V617 (V617F) | | |
|---|---|---|---|
| | G (>T) | T | C | T |
| ABEmax-Cas9NG_AAT_PAM | NA | 0.78 | NA | 7.35 |
| ABEmax-Cas9NG_ZFP_2_AAT_PAM | NA | 1.37 | NA | 15.24 |
| ABEmax-Cas9NG_ZFP_4_AAT_PAM | NA | 1.16 | NA | 11.15 |
| ABEmax-Cas9NG_ZFP_6_AAT_PAM | NA | 1.57 | NA | 14.72 |
| ABEmax-Cas9NG_ZFP_7_AAT_PAM | NA | 1.25 | NA | 10.64 |
| ABEmax-Cas9NG_TAA_PAM | NA | 0.17 | NA | 0.13 |
| ABEmax-Cas9NG_ZFP_2_TAA_PAM | NA | 1.69 | NA | 0.25 |
| ABEmax-Cas9NG_ZFP_4_TAA_PAM | NA | 1.31 | NA | 0.40 |
| ABEmax-Cas9NG_ZFP_6_TAA_PAM | NA | 1.13 | NA | 0.12 |
| ABEmax-Cas9NG_ZFP_7_TAA_PAM | NA | 0.97 | NA | 0.19 |

(T column values, leftmost: 0.38, 0.76, 0.58, 0.59, 0.64, 0.45, 7.85, 4.92, 4.84, 3.45)

Figure 8A

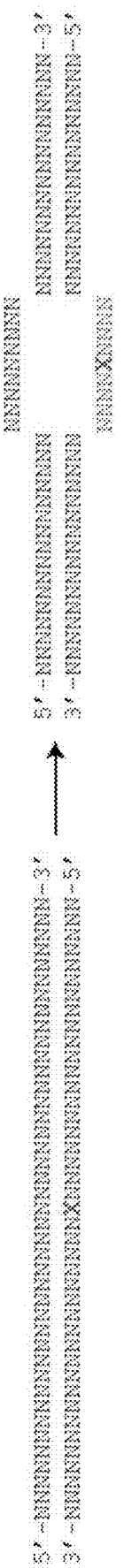

X = target base

Accessible single-stranded substrate for base editing

Figure 8F

LNA#1  5'-NnNnNnNnNnNnN$_{tct}$
NNNNNNNNNNNNNNNNNNNN$_c$NNNNNNNNNNNNNNNN-3'
3'-nNnnNnnNnnNnnNnNn$_t$

5'-NNNNNNNNNNNNNNN
3'-NNNNNNNNNNNNNNN

NNNNNNNNNNNNNNNNNNNNXNNNNNNNNNNNNNNNN

LNA#1a: 5'-NnNnNnNnNnNnNntctnNnNnNnNnNnNnNnNnNn-3'
LNA#1b: 5'-N'n'NnNnNnNnNntctnnNnNnNnNnNnNnN'n-3'
LNA#1c: 5'-NnNnNnNnNnNnNntctnNnNnNnNnNnNnNnNnNn-Chol-TEG-3'

Figure 8G

LNA#2  5'-NnNnNnNnNn$_t$NnNnNnNn-3'    LNA#3   NNNNNNNNNNNN-3'
NNNNNNNNNNNN$_g$NN$_c$NNNNNNNNNN           NNNNNNNNNNNN-5'
3'-nNnnNnnNn$_t$       $_t$nNnnNnnNn-5'

5'-NNNNNNNNNNNNNN
3'-NNNNNNNNNNNNNN

NNNNNNNNNNNNNXNNNNNNNNNNNNN

LNA#2: 5'-NnNnNnNnNntcctnNnNnNnNn-3'
LNA#3: 5'-NnNnNnNnNntctnNnNnNnNn-3'

ENGINEERED TARGET SPECIFIC BASE EDITORS

CROSS-REFERENCE TO RELATED APPLICATIONS

The present application claims the benefit of U.S. Provisional Application No. 62/721,903, filed Aug. 23, 2018; U.S. Provisional Application No. 62/753,696, filed Oct. 31, 2018; U.S. Provisional Application No. 62/817,153, filed Mar. 12, 2019; and U.S. Provisional Application No. 62/867,565, filed Jun. 27, 2019, the disclosures of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Aug. 20, 2019, is named 8325-0180-S180-US1_SL.txt and is 225,511 bytes in size.

TECHNICAL FIELD

The present disclosure is in the fields of polypeptide and genome engineering.

BACKGROUND

Artificial nucleases, such as engineered zinc finger nucleases (ZFN), transcription-activator like effector nucleases (TALENs), the CRISPR/Cas system with an engineered crRNA/tracr RNA ('single guide RNA'), also referred to as RNA guided nucleases, and/or nucleases based on the Argonaute system are revolutionizing the fields of medicine, biotechnology and agriculture. These molecular tools are allowing the genetic manipulation (e.g. editing) of genomes in organisms to a level never before possible. Artificial nucleases are capable of cleaving DNA such that following such cleavage, the cell is forced to 'heal' the break by either error-prone non-homologous end joining (NHEJ) or, in the presence of a substrate DNA with homology to the regions flanking the cut site, by insertion of the substrate DNA through homology-directed repair (HDR). Both of these processes start with a double strand break (DSB) in the DNA.

In some instances, engineered nucleases could possibly result in unwanted consequences (e.g. translocations, inversions and deletions) that may occur due to the induction of multiple DSB in the chromosome of a genetically-edited cell. For example, some evidence of chromosomal rearrangements including translocations, inversions and deletions have been observed following nuclease treatment (Kosicki, et al. (2018) *Nat Biotechnol* 36:765 and Shin, et al. (2017) *Nat Comm* doi:10.1038/ncomms15646), and more recently, there has been concern about induction of the p53 pathway following cleavage in some cells leading to apoptosis using the CRISPR/Cas system (Ihry, et al. (2018) *Nat Med* 24:939-946 and Haapaniemi, et al. (2018) *Nat Med* 24:927-930). Also, HDR typically is very inefficient in most eukaryotes, making gene correction difficult (Eid, et al. (2018) *Biochem J* 475:1955-1964).

In addition, Cas9 base editors such as AID-dCas9, APOBEC-dCas9 (e.g. APOBEC3G or APOBEC1), BE2, BE3 and BE4 (see, e.g., Komor, et al. (2016) *Nature* 533(7603):420-424; Komor, et al. (2017) *Science Advances* 3(8)_eaao4774; Kim, et al. (2017) *Nat Biotechnol* 35(4): 371-376) can exhibit a lack of specificity (see Kim, et al. (2019) *Nat Biotechnol* 10.1038/s41587-019-0050-1; Zuo, et al. (2019) *Science* DOI:10.1126/science.aav9973), rendering them unsuitable for a variety of purposes, including in vivo and ex vivo therapeutic applications.

Thus, there remains a need to accomplish genome (base) editing without inducing a double strand break and with high specificity.

SUMMARY

The present disclosure provides methods and compositions to selectively edit DNA in a cell (for example, a base editor), including editing (e.g., of a single base) without making a double-stranded cut in the target DNA (e.g., the edited genome). Such base editors can be cytosine base editors (CBEs) which change a C:G to a T:A or adenine base editors (ABEs) which change A:T to G:C. Furthermore, because no double-stranded break is induced, there are no free DNA ends in the endogenous target and no translocations occur. Base editors as described herein can be used for gene knock out (e.g., changing a regular codon into a stop codon, for instance using a cytosine base editor and/or mutating a splice acceptor site using either cytosine or adenine base editors); introducing mutations (e.g., activating or repressing mutations) into a control element (e.g., promoter region) of a gene; correcting (reversing) disease-causing mutations (such as point mutations); and/or inducing mutations that that result in therapeutic benefits. The base editors as described herein may be provided (to a cell for in vitro or ex vivo uses or in vivo to a subject) for base editing in polypeptide and/or polynucleotide form. Among other advantages, the base editors of the invention can (1) increase specificity due to the additional DNA binding domain/length of the binding site an increased precision or targeting density due to reduced PAM requirements.; (2) expand (relax) PAM restrictions to allow targeting of sites not currently targetable; (3) increase editing efficiency at poorly performing PAM sites; and/or (4) improve efficiency at target sites targetable with non ZFP-anchored reagents and therefore supports a lower dose which then also results in lower off-target activity.

Thus, described herein are base editing compositions comprising at least one functional domain (e.g., a DNA destabilizing molecule such as a nickase, a protein and/or a nucleotide) and at least one DNA-binding domain (e.g., a zinc finger protein). In certain embodiments, the base editing composition edits an adenine (A) or cytidine (C) base in DNA, wherein the composition comprises: (1) at least one zinc finger protein (ZFP) DNA-binding domain; (2) at least one DNA destabilizing molecule; and (3) at least one adenine or cytosine deaminase, wherein the composition does not make a double-stranded cut in the DNA.

Any DNA destabilizing molecule may be used in the compositions described herein in any combination, including but not limited to a Cas9 nickase, a Cas9 protein (e.g., dCas) operably linked to a single guide RNA (sgRNA), any RNA programmable system, a zinc finger nuclease nickase (ZFN nickase), a TALEN nickase, one or more proteins such as those shown in Table A, and/or one or more nucleotides (e.g., one or more peptide nucleic acids (PNAs), locked nucleic acids (LNAs) and/or bridged nucleic acids (BNAs)). In certain embodiments, the base editing composition comprises more than one DNA destabilizing molecule, for example one or more proteins (e.g., Table A, nickases, etc.) and/or one or more nucleotides. In certain embodiments, the composition comprises a ZFN nickase and one or more additional proteins and/or nucleotide DNA destabilizing molecules (e.g., one or more proteins of Table A and/or one or more nucleotides as described herein). In certain aspects, the base editing composition does not comprise a Cas9 protein, but may comprise other Cas protein (e.g, non-Cas9 RNA programmable systems). In certain embodiments, the DNA-destabilizing molecule comprises a zinc finger nuclease (ZFN) nickase.

The at least one zinc finger protein (ZFP) DNA-binding domain of the base editing composition may be operably linked to one or more of the other components of the base editing composition, for example to one or more of the DNA destabilizing molecules (e.g., to Cas9 nickase, dCas9, etc.) and/or to the at least one adenine or cytosine deaminase. In certain embodiments, at least one ZFP DNA-binding domain is operably linked to the adenine or cytosine deaminase. In other embodiments, the base editing composition comprises first and second ZFP DNA-binding domains, wherein the first ZFP DNA-binding domain is operably linked to the Cas9 nickase. The ZFP DNA-binding domain may comprise 3, 4, 5, 6 or more fingers and may bind to a target site on either side (5' or 3') of the targeted base to be edited. In certain embodiments, the ZFP binds to a target site that is 1 to 100 (or any number therebetween) nucleotides on either side of the targeted base. In other embodiments, the ZFP binds to a target site that is 1 to 50 (or any number therebetween) nucleotides on either side of the targeted base.

Any adenine or cytosine deaminase can be used in the compositions described herein, including wild-type and/or evolved domains. In certain embodiments, the adenine or cytosine deaminase is comprised of first and second inactive domains that dimerize to form an active adenine or cytosine deaminase. In certain embodiments, the first inactive domain of the adenine or cytosine deaminase is operably linked to the Cas9 nickase and the second inactive domain of the adenine or cytosine deaminase is operably linked to a ZFP DNA-binding domain. In still further embodiments, the adenine or cytosine deaminase and the ZFP DNA-binding domain are both operably linked to the Cas9 nickase. In other embodiments, the base editor comprises first and second ZFP DNA-domains, the first ZFP operably linked to the Cas9 nickase and the second ZFP DNA-binding domain operably linked to the adenine or cytosine deaminase.

One or more polynucleotides encoding one or more base editing compositions as described herein are also provided. The polynucleotides may be carried on viral (e.g., AAV, Ad, etc.) and/or non-viral (e.g., plasmid, mRNA, etc.) vectors. Furthermore, a cell or population of cells comprising one or more compositions and/or the one or more polynucleotides as described herein are also provided, as well as descendants of such cells, wherein the cells comprise an edited base.

Also provided are methods of editing a base in a target DNA (e.g., DNA double stranded endogenous gene or extrachromosomal (episomal) sequence) using one or more of the compositions and/or polynucleotides as described herein. In certain embodiments, the methods comprise: (i) editing a cytidine base ("C") to a uracil base ("U"), optionally wherein the U is replaced with a thymidine base ("T") during DNA replication; (ii) editing an adenine base ("A") to an inosine ("I"), optionally wherein the I replaced with a guanine base ("G") during replication; and/or (iii) editing a CA or AC dinucleotide to a UI or an IU. In other embodiments, the editing in the cell results in: (i) changing a C:G base pair to an T:A base pair; (ii) changing a C:G base pair to a G:C base pair; (iii) changing an A:T base pair to a G:C base pair; (iv) introduction of a stop codon; and/or (v) editing or creating a splicing sequence. The methods may be used to correct any disease mutation (e.g., point mutation), including in an exon or in an intron. wherein DNA in a chromosome or an extrachromosomal episome in the cell or the subject is edited. The method may be performed in vitro, ex vivo, or in vivo.

In one aspect, described herein are compositions and systems comprising a DNA-editing composition (e.g., a base editing composition, also referred to herein as a base editing complex). The DNA-editing complex comprises at least one functional domain and a DNA-binding domain. In certain embodiments, the DNA-editing composition complex comprises a fusion molecule comprising a DNA-binding domain and, in addition, at least one DNA destabilizing molecule such as a nickase domain that makes a single-stranded cut in double-stranded DNA (e.g., a DNA-nickase). In other embodiments, the DNA-editing composition (complex) comprises multiple (two or more) fusion molecules, for example a first catalytically active fusion molecule comprising a nickase including a first DNA-binding domain and nickase domain and a second catalytically inactive fusion molecule comprising a second DNA-binding domain and optionally one or more additional fusion molecules, each comprising an additional DNA-binding domain and one or more functional domains as described herein. In certain embodiments, the base editor comprises a composition as shown in any of FIGS. 1A through 1D. In certain embodiments, binding of the first and second (and optionally additional DNA binding domains) results in base-editing, for example when the catalytically active and catalytically inactive fusion molecules dimerize. In some embodiments, the optional additional DNA binding domains bind to double stranded DNA, while in other embodiments, the DNA binding domains bind to single stranded DNA. In some embodiments, the DNA nickase is a ZFN nickase, a TALEN nickase or a CRISPR/Cas nickase, in which at least one functional (nickase) domain is operably linked to a DNA binding domain (e.g. a ZFP DNA binding domain, a TALE DNA binding domain and a sgRNA for use with a CRISPR/Cas system). In some embodiments, the DNA nickase (e.g., fusion molecule) comprises a linker sequence between the nickase domain and the DNA binding domain. The nickase domain(s) may be positioned on either side of the DNA-binding domain, including at the N- or C-terminal side of the fusion molecule (N- and/or C-terminal to DNA-binding domain). In some embodiments, the linkers are selected from a bacterial selection system from a large linker library (>10e8 members). In some embodiments, the linkers range from four to 22 amino acid residues. In some embodiments, the linkers allow for specific positioning of a functional domain (for example a nickase domain) relative to a DNA binding domain (for example, linkage of the nickase domain to the N- or C-terminal side of the DNA binding domain). In some examples, the linker is selected using the method disclosed in Paschon, et al. (2019) *Nat Commun.* 10:1133. One or more polynucleotides (e.g., constructs) encoding base editors (or components thereof) are also provided.

The DNA-editing complexes as described herein comprise one or more functional domains, including, but not limited to, one or more adenine deaminase domains, one or more cytidine deaminases, and/or one or more uracil DNA glycosylase inhibitors. One or more functional domains may be included in the catalytically active and/or the catalytically inactive fusion molecule of the DNA-editing complexes described herein. In some embodiments, the cytidine deaminase is an apolipoprotein B mRNA-editing complex 1 (APOBEC1) domain. In some embodiments, the cytidine deaminase is an Activation Induced Deaminase (AID). In some embodiments, the deaminase is an adenine deaminase. In some embodiments, the adenine deaminase is a wild-type or mutated (evolved) TadA (tRNA adenine deaminase (see Gaudelli, et al. (2017) *Nature* 551:464-471). In some embodiments, the adenine deaminase is ABE 7.8, ABE 7.9 or ABE 7.10 (Gaudelli, ibid) or ABEmax (Koblan, et al. (2018) *Nat Biotechnol.* 36(9):843-846). In some embodiments, the deaminase (adenine or cytidine) functional domain is assembled from two polypeptides comprising operably linked zinc fingers (e.g., a split enzyme) or from one or more ZFPs operably linked to one part of the split enzyme and a Cas9 nickase operably linked to the other component of the split enzyme (see, e.g., FIG. 1B). In some embodiments, assembly of the deaminase is driven by the binding of the operably linked zinc fingers to DNA targets such that the polypeptides are positioned to allow assembly. In some embodiments, the base editor further comprises a uracil DNA glycosylase inhibitor (UGI).

In one aspect, the base editor comprises a DNA-unwinding (also referred to as DNA-destabilizing) system derived from a CRISPR system, for instance a Cas9 (e.g., naturally occurring and/or engineered Cas9) protein (e.g., nickase) or a non-Cas9 protein. In certain embodiments, the base editor is a Cas9 base editor further comprises a zinc finger protein DNA-binding domain, which ZFP may be operably linked to any component of the Cas9 protein (e.g., wild-type or engineered nickase) in any orientation, for example a base editor comprising a ZFP (a ZFP anchor) operably linked to the Cas9 protein, the sgRNA of the Cas9 nickase or the deamimase (wild-type or engineered (evolved) ABE or CBE). In certain embodiments, the ZFP is operably linked to the Cas9 domain of the base editor. In certain embodiments, the base editor comprises the components as shown in the Cas9 base editors of FIG. 3.

In another aspect, the base editor does not comprise a DNA-unwinding (DNA-destabilizing) element derived from a Cas9 protein (also referred to as "Cas9-free"). In certain embodiments, the Cas9-free base editors of the invention comprise a ZFP-deaminase fusion protein and a ZFN nickase, and optionally one or more DNA-destabilizing factors. In certain embodiments, the DNA-destabilizing factor is a protein (e.g., as shown in Table A) or an oligonucleotide (e.g., one or more PNAs, LNAs and/or BNAs). The one or more non Cas9 DNA-destabilizing (unwinding) factor(s) (e.g., proteins of Table A, LNAs, PNAs, BNAs, etc.) may be operably linked to any component of the base editor, for example either component of the ZFP-deaminase fusion protein and/or any of the components of the ZFN nickase. In some embodiments, the base editor comprises one or more protein and one or more nucleotide DNA-destabilizing (unwinding) factors. In still further embodiments, the Cas9-free base editors described herein comprise one or more proteins derived from a CRISPR system, which proteins are not Cas9 but have DNA-destabilizing (unwinding) properties.

In certain embodiments, the base editor comprises one or more nucleotide sequences, for example one or more DNA oligonucleotides, RNA oligonucleotides, peptide nucleic acids (PNAs), locked nucleic acids (LNAs) and/or bridged nucleic acids (BNAs), which can be used to provide a single stranded DNA substrate for base editors at the target site. This can be facilitated by e.g. duplex invasion, triplex invasion or a tail-clamp (Quijano, et al. (2017) *Yale J. Biol and Med.* 90:583-598; Pellestor and Paulasova (2004) *European J. Human Genetics* 12:694-700; Schleifman, et al. (2011) *Chem Biol.* 18:1189-1198). The structure of the one or more nucleotide sequences of the base editor will vary in length; number and position of DNA and/or RNA and/or LNA and/or LNA and/or BNA bases; phosphorothioate bonds; other common modifications of these oligonucleotides depending on the target sequence composition.

In certain embodiments, the base editor comprises one or more PNAs, for example, gamma PNAs containing mini-PEG substitutions and the gamma position for enhanced binding, increased solubility and improved delivery (Bahal, et al. (2014) *Current Gene Ther.* 14(5):331-342. In certain embodiments, the PNAs comprise one or more O indicates 8-amino-2,6-dioxaoctanoic acid linkers and/or one or more cytosines (C) or pseudoisocytosine residues. Optionally, one or more lysine (Lys) residues are included in the PNA, for example on the N- and/or C-terminals of the PNA sequence. In certain embodiments, 1, 2, 3, 4, 5 or more Lys residues are included at one or both terminals of the PNA. In certain embodiments, two or more PNAs are used in the base editor, for example in the same or reverse orientation relative to each other. In certain embodiments, the PNA comprises one or more PNAs as shown in FIGS. 8B to 8E, including but not limited to one or more PNAs of the structure: N-Lys-Lys-Lys-NNNNNNNNNN-OOO-NNNNNNNNNN-Lys-Lys-Lys-C; N-Lys-Lys-Lys-NNNNNNNNNN-OOO-NNNNN NNNNNNNNNN-Lys-Lys-Lys-C; N-Lys-Lys-Lys-NNNN NNNNNN-OOO-NNNNNNNNNN-Lys-Lys-Lys-C; N-Lys-Lys-Lys-NNNNNNNNNN-OOO-NNNNNNNNNN-Lys-Lys-Lys-C; and/or N-Lys-Lys-Lys-NNNNNNNNN NNNNNN-Lys-Lys-Lys-C, where O indicates 8-amino-2,6-dioxaoctanoic acid linkers and C indicates cytosine. The Lys resides on the N- and/or C-terminals of the PNA sequence are optional and pseudoisocytosine be can substituted for cytosine.

In other embodiments the base editor comprises one or more LNAs. LNAs can include a stacking linker and 2'-glycylamino-LNA for improved performance (Geny, et al. (2016) *Nucleic Acids Res.* 44(5):2007-2019). In certain embodiments, the LNA comprise one or more phosphorothioate bonds, optionally between one or more LNA residues and/or DNA residues. In other embodiments, the LNA comprises one or more Cholesterol-TEG, which may increase uptake into cells. In certain embodiments, the base editor comprises one or more LNAs as shown in FIG. 8F or 8G, including but not limited to one or more LNAs of the structure: 5'-NnNnNnNnNnNnNnNtctct nNnNnNnNnNn Nnn NnnNnnNn-3' (SEQ ID NO: 1); 5'-N*n*NnNnNnNn NnNnNtctctnNnNnNnNnNnNnNnNnNnnNnnNnnNnn*N*n-3' (SEQ ID NO:69); and/or 5'-NnNnNnNnNnNnNnNnNtctct nNnNnNnNnNnNnnNnnNnnNn-Chol-TEG-3' (SEQ ID NO:70), where LNA nucleotides are shown in uppercase; DNA nucleotides are in lower case; "*" indicates phosphorothioate bonds; and Chol-TEG indicates 3' Cholesterol-TEG for increased uptake into cells.

The components of the base-editing compositions described herein may be included in any combination (one or more nickase domains, one or more DNA-binding domains, one or more functional domains, etc.) and these components may be positioned in any order relative to each other. In some embodiments, the UGI, cytidine and/or adenine deaminase is(are) N-terminal of the DNA-binding domain of the catalytically inactive fusion molecule and/or N-terminal to the nickase domain of the catalytically active fusion molecule of the DNA-editing complex. In some embodiments, cytidine and/or adenine deaminase and/or UGI is(are) C-terminal of the DNA-binding domain of the catalytically inactive fusion molecule and/or C-terminal to the nickase domain of the catalytically active fusion molecule. In some embodiments, the one or more UGIs, cytidine and/or adenine deaminase(s) is(are) positioned between the DNA binding domain and the nickase domain(s) (in the catalytically active domain). In some embodiments, the fusion molecule comprises a cytidine deaminase and an adenine deaminase domain or a UGI, wherein the UGI, cytidine and adenine deaminases are positioned in any way with regard to the DNA-binding domain, each other and/or the nickase domain (e.g., both N-terminal to the DNA-binding domain of the catalytically inactive fusion molecule in any order, both C-terminal to the DNA-binding domain of the catalytically inactive fusion molecule in any order, one N-terminal to the DNA-binding domain of the catalytically inactive fusion molecule, one C-terminal to the DNA-binding domain of the catalytically inactive fusion molecule, N-terminal to the nickase domain and/or DNA-binding domain of the catalytically active fusion molecule, C-terminal to the nickase domain and/or DNA-binding domain of the catalytically active fusion molecule, one C-terminal to the nickase domain and/or DNA-binding domain of the catalytically active fusion molecule, one N-terminal to the nickase domain and/or DNA-binding domain of the catalytically active fusion molecule, between the nickase domain and the DNA-binding domain of the catalytically active fusion molecule, etc.). Non-limiting examples of configurations of one or more fusion molecules of the base-editing compositions are shown in the appended Figures and Examples. In some embodiments, the UGI, cytidine and/or adenine deaminase domains are linked to the other members of the DNA-editing complex using linkers known in the art. One or more polynucleotides encoding the base editors or components thereof are also provided.

In still further aspects, the DNA-editing complex comprises one or more functional domains comprising at least one uracil DNA glycosylase inhibitor (e.g. UGI) domain. The, which UGI domain(s) is(are) incorporated into the DNA-editing complex in any way such that the DNA-editing complex is operable. In some embodiments, the base editing complex comprises a bacteriophage Gam protein. In some embodiments, the base editing complex comprises a deaminase, a nickase, a UGI and/or a GAM protein. In some embodiments, the components of the base editing complex are provided in one, two or more gene expression constructs encoding one, two or more fusion proteins. In some embodiments, one or more uracil DNA glycosylase inhibitor domain(s) is/are linked to the other members of the complex using the linkers described above and known in the art. In some embodiments, a linker is used to link the uracil DNA glycosylase inhibitor to other members of the complex wherein the linker is identified using the method disclosed in Paschon, et al. (2019) *Nat Commun.* 10:1133.

In some embodiments, the DNA-editing (base editing) complex further comprises a molecule to assist in opening a double-strand DNA helix. In some embodiments, the molecule comprises an enzyme. In some embodiments, the enzyme is a helicase (for example, RecQ helicases (WRN, BLM, RecQL4 and RecQ5, (see Mo, et al. (2018) *Cancer Lett.* 413:1-10), DNA2 (Jia, et al. (2017) *DNA Repair (Amst).* 59:9-19) and any other eukaryotic helicases including for example, FANCJ, XPD, XPB, RTEL1, and PIF1 (Brosh (2013) *Nat Rev Canc* 13(8):542-558)). In some embodiments, the enzyme is a bacterial and/or a viral helicase. Exemplary viral helicases include those encoded by the Myoviridae family of viruses (for example gp41, Dda, UvsW, Gene α, and Ban); those encoded by the Podpviridae family of viruses (for example 4B); those encoded by the Siphoviridae, Baculoviridae, Herpesviridae, Polyomaviridae, Palillomaviridae and Poxviridae families (for example, G40P, p143, UL5, UL9, Tag, E1, NPH—I, NPH-II, A18R, and VETF), or any other viral helicase known in the art (see e.g. Frick and Lam (2006) *Curr Pharm Des* 12(11): 1315-1338). In some embodiments, the helicase enzyme is a bacterial enzyme. Exemplary bacterial helicases include the *P. aeruginosa* SF4 DnaB-like helicase, or the RecB and RecD helicases that are part of the bacterial RecBCD complex in bacteria such as *E coli* and *H. pylori* (Shadrick, et al. (2013) *J. Biomol Screen* 18(7):761-781). In some embodiments, engineered or evolved variants of multimeric helicases are used which result in monomeric helicase activity (see e.g. Brendza, et al. (2005) *PNAS* 102(29): 10076-70081). In some embodiments, the molecule comprises a CRISPR/Cas complex. In some embodiments, the CRISPR/Cas complex comprises a guide RNA. In some embodiments, the complex comprises a Cas enzyme that is catalytically defective in its nuclease domains. In some embodiments, the complex comprises a Cas enzyme that is catalytically defective in one of its nuclease domains (for example a nickase). In some embodiments, the Cas enzyme is defective in its PAM recognition (Anders, et al. (2014) *Nature* 513(7519):569-573). In some embodiments, the Cas enzyme has relaxed (expanded) PAM requirements as compared to native PAM sequences (see for example Nishimasu, et al. (2018) *Science* 361:1259-1262). In certain embodiments, the Cas base editor as described herein exhibits relaxed (expanded) PAM requirements as compared to the NGG PAM sequence of SpCas9. In some embodiments, the molecule has helix-destabilizing properties. Exemplary helix-destabilizing molecules include ICP8 from herpes simplex virus type I (Boehmer and Lehman (1993) *J Virol* 67(2):711-715), Puralpha (Darbinian, et al. (2001) *J Cell Biochem* 80(4):589-95), and calf thymus DNA helix-destabilizing protein (Kohwi-Shigematsu, et al. (1978) *Proc Natl Acad Sci USA* 75(10):4689-93). In some embodiments, the molecule is involved in transcription and/or D loop formation/stabilization. Exemplary molecules of this class include Rad51, Rad52, RPA1, RPA2 and RPA3, Exol, BLM, and HMGB1 and HMGB2. Other proteins that can be utilized include Bovin ROA1 and *E. coli* RecA or *E. coli* rad51. Other protein domains that may act as DNA helix destabilizers include the RecI and Rec II domain from Cas9 or the RecII domain on its own, as well as any other helix destabilizing region from Cas9. Other non-limiting examples of suitable protein domains for use in the base editors described herein are shown in Table A.

In some embodiments, the molecule is a nucleic acid, including but not limited to oligonucleotides, PNAs, LNAs, BNAs and the like. In some embodiments, the nucleic acid is a DNA with homology to the region near the targeted editing. In some embodiments, the nucleic acid is an RNA with homology to the region near the targeted editing. In some embodiments, the RNA is modified. In some embodiments, the fusion molecule comprises amino acid linker sequences between one or more domains of the fusion molecule. In some embodiments, the molecule(s) used to assist in opening a double-strand DNA helix is/are linked to the other members of the DNA-editing complex using the linkers described above. In some embodiments, the molecule(s) used to assist in opening a double strand DNA helix is linked to the other members of the DNA editing complex is identified using known methods.

In certain embodiments, the nucleic acid comprises a PNA, for example a PNA comprising one or more O indicates 8-amino-2,6-dioxaoctanoic acid linkers and/or one or more cytosines (C) or pseudoisocytosine residues. Optionally, one or more lysine (Lys) residues are included in the PNA, for example on the N- and/or C-terminals of the PNA sequence. In certain embodiments, 1, 2, 3, 4, 5 or more Lys residues are included at one or both terminals of the PNA. In certain embodiments, two or more PNAs are used in the base editor, for example in the same or reverse orientation relative to each other. In certain embodiments, the one or more PNAs comprise: N-Lys-Lys-Lys-NNN NNNNNNN-OOO-NNNNNNNNNN-Lys-Lys-Lys-C; N-Lys-Lys-Lys-NNNNNNNNNN-OOO-NNNNNNNNNN NNNNN-Lys-Lys-Lys-C; N-Lys-Lys-Lys-NNNNNNNN N NOOO-NNNNNNNNNN-Lys-Lys-Lys-C; N-Lys-Lys-Lys- NNNNNNNNNN-OOO-NNNNNNNNNN-Lys-Lys-Lys-C; and/or N-Lys-Lys-Lys-NNNNNNNNNNNNNNN-Lys-Lys- Lys-C(PNA #5), wherein O indicates 8-amino-2,6-dioxaoc- tanoic acid linkers and C indicates cytosine. The Lys resides on the N- and/or C-terminals of the PNA sequence are optional and pseudoisocytosine be can substituted for cytosine. See, also, FIGS. 8B to 8E.

In other embodiments the base editor comprises one or more LNAs. LNAs can include a stacking linker and 2'-glycylamino-LNA for improved performance (Geny, et al. (2016) *Nucleic Acids Res.* 44(5):2007-2019. In certain embodiments, the LNA comprise one or more phosphoro- thioate bonds, optionally between one or more LNA residues and/or DNA residues. In other embodiments, the LNA comprises one or more Cholesterol-TEG, which may increase uptake into cells. In certain embodiments, the one or more LNAs comprise: 5'-NnNnNnNnNnNnNnNntctct nNnNnNnNnNnNnnNnnNnnNn-3' (SEQ ID NO: 1); 5'-N*n*NnNnNnNnNnNnNtctctnNnNnNnNnNnNnNn- NnnNnnNnnNnn*N*n-3' (SEQ ID NO:69); and/or 5'-Nn NnNnNnNnNnNnNtctct nNnNnNnNnNnNnnNnnNnnNn- Chol-TEG-3' (SEQ ID NO:70), where LNA nucleotides are in uppercase; DNA nucleotides are in lower case; "*" indicates phosphorothioate bonds; and "Chol-TEG" indicates 3' Cholesterol-TEG for increased uptake into cells. See, also, FIGS. 8F and 8G.

These molecules may all be incorporated into the base editing system described herein, and may act to increase editing efficiency, decrease off target base editing, adjust the base editing window or alter the targeted type of nucleic acid base.

In some embodiments, functional domains as described herein are included in single fusion molecule. Alternatively, DNA-editing complexes that include multiple functional domains may be separated into separate fusion molecules in any way. In some embodiments, one fusion molecule comprises a DNA binding domain, a cytidine and/or adenine deaminase and a UGI, while a second fusion molecule comprises a nickase or half-nickase domain. In some embodiments, one fusion molecule comprises a catalytically inactive (dead) FokI domain fused to a DNA binding domain fused to a deaminase domain, and the second fusion protein comprises a half FokI nickase protein, a DNA binding domain and a UGI domain. In some embodiments, one fusion protein comprises a catalytically inactive (dead) FokI domain fused to a deaminase domain fused to a UGI domain while a second fusion molecule comprises a functional nickase protein. In some embodiments, the one or more fusion proteins disclosed herein are fused in any order of domains within the fusion molecule that is operable. In some embodiments, the nickase domain is a Cas nickase domain, and in some embodiments, the nickase domain is a TALEN nickase domain. In some embodiments, one or more of the functional domains are linked to one or more other members of the complex using the linkers described above. In some embodiments, the one or more functional domains are linked to one or more other members of the complex using linkers identified using the methods disclosed in Paschon, et al. (2019) *Nat Commun.* 10:1133.

The base editor(s) described herein may be encoded by one or more polynucleotides. The one or more polynucleotides may be carried on viral vectors (AAV, Ad, etc.), non-viral vectors (plasmid, mRNA, etc.) or combinations thereof. In certain embodiments, one polynucleotide includes all the components of the base editor while in other embodiments, the components of the base editor are carried by two or more polynucleotides (e.g., separate polynucleotides carrying split enzymes and/or ZFPs).

In another aspect, described herein are methods of editing (e.g., gene editing) of a DNA molecule using one or more DNA-editing complexes as described herein. The methods described introducing one or more DNA-editing complexes into a cell such that the DNA molecule is edited. The cell may be isolated or may be in living subject (e.g., via intravenous or other administration to the subject). In some embodiments, the DNA molecule is a chromosome or an extrachromosomal episome in a cell. In some embodiments, the chromosome or extrachromosomal episome comprises a cytidine base ("C") that is deaminated to a uracil base ("U") by the fusion protein disclosed herein. In some embodiments, the U is replaced with a thymidine base ("T") during DNA replication. In some embodiments, the chromosome or extrachromosomal episome comprises an adenine base ("A") that is deaminated to an inosine ("I") base by the fusion protein disclosed herein. In some embodiments, the I is replaced with a guanine base ("G") during replication. In some embodiments, the chromosome or extrachromosomal episome comprises an adenine and a cytidine base that are deaminated by the deaminases disclosed herein such that a CA or AC dinucleotide is deaminated into a UI or an IU dinucleotide (FIG. 1 for exemplary systems).

In some embodiments, the nickase domain is derived from a FokI DNA cleavage domain (see U.S. Pat. Nos. 5,436,150; 8,703,489; 9,200,266; and 9,631,186). In some embodiments, the FokI nickase comprises one or more mutations as compared to a parental FokI nickase. Mutations as described herein, include but are not limited to, mutations that change the charge of the cleavage domain, for example mutations of positively charged residues to non-positively charged residues (e.g., mutations of K and R residues (e.g., mutated to S); N residues (e.g., to D), and Q residues (e.g., to E); mutations to residues that are predicted to be close to the DNA backbone based on molecular modeling and that show variation in FokI homologs; and/or mutations at other residues (e.g., U.S. Pat. No. 8,623,618 and Guo, et al. (2010)*J. Mol. Biol.* 400(1):96-107). Nickases can be ZFN nickases, TALEN nickases and CRISPR/Cas systems such as Cas nickases.

In some embodiments, the base editors comprise DNA-binding domains (e.g., engineered nickase domains) comprising cleavage domains that are derived from FokI or FokI homologues and comprise a mutation in one or more of amino acid residues 416, 418, 422, 447, 448, 476, 479, 481 and/or 525, numbered relative to the wild-type full length FokI as shown in SEQ ID NO:5, or corresponding residues in FokI homologues. In some embodiments, the cleavage half domains derived from FokI comprises a mutation in one or more of amino acid residues 414-426, 443-450, 467-488, 501-502, and/or 521-531, including one or more of 387, 393, 394, 398, 400, 416, 418, 422, 427, 434, 439, 441, 442, 444, 446, 448, 472, 473, 476, 478, 479, 480, 481, 487, 495, 497, 506, 516, 523, 525, 527, 529, 534, 559, 569, 570, and/or 571. The mutations may include mutations to residues found in natural restriction enzymes homologous to FokI at the corresponding positions. In some embodiments, the mutations are substitutions, for example substitution of the wild-type residue with any different amino acid, for example alanine (A), cysteine (C), aspartic acid (D), glutamic acid (E), histidine (H), phenylalanine (F), glycine (G), asparagine (N), serine (S) or threonine (T). In some embodiments, the FokI nuclease domain comprises a mutation at one or more of 416, 418, 422, 476, 447, 479, 481 and/or 525 (numbered relative to wild-type, SEQ ID NO:5). The nuclease domains may also comprise one or more mutations at positions 418, 432, 441, 448, 476, 481, 483, 486, 487, 490, 496, 499, 523, 527, 537, 538 and 559, including but not limited to ELD, KKR, ELE, KKS. See, e.g., U.S. Pat. No. 8,623,618. In some embodiments, the cleavage domain includes mutations at one or more of the residues 419, 420, 425, 446, 447, 470, 471, 472, 475, 478, 480, 492, 500, 502, 521, 523, 526, 530, 536, 540, 545, 573 and/or 574. In certain embodiments, the variant cleavage domains described herein include mutations to the residues involved in nuclease dimerization (dimerization domain mutations), and one or more additional mutations; for example to phosphate contact residues: e.g. dimerization mutants (such as ELD, KKR, ELE, KKS, etc.) in combination with one, two, three, four, five, six or more mutations at amino acid positions outside of the dimerization domain, for example in amino acid residues that may participate in phosphate contact. In some embodiments, the mutation at positions 416, 418, 422, 447, 448, 476, 479, 481 and/or 525 comprise replacement of a positively charged amino acid with an uncharged or a negatively charged amino acid. In other embodiments, mutations at positions 446, 472 and/or 478 (and optionally additional residues for example in the dimerization or catalytic domains) are made. In some embodiments, the mutations comprise I479Q and/or Q481A mutations.

In some embodiments, the engineered cleavage half domain comprises mutations in the dimerization domain, for example, amino acid residues 490, 537, 538, 499, 496 and 486 in addition to the mutations described herein. In some embodiments, the invention provides fusion proteins wherein the engineered cleavage half-domain comprises a polypeptide in which the wild-type Gln (Q) residue at position 486 is replaced with a Glu (E) residue, the wild-type Ile (I) residue at position 499 is replaced with a Leu (L) residue and the wild-type Asn (N) residue at position 496 is replaced with an Asp (D) or a Glu (E) residue ("ELD" or "ELE") in addition to one or more mutations described herein. In some embodiments, the engineered nickase half domains are derived from a wild-type FokI or FokI homologue cleavage half domain and comprise mutations in the amino acid residues 490, 538 and 537, numbered relative to wild-type FokI (SEQ ID NO:5) in addition to the one or more mutations at amino acid residues 416, 418, 422, 447, 448, 476, 479, 481 or 525. In some embodiments, the invention provides a fusion protein, wherein the engineered nickase half-domain comprises a polypeptide in which the wild-type Glu (E) residue at position 490 is replaced with a Lys (K) residue, the wild-type Ile (I) residue at position 538 is replaced with a Lys (K) residue, and the wild-type His (H) residue at position 537 is replaced with a Lys (K) residue or an Arg (R) residue ("KKK" or "KKR") (see U.S. Pat. No. 8,962,281, incorporated by reference herein) in addition to one or more mutations described herein (see U.S. Patent Publication No. 2018/0087072).

In some embodiments, fusion molecules comprising a DNA binding domain and an engineered FokI or homologue thereof cleavage half-domain as described herein that produce an artificial nuclease are provided. In some embodiments, the DNA-binding domain of the fusion molecule is a zinc finger binding domain (for example, an engineered zinc finger binding domain, ZFP). In some embodiments, the one or more of the zinc fingers are linked together using linkers identified using the methods disclosed in Paschon, et al., supra. In some embodiments, the DNA-binding domain is a TALE DNA-binding domain (TALE). In some embodiments, the DNA binding domain comprises a DNA binding molecule (e.g. guide RNA) and a catalytically inactive Cas or Cpf1 (also known as Cas12a) protein (for example dCas9 or dCpf1). In some embodiments, the DNA binding domain comprises a ZFP fused to a catalytically inactive Cas (dCas) protein. In some embodiments, the ZFP-dCas fusion protein comprises mutations to alter the PAM specificity. In some embodiments, the ZFP-dCas protein is not dependent on PAM recognition to specifically bind to a DNA sequence. In some embodiments, the DNA binding domain comprises a TALE fused to a dCas protein. In some embodiments, the TALE-dCas fusion protein comprises mutations to alter the PAM specificity. In some embodiments, the TALE-dCas protein is not dependent on PAM recognition to specifically bind to a DNA sequence. In any of the above embodiments, the linkers used to link the DNA binding domain (for example, ZFP, TALE or guide RNA and Cas system) to the engineered FokI or homologue thereof are identified using the methods known in the art. See, e.g., Paschon, et al. (2019) Nat Commun. 10:1133.

In some embodiments, the DNA-editing complex edits specific DNA bases in a double stranded DNA. In some embodiments, the edits are made in a DNA molecule within a cell. In some embodiments, the DNA is in a chromosome in a cell. In some embodiments, the editing results in the change from a C:G base pair to a T:A base pair. In some embodiments, the editing results in a change from a C:G base pair to a G:C base pair. In some embodiments, the editing results in a change from a A:T base pair to a G:C base pair. In some embodiments, the editing is done in an exon. In some embodiments, the editing results in the introduction of a stop codon (for example TAA, TAG, TGA). In some embodiments, the base editing results in the knock-out of gene expression of a targeted gene. In some embodiments, the editing is done in a sequence encoding a splicing sequence (for example, a U2 splice sequence wherein a 5' consensus sequence is G T A/G A/C/T G T/G/A/C A/G/T/C (T/C/G/A)$_3$ (SEQ ID NO:73) and the 3' consensus sequence is (T/C)$_{10}$ T/C/A/G C/T A G (SEQ ID NO:74); and a U12 splice sequence wherein a 5' consensus sequence is G/A T A T C T T/C and a 3' consensus sequence is (T/G/A/G)$_2$ T/A/C/G (T/C/A/G)$_2$ C/T A G/C, see Turunen, et al. (2013) Wiley Interdiscip Rev RNA. 4(1):61-76). In some embodiments, a new splicing sequence is created. In some embodiments, a splicing sequence is altered such that it no longer functions as a splicing sequence. In some embodiments, alteration of a splicing sequence causes exon skipping. In some embodiments, a sequence is altered such that a rare codon in created. In some embodiments, base editing causes correction of a point mutation in a DNA sequence such that a gene associated with a disease is corrected. Non-limiting examples of base editing for treatment and/or prevention of disease include editing of JAK2 such that the V617F version is no longer expressed (thereby reducing activation of this gene which leads to uncontrolled blood cell production); base editing to knock out or repress other cancer genes such as BCR/ABL; base editing of A1AT; and the like. Exemplary diseases that may be treated include sickle cell disease, hemophilia, cystic fibrosis, phenylketonuria, Tay-Sachs, color blindness, Fabry disease, Friedreich's ataxia, prostate cancer, and many others.

In some embodiments, the base editing complexes as disclosed herein act on RNA molecules. In some embodiments, the base editors utilize an RNA-specific deaminase such as ADAR2 (adenosine deaminase acting on RNA type 2) (see Cox, et al. (2017) *Science* 358(6366):1019-1027).

Also disclosed herein are cells comprising any of the compositions (base-editing compositions and/or one or more polynucleotides encoding these compositions) as well as cells descended from these cells that have been modified by the methods and compositions disclosed herein. In some embodiments, the cell is a bacterial cell or a eukaryotic cell. In some embodiments, the cells comprise a base-editor complex and a base-editor complex induced DNA or RNA modification. The modified cells, and any cells derived from the modified cells do not necessarily comprise the base editor complex of the disclosure more than transiently, but the genomic modifications mediated by such base editor complexes remain.

In yet another aspect, methods for targeted editing of cellular chromatin in a region of interest; methods of treating infection; and/or methods of treating disease are disclosed herein. These methods maybe practiced in vitro, ex vivo or in vivo or a combination thereof. The methods involve editing cellular chromatin at a predetermined region of interest in cells by expressing a base editing complex as described herein (for example fusion polypeptides and optionally any associated nucleic acids in which one or more fusion polypeptide(s) comprise the engineered nickases as disclosed herein). In certain embodiments, the targeted editing of the on-target site is found in 5%, 10%, 15%, 20%, 25%, 30%, 35%, 40%, 45%, 50%, 55%, 60%, 65%, 70%, 75%, 80%, 85%, 90%, 95% or 100% of the cells.

The base editing complex as disclosed herein can be used in methods for targeted editing of cellular chromatin in a region of interest. Cells include cultured cells, cell lines, cells in an organism, cells that have been removed from an organism for treatment in cases where the cells and/or their descendants will be returned to the organism after treatment, and cells removed from an organism, modified using the fusion molecules of the invention, and then returned to the organism in a method of treatment (cell therapy). A region of interest in cellular chromatin can be, for example, a genomic sequence or portion thereof.

A fusion molecule can be expressed in a cell, e.g., by delivering the fusion molecule to the cell as a polypeptide, or by delivering a polynucleotide encoding the fusion molecule to a cell, wherein the polynucleotide, if DNA, is transcribed and is translated, to generate the fusion molecule. Further, if the polynucleotide is an mRNA encoding the fusion molecule, following delivery of the mRNA to the cell, the mRNA is translated, thus generating the fusion molecule.

In other aspects of the invention are provided methods and compositions for increasing base editing specificity. In some embodiments, methods are provided for increasing overall on-target editing specificity by decreasing off-target editing activity. In some embodiments, methods are provided for decreasing indel formation associated with base editing. In some embodiments, the engineered nickase components (nickase partners, for example a catalytically inactive ZFN partner and a catalytically active ZFN partner that form a ZFN nickase) of an engineered base editing complex are used to contact a cell, where each nickase partner of the complex is given in a ratio to the other partner other than one to one. In some embodiments, the ratio of the two partners is given at a 1:2, 1:3, 1:4, 1:5, 1:6, 1:8, 1:9, 1:10 or 1:20 ratio, or any value therebetween. In other embodiments, the ratio of the two partners is greater than 1:30. In some aspects, each partner is delivered to the cell as an mRNA or is delivered in a viral or non-viral vector where different quantities of mRNA or vector encoding each partner are delivered. In further embodiments, each partner of the nuclease complex may be comprised on a single viral or non-viral vector, but is deliberately expressed such that one partner is expressed at a higher or lower value that the other, ultimately delivering the cell a ratio of cleavage half domains that is other than one to one. In some embodiments, each cleavage half domain is expressed using different promoters with different expression efficiencies. In some embodiments, the two cleavage domains are delivered to the cell using a viral or non-viral vector where both are expressed from the same open reading frame, but the genes encoding the two partners are separated by a sequence (e.g. self-cleaving 2A sequence or IRES) that results in the 3' partner being expressed at a lower rate, such that the ratios of the two partners are 1:2, 1:3, 1:4, 1:5, 1:6, 1:8, 1:9, 1:10 or 1:20 ratio, or any value therebetween. In other embodiments, the two partners are deployed at a ratio that is chosen to be different from 1:1.

In another aspect, described herein is a population of cells produced using one or more base editors as described herein. In certain embodiments, more than 5%-20% (or any value therebetween), preferably more than 20%, even more preferably more than 50% and even more preferably between 80% and 100% of the cells include the modification to the targeted base (e.g., are base edited cells). In still further embodiments, the edited cells exhibit few or no off-target edits (unintended edits anywhere in the genome) and/or bystander (editing events in close proximity, for example 1-20 (or any value therebetween) nucleotides on either side of the intended target base, for example within the protospacer region of Cas9) mutations. Isolated populations of base edited cells as described herein can be used for ex vivo treatment of disease in a subject and/or can be further manipulated ex vivo (e.g., via further rounds of base editing as described herein) prior to use as an ex vivo treatment. In addition, base editing can be conducted in vivo such that the disease or condition is treated in the subject following correction of the disease-related mutations in vivo.

In some embodiments, the nickase partners are fused to additional active domains. In some embodiments, the additional domains include one or more exemplary domains selected from one or more deaminases (for example A specific or C specific), a UGI domain, a helicase, and a GAM domain. In another aspect, described herein is a kit comprising a base editing complex as described herein or one or more polynucleotide(s) encoding one or more base editing complex proteins as described herein; ancillary reagents; and optionally instructions and suitable containers.

These and other aspects will be readily apparent to the skilled artisan in light of disclosure as a whole.

BRIEF DESCRIPTION OF THE DRAWINGS

FIG. 1A shows systems comprising one catalytically inactive (indicated by "X") fusion molecule comprising a DNA-binding domain (e.g., ZFP, TALE, sgRNA) and one catalytically active nickase fusion molecule (indicated by the scissors), also comprising a DNA-binding domain (e.g., ZFP, TALE, sgRNA). The catalytically active and inactive fusion molecules dimerize upon binding of the DNA-binding domains to their respective target sites and, following binding, edit the target DNA (e.g., base editing). FIG. 1A also shows complexes comprising two UGI domains. FIG. 1B shows further exemplary Cas9 and Cas9-free systems for base editing. The top panel shows a base editor that functions via dimerization of the components of any adenosine or cytosine deaminase domains. The bottom panel of FIG. 1B shows various embodiments of ABE and CBE base editors as described herein. FIG. 1C shows another embodiment of a base editor as described herein comprising a Cas9 DNA destabilizing molecule (e.g., RNA programmable system comprising dCas9 operably linked to a sgRNA), optionally linked to a ZFP anchor; a ZFP-deaminase fusion protein; and a ZFN nickase. In certain embodiments, the ZFN nickase is not present and the DNA destabilizing molecule comprises any RNA-programmable molecule. The schematic shows the ZFN nickase on the opposite side of the Cas9 nickase from the ZFP-deaminase fusion protein but it will be apparent the ZFN nickase and ZFP-deaminase can both be 3' or 5' to the Cas9 nickase. FIG. 1D shows further Cas9-free (also referred to as non-Cas9) base editing systems. The triangle indicates where nicking occurs and "PNA" refers to peptide nucleic acid; "LNA" refers to locked nucleic acid and "BNA" refers to bridged nucleic acid. The nucleotides in these base editors (e.g., DNA oligonucleotides, RNA oligonucleotides, peptide nucleic acids (PNAs), locked nucleic acids (LNAs) and/or bridged nucleic acids (BNAs)) can provide a single stranded DNA substrate for base editors at the target site.

FIGS. 3A and 3B are schematics depicting exemplary ZFP base editors. FIG. 3A shows exemplary ZFP adenine base editors. The top panel shows an exemplary editor with the indicated components. The middle panel shows an exemplary ABE that uses two E. coli tRNA-specific adenosine deaminases (tadA), where one is the wild type sequence and the other is an evolved sequence (Gaudelli, et al. (2017) Nature 551(7681):464-471)). The TadA domains are attached to each other and to the SPCas9 sequence using the linker shown (SEQ ID NO:2). The SpCas9 used is a VRVR-FRR variant with a known relaxed PAM requirement (see Nishimasu, et al. (2018) Science 361:1259-1262). The Cas9 sequence is then linked to a ZFP DNA binding domain, where the linker used (SEQ ID NO:3) can comprise two NLS sequences and three HA tags. Cas9VR is also referred to as Cas9NG. FIG. 3B shows exemplary Cas9 and Cas9-free base editors as described herein. The following abbreviations are used: "TadA" refers to wild-type adenine deaminase domain; TadA* refers to an evolved (engineered) adenine deaminase domain; "7.8" "7.9" "7.10" and "MAX" refer to evolved (engineered) adenine deaminase domains as described in Gaudelli, et al. (2017) Nature 551(7681):464-471) and Koblan, et al. (2018) Nat Biotechnol. 36(9):843-846; "SpCas9 [PAMs: NGG]" refers to Cas9 from Streptococcus pyogenes as described in Jinek, et al. (2012) Science 337(6096):816-21; "SpXCas9-3.7 [PAMs: NGN, GAA & GAT]" refers to a SpCas9 variant with broad PAM compatibility as described in Hu, et al. (2018) Nature 556(7699): 57-63; "SpCas9-NG [PAMs: NGN; NAN in vitro]" refers to a SpCas9 variant with relaxed PAM requirements as described in Nishimasu, et al. (2018) Science 361(6408): 1259-1262; "ScCas9 [PAMs: TGT, . . . ]" refers to a SpCas9 ortholog with minimal PAM specificity as described in Chatterjee, et al. (2018) Sci Adv 4(10):eaau0766. doi: 10.1126/sciadv.aau0766; "NO CAS9" means this domain is not present (Cas9-free base editor); "5F ZFP" refers to a five-finger ZFP; "6F ZFP" refers to a six finger ZFP; ">6F ZFP" refers to a ZFP having more than 6 fingers; "ZFP RQ" and "( . . . )" refers to modified ZFPs as described in Miller, et al. (2019) Nature Biotechnology 37(8):945-952

FIGS. 5A and 5B show base editor constructs comprising sequences encoding two UGI proteins linked to a ZFP DNA binding domain, further linked to sequences encoding either the APOBEC1 (FIG. 5A) or AID (FIG. 5B) cytidine enzymes capable of deaminating C nucleotides to U. FIGS. 5C and 5D depict two cytidine base editor constructs which lack the UGI domains of the constructs of FIGS. 5A and 5B. FIGS. 5E and 5F depict two constructs that utilize sequences encoding a FokI nickase. These constructs can be used as a pair where the sequences encoding the cytidine base editor are linked to a ZFP DNA binding domain which is then linked to a FokI catalytically inactive nuclease domain. The second construct (FIG. 5F) comprises sequences encoding two UGI domains linked to a ZFP DNA binding domain which is linked to sequences encoding a catalytically active FokI nuclease domain. The pair may be constructed in any manner to make an active base editor wherein the active and inactive FokI domains may be on either of the two partner constructs, and the UGI sequences and the cytidine base editor sequence can be on either partner.

FIG. 6A shows a construct comprising sequences encoding two TadA domains, one wild type and one evolved, and linked to a ZFP DNA binding domain. As shown in FIG. 6B, in some variations, the construct further comprises a catalytically inactive FokI domain.

FIGS. 7A through 7C illustrate base editing of the JAK2 V617F target. FIG. 7A shows the wildtype DNA double stranded sequence on the left (SEQ ID NO:30) with the encoded valine (V) indicated on top. The middle sequence shows the mutated DNA double strand sequence (SEQ ID NO:31) where the mutant phenylalanine (F) is indicated on the top. At the right is shown two possible base edited outcomes (SEQ ID NO:32 and 33) where the edited nucleotides are shown in bold with the changes to either a serine (S) or a proline (P) at the top. FIG. 7B shows the DNA sequence (SEQ ID NO:34) surrounding the JAK2 V617F mutation, with the two closest PAM sites indicated. FIG. 7B discloses the protein sequence as SEQ ID NO:79. FIG. 7C shows exemplary results with the indicated base editors in K562 cells without the V617F mutation. Other A:T pairs within the base editing window were used to evaluate the activity of the tested base editors. ABEmax-Cas9NG indicates a Cas9NG nickase fused to ABEmax. ABEmax-Cas9 was anchored with 7 different ZFPs (shown are ZFP 2, ZFP 4, ZFP 6 and ZFP 7). FIG. 7C shows the results for three different PAM sites (AAT, TAA, AAA; see FIG. 7B) on the left. Here, both the ABEmax expression constructs as well as the corresponding sgRNAs were supplied as plasmid DNA (600 ng each). The ZFP anchored ABEmax-Cas9NG constructs show increased efficiency for all three PAM sites (approx. 2× for the AAT and AAA PAM sites; approx. 12× for the TAA PAM site). The base editors for the AAT and TAA PAM sites were also tested at a higher dose (800 ng plasmid DNA) and show similar results. ZFP 6 results in approx. 2.5× higher activity for the AAT PAM site and ZFP 2 results in approximately 17× higher activity for the TAA PAM site.

FIGS. 8A through 8G are schematics showing exemplary base editors comprising nucleotides (e.g., DNA oligonucleotides, RNA oligonucleotides, peptide nucleic acids (PNAs), locked nucleic acids (LNAs) and/or bridged nucleic acids (BNAs) used to provide a single stranded DNA substrate for base editors at the target site as shown in FIG. 1D). FIG. 8A depicts the targeted base to be edited ("X") before (left side) and after (right side) contact with the nucleotide-containing single stranded substrate of the base editor. FIG. 8B depicts an exemplary PNA (PNA #1) for use in a base editor as described herein, the PNA having the structure: N-Lys-Lys-Lys-NNNNNNNNNN-OOO-NNNNNNNNNN-Lys-Lys-Lys-C. FIG. 8C depicts an exemplary PNA (PNA #2) or use in a base editor as described herein, the PNA having the structure: N-Lys-Lys-Lys-NNNNNNNNNN-OOO-NNN NNNNNNNNNNN-Lys-Lys-Lys-C. FIG. 8D depicts an exemplary embodiment in which the base editor comprises 2 PNAs (PNA #3 having the structure N-Lys-Lys-Lys-NNNNNNNNNN-OOO-NNNNNNNNNN-Lys-Lys-Lys-C and PNA #4 having the structure N-Lys-Lys-Lys-NN NNNNNNNN-OOO-NNNNNNNNNN-Lys-Lys-Lys-C in reverse orientations relative to each other. FIG. 8E depicts an exemplary embodiment in which the PNA comprises the structure N-Lys-Lys-Lys-NNNNNNNNNNNNNNNN-Lys-Lys-Lys-C(PNA #5). In FIGS. 8B through 8E, O indicates 8-amino-2,6-dioxaoctanoic acid linkers and C indicates cytosine. The Lys resides on the N- and/or C-terminals of the PNA sequence are optional and pseudoisocytosine be can substituted for cytosine. FIGS. 8F and 8G depict exemplary embodiments of a base editor comprising an LNA. FIG. 8F shows an exemplary LNA (LNA #1) (SEQ ID NO:80). Exemplary LNA #1 sequences include LNA #1a: 5'-NnNn NnNnNnNnNtctct nNnNnNnNnNn nNnNnnNn-3' (SEQ ID NO:1); LNA #b: 5'-N*n*NnNnNnNnNnNnNtctct nNnNnNnNnNnNnNnnNn n*N*n-3' (SEQ ID NO:69); and LNA #1c: 5'-NnNnNnNnNnNnNnNtctct nNnNnNnNn NnnNnnNnnNn-Chol-TEG-3' (SEQ ID NO:70). FIG. 8G shows an exemplary embodiment in which the base editor comprises 2 LNAs, shown in reverse orientation with respect to each other (LNA #2: 5'-NnNnNnNn NntctctNnNnNnNnNn-3' (SEQ ID NO:71) and LNA #3: 5'-NnNnNnNnNntctctNnNnNnNnNn-3' (SEQ ID NO:72)). In FIGS. 8F and 8G, LNA nucleotides are in uppercase; DNA nucleotides are in lower case; "*" indicates phosphorothioate bonds; and "Chol-TEG" indicates 3' Cholesterol-TEG for increased uptake into cells.

DETAILED DESCRIPTION

Figure 1A:
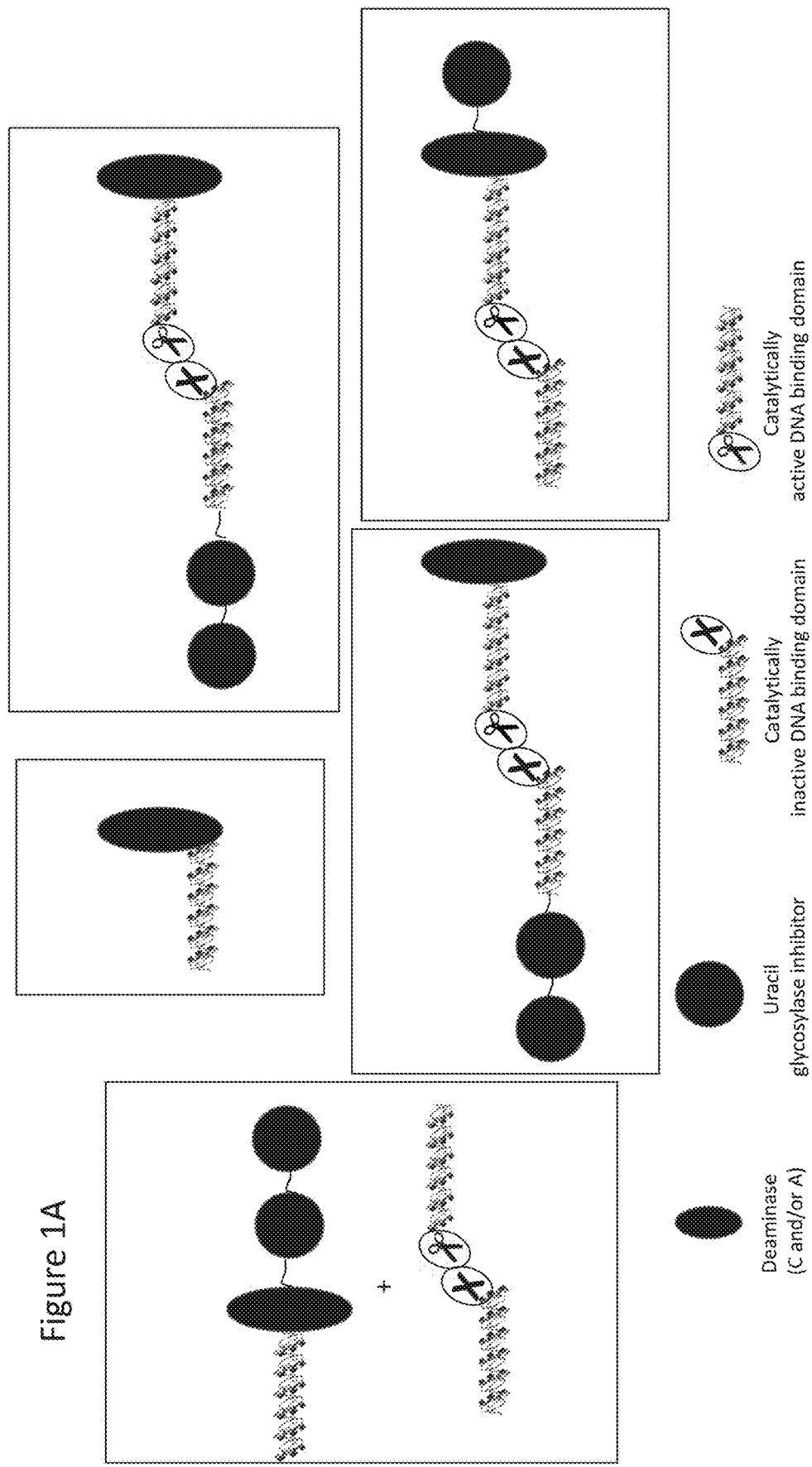
FIGS. 1A through 1D are schematics depicting exemplary DNA-editing systems and complexes.

Artificial nucleases, such as engineered zinc finger nucleases (ZFN), transcription-activator like effector nucleases (TALENs), the CRISPR/Cas system with an engineered crRNA/tracr RNA ('single guide RNA'), also referred to as RNA guided nucleases, and/or nucleases based on the Argonaute system are revolutionizing the fields of medicine, biotechnology and agriculture. These molecular tools are allowing the genetic manipulation (e.g. editing) of genomes in organisms to a level never before possible. Artificial nucleases are capable of cleaving DNA such that following such cleavage, the cell is forced to 'heal' the break by either error-prone non-homologous end joining (NHEJ) or, in the presence of a substrate DNA with homology to the regions flanking the cut site, by insertion of the substrate DNA through homology-directed repair (HDR). Both of these processes start with a double strand break (DSB) in the DNA.

Described herein are compositions (systems) and methods for base editing that do not use a double-stranded cut for genetic modification. Base editing essentially relies on altering the identity of a specific base in a DNA strand and involved site-specific modification of the DNA base along with manipulation of the DNA repair machinery to avoid repair of the edited base. It is generally accomplished by using a system to open up the DNA double helix such that there are regions of single stranded DNA present. Next, the bases themselves are acted on by base modifying enzymes such as deaminases to change the nucleoside structure. For example, the Activation Induced Deaminase (AID) and apolipoprotein B mRNA editing enzyme catalytic polypeptide-like family proteins (APOBECs) are cytidine deaminases critical to antibody diversification and innate immunity against retroviruses. These enzymes convert cytidines (C) to uracils (U) in DNA. If DNA replication occurs before uracil repair, the replication machinery will treat the uracil as thymine (T), leading to a C:G to T:A base pair conversion (Yang, et al. (2016) Nat Commun doi 10.1038/ncomms13330) so the system can be used to generate C to T point mutations.

Any of the base editors as described herein can be used for targeted base editing for any use, including but not limited to gene knockout (e.g., alteration of a base to produce a stop codon in place of a regular codon; alteration of a base in a splice acceptor site); introduction of mutations in control (promoter) regions of a gene to activate or repress gene expression; and/or correction of disease-causing mutations by reversing a point mutation. Cells and cell lines comprising the base editors and/or targeted changes made by base editors (but no longer comprising the base editors themselves) are also provided.

The base editors of the present invention provide unexpectedly superior editing efficiencies and/or specificity as compared currently used based editors.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide," and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$. "Non-specific binding" refers to, non-covalent interactions that occur between any molecule of interest (e.g. an engineered nuclease) and a macromolecule (e.g. DNA) that are not dependent on-target sequence.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity. In the case of an RNA-guided nuclease system, the RNA guide is heterologous to the nuclease component (Cas9 or Cfp1) and both may be engineered.

A "DNA binding molecule" is a molecule that can bind to DNA. Such DNA binding molecule can be a polypeptide, a domain of a protein, a domain within a larger protein or a polynucleotide. In some embodiments, the polynucleotide is DNA, while in other embodiments, the polynucleotide is RNA. In some embodiments, the DNA binding molecule is a protein domain of a nuclease (e.g. the FokI domain), while in other embodiments, the DNA binding molecule is a guide RNA component of an RNA-guided nuclease (e.g. Cas9 or Cpf1). DNA-binding molecules can comprise a protein, or a domain within a larger protein, that binds DNA in a sequence-specific manner, for example through one or more zinc fingers or through interaction with one or more ZFP recognition helix regions of a zinc finger protein (ZFP) or the RVDs of a TALE. DNA-binding molecules also include single guide RNA (sgRNA) of a CRISPR/Cas system and/or DNA-binding domains of a Ttago system. The term zinc finger DNA binding protein is often abbreviated as zinc finger protein or ZFP.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. See, e.g., U.S. Pat. No. 8,586,526, incorporated by reference herein in its entirety.

DNA-binding domains can be "engineered" to bind to a predetermined nucleotide sequence, for example via engineering (altering one or more amino acids) of the recognition helix region of a naturally occurring zinc finger protein or by engineering of the amino acids involved in DNA binding (the "repeat variable diresidue" or RVD region). Therefore, engineered zinc finger proteins or TALE proteins are proteins that are non-naturally occurring. Non-limiting examples of methods for engineering zinc finger proteins and TALEs are design and selection. A designed protein is a protein not occurring in nature whose design/composition results principally from rational criteria. Rational criteria for design include application of substitution rules and computerized algorithms for processing information in a database storing information of existing ZFP or TALE designs and binding data. See, for example, U.S. Pat. Nos. 8,586,526; 6,140,081; 6,453,242; and 6,534,261; see also International Patent Publication Nos. WO 98/53058; WO 98/53059; WO 98/53060; WO 02/016536; and WO 03/016496.

A "selected" zinc finger protein, TALE protein or CRISPR/Cas system is not found in nature whose production results primarily from an empirical process such as phage display, interaction trap, rational design or hybrid selection. See e.g., U.S. Pat. Nos. 5,789,538; 5,925,523; 6,007,988; 6,013,453; and 6,200,759; and International Patent Publication Nos. WO 95/19431; WO 96/06166; WO 98/53057; WO 98/54311; WO 00/27878; WO 01/60970; WO 01/88197; and WO 02/099084.

"TtAgo" is a prokaryotic Argonaute protein thought to be involved in gene silencing. TtAgo is derived from the bacteria *Thermus thermophilus*. See, e.g. Swarts, et al. (2014) *Nature* 507(7491):258-261; Swarts, et al. (2012) *PLoS One* 7(4):e35888; Sheng, et al. (2014) *Proc. Natl. Acad. Sci. U.S.A.* 111, 652-657. A "TtAgo system" is all the components required including e.g. guide DNAs for cleavage by a TtAgo enzyme.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize. The term "cleavage domain" is used interchangeably with the term "cleavage half-domain." The term "FokI cleavage domain" includes the FokI sequence as shown in SEQ ID NO:5 as well as any FokI homologues.

An "engineered cleavage half-domain" is a cleavage half-domain that has been modified so as to form obligate heterodimers with another cleavage half-domain (e.g., another engineered cleavage half-domain).

The term "editing" as used herein refers to a process wherein a nucleotide base is modified as compared to the initial (e.g., wild-type) base at the same position. Base editing (e.g., targeted point mutations) will necessarily reproduce the change in any mRNA that is transcribed from the edited DNA. Adenine and cytidine deaminases remove an amino group from their respective nucleotide targets, converting them into inosine and uridine respectively. During DNA repair or replication, inosine is recognized as guanine and uridine is recognized as thymine by polymerase enzymes, resulting in conversion of an A:T base pair into a G:C base pair, or C:G base pair into a T:A base pair in the double stranded DNA that has been edited. The "base editing window" refers to any bases that are subject to editing by the base editors as described herein may be any distance from any component of the editing system, typically within a region that is accessible following binding of at least one component of the base editing system to the target DNA. Base editors requiring a PAM sequence (e.g., Cas9-containing editors) typically have a base editing window of 3, 4, 5, 6, 7 or more nucleotides that can be 13-16 or more nucleotides from the PAM sequence. Base editors as described herein can be used for targeted base editing for any use, including but not limited to gene knockout (e.g., alteration of a base to produce a stop codon in place of a regular codon; alteration of a base in a splice acceptor site); introduction of mutations in control (promoter) regions of a gene to activate or repress gene expression; and/or correction of disease-causing mutations by reversing a point mutation. Cell lines comprising the base editors and/or targeted changes made by base editors (but no longer comprising the base editors themselves).

The term "sequence" refers to a nucleotide sequence of any length, which can be DNA or RNA; can be linear, circular or branched and can be either single-stranded or double stranded. The term "transgene" refers to a nucleotide sequence that is inserted into a genome. A transgene can be of any length, for example between 2 and 100,000,000 nucleotides in length (or any integer value therebetween or thereabove), preferably between about 100 and 100,000 nucleotides in length (or any integer therebetween), more preferably between about 2000 and 20,000 nucleotides in length (or any value therebetween) and even more preferable, between about 5 and 15 kb (or any value therebetween).

A "chromosome" is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids, minicircles and certain viral genomes. The liver specific constructs described herein may be episomally maintained or, alternatively, may be stably integrated into the cell.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, ligases, deubiquitinases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster. Methods for the introduction of exogenous molecules into plant cells are known to those of skill in the art and include, but are not limited to, protoplast transformation, silicon carbide (e.g., WHISKERS™), *Agrobacterium*-mediated transformation, lipid-mediated transfer (i.e., liposomes, including neutral and cationic lipids), electroporation, direct injection, cell fusion, particle bombardment (e.g., using a "gene gun"), calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

As used herein, the term "product of an exogenous nucleic acid" includes both polynucleotide and polypeptide products, for example, transcription products (polynucleotides such as RNA) and translation products (polypeptides).

A "fusion" molecule is a molecule in which two or more subunit molecules are linked, preferably covalently. The subunit molecules can be the same chemical type of molecule, or can be different chemical types of molecules. Examples of fusion molecules include, but are not limited to, fusion proteins (for example, a fusion between a protein DNA-binding domain and a cleavage domain), fusions between a polynucleotide DNA-binding domain (e.g., sgRNA) operatively associated with a cleavage domain, and fusion nucleic acids (for example, a nucleic acid encoding the fusion protein).

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "split enzyme" is an enzyme that has been split into two or more inactive polypeptide chains and then reassembled into an operable enzyme. The assembly of the split enzyme into an active protein often is driven by proximity where each inactive polypeptide chain is fused to other molecules that are capable of bringing the inactive chains physically together so that they can assemble, overcoming the entropic costs of fragmentation. The fused molecules can be other proteins that interact with each other, or any type of molecules that interact either with each other or with a common ligand, such that the interaction causes the assembly of the polypeptides that make up the split enzyme. See for example Shekhawat and Ghosh (2011) *Curr Opin Chem Biol* 15(6): 789-797.

A "gene" for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP, TALE or CRISPR/Cas system as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells), including stem cells (pluripotent and multipotent).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid or protein (e.g., coding function, ability to hybridize to another nucleic acid, enzymatic activity assays) are well-known in the art.

A polynucleotide "vector" or "construct" is capable of transferring gene sequences to target cells. Typically, "vector construct," "expression vector," "expression construct," "expression cassette," and "gene transfer vector" mean any nucleic acid construct capable of directing the expression of a gene of interest and which can transfer gene sequences to target cells. Thus, the term includes cloning, and expression vehicles, as well as integrating vectors.

The terms "subject" and "patient" are used interchangeably and refer to mammals such as human patients and non-human primates, as well as experimental animals such as rabbits, dogs, cats, rats, mice, and other animals. Accordingly, the term "subject" or "patient" as used herein means any mammalian patient or subject to which the expression cassettes of the invention can be administered. Subjects of the present invention include those with a disorder.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. Cancer, monogenic diseases and graft versus host disease are non-limiting examples of conditions that may be treated using the compositions and methods described herein.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease. An "intended" or "on-target" sequence is the sequence to which the binding molecule is intended to bind and an "unintended" or "off-target" sequence includes any sequence bound by the binding molecule that is not the intended target.

The terms "DNA destabilizing molecule" and "DNA unwinding molecule" are used interchangeably to refer to any molecule (e.g., protein, nucleotide, small molecule, etc.) that aid in increasing the accessibility of (e.g., by exposing) the base targeted by the base editor. The term includes, but is not limited to, nickases, oligonucleotides (LNAs, PNAs, BNAs, etc.), RNA-programmable systems (e.g., Cas proteins operably linked to sgRNAs), and other proteins (e.g., Table A).

Base Editors

The base editing compositions (systems) described herein can directly change the identity of individual DNA base pairs without inducing double-stranded breaks. Thus, the base editors are not reliant on the DNA repair pathway preference to the target cell. Furthermore, because there is no double-stranded break made in the target DNA, there are no free DNA ends and, accordingly, no translocations.

The base editors described herein may be cytosine based editors (CBEs), which change a C:G pair to a T:A pair or adenine base editors (ABEs), which change an A:T pair to a G:C pair. These base editors can be used for inactivation (gene knock out) for example by turning regular codons into stop codons (e.g., using a cytosine base editor) and/or by mutating splice acceptor sites using either cytosine or adenine base editors. In addition, base editors as described herein can be used for altering control (e.g., promoter regions) of a gene to activate or repress expression of the gene. Furthermore, base editing can be used to correct mutations, particularly disease-causing mutations.

Subsequent to the development of the first APOBEC-dCas9 base editors, a second base editor called BE2 was developed in which uracil DNA glycosylase (UGI) was added. Base excision repair is the cell's primary response to G:U mismatches and is initiated by excision of the uracil by uracil N-glycosylase (UNG). In an effort to protect the edited G:U intermediate from excision by UNG, a 83-amino acid uracil glycosylase inhibitor (UGI) was directly added to the C terminus of catalytically dead Cas9 (dCas9) resulting in an increase in efficiency (Komor, et al. (2017) *Science Advances* 3(8):eaao4774). In the early versions of base editors, a dead Cas9 was typically used such that the DNA replication machinery was used to carry out the final conversion of the nucleotide base opposite the edited base. In addition, Cas nickases have used to create a nick on the strand opposite of the one comprising the edited base. The creation of the nick attracts the DNA repair machinery such that the region downstream of the nick is excised and replaced using the edited strand as a template. The cytidine base editor BE3 used a Cas that was a nickase, Cas9 D10A, which also increased efficiency (Kim, et al. (2017) *Nat Biotechnol* 35(4):371-376). In yet another variant, the BE4 system uses two UGI domains, at both the N- and C-terminal ends of the complex for even greater efficiency. Another cytidine deaminase system relies on the activation-induced cytidine deaminase (AID) in combination with a nickase Cas9 ("target-AID").

Figure 2:
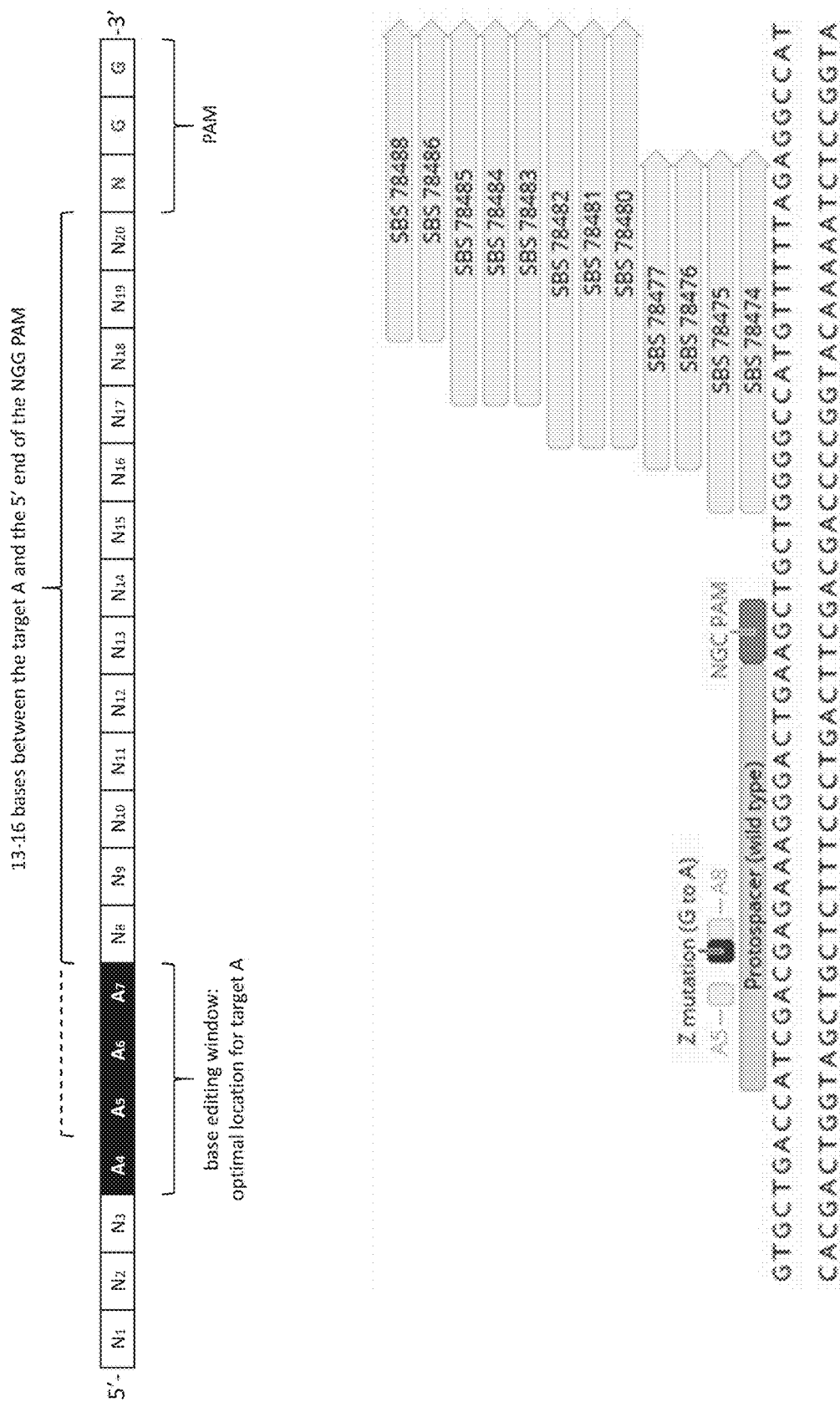
FIG. 2 is a schematic showing DNA targeted by an exemplary adenine base editor. The drawing shows the DNA sequence near the A1AT Z mutation with a wildtype mRNA protospacer and PAM aligned on top (SEQ ID NO:78). To the right of the protospacer is shown the DNA targets of several different ZFPs. As shown, for ABE requiring a PAM sequence the target for base editing (also referred to as the base editing window) is typically 13-16 nucleotides from the PAM sequence and may be 3, 4, 5, 6, 7 or more nucleotides in size (shown in Figure is base editing window of 4 nucleotides) (SEQ ID NO:77).

When the base editor interacts with the DNA, the Cas-based editors require a PAM sequence to interact with, and then the window for activity (base editing window) is typically 13-16 bases from the 5' end of the PAM sequence (see, also, FIG. 2). The activity window of the different editing systems described above vary. The target-AID system edits bases farther from the PAM sequence while the BE4 system edits those nearer to the PAM. Base editors have also been constructed based on the Cpf1 CRISPR system (Eid, et al., ibid). In addition, the BE4 configuration of base editors has been developed using both *S. pyogenes* and *S. aureus* derived CRISPR systems (BE4 and SaBE4 respectively). Therefore, Cas9 base editing systems are limited by the availability of a PAM sequence appropriately spaced from the target site (as the distance can significantly impact efficiency and/or specificity of the based editors) and/or the distance of the PAM sequence from the base editing window (as shown in FIG. 2A, 13-16 bases between the target base (e.g., A) and the 5' end of the NGG PAM.

Thus, prior to the present invention, Cas9 base editors were known to induce genome-wide off-target effects as well as bystander effects (unintended edits near the targeted base). See, e.g., Zuo, et al. (2019) *Science* 364(6437):289-292; Jin, et al. (2019) *Science* 364(6437):292-295; Gruenewald, et al. (2019) *Nature* 569(7756):433-437.

Additional base editor configurations have included the use of a GAM protein from bacteriophage Mu. In some instances, indels (insertions and deletions) have been observed as a result of some types of base editing. Because some base editors nick the strand opposite a U, cleavage of the glycosidic bond by UNG, followed by processing of the resulting apurinic or apyrimidinic site by AP lyase might result in a double stranded DNA break (DSB), potentially resulting in indel formation. The Gam protein of bacteriophage Mu binds to the ends of DSBs and protects them from degradation thus using Gam to bind the free ends of DSB may reduce indel formation during the process of base editing (Komor, et al. (2016) Nature 533(7603):420-424; Komor, et al. (2017) Science Advances 3(8):eaao4774). In addition to the cytidine deaminase editors, base editors have been developed with synthetic adenosine deaminases, which convert the adenine base into inosine (adenine base editors: "ABEs", see Gaudelli, et al. (2017) Nature 551(7681):464-471). Inosine can base pair with cytidine and subsequently be corrected to guanine, thereby converting A into G, or A:T into G:C.

As described above, base editors as described herein can further comprise molecules that "open up" the DNA helix to expose the targeted base within a single stranded region of the DNA. Commonly known molecules that can accomplish this include but are not limited to DNA helicases, helix-destabilizing molecules and the bacterial DnaA protein, single-strand DNA binding proteins, triplex forming oligonucleotides or oligonucleotides.

In certain embodiments, the base editor comprises a protein domain that aids in unwinding (opening up) of the DNA helix to expose the targeted base for editing. Non-limiting examples of suitable proteins are shown in Table A.

TABLE A

| Protein Name | Organism | Protein Sequence |
|---|---|---|
| ROA1 | Bovine | MSKSESPKEPEQLRKLFIGGLSFETTDESLRSHFEQWGTLTDCVVMRDPNTKRS RGFGFVTYATVEEVDAAMNARPHKVDGRVVEPKRAVSREDSQRPGAHLTVKKIF VGGIKEDTEEHEILRDYFEQYGKIEVIEIMTDRGSGKKRGFAFVTFDDHDSVDK IVIQKYHTVNGHNCEVRKALSKQEMASASSSQRGRSGSGNFGGGRGGGFGGNDN FGRGGNFSGRGGFGGSRGGGGYGGSGDGYNGFGNDGSNFGGGGSYNDFGNYNNQ SSNFGPMKGGNFGGRSSGPYGGGGQYFAKPRNQGGYGGSSSSSSYGSGRRF (SEQ ID NO: 35) |
| UvsW | BPT4 | MDIKVHFHDFSHVRIDCEESTFHELRDFFSFEADGYRFNPRFRYGNWDGRIRLL DYNRLLPFGLVGQIKKFCDNFGYKAWIDPQINEKEELSRKDFDEWLSKLEIYSG NKRIEPHWYQKDAVFEGLVNRRRILNLPTSAGKSLIQALLARYYLENYEGKILI IVPTTALTTQMADDFVDYRLFSHAMIKKIGGGASKDDKYKNDAPVVVGTWQTVV KQPKEWFSQFGMMMNDECHLATGKSISSIISGLNNCMFKFGLSGSLRDGKANIM QYVGMFGEIFKPVTTSKLMEDGQVTELKINSIFLRYPDEFTTKLKGKTYQEEIK IITGLSKRNKWIAKLAIKLAQKDENAFVMPKHVSHGKAIFDLIKNEYDKVYYVS GEVDTETRNIMKTLAENGKGIIIVASYGVFSTGISVKNLHHVVLAHGVKSKIIV LQTIGRVLRKHGSKTIATVWDLIDSAGVKPKSANTKKKYVHLNYLLKHGIDRIQ RYADEKFNYVMKTVNLISFGPLEKKMLLEFKQFLYEASIDEFMGKIASCQTLEG LEELEAYYKKRVKETELKDTDDISVRDALAGKRAELEDSDDEVEESF (SEQ ID NO: 36) |
| RECDL | D. radiourans | MSAALPAEPFRVSGGVNKVRFRSDTGFTVMSATLRNEQGEDPDATVIGVMPPLD VGDTFSAEVLMEEHREYGYQYRVVNMVLEAMPADLSEEGVAAYFEARVGGVGKV LAGRIAKTFGAAAFDLLEDDPQKFLQVPGITESTLHKMVSSWSQQGLERRLLAG LQGLGLTINQAQRAVKHFGADALDRLEKDLFTLTEVEGIGFLTADKLWQARGGA LDDPRRLTAAAVYALQLAGTQAGHSFLPRSRAEKGVVHYTRVTPGQARLAVETA VELGRLSEDDSPLFAAEAAATGEGRIYLPHVLRAEKKLASLIRTLLATPPADGA GNDDWAVPKKARKGLSEEQASVLDQLAGHRLVVLTGGPGTGKSTTTKAVADLAE SLGLEVGLCAPTGKAARRLGEVTGRTASTVHRLLGYGPQGFRHNHLEPAPYDLL IVDEVSMMGDALMLSLLAAVPPGARVLLVGDTDQLPPVDAGLPLLALAQAAPTI KLTQVYRQAAKNPIIQAAHGLLHGEAPAWGDKRLNLTEIEPDGGARRVALMVRE LGGPGAVQVLTPMRKGPLGMDHLNYHLQALFNPGEGGVRIAEGEARPGDTVVQT KNDYNNEIFNGTLGMVLKAEGARLTVDFDGNVVELTGAELFNLQLGYALTVHRA QGSEWGTVLGVLHEAHMPMLSRNLVYTALTRARDRFFSAGSASAWQIAAARQRE ARNTALLERIRAH (SEQ ID NO: 37) |
| RecA | E. coli | MAIDENKQKALAAALGQIEKQFGKGSIMRLGEDRSMDVETISTGSLSLDIALGA GGLPMGRIVEIYGPESSGKTTLTLQVIAAAQREGKTCAFIDAEHALDPIYARKL GVDIDNLLCSQPDTGEQALEICDALARSGAVDVIVVDSVAALTPKAEIEGEIGD SHMGLAARMMSQAMRKLAGNLKQSNTLLIFINQIRMKIGVMFGNPETTTGGNAL KFYASVRLDIRRIGAVKEGENVVGSETRVKVVKNKIAAPFKQAEFQILYGEGIN FYGELVDLGVKEKLIEKAGAWYSYKGEKIGQGKANATAWLKDNPETAKEIEKKV RELLLSNPNSTPDFSVDDSEGVAETNEDF (SEQ ID NO: 38) |
| RecB | E. coli | MSDVAETLDPLRLPLQGERLIEASAGTGKTFTIAALYLRLLLGLGGSAAFPRPL TVEELLVTFTEAATAELRGRIRSNIHELRIACLRETTDNPLYERLLEEIDDKA QAAQWLLLAERQMDEAAVFTIHGFCQRMLNLNAFESGMLFEQQLIEDESLLRYQ ACADFWRRHCYPLPREIAQVVFETWKGPQALLRDINRYLQGEAPVIKAPPPDDE TLASRHAQIVARIDTVKQQWRDAVGELDALIESSGIDRRKFNRSNQAKWIDKIS AWAEEETNSYQLPESLEKFSQRFLEDRTKAGGETPRHPLFEAIDQLLAEPLSIR DLVITRALAEIRETVAREKRRRGELGFDDMLSRLDSALRSESGEVLAAAIRTRF PVAMIDEFQDTDPQQYRIFRRIWHHQPETALLLIGDPKQAIYAFRGADIFTYMK ARSEVHAHYTLDTNWRSAPGMVNSVNKLFSQTDDAFMFREIPFIPVKSAGKNQA LRFVFKGETQPAMKMWLMEGESCGVGDYQSTMAQVCAAQIRDWLQAGQRGEALL MNGDDARPVRASDISVLVRSRQEAAQVRDALTLLEIPSVYLSNRDSVFETLEAQ EMLWLLQAVMTPERENTLRSALATSMMGLNALDIETLNNDEHAWDVVVEEFDGY |

TABLE A-continued

| Protein Name | Organism | Protein Sequence |
|---|---|---|
| | | RQIWRKRGVMPMLRALMSARNIAENLLATAGGERRLTDILHISELLQEAGTQLE<br>SEHALVRWLSQHILEPDSNASSQQMRLESDKHLVQIVTIHKSKGLEYPLVWLPF<br>ITNFRVQEQAFYHDRHSFEAVLDLNAAPESVDLAEAERLAEDLRLLYVALTRSV<br>WHCSLGVAPLVRRRGDKKGDTDVHQSALGRLLQKGEPQDAAGLRTCIEALCDDD<br>IAWQTAQTGDNQPWQVNDVSTAELNAKTLQRLPGDNWRVTSYSGLQQRGHGIAQ<br>DLMPRLDVDAAGVASVVEEPTLTPHQFPRGASPGTFLHSLFEDLDFTQPVDPNW<br>VREKLELGGFESQWEPVLTEWITAVLQAPLNETGVSLSQLSARNKQVEMEFYLP<br>ISEPLIASQLDTLIRQFDPLSAGCPPLEFMQVRGMLKGFIDLVFRHEGRYYLLD<br>YKSNWLGEDSSAYTQQAMAAAMQAHRYDLQYQLYTLALHRYLRHRIADYDYEFI<br>FIFGGVIYLFLRGVDKEHPQQGIYTTRPNAGLIALMDEMFAGMTLEEA<br>(SEQ ID NO: 39) |
| RecC | E. coli | MLRVYHSNRLDVLEALMEFIVERERLDDPFEPEMILVQSTGMAQWLQMTLSQKF<br>GIAANIDFPLPASFIWDMFVRVLPEIPKESAFNKQSMSWKLMTLLPQLLEREDF<br>TLLRHYLTDDSDKRKLFQLSSKAADLFDQYLVYRPDWLAQWETGHLVEGLGEAQ<br>AWQAPLWKALVEYTHQLGQPRWHRANLYQRFIETLESATTCPPGLPSRVFICGI<br>SALPPVYLQALQALGKHIEIHLLFTNPCRYYWGDIKDPAYLAKLLTRQRRHSFE<br>DRELPLFRDSENAGQLFNSDGEQDVGNPLLASWGKLGRDYIYLLSDLESSQELD<br>AFVDVTPDNLLHNIQSDILELENRAVAGVNIEEFSRSDNKRPLDPLDSSITFHV<br>CHSPQREVEVLHDRLLAMLEEDPTLTPRDIIVMVADIDSYSPFIQAVFGSAPAD<br>RYLPYAISDRRARQSHPVLEAFISLLSLPDSRFVSEDVLALLDVPVLAARFDIT<br>EEGLRYLRQWVNESGIRWGIDDDNVRELELPATGQHTWRFGLTRMLLGYAMESA<br>QGEWQSVLPYDESSGLIAELVGHLASLLMQLNIWRRGLAQERPLEEWLPVCRDM<br>LNAFFLPDAETEAAMTLIEQQWQAIIAEGLGAQYGDAVPLSLLRDELAQRLDQE<br>RISQRFLAGPVNICTLMPMRSIPFKVVCLLGMNDGVYPRQLAPLGFDLMSQKPK<br>RGDRSRRDDDRYLFLEALISAQQKLYISYIGRSIQDNSERFPSVLVQELIDYIG<br>QSHYLPGDEALNCDESEARVKAHLTCLHTRMPFDPQNYQPGERQSYAREWLPAA<br>SQAGKAHSEFVQPLPFTLPETVPLETLQRFWAHPVRAFFQMRLQVNFRTEDSEI<br>PDTEPPFILEGLSRYQINQQLLNALVEQDDAERLFRRFRAAGDLPYGAFGEIFWE<br>TQCQEMQQLADRVIACRQPGQSMEIDLACNGVQITGWLPQVQPDGLLRWRPSLL<br>SVAQGMQLWLEHLVYCASGGNGESRLFLRKDGEWRFPPLAAEQAHLYLSQLIEG<br>YREGMSAPLLVLPESGGAWLKTCYDAQNDAMLDDDSTLQKARTKFLQAYEGNMM<br>VRGEGDDIWYQRLWRQLTPETMEAIVEQSQRFLLPLFRFNQS<br>(SEQ ID NO: 40) |
| RecD | E. coli | MKLQKQLLEAVEHKQLRPLDVQFALTVAGDEHPAVTLAAALLSHDAGEGHVCLP<br>LSRLENNEASHPLLATCVSEIGELQNWEECLLASQAVSRGDEPTPMILCGDRLY<br>LNRMWCNERTVARFFNEVNHAIEVDEALLAQTLDKLFPVSDEINWQKVAAAVAL<br>TRRISVISGGPGTGKTTTVAKLLAALIQMADGERCRIRLAAPTGKAAARLTESL<br>GKALRQLPLTDEQKKRIPEDASTLHRLLGAQPGSQRLRFIHAGNPLHLDVLVVD<br>EASMIDLPMMSRLIDALPDHARVIFLGDRDQLASVEAGAVLGDICAYANAGFTA<br>ERARQLSRLTGTHVPAGTGTEAASLRDSLCLLQKSYRFGSDSGIGQLAAAINRG<br>DKTAVKTVFQQDFTDIEKRLLQSGEDYIAMLEEALAGYGRYLDLLQARAEPDLI<br>IQAFNEYQLLCALREGPFGVAGLNERIEQFMQQKRKIHRHPHSRWYEGRPVMIA<br>RNDSALGLFNGDIGIALDRGQGTRVWFAMPDGNIKSVQPSRLPEHETTWAMTVH<br>KSQGSEFDHAALILPSQRTPVVTRELVYTAVIRARRRLSLYADERILSAAIATR<br>TERRSGLAALFSSRE<br>(SEQ ID NO: 41) |
| RecQ | E. coli | MAQAEVLNLESGAKQVLQETFGYQQFRPGQEEIIDTVLSGRDCLVVMPTGGGKS<br>LCYQIPALLLNGLTVVVSPLISLMKDQVDQLQANGVAAACLNSTQTREQQLEVM<br>TGCRTGQIRLLYIAPERLMLDNFLEHLAHWNPVLLAVDEAHCISQWGHDFRPEY<br>AALGQLRQRFPTLPFMALTATADDTTRQDIVRLLGLNDPLIQISSFDRPNIRYM<br>LMEKFKPLDQLMRYVQEQRGKSGIIYCNSRAKVEDTAARLQSKGISAAAYHAGL<br>ENNVRADVQEKFQRDDLQIVVATVAFGMGINKPNVRFVVHFDIPRNIESYYQET<br>GRAGRDGLPAEAMLFYDPADMAWLRRCLEEKPQGQLQDIERHKLNAMGAFAEAQ<br>TCRRLVLLNYFGEGRQEPCGNCDICLDPPKQYDGSTDAQIALSTIGRVNQRFGM<br>GYVVEVIRGANNQRIRDYGHDKLKVYGMGRDKSHEHWVSVIRQLIHLGLVTQNI<br>AQHSALQLTEAARPVLRGESSLQLAVPRIVALKPKAMQKSFGGNYDRKLFAKLR<br>KLRKSIADESNVPPYVVFNDATLIEMAEQMPITASEMLSVNGVGMRKLERFGKP<br>FMALIRAHVDGDDEE<br>(SEQ ID NO: 42) |
| Rep_Delta_2B | E. coli | MRLNPGQQQAVEFVTGPCLVLAGAGSGKTRVITNKIAHLIRGCGYQARHIAAVT<br>FTNKAAREMKERVGQTLGRKEARGLMISTFHTLGLDIIKREYAALGMKANFSLF<br>DDTDQLALLKELTEGLIEDDKVLLQQLISTISNWKNDLKTPAQAAAEAKGERDR<br>IFAHCYGLYDAHLKACNVLDFDDLILLPTLLLQRNEEVRERWQNKIRYLLVDEY<br>QDTNTSQYELVKLLVGSRARFTVVGDDDQSIYSWRGARPQNLVLLSQDFPALKV<br>IKLEQNYRSSGRILKAANILIANNPHVFEKRLFSELGYGTELKVLSANNEEHEA<br>ERVTGELIAHHFVNKTQYKDYAILYRGNHQSRVFEKFLMQNRIPYKISGGGGGG<br>ESEEELDQVQLMTLHASKGLEFPYVYMVGMEEGFLPHQSSIDEDNIDEERRLAY<br>VGITRAQKELTFTLCKERRQYGELVRPEPSRFLLELPQDDLIWEQERKVVSAEE<br>RMQKGQSHLANLKAMMAAKRGK<br>(SEQ ID NO: 43) |
| UvrD | E. coli | MDVSYLLDSLNDKQREAVAAPRSNLLVLAGAGSGKTRVLVHRIAWLMSVENCSP<br>YSIMAVTFTNKAAAEMRHRIGQLMGTSQGGMWVGTFHGLAHRLLRAHHMDANLP<br>QDFQILDSEDQLRLLKRLIKAMNLDEKQWPPRQAMWYINSQKDEGLRPHHIQSY |

TABLE A-continued

| Protein Name | Organism | Protein Sequence |
|---|---|---|
| | | GNPVEQTWQKVYQAYQEACDRAGLVDFAELLLRAHELWLNKPHILQHYRERFTN<br>ILVDEFQDTNNIQYAWIRLLAGDTGKVMIVGDDDQSIYGWRGAQVENIQRFLND<br>FPGAETIRLEQNYRSTSNILSAANALIENNNGRLGKKLWTDGADGEPISLYCAF<br>NELDEARFVVNRIKTWQDNGGALAECAILYRSNAQSRVLEEALLQASMPYRIYG<br>GMRFFERQEIKDALSYLRLIANRNDDAAFERVVNTPTRGIGDRTLDVVRQTSRD<br>RQLTLWQACRELLQEKALAGRAASALQRFMELIDALAQETADMPLHVQTDRVIK<br>DSGLRTMYEQEKGEKGQTRIENLEELVTATRQFSYNEEDEDLMPLQAFLSHAAL<br>EAGEGQADTWQDAVQLMTLHSAKGLEFPQVFIVGMEEGMFPSQMSLDEGGRLEE<br>ERRLAYVGVTRAMQKLTLTYAETRRLYGKEVYHRPSRFIGELPEECVEEVRLRA<br>TVSRPVSHQRMGTPMVENDSGYKLGQRVRHAKFGEGTIVNMEGSGEHSRLQVAF<br>QGQGIKWLVAAYARLESV<br>(SEQ ID NO: 44) |
| RAPA | E. coli | MPFTLGQRWISDTESELGLGTVVAVDARTVTLLFPSTGENRLYARSDSPVTRVM<br>FNPGDTITSHDGWQMQVEEVKEENGLLTYIGTRLDTEESGVALREVFLDSKLVF<br>SKPQDRLFAGQIDRMDRFALRYRARKYSSEQFRMPYSGLRGQRTSLIPHQLNIA<br>HDVGRRHAPRVLLADEVGLGKTIEAGMILHQQLLSGAAERVLIIVPETLQHQWL<br>VEMLRRFNLRFALFDDERYAEAQHDAYNPFDTEQLVICSLDFARRSKQRLEHLC<br>EAEWDLLVVDEAFIEILVWSEDAPSREYQAIEQLAEHVPGVLLLTATPEQLGME<br>SHFARLRLLDPNRFHDFAQFVEEQKNYRPVADAVAMLLAGNKLSNDELNMLGEM<br>IGEQDIEPLLQAANSDSEDAQSARQELVSMLMDRHGTSRVLFRNTRNGVKGFPK<br>RELHTIKLPLPTQYQTAIKVSGIMGARKSAEDRARDMLYPERIYQEFEGDNATW<br>WNFDPRVEWLMGYLTSHRSQKVLVICAKAATALQLEQVLREREGIRAAVFHEGM<br>SIIERDRAAAWFAEEDTGAQVLLCSEIGSEGRNFQFASHMVMFDLPFNPDLLEQ<br>RIGRLDRIGQAHDIQIHVPYLEKTAQSVLVRWYHEGLDAFEHTCPTGRTIYDSV<br>YNDLINYLASPDQTEGFDDLIKNCREQHEALKAQLEQGRDRLLEIHSNGGEKAQ<br>ALAESIEEQDDDTNLIAFAMNLFDIIGINQDDRGDNMIVLTPSDHMLVPDFPGL<br>SEDGITITFDREVALAREDAQFITWEHPLIRNGLDLILSGDTGSSTISLLKNKA<br>LPVGTLLVELIYVVEAQAPKQLQLNRFLPPTPVRMLLDKNGNNLAAQVEFETFN<br>RQLNAVNRHTGSKLVNAVQQDVHAILQLGEAQIEKSARALIDAARNEADEKLSA<br>ELSRLEALRAVNPNIRDDELTAIESNRQQVMESLDQAGWRLDALRLIVVTHQ<br>(SEQ ID NO: 45) |
| RECG | E. coli | MKGRLLDAVPLSSLTGVGAALSNKLAKINLHTVQDLLLHLPLRYEDRTHLYPIG<br>ELLPGVYATVEGEVLNCNISFGGRRMMTCQISDGSGILTMRFFNFSAAMKNSLA<br>AGRRVLAYGEAKRGKYGAEMIHPEYRVQGDLSTPELQETLTPVYPTTEGVKQAT<br>LRKLTDQALDLLDTCAIEELLPPELSQGMMTLPEALRTLHRPPPTLQLSDLETG<br>QHPAQRRLILEELLAHNLSMLALRAGAQRFHAQPLSANDTLKNKLLAALPFKPT<br>GAQARVVAEIERDMALDVPMMRLVQGDVGSGKTLVAALAALRAIAHGKQVALMA<br>PTELLAEQHANNFRNWFAPLGIEVGWLAGKQKGKARLAQQEAIASGQVQMIVGT<br>HAIFQEQVQFNGLALVIIDEQHRFGVHQRLALWEKGQQQGFHPHQLIMTATPIP<br>RTLAMTAYADLDTSVIDELPPGRTPVTTVAIPDTRRTDIIDRVHHACITEGRQA<br>YWVCTLIEESELLEAQAAEATWEELKLALPELNVGLVHGRMKPAEKQAVMASFK<br>QGELHLLVATTVIEVGVDVPNASLMIIENPERLGLAQLHQLRGRVGRGAVASHC<br>VLLYKTPLSKTAQIRLQVLRDSNDGFVIAQKDLEIRGPGELLGTRQTGNAEFKV<br>ADLLRDQAMIPEVQRLARHIHERYPQQAKALIERWMPETERYSNA<br>(SEQ ID NO: 46) |
| DnaA | E. coli | MSLSLWQQCLARLQDELPATEFSMWIRPLQAELSDNTLALYAPNRFVLDWVRDK<br>YLNNINGLLTSFCGADAPQLRFEVGTKPVTQTPQAAVTSNVAAPAQVAQTQPQR<br>AAPSTRSGWDNVPAPAEPTYRSNVNVKHTFDNFVEGKSNQLARAAARQVADNPG<br>GAYNPLFLYGGTGLGKTHLLHAVGNGIMARKPNAKVVYMHSERFVQDMVKALQN<br>NAIEEFKRYYRSVDALLIDDIQFFANKERSQEEFFHTFNALLEGNQQTILTSDR<br>YPKEINGVEDRLKSRFGWGLTVAIEPPELETRVAILMKKADENDIRLPGEVAFF<br>IAKRLRSNVRELEGALNRVIANANFTGRAITIDFVREALRDLLALQEKLVTIDN<br>IQKTVAEYYKIKVADLLSKRRSRSVARPRQMAMALAKELTNHSLPEIGDAFGGR<br>DHTTVLHACRKIEQLREESHDIKEDFSNLIRTLSS<br>(SEQ ID NO: 47) |
| HMGB1 | H. sapiens | MGKGDPKKPRGKMSSYAFFVQTCREEHKKKHPDASVNFSEFSKKCSERWKTMSA<br>KEKGKFEDMAKADKARYEREMKTYIPPKGETKKKFKDPNAPKRPPSAFFLFCSE<br>YRPKIKGEHPGLSIGDVAKKLGEMWNNTAADDKQPYEKKAAKLKEKYEKDIAAY<br>RAKGKPDAAKKGVVKAEKSKKKKEEEEDEEDEEEEEDEEDEDEEEDDDDE<br>(SEQ ID NO: 48) |
| HMGB2 | H. sapiens | MGKGDPNKPRGKMSSYAFFVQTCREEHKKKHPDSSVNFAEFSKKCSERWKTMSA<br>KEKSKFEDMAKSDKARYDREMKNYVPPKGDKKGKKKDPNAPKRPPSAFFLFCSE<br>HRPKIKSEHPGLSIGDTAKKLGEMWSEQSAKDKQPYEQKAAKLKEKYEKDIAAY<br>RAKGKSEAGKKGPGRPTGSKKKNEPEDEEEEEEEEDEDEEEEDEDEE<br>(SEQ ID NO: 49) |
| RFA1 | H. sapiens | MVGQLSEGAIAAIMQKGDTNIKPILQVINIRPITTGNSPPRYRLLMSDGLNTLS<br>SFMLATQLNPLVEEEQLSSNCVCQIHRFIVNTLKDGRRVVILMELEVLKSAEAV<br>GVKIGNPVPYNEGLGQPQVAPPAPAASPAASSRPQPQNGSSGMGSTVSKAYGAS<br>KTFGKAAGPSLSHTSGGTQSKVVPIASLTPYQSKWTICARVTNKSQIRTWSNSR<br>GEGKLFSLELVDESGEIRATAFNEQVDKFFPLIEVNKVYYFSKGTLKIANKQFT<br>AVKNDYEMTFNNETSVMPCEDDHEILPTVQFDFTGIDDLENKSKDSLVDIIGIC<br>KSYEDATKITVRSNNREVAKRNIYLMDTSGKVVTATLWGEDADKFDGSRQPVLA |

TABLE A-continued

| Protein Name | Organism | Protein Sequence |
|---|---|---|
| | | IKGARVSDFGGRSLSVLSSSTIIANPDIPEAYKLRGWFDAEGQALDGVSISDLK<br>SGGVGGSNTNWKTLYEVKSENLGQGDKPDYFSSVATVVYLRKENCMYQACPTQD<br>CNKKVIDQQNGLYRCEKCDTEFPNFKYRMILSVNIADFQENQWVTCFQESAEAI<br>LGQNAAYLGELKVKPVDYREYGRRLVMSIRRSALM<br>(SEQ ID NO: 50) |
| RFA2 | H. sapiens | MWNSGFESYGSSSYGGAGGYTQSPGGFGSPAPSQAEKKSRARAQHIVPCTISQL<br>LSATLVDEVFRIGNVEISQVTIVGIIRHAEKAPTNIVYKIDDMTAAPMDVRQWV<br>DTDDTSSENTVVPPETYVKVAGHLRSFQNKKSLVAFKIMPLEDMNEFTTHILEV<br>INAHMVLSKANSQPSAGRAPISNPGMSEAGNFGGNSFMPANGLTVAQNQVLNLI<br>KACPRPEGLNFQDLKNQLKHMSVSSIKQAVDFLSNEGHIYSTVDDDHFKSTDAE<br>(SEQ ID NO: 51) |
| RFA3 | H. sapiens | MVDMMDLPRSRINAGMLAQFIDKPVCFVGRLEKIHPTGKMFILSDGEGKNGTIE<br>LMEPLDEEISGIVEVVGRVTAKATILCTSYVQFKEDSHPFDLGLYNEAVKIIHD<br>FPQFYPLGIVQHD<br>(SEQ ID NO: 52) |
| RAD51 | H. sapiens | MAMQMQLEANADTSVEEESFGPQPISRLEQCGINANDVKKLEEAGFHTVEAVAY<br>APKKELINIKGISEAKADKILAEAAKLVPMGFTTATEFHQRRSEIIQITTGSKE<br>LDKLLQGGIETGSITEMFGEFRTGKTQICHTLAVTCQLPIDRGGGEGKAMYIDT<br>EGTFRPERLLAVAERYGLSGSDVLDNVAYARAFNTDHQTLLYQASAMMVESRY<br>ALLIVDSATALYRTDYSGRGELSARQMHLARFLRMLLRLADEFGVAVVITNQVV<br>AQVDGAAMFAADPKKPIGGNIIAHASTTRLYLRKGRGETRICKIYDSPCLPEAE<br>AMFAINADGVGDAKD<br>(SEQ ID NO: 53) |
| RAD52 | H. sapiens | MSGTEEAILGGRDSHPAAGGGSVLCFGQCQYTAEEYQAIQKALRQRLGPEYISS<br>RMAGGGQKVCYIEGHRVINLANEMFGYNGWAHSITQQNVDFVDLNNGKFYVGVC<br>AFVRVQLKDGSYHEDVGYGVSEGLKSKALSLEKARKEAVTDGLKRALRSFGNAL<br>GNCILDKDYLRSLNKLPRQLPLEVDLTKAKRQDLEPSVEEARYNSCRPNMALGH<br>PQLQQVTSPSRPSHAVIPADQDCSSRSLSSSAVESEATHQRKLRQKQLQQQFRE<br>RMEKQQVRVSTPSAEKSEAAPPAPPVTHSTPVTVSEPLLEKDFLAGVTQELIKT<br>LEDNSEKWAVTPDAGDGVVKPSSRADPAQTSDTLALNNQMVTQNRTPHSVCHQK<br>PQAKSGSWDLQTYSADQRTTGNWESHRKSQDMKKRKYDPS<br>(SEQ ID NO: 54) |
| BLM | H. sapiens | MAAVPQNNLQEQLERHSARTLNNKLSLSKPKFSGFTFKKKTSSDNNVSVTNVSV<br>AKTPVLRNKDVNVTEDFSFSEPLPNTTNQQRVKDFFKNAPAGQETQRGGSKSLL<br>PDFLQTPKEVVCTTQNTPTVKKSRDTALKKLEFSSSPDSLSTINDWDDMDDFDT<br>SETSKSFVTPPQSHFVRVSTAQKSKKGKRNFFKAQLYTTNTVKTDLPPPSSESE<br>QIDLTEEQKDDSEWLSSDVICIDDGPIAEVHINEDAQESDSLKTHLEDERDNSE<br>KKKNLEEAELHSTEKVPCIEFDDDDYDTDTDFVPPSPEEIISASSSSSKCLSTLKD<br>LDTSDRKEDVLSTSKDLLSKPEKMSMQELNPETSTDCDARQISLQQQLIHVMEH<br>ICKLIDTIPDDKLKLLDCGNELLQQRNIRRKLLTEVDFNKSDASLLGSLWRYRP<br>DSLDGPMEGDSCPTGNSMKELNFSHLPSNSVSPGDCLLTTTLGKTGFSATRKNL<br>FERPLFNTHLQKSFVSSNWAETPRLGKKNESSYFPGNVLTSTAVKDQNKHTASI<br>NDLERETQPSYDIDNFDIDDFDDDDDWEDIMHNLAASKSSTAAYQPIKEGRPIK<br>SVSERLSSAKTDCLPVSSTAQNINFSESIQNYTDKSAQNLASRNLKHERFQSLS<br>FPHTKEMMKIFHKKFGLHNFRTNQLEAINAALLGEDCFILMPTGGGKSLCYQLP<br>ACVSPGVTVVISPLRSLIVDQVQKLTSLDIPATYLTGDKTDSEATNIYLQLSKK<br>DPIIKLLYVTPEKICASNRLISTLENLYERKLLARFVIDEAHCVSQWGHDFRQD<br>YKRMNMLRQKFPSVPVMALTATANPRVQKDILTQLKILRPQVFSMSFNRHNLKY<br>YVLPKKPKKVAFDCLEWIRKHHPYDSGIIYCLSRRECDTMADTLQRDGLAALAY<br>HAGLSDSARDEVQQKWINQDGCQVICATIAFGMGIDKPDVRFVIHASLPKSVEG<br>YYQESGRAGRDGEISHCLLFYTYHDVTRLKRLIMMEKDGNHEITRETHFNNLYS<br>MVHYCENITECRRIQLLAYFGENGFNPDFCKKHPDVSCDNCCKTKDYKTRDVTD<br>DVKSIVRFVQEHSSSQGMRNIKHVGPSGRFTMNMLVDIFLGSKSAKIQSGIFGK<br>GSAYSRHNAERLFKKLILDKILDEDLYINANDQAIAYVMLGNKAQTVLNGNLKV<br>DFMETENSSSVKKQKALVAKVSQREEMVKKCLGELTEVCKSLGKVFGVHYFNIF<br>NTVTLKKLAESLSSDPEVLLQIDGVTEDKLEKYGAEVISVLQKYSEWTSPAEDS<br>SPGISLSSSRGPGRSAAEELDEEIPVSSHYFASKTRNERKRKKMPASQRSKRRK<br>TASSGSKAKGGSATCRKISSKTKSSSIIGSSSASHTSQATSGANSKLGIMAPPK<br>PINRPFLKPSYAFS<br>(SEQ ID NO: 55) |
| EXO1 | H. sapiens | MGIQGLLQFIKEASEPIHVRKYKGQVVAVDTYCWLHKGAIACAEKLAKGEPTDR<br>YVGFCMKFVNMLLSHGIKPILVFDGCTLPSKKEVERSRRERRQANLLKGKQLLR<br>EGKVSEARECFTRSINITHAMAHKVIKAARSQGVDCLVAPYEADAQLAYLNKAG<br>IVQAIITEDSDLLAFGCKKVILKMDQFGNGLEIDQARLGMCRQLGDVFTEEKFR<br>YMCILSGCDYLSSLRGIGLAKACKVLRLANNPDIVKVIKKIGHYLKMNITVPED<br>YINGFIRANNTFLYQLVFDPIKRKLIPLNAYEDDVDPETLSYAGQYVDDSIALQ<br>IALGNKDINTFEQIDDYNPDTAMPAHSRSHWDLKTCQKSANVSSIWHRNYSPR<br>PESGTVSDAPQLKENPSTVGVERVISTKGLNLPRKSSIVKRPRSAELSEDDLLS<br>QYSLSFTKKTKKNSSEGNKSLSFSEVFVPDLVNGPTNKKSVSTPPRTRNKFATF<br>LQRKNEESGAVVVPGTRSRFFCSSDSTDCVSNKVSIQPLDETAVTDKENNLHES<br>EYGDQEGKRLVDTDVARNSSDDIPNNHIPGDHIPDKATVFTDEESYSFESSKFT<br>RTISPPTLGTLRSCFSWSGGLGDFSRTPSPSPSTALQQFRRKSDSPTSLPENNM |

TABLE A-continued

| Protein Name | Organism | Protein Sequence |
|---|---|---|
| | | SDVSQLKSEESSDDESHPLREEACSSQSQESGEFSLQSSNASKLSQCSSKDSDS<br>EESDCNIKLLDSQSDQTSKLRLSHFSKKDTPLRNKVPGLYKSSSADSLSTTKIK<br>PLGPARASGLSKKPASIQKRKHHNAENKPGLQIKLNELWKNFGFKKDSEKLPPC<br>KKPLSPVRDNIQLTPEAEEDIFNKPECGRVQRAIFQ<br>(SEQ ID NO: 56) |
| RECQ1 | H. sapiens | MASVSALTEELDSITSELHAVEIQIQELTERQQELIQKKKVLTKKIKQCLEDSD<br>AGASNEYDSSPAAWNKEDFPWSGKVKDILQNVFKLEKFRPLQLETINVTMAGKE<br>VFLVMPTGGGKSLCYQLPALCSDGFTLVICPLISLMEDQLMVLKQLGISATMLN<br>ASSSKEHVKWVHAEMVNKNSELKLIYVTPEKIAKSKMFMSRLEKAYEARRFTRI<br>AVDEVHCCSQWGHDFRPDYKALGILKRQFPNASLIGLTATATNHVLTDAQKILC<br>IEKCFTFTASFNRPNLYYEVRQKPSNTEDFIEDIVKLINGRYKGQSGIIYCFSQ<br>KDSEQVTVSLQNLGIHAGAYHANLEPEDKTTVHRKWSANEIQVVVATVAFGMGI<br>DKPDVRFVIHEISMSKSMENYYQESGRAGRDDMKADCILYYGFGDIFRISSMVV<br>MENVGQQKLYEMVSYCQNISKCRRVLMAQHFDEVWNSEACNKMCDNCCKDSAFE<br>RKNITEYCRDLIKILKQAEELNEKLTPLKLIDSWMGKGAAKLRVAGVVAPTLPR<br>EDLEKIIAHFLIQQYLKEDYSFTAYATISYLKIGPKANLLNNEAHAITMQVTKS<br>TQNSFRAESSQTCHSEQGDKKMEEKNSGNFQKKAANMLQQSGSKNTGAKKRKID<br>DA<br>(SEQ ID NO: 57) |
| ERCC2 | H. sapiens | MKLNVDGLLVYFPYDYIYPEQFSYMRELKRTLDAKGHGVLEMPSGTGKTVSLLA<br>LIMAYQRAYPLEVTKLIYCSRTVPEIEKVIEELRKLLNFYEKQEGEKLPFLGLA<br>LSSRKNLCIHPEVTPLRFGKDVDGKCHSLTASYVRAQYQHDTSLPHCRFYEEFD<br>AHGREVPLPAGIYNLDDLKALGRRQGWCPYFLARYSILHANVVVYSYHYLLDPK<br>IADLVSKELARKAVVVFDEAHNIDNVCIDSMSVNLTRRTLDRCQGNLETLQKTV<br>LRIKETDEQRLRDEYRRLVEGLREASAARETDAHLANPVLPDEVLQEAVPGSIR<br>TAEHFLGFLRRLLEYVKWRLRVQHVVQESPPAFLSGLAQRVCIQRKPLRFCAER<br>LRSLLHTLEITDLADFSPLTLLANFATLVSTYAKGFTIIIEPFDDRTPTIANPI<br>LHFSCMDASLAIKPVFERFQSVIITSGTLSPLDIYPKILDFHPVTMATFTMTLA<br>RVCLCPMIIGRGNDQVAISSKFETREDIAVIRNYGNLLLEMSAVVPDGIVAFFT<br>SYQYMESTVASWYEQGILENIQRNKLLFIETQDGAETSVALEKYQEACENGRGA<br>ILLSVARGKVSEGIDFVFIHYGRAVIMFGVPYVYTQSRILKARLEYLRDQFQIR<br>ENDFLTFDAMRHAAQCVGRAIRGKTDYGLMVFADKRFARGDKRGKLPRWIQEHL<br>TDANLNLTVDEGVQVAKYFLRQMAQPFHREDQLGLSLLSLEQLESEETLKRIEQ<br>IAQQL<br>(SEQ ID NO: 58) |
| ERCC3 | H. sapiens | MGKRDRADRDKKKSRKRHYEDEEDDEEDAPGNDPQEAVPSAAGKQVDESGTKVD<br>EYGAKDYRLQMPLKDDHTSRPLWVAPDGHIFLEAFSPVYKYAQDFLVAIAEPVC<br>RPTHVHEYKLTAYSLYAAVSVGLQTSDITEYLRKLSKTGVPDGIMQFIKLCTVS<br>YGKVKLVLKHNRYFVESCHPDVIQHLLQDPVIRECRLRNSEGEATELITETFTS<br>KSAISKTAESSGGPSTSRVTDPQGKSDIPMDLFDFYEQMDKDEEEEEETQTVSF<br>EVKQEMIEELQKRCIHLEYPLLAEYDFRNDSVNPDINIDLKPTAVLRPYQEKSL<br>RKMFGNGRARSGVIVLPCGAGKSLVGVTAACTVRKRCLVLGNSAVSVEQWKAQF<br>KMWSTIDDSQICRFTSDAKDKPIGCSVAISTYSMLGHTTKRSWEAERVMEWLKT<br>QEWGLMILDEVHTIPAKMFRRVLTIVQAHCKLGLTATLVREDDKIVDLNFLIGP<br>KLYEANWMELQNNGYIAKVQCAEVWCPMSPEFYREYVAIKTKKRILLYTMNPNK<br>FRACQFLIKFPHERRNDKIIVFADNVFALKEYAIRLNKPYIYGPTSQGERMQILQ<br>NFKHNPKINTIFISKVGDTSFDLPEANVLIQISSHGGSRRQEAQRLGRVLRAKK<br>GMVAEEYNAFFYSLVSQDTQEMAYSTKRQRFLVDQGYSFKVITKLAGMEEEDLA<br>FSTKEEQQQLLQKVLAATDLDAEEEVVAGEFGSRSSQASRRFGTMSSMSGADDT<br>VYMEYHSSRSKAPSKHVPLFKRFRK<br>(SEQ ID NO: 59) |
| WRN | H. sapiens | MSEKKLETTAQQRKCPEWMNVQNKRCAVEERKACVRKSVFEDDLPFLEFTGSIV<br>YSYDASDCSFLSEDISMSLSDGDVVGFDMEWPPLYNRGKLGKVALIQLCVSESK<br>CYLFHVSSMSVFPQGLKMLLENKAVKKAGVIEGDQWKLLRDFDIKLKNPVELT<br>DVANKKLKCTETWSLNSLVKHLLGKQLLKDKSIRCSNWSKFPLTEDQKLYAATD<br>AYAGFIIYRNLEILDDTVQRFAINKEEEILLSDMNKQLTSISEEVMDLAKHLPH<br>AFSKLENPRRVSILLKDISENLYSLRRMIIGSTNIETELRPSNNLNLLSFEDST<br>TGGVQQKQIREHEVLIHVEDETWDPTLDHLAKHDGEDVLGNKVERKEDGFEDGV<br>EDNKLKENMERACLMSLDITEHELQILEQQSQEEYLSDIAYKSTEHLSPNDNEN<br>DTSYVIESDEDLEMEMLKHLSPNDNENDTSYVIESDEDLEMEMLKSLENLNSGT<br>VEPTHSKCLKMERNLGLPTKEEEEDDENEANEGEEDDDKDFLWPAPNEEQVTCL<br>KMYFGHSSFKPVQWKVIHSVLEERRDNVAVMATGYGKSLCFQYPPVYVGKIGLV<br>ISPLISLMEDQVLQLKMSNIPACFLGSAQSENVLTDIKLGKYRIVYVTPEYCSG<br>NMGLLQQLEADIGITLIAVDEAHCISEWGHDFRDSFRKLGSLKTALPMVPIVAL<br>TATASSSIREDIVRCLNLRNPQITCTGFDRPNLYLEVRRKTGNILQDLQPFLVK<br>TSSHWEFEGPTIIYCPSRKMTQQVTGELRKLNLSCGTYHAGMSFSTRKDIFIHR<br>FVRDEIQCVIATIAFGMGINKADIRQVIHYGAPKDMESYYQEIGRAGRDGLQSS<br>CHVLWAPADINLNRHLLTEIRNEKFRLYKLKMMAKMEKYLHSSRCRRQIILSHF<br>EDKQVQKASLGIMGTEKCCDNCRSRLDHCYSMDDSEDTSWDFGPQAFKLLSAVD<br>ILGEKFGIGLPILFLRGSNSQRLADQYRRHSLFGTGKDQTESWWKAFSRQLITE<br>GFLVEVSRYNKFMKICALTKKGRNWLHKANTESQSLILQANEELCPKKLLLPSS<br>KTVSSGTKEHCYNQVPVELSTEKKSNLEKLYSYKPCDKISSGSNISKKSIMVQS<br>PEKAYSSSQPVISAQEQETQIVLYGKLVEARQKHANKMDVPPAILATNKILVDM<br>AKMRPTTVENVKRIDGVSEGKAAMLAPLLEVIKHFCQTNSVQTDLFSSTKPQEE |

TABLE A-continued

| Protein Name | Organism | Protein Sequence |
|---|---|---|
| | | QKTSLVAKNKICTLSQSMAITYSLFQEKKMPLKSIAESRILPLMTIGMHLSQAV<br>KAGCPLDLERAGLTPEVQKIIADVIRNPPVNSDMSKISLIRMLVPENIDTYLIH<br>MAIEILKHGPDSGLQPSCDVNKRRCFPGSEEICSSSKRSKEEVGINTETSSAER<br>KRRLPVWFAKGSDTSKKLMDKTKRGGLFS<br>(SEQ ID NO: 60) |
| RECQ5 | H. sapiens | MSSHEITTFPFDPERRVRSTLKKVFGFDSFKTPLQESATMAVVKGNKDVFVCMP<br>TGAGKSLCYQLPALLAKGITIVVSPLIALIQDQVDHLLTLKVRVSSLNSKLSAQ<br>ERKELLADLEREKPQTKILYITPEMAASSSFQPTLNSLVSRHLLSYLVVDEAHC<br>VSQWGHDFRPDYLRLGALRSRLGHAPCVALTATATPQVQEDVFAALHLKKPVAI<br>FKTPCFRANLFYDVQFKELISDPYGNLKDFCLKALGQEADKGLSGCGIVYCRTR<br>EACEQLAIELSCRGVNAKAYHAGLKASERTLVQNDWMEEKVPVIVATISFGMGV<br>DKANVRFVAHWNIAKSMAGYYQESGRAGRDGKPSWCRLYYSRNDRDQVSFLIRK<br>EVAKLQEKRGNKASDKATIMAFDALVTFCEELGCRHAAIAKYFGDALPACAKGC<br>DHCQNPTAVRRRLEALERSSSWSKTCIGPSQGNGFDPELYEGGRKGYGDFSRYD<br>EGSGGSGDEGRDEAHKREWNLFYQKQMQLRKGKDPKIEEFVPPDENCPLKEASS<br>RRIPRLTVKAREHCLRLLEEALSSNRQSTRTADEADLRAKAVELEHETFRNAKV<br>ANLYKASVLKKVADIHRASKDGQPYDMGGSAKSCSAQAEPPEPNEYDIPPASHV<br>YSLKPKRVGAGFPKGSCPFQTATELMETTRIREQAPQPERGGEHEPPSRPCGLL<br>DEDGSEPLPGPRGEVPGGSAHYGGPSPEKKAKSSSGGSSLAKGRASKKQQLLAT<br>AAHKDSQSIARFFCRRVESPALLASAPEAEGACPSCEGVQGPPMAPEKYTGEED<br>GAGGHSPAPPQTEECLRERPSTCPPRDQGTPEVQPTPAKDTWKGKRPRSQQENP<br>ESQPQKRPRPSAKPSVVAEVKGSVSASEQGTLNPTAQDPPFQLSAPGVSLKEAAN<br>VVVKCLTPFYKEGKFASKELFKGFARHLSHLLTQKTSPGRSVKEEAQNLIRHFF<br>HGRARCESEADWHGLCGPQR<br>(SEQ ID NO: 61) |
| RECQ4 | H. sapiens | MERLRDVRERLQAWERAFRRQRGRRPSQDDVEAAPEETRALYREYRTLKRTTGQ<br>AGGGLRSSESLPAAAEEAPEPRCWGPHLNRAATKSPQSTPGRSRQGSVPDYGQR<br>LKANLKGTLQAGPALGRRPWPLGRASSKASTPKPPGTGPVPSFAEKVSDEPPQL<br>PEPQPRPGRLQHLQASLSQRLGSLDPGWLQRCHSEVPDFLGAPKACRPDLGSEE<br>SQLLIPGESAVLGPGAGSQGPEASAFQEVSIRVGSPQPSSSGGEKRRWNEEPWE<br>SPAQVQQESSQAGPPSEGAGAVAVEEDPPGEPVQAQPPQPCSSPSNPRYHGLSP<br>SSQARAGKAEGTAPLHIFPRLARHDRGNYVRLNMKQKHYVRGRALRSRLLRKQA<br>WKQKWRKKGECFGGGGATVTTKESCFLNEQFDHWAAQCPRPASEEDTDAVGPEP<br>LVPSPQPVPEVPSLDPTVLPLYSLGPSGQLAETPAEVFQALEQLGHQAFRPGQE<br>RAVMRILSGISTLLVLPTGAGKSLCYQLPALLYSRRSPCLTLVVSPLLSLMDDQ<br>VSGLPPCLKAACIHSGMTRKQRESVLQKIRAAQVHVLMLTPEALVGAGGLPPAA<br>QLPPVAFACIDEAHCLSQWSHNFRPCYLRVCKVLRERMGVHCFLGLTATATRRT<br>ASDVAQHLAVAEEPDLHGPAPVPTNLHLSVSMDRDTDQALLTLLQGKRFQNLDS<br>IIIYCNRREDTERIAALLRTCLHAAWVPGSGGRAPKTTAEAYHAGMCSRERRRV<br>QRAFMQGQLRVVVATVAFGMGLDRPDVRAVLHLGLPPSFESYVQAVGRAGRDGQ<br>PAHCHLFLQPGEDLRELRRHVHADSTDFLAVKRLVQRVFPACTCTCTRPPSEQ<br>EGAVGGERPVPKYPPQEAEQLSHQAAPGPRRVCMGHERALPIQLTVQALDMPEE<br>AIETLLCYLELHPHHWLELLATTYTHCRLNCPGGPAQLQALAHRCPPLAVCLAQ<br>QLPEDPGQGSSSVEFDMVKLVDSMGWELASVRRALCQLQWDHEPRTGVRRGTGV<br>LVEFSELAFHLRSPGDLTAEEKDQICDFLYGRVQARERQALARLRRTFQAFHSV<br>AFPSCGPCLEQQDEERSTRLKDLLGRYFEEEEGQEPGGMEDAQGPEPGQARLQD<br>WEDQVRCDIRQFLSLRPEEKFSSRAVARIFHGIGSPCYPAQVYGQDRRFWRKYL<br>HLSFHALVGLATEELLQVAR<br>(SEQ ID NO: 62) |
| HELQ | H. sapiens | MDECGSRIRRRVSLPKRNRPSLGCIFGAPTAAELVPGDEGKEEEEMVAENRRRK<br>TAGVLPVEVQPLLLSDSPECLVLGGGDTNPDLLRHMPTDRGVGDQPNDSEVDMF<br>GDYDSFTENSFIAQVDDLEQKYMQLPEHKKHATDFATENLCSESIKNKLSITTI<br>GNLTELQTDKHTENQSGYEGVTIEPGADLLYDVPSSQAIYFENLQNSSNDLGDH<br>SMKERDWKSSSHNTVNEELPHNCIEQPQQNDESSSKVRTSSDMNRRKSIKDHLK<br>NAMTGNAKAQTPIFSRSKQLKDTLLSEEINVAKKTVESSSNDLGPFYSLPSKVR<br>DLYAQFKGIEKLYEWQHTCLTLNSVQERKNLIYSLPTSGGKTLVAEILMLQELL<br>CCRKDVLMILPYVAIVQEKISGLSSFGIELGFFVEEYAGSKGRFPPTKRREKKS<br>LYIATIEKGHSLVNSLIETGRIDSLGLVVVDELHMIGEGSRGATLEMTLAKILY<br>TSKTTQIIGMSATLNNVEDLQKFLQAEYYTSQFRPVELKEYLKINDTIYEVDSK<br>AENGMTFSRLLNYKYSDTLKKMDPDHLVALVTEVIPNYSCLVFCPSKKNCENVA<br>EMICKFLSKEYLKHKEKEKCEVIKNLKNIGNGNLCPVLKRTIPFGVAYFIHSGL<br>TSDERKLLEEAYSTGVLCLFTCTSTLAAGVNLPARRVILRAPYVAKEFLKRNQY<br>KQMIGRAGRAGIDTIGESILILQEKDKQQVLELITKPLENCYSHLVQEFTKGIQ<br>TLFLSLIGLKIATNLDDIYHFPMNGTFFGVQQKVLLKEKSLWEITVESLRYLTEK<br>GLLQKDTIYKSEEEVQYNFHITKLGRASFKGTIDLAYCDILYRDLKKGLEGLVL<br>ESLLHLIYLTTPYDLVSQCNPDWMIYFRQFSQLSPAEQNVAAILGVSESPIGKK<br>ASGQAIGKKVDKNVVNRLYLSFVLYTLLKETNIWTVSEKFNMPRGYIQNLLTGT<br>ASFSSCVLHFCEELEEFWVYRALLVELTKKLTYCVKAELIPLMEVTGVLEGRAK<br>QLYSAGYKSLMHLANANPEVLVRTIDHLSRRQAKQIVSSAKMLLHEKAEALQEE<br>VEELLRLPSDFPGAVASSTDKA<br>(SEQ ID NO: 63) |
| ICP8 | H. simplex | METKPKTATTIKVPPGPLGYVYARACPSEGIELLALLSARSGDSDVAVAPLVVG<br>LTVESGFEANVAVVVGSRTTGLGGTAVSLKLTPSHYSSSVYVFHGGRHLDPSTQ<br>APNLTRLCERARRHFGFSDYTPRPGDLKHETTGEALCERLGLDPDRALLYLVVT |

TABLE A-continued

| Protein Name | Organism | Protein Sequence |
|---|---|---|
| | | EGFKEAVCINNTFLHLGGSDKVTIGGAEVHRIPVYPLQLFMPDFSRVIAEPFNA<br>NHRSIGEKFTYPLPFFNRPLNRLLFEAVVGPAAVALRCRNVDAVARAAAHLAFD<br>ENHEGAALPADITFTAFEASQGKTPRGGRDGGGKGAAGGFEQRLASVMAGDAAL<br>ALESIVSMAVFDEPPTDISAWPLFEGQDTAAARANAVGAYLARAAGLVGAMVFS<br>TNSALHLTEVDDAGPADPKDHSKPSFYRFFLVPGTHVAANPQVDREGHVVPGFE<br>GRPTAPLVGGTQEFAGEHLAMLCGFSPALLAKMLFYLERCDGAVIVGRQEMDVF<br>RYVADSNQTDVPCNLCTFDTRHACVHTTLMRLRARHPKFASAARGAIGVFGTMN<br>SMYSDCDVLGNYAAFSALKRADGSETARTIMQETYRAATERVMAELETLQYVDQ<br>AVPTAMGRLETIITNREALHTVVNNVRQVVDREVEQLMRNLVEGRNFKFRDGLG<br>EANHAMSLTLDPYACGPCPLLQLLGRRSNLAVYQDLALSQCHGVFAGQSVEGRN<br>FRNQFQPVLRRRVMDMFNNGFLSAKTLTVALSEGAAICAPSLTAGQTAPAESSF<br>EGDVARVTLGFPKELRVKSRVLFAGASANASEAAKARVASLQSAYQKPDKRVDI<br>LLGPLGFLLKQFHAAIFPNGKPPGSNQPNPQWFWTALQRNQLPARLLSREDIET<br>IAFIKKFSLDYGAINFINLAPNNVSELAMYYMANQILRYCDHSTYFINTLTAII<br>AGSRRPPSVQAAAAWSAQGGAGLEAGARALMDAVDAHPGAWTSMFASCNLLRPV<br>MAARPMVVLGLSISKYYGMAGNDRVFQAGNWASLMGGKNACPLLIFDRTRKFVL<br>ACPRAGFVCAASSLGGGAHESSLCEQLRGIISEGGAAVASSVFVATVKSLGPRT<br>QQLQIEDWLALLEDEYLSEEMMELTARALERGNGEWSTDAALEVAHEAEALVSQ<br>LGNAGEVFNFGDFGCEDDNATPFGGPGAPGPAFAGRKRAFHGDDPFGEGPPDKK<br>GDLTLDML<br>(SEQ ID NO: 64) |
| RAD25 | S. cerevisiae | MTDVEGYQPKSKGKIFPDMGESFFSSDEDSPATDAEIDENYDDNRETSEGRGER<br>DTGAMVTGLKKPRKKTKSSRHTAADSSMNQMDAKDKALLQDTNSDIPADFVPDS<br>VSGMFRSHDFSYLRLRPDHASRPLWISPSDGRIILESFSPLAEQAQDFLVTIAE<br>PISRPSHIHEYKITAYSLYAAVSVGLETDDIISVLDRLSKVPVAESIINFIKGA<br>TISYGKVKLVIKHNRYFVETTQADILQMLLNDSVIGPLRIDSDHQVQPPEDVLQ<br>QQLQQTAGKPATNVNPNDVEAVFSAVIGGDNEREEEDDDIDAVHSFEIANESVE<br>VVKKRCQEIDYPVLEEYDFRNDHRNPDLDIDLKPSTQIRPYQEKSLSKMFGNGR<br>ARSGIIVLPCGAGKTLVGITAACTIKKSVIVLCTSSVSVMQWRQQFLQWCTLQP<br>ENCAVFTSDNKEMFQTESGLVVSTYSMVANTRNRSHDSQKVMDFLTGREWGFII<br>LDEVHVVPAAMFRRVVSTIAAHAKLGLTATLVREDDKIGDLNFLIGPKLYEANW<br>MELSQKGHIANVQCAEVWCPMTAEFYQEYLRETARKRMLLYIMNPTKFQACQFL<br>IQYHERRGDKIIVFSDNVYALQEYALKMGKPFIYGSTPQQERMNILQNFQYNDQ<br>INTIFLSKVGDTSIDLPEATCLIQISSHYGSRRQEAQRLGRILRAKRRNDEGFN<br>AFFYSLVSKDTQEMYYSTKRQAFLVDQGYAFKVITHLHGMENIPNLAYASPRER<br>RELLQEVLLKNEEAAGIEVGDDADNSVGRGSNGHKRFKSKAVRGEGSLSGLAGG<br>EDMAYMEYSTNKNKELKEHHPLIRKMYYKNLKK<br>(SEQ ID NO: 65) |
| RAD3 | S. cerevisiae | MKFYIDDLPVLFPYPKIYPEQYNYMCDIKKTLDVGGNSILEMPSGTGKTVSLLS<br>LTIAYQMHYPEHRKIIYCSRTMSEIEKALVELENLMDYRTKELGYQEDFRGLGL<br>TSRKNLCLHPEVSKERKGTVVDEKCRRMTNGQAKRKLEEDPEANVELCEYHENL<br>YNIEVEDYLPKGVFSFEKLLLKYCEEKTLCPYFIVRRMISLCNIIIYSYHYLLDP<br>KIAERVSNEVSKDSIVIFDEAHNIDNVCIESLSLDLTTDALRRATRGANALDER<br>ISEVRKVDSQKLQDEYEKLVQGLHSADILTDQEEPFVETPVLPQDLLTEAIPGN<br>IRRAEHFVSFLKRLIEYLKTRMKVLHVISETPKSFLQHLKQLTFIERKPLRFCS<br>ERLSLLVRTLEVTEVEDFTALKDIATFATLISTYEEGFLLIIEPYEIENAAVPN<br>PIMRFTCLDASIAIKPVFERFSSVIITSGTISPLDMYPRMLNFKTVLQKSYAMT<br>LAKKSFLPMIITKGSDQVAISSRFEIRNDPSIVRNYGSMLVEFAKITPDGMVVF<br>FPSYLYMESIVSMWQTMGILDEVWKHKLILVETPDAQETSLALETYRKACSNGR<br>GAILLSVARGKVSEGIDFDHQYGRTVLMIGIPFQYTESRILKARLEFMRENYRI<br>RENDFLSFDAMRHAAQCLGRVLRGKDDYGVMVLADRRFSRKRSQLPKWIAQGLS<br>DADLNLSTDMAISNTKQFLRTMAQPTDPKDQEGVSVWSYEDLIKHQNSRKDQGG<br>FIENENKEGEQDEDEDEDIEMQ<br>(SEQ ID NO: 66) |
| Cas9_RecII | S. pyogenes | DVDKLFIQLVQTYNQLFEENPINASGVDAKAILSARLSKSRRLENLIAQLPGEK<br>KNGLFGNLIALSLGLTPNFKSNFDLAEDAKLQLSKDTYDDDLDNLLAQIGDQYA<br>DLFLAAKNLSDAILLSDILRV<br>(SEQ ID NO: 67) |
| Cas9_RecI_<br>RecII_RecI | S. pyogenes | DDSFFHRLEESFLVEEDKKHERHPIFGNIVDEVAYHEKYPTIYHLRKKLVDSTD<br>KADLRLIYLALAHMIKFRGHFLIEGDLNPDNSDVDKLFIQLVQTYNQLFEENPI<br>NASGVDAKAILSARLSKSRRLENLIAQLPGEKKNGLFGNLIALSLGLTPNFKSN<br>FDLAEDAKLQLSKDTYDDDLDNLLAQIGDQYADLFLAAKNLSDAILLSDILRVN<br>TEITKAPLSASMIKRYDEHHQDLTLLKALVRQQLPEKYKEIFFDQSKNGYAGYI<br>DGGASQEEFYKFIKPILEKMDGTEELLVKLNREDLLRKQRTFDNGSIPHQIHLG<br>ELHAILRRQEDFYPFLKDNREKIEKILTFRIPYYVGPLARGNSRFAWMTRKSEE<br>TITPWNFEEVVDKGASAQSFIERMTNFDKNLPNEKVLPKHSLLYEYFTVYNELT<br>KVKYVTEGMRKPAFLSGEQKKAIVDLLFKTNRKVTVKQLKEDYFKKIECFDSVE<br>ISGVEDRFNASLGTYHDLLKIIKDKDFLDNEENEDILEDIVLTLTLFEDREMIE<br>ERLKTYAHLFDDKVMKQLKRRRYTGWGRLSRKLINGIRDKQSGKTILDFLKSDG<br>FANRNFMQLIHDDSLTFKEDIQKAQVSGQGD<br>(SEQ ID NO: 68) |

In certain embodiments, the base editor (e.g., a Cas-free base editor) comprises one or more DNA oligonucleotides, one or more RNA oligonucleotides and/or one or more synthetic oligonucleotides including one or more peptide nucleic acids (PNA), one or more locked nucleic acids (LNA) and/or one or more bridged nucleic acids (BNA). See, e.g., FIG. 1D. See, e.g., Nielsen, et al. (1991) *Science* 254:1497-1500 and Bahal, et al. (2014) *Curr Gene Ther.* 14(5):331-342 regarding PNA; Moreno, et al. (2013) *Nucleic Acid Res.* 41(5):3257-3273 and Geny, et al. (2016) *Nucleic Acid Res.* 44(5):2007-2019 regarding LNA; and Rahman, et al. (2007) *Nucleosides Nucleotides Nucleic Acids* 26(10-12):1625-1628 regarding BNA.

In certain embodiments, the Cas9-free base editors of the invention comprise a ZFP-deaminase fusion protein and a ZFN nickase, and optionally one or more DNA-destabilizing factors. In certain embodiments, the DNA-destabilizing factor is a protein (e.g., as shown in Table A) or an oligonucleotide (e.g., an LNA, PNA or BNA). In other embodiments, the Cas9-free base editors comprise non-Cas9 CRISPR proteins with DNA destabilizing (unwinding) properties, including any Cas9 equivalents such as Cas12a (including a full length or truncated Cas12 protein). In other embodiments, the Cas9-free base editors do not comprise any elements from a CRISPR system. The one or more non-Cas9 DNA-destabilizing (unwinding) factor(s) (e.g., proteins of Table A, LNAs, PNAs, BNAs, etc.) may be operably linked to any component of the base editor, for example either component of the ZFP-deaminase fusion protein and/or any of the components of the ZFN nickase.

In certain embodiments, the base editor comprises one or more nucleotide sequences, for example one or more DNA oligonucleotides, RNA oligonucleotides, peptide nucleic acids (PNAs), locked nucleic acids (LNAs) and/or bridged nucleic acids (BNAs), which can be used to provide a single stranded DNA substrate for base editors at the target site. This can be facilitated by e.g. duplex invasion, triplex invasion or a tail-clamp (Quijano, et al. (2017) *Yale J. Biol and Med.* 90:583-598; Pellestor and Paulasova (2004) *European J. Human Genetics* 12:694-700; Schleifman, et al. (2011) *Chem Biol.* 18:1189-1198. The structure of the one or more nucleotide sequences of the base editor will vary in length; number and position of DNA and/or RNA and/or LNA and/or LNA and/or BNA bases; phosphorothioate bonds; other common modifications) of these oligonucleotides depending on the target sequence composition.

In certain embodiments, the base editor comprises one or more PNAs, for example gamma PNAs containing miniPEG substitutions and the gamma position for enhanced binding, increased solubility and improved delivery (Bahal, et al. (2014) *Current Gene Ther.* 14(5):331-342. In certain embodiments, the PNAs comprise one or more Q indicating 8-amino-2,6-dioxaoctanoic acid linkers and/or one or more cytosines (C) or pseudoisocytosine residues. Optionally, one or more lysine (Lys) residues are included in the PNA, for example on the N- and/or C-terminals of the PNA sequence. In certain embodiments, 1, 2, 3, 4, 5 or more Lys residues are included at one or both terminals of the PNA. In certain embodiments, two or more PNAs are used in the base editor, for example in the same or in reverse orientation relative to each other. In certain embodiments, the one or more PNAs have the structure: N-Lys-Lys-Lys-NNNNNNNNNN-OOO-NNNNNNNNNN-Lys-Lys-Lys-C; N-Lys-Lys-Lys-NNNN NNNNNN-OOO-NNNNNNNNNNNNNNN-Lys-Lys-Lys-C; N-Lys-Lys-Lys-NNNNNNNNNN-OOO-NNNNNNNN NN-Lys-Lys-Lys-C; N-Lys-Lys-Lys-NNNNNNNNNN-OO O-NNNNNNNNNN-Lys-Lys-Lys-C; and/or N-Lys-Lys-Lys-NNNNNNNNNNNNNNNN-Lys-Lys-Lys-C, wherein O indicates 8-amino-2,6-dioxaoctanoic acid linkers and C indicates cytosine. The Lys residues on the N- and/or C-terminals of the PNA sequence are optional and pseudoisocytosine be can substituted for cytosine. In the certain embodiments, the one or more PNAs comprises one or more PNAs as shown in FIGS. 8B to 8E.

In other embodiments the base editor comprises one or more LNAs. LNAs can include a stacking linker and 2'-glycylamino-LNA for improved performance (Geny, et al. (2016) *Nucleic Acids Res.* 44(5):2007-2019. In certain embodiments, the LNA comprise one or more phosphorothioate bonds, optionally between one or more LNA residues and/or DNA residues. In other embodiments, the LNA comprises one or more Cholesterol-TEG, which may increase uptake into cells. In certain embodiments, the one or more LNAs have the following structure: 5'-NnNnNn NnNnNnNnNtctct nNnNnNnNnNnNnnNnnNnnNn-3' (SEQ ID NO: 1); 5'-N*n*NnNnNnNnNnNnNtctctnNnNnNnNn Nn Nn NnNnnNnnNnnNnn*N*n-3' (SEQ ID NO:69); and/or 5'-NnNnNnNnNnNnNnNtctct nNnNnNnNnNnNnnNnn Nnn Nn-Chol-TEG-3' (SEQ ID NO:70), where LNA nucleotides are in uppercase; DNA nucleotides are in lower case; "*" indicates phosphorothioate bonds; and "Chol-TEG" indicates 3' Cholesterol-TEG (see, e.g., Bijsterbosch, et al. (2000) *Nucleic Acids Res.* 28:2717-2725; Bijsterbosch, et al. (2002) *J. Pharmacol. Exp. Ther.* 302:619-626; Manoharan (2002) *Antisense Nucleic Acid Drug Dev* 12:103-28; M. Manoharan (2004) *Curr Opin Chem Biol.* 8:570-9) for increased uptake into cells. In certain embodiments, the base editor comprises one or more LNAs as shown in FIG. 8F or FIG. 8G.

The one or more DNA destabilizing factors may be provided independently from and/or with a base editor (e.g., ABE and/or CBE) and/or a nickase. In certain embodiments, the DNA de-stabilizing factor(s) is(are) fused to the ZFP and/or ZFN nickase in any orientation (e.g., N- and/or C-terminal). The DNA destabilizing factor(s) can bind within a 1 kb window of the base editor target site.

Figure 3B:
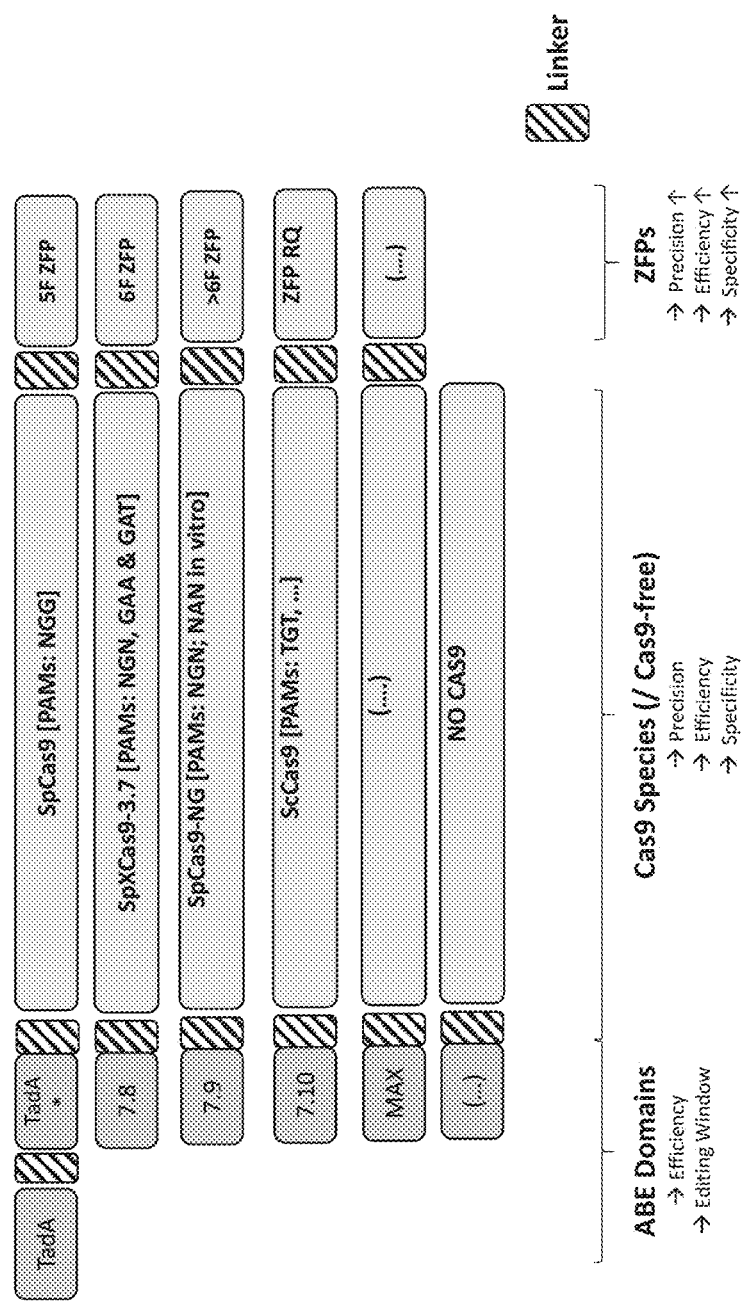

In certain embodiments, described herein is a base editing system comprising a base editor (e.g., a Cas9 adenine or cytosine base editor) and one or more additional DNA-binding domains (e.g., ZFPs, TALEs, additional sgRNA) that specifically binds to a target site near (RANGE) the base editor. In certain embodiments, the Cas9-containing base editing system comprises: a Cas9 nickase and one or more DNA-binding molecules (e.g., ZFPs) that serve to anchor the Cas9 nickase and/or position one or more components of the base editor in relation to the other components, thereby increasing specificity and/or efficiency of base editing. The one or more DNA-binding molecules (e.g., ZFP anchor(s)) typically bind to a target site within 1-50 (or any value therebetween) nucleotides of the base editor (e.g., Cas9 or Cas9-free base editor) and/or targeted base. The DNA-binding molecule may bind 5' and/or 3' to the base editor and/or targeted base. In certain embodiments, the Cas9 base editor as described herein comprises two more ZFP domains, for example a ZFP domain operably linked to a deaminase domain or component thereof and a ZFP anchor domain. See, e.g., FIG. 1B. In certain embodiments, the at least one DNA-binding domain binds to a target site 5' of the base editor, optionally on the same or different strand as bound by the base editor. See, e.g., FIG. 1B, bottom right schematic; FIG. 3; and FIG. 7A for exemplary embodiments in which one or more additional ZFP anchors are used and specifically binds to a target site 5' of the base editor of the system and on the same strand as bound by the base editor.

The inclusion of one or more ZFP anchors can increase efficiency and/or specificity of the base editor, for example in some cases, 2-fold to 5-fold (or any value therebetween), 10-fold to 100-fold (or any value therebetween), or more than 100-fold as compared to base editors not including a ZFP anchor.

In other embodiments, described herein is a base editing system comprising: (1) a Cas9 nickase (e.g., comprising a catalytically inactive monomer of an adenosine deaminase); (2) an anchor DNA-binding domain (e.g., ZFP) that specifically binds to a target site 5' or 3' to the Cas9 nickase; and (3) a non-Cas9 nickase (e.g., a ZFP-nickase) comprising a catalytically inactive monomer of the adenosine deaminase and a DNA-binding domain (e.g., ZFP) that binds to a target site 5' or 3' to the Cas9 nickase. Upon dimerization of the A deaminase monomers of the Cas9 nickase and non-Cas9 nickase (e.g., ZFN nickase) dimerize form a functional deaminase. The anchor DNA-binding domain and non-Cas9 nickase may bind on the same or different strands of the target and/or on the same (5' or 3') or different (one on 5' and one on 3') sides of the Cas9 nickase. In certain embodiments, the anchor DNA-binding domain and the non-Cas9 nickase bind to opposite strands on opposite sides of the Cas9 nickase. See, e.g., FIG. 1B, top schematics.

In other embodiments, described herein is a base editing system comprising: (1) a Cas9 nickase; (2) an optional anchor DNA-binding domain (e.g., ZFP) that specifically binds to a target site 5' or 3' to the Cas9 nickase; and (3) a non-Cas9 nickase (e.g., a ZFP-nickase) comprising an A or C deaminase. The anchor DNA-binding domain and non-Cas9 nickase may bind on the same or different strands of the target and/or on the same (5' or 3') or different (one on 5' and one on 3') sides of the Cas9 nickase. In certain embodiments, the anchor DNA-binding domain and the non-Cas9 nickase base editor bind to opposite strands on opposite sides of the Cas9 nickase. See, e.g., FIG. 1B, bottom middle schematic.

In other embodiments, described herein is a base editing system comprising: (1) a Cas9 protein (e.g., dCas9) operably linked to a sgRNA; (2) an optional anchor DNA-binding domain (e.g., ZFP anchor) that specifically binds to a target site 5' or 3' to the Cas9 nickase; (3) a fusion protein comprising a ZFP operably linked to an A or C deaminase, which fusion protein is 3' or 5' to the Cas9 protein; and (4) a ZFN nickase that binds 3' or 5' of the Cas9 protein and/or the ZFP. The anchor DNA-binding domain and non-Cas9 protein may bind on the same or different strands of the target and/or on the same (5' or 3') or different (one on 5' and one on 3') sides of the Cas9 protein. In certain embodiments, the ZFP of the ZFP-deaminase fusion protein and the optional anchor ZFP bind to opposite strands. See, e.g., FIG. 1C. In further embodiments, the base editor does not comprise a ZFN nickase.

The Cas9 base editors described herein provide surprising and unexpected advantages in terms of PAM sequences that may be used for efficient and targeted base editing, including expanding (relaxing) the available PAM sequence for base editors comprising sgRNAs.

Also described herein are base editors (ABEs or CBEs) that do not comprise a Cas9 base editor (e.g., lack a Cas9 nickase or Cas9 protein). See, e.g., FIG. 1A through FIG. 1D.

In certain embodiments, the base editor comprises: (1) a non-Cas9 nickase, for example a ZFN nickase comprising a pair of ZFNs (ZFP operably linked to a nuclease domain) in which one of the nuclease domains of the pair is catalytically inactive (see, e.g., U.S. Pat. Nos. 8,703,489; 9,200,266; 9,631,186; and 10,113,207); and (2) a ZFP base editor comprising a ZFP operably linked to an A or C deaminase. See, e.g., FIG. 1B, bottom left schematic.

In other embodiments, the base editor comprises a DNA destabilizing molecule comprising any RNA-programmable molecule. In certain embodiments, the DNA destabilizing molecule comprises an RNA-programmable molecule comprising Cas9 protein (e.g., dCas9) and sgRNA. In other embodiments, the RNA-programmable molecule is not a Cas9 protein (e.g., Cpf1 (also known as Cas12a), C2c1, C2c2 (also known as Cas13a), C2c3, Cas1, Cas2, Cas4, CasX and CasY); and an adenosine or cytosine deaminase. Optionally, the base editor further comprises at least one ZFP DNA-binding domain (e.g., any combination of a ZFP DNA-binding domain operably linked to the adenosine or cytosine deaminase; a ZFP anchor on either side of the DNA destabilizing molecule; and/or a ZFN nickase).

In other embodiments, the Cas9-free base editor comprises a ZFN nickase, and ABE or CBE (e.g. operably linked to a ZFP) and one or more DNA destabilizing molecules that makes the target base accessible (e.g., unwinds the DNA). See, e.g., FIG. 1D. Non-limiting examples of DNA destabilizing (unwinding) molecules include protein domains as shown in Table A and nucleic acids, including LNAs and/or PNAs as shown in FIG. 8. The ZFN nickase may include one or more mutations in the catalytically active and/or catalytically inactive FokI domains and/or one or more mutations to the ZFP backbone. See, e.g., U.S. Patent Publication No. 2018/0087072. In certain embodiments, the base editors as described herein may be Cas9-free but may include non-Cas9 CRISPR proteins.

Figure 1B:
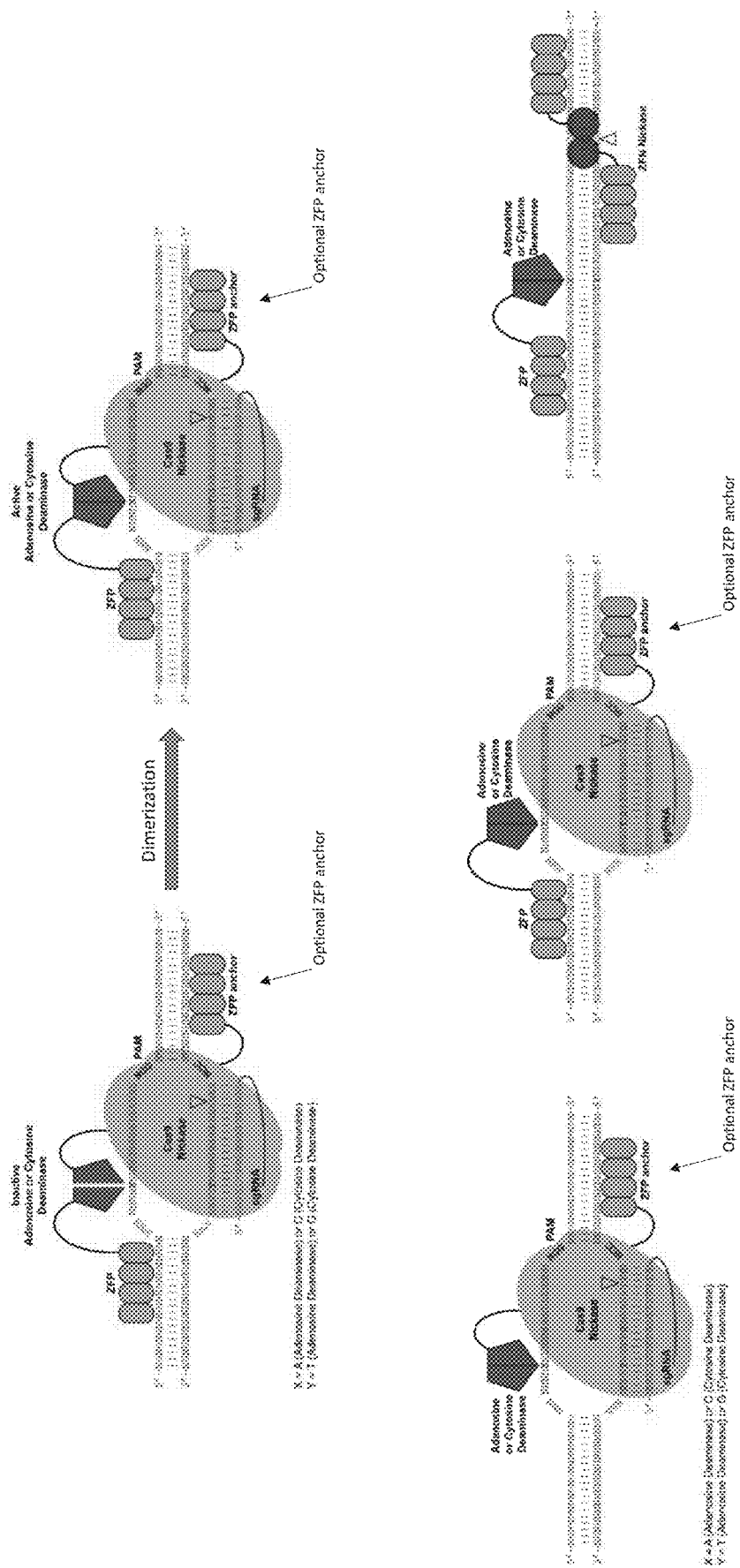
Figure 1C:
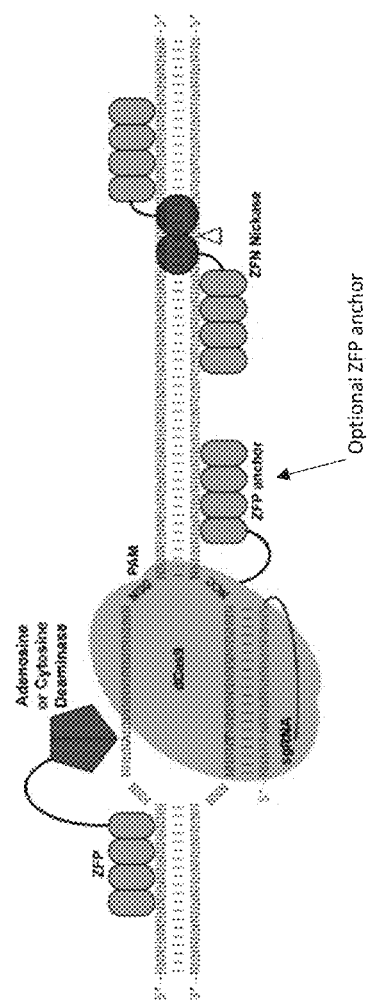
Figure 1D:
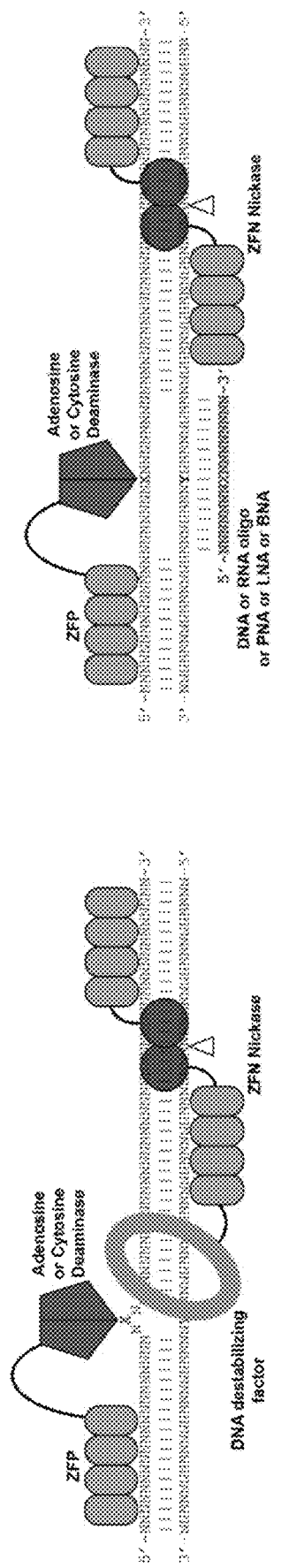

Any of the Cas9-free (e.g., ZFP) base editors may further comprise (or recruit) one or more additional DNA destabilizing factors (e.g., DNA helicases, helix-destabilizing molecules and the bacterial DnaA protein, single-strand DNA binding proteins, oligonucleotides, etc.), for example if further unwinding of the DNA augments base editor function by increasing accessibility of the target. The one or more DNA destabilizing factors can be associated with the nickase and/or the A or C deaminase-containing molecule. In certain embodiments, the DNA destabilizing factor (e.g., DNA oligo) is associated with the ZFN nickase as depicted in FIG. 1D.

In other embodiments, described herein is a base editing system comprising: (1) at least one DNA destabilizing molecule (e.g., non-Cas9 protein); (2) an optional DNA-binding domain (e.g., ZFN anchor) that specifically binds to a target site 5' or 3' to the DNA destabilizing molecule; and (3) a fusion protein comprising a ZFP operably linked to an A or C deaminase, which fusion protein is 3' or 5' to the DNA-destabilizing molecule.

Cas9-free base editors offer several surprising and unexpected advantages over Cas9 base editors including, but not limited to: (i) No Cas9 dependent off-target effects as we can build ZFNs with 99% or more cutting efficiency (no off-target effects); (ii) eliminating PAM restrictions as ZFPs can target essentially any sequence in the human genome; (iii) reducing and/or eliminating bystander mutations (e.g., within the target window) prevalent with current Cas9 base editors; and/or (iv) facilitate AAV delivery (known to be functional in vivo) due to reduced construct size.

Thus, cas9-free base editors provide significant advantages over conventional Cas9 base editors including but not limited to: target specificity; versatility; control or elimination of bystander mutations; and ease of delivery. In terms of target specificity, Cas9-free ZFP base editors can be designed that are 99% efficient at editing with few or no off-target effects, whereas Cas9 base editors exhibit higher rates of off-target effects. Similarly, non-Cas9 ZFP base editors control (reduce) or eliminate bystander mutations as seen with Cas9 base editors. Furthermore, whereas the selection of target sites for non-Cas9 ZFP base editors is limited by PAM requirements, Cas9 free ZFP base editors can target essentially any target sequence). In addition, due to the reduced construct size of non-Cas9 base editors, they can be delivered using AAV vectors, thereby greatly expanding therapeutic (in vivo) uses.

In certain embodiments, the base editors (base editing systems) described herein include a single base to be changed (target base) within: (1) the base editing window and/or (2) bases between the base editing window and the 5' end of the PAM sequence intervening. See, also FIG. 2. The opening of the DNA editing window leaves other non-target bases (adenines and/or cytosines) open for potential modification by base editors. This means that although the target may be 13-16 nucleotides away from the 5' end of the PAM sequence, targeted bases (e.g., adenines or cytosines) present in those intervening nucleotides and/or in the base editing window may also be altered. Such non-targeted mutations, also referred to as "bystander" mutations, which may be undesirable in the base editing process. In some situations, bystander mutations may be avoided by choosing a PAM sequence that do not comprise the base to be targeted (an adenine for adenine base editors or cytidine for cytidine base editor) in the editing window. Alternatively, and/or in addition to selection of a PAM sequences, the present invention reduces or eliminates bystander mutations by using a base editor as described herein comprising a ZFP anchor paired with a ZFN nickase functional domains, eliminating the PAM requirement, and allowing the user to place the editor at any optimal location.

In some embodiments, disclosed herein are complexes (systems) comprising a variety of fusion proteins. In some embodiments, Cas proteins can be fused to alternate DNA binding domains to increase the specificity of binding of the fusion protein to a DNA (see Bolukbashi, et al. (2015) *Nat Methods* 12(12):1150-1156). For example, ZFP, TtAgo and TALE DNA binding domains may be fused to a dCas. In some embodiments, the dCas comprises mutations to alter PAM specificity (see Gao, et al. (2017) *Nature Biotechnology* 35:789-792; Virginijus Siksnys (2016) *Mol Cell* 61:793) or to alter the requirement for PAM recognition. In some embodiments, the base editor lacks a Cas nuclease.

Potential targets for this approach are many. Non-limiting examples of base editing for treatment and/or prevention of disease editing of gene involved in exemplary diseases that may be treated include sickle cell disease, hemophilia, cystic fibrosis, phenylketonuria, Tay-Sachs, color blindness, Fabry disease, Friedreich's ataxia, prostate cancer, and many others.

Thus, the base editing systems as described herein may be used to alter expression of any disease-associate gene. In certain embodiments, the gene is associated with a cancer, for example, the JAK2 V617F mutation. This mutation plays a critical role in the expansion of myeloproliferative neoplasms. JAK2 transduces cytokine and growth factor signals from membrane-bound receptors through phosphorylation of the STAT family of transcription factors. The V617F mutation leads to constitutive tyrosine phosphorylation activity and promotes cytokine hypersensitivity (James, et al. (2005) *Nature* 434:1144-1148) and the ability to drive cells to proliferate in the absence of cytokines (Zhao, et al. (2005) *J. Biol Chem* 280 (24):22788-22792). For some JAK2 V617F disorders (e.g. primary myelofibrosis), the only cure is hematopoietic cell transplant, however current approaches are often associated with disease relapse and graft versus host disease (Byrne, et al. (2018) *Ther Avd Hematol* 9(9):251-259). Editing of a subject's hematopoietic stem cells/progenitor cells (HSC/PC) to remove the mutation may allow successful treatment of these diseases.

In certain embodiments, base targets an alpha-1 antitrypsin (within the SERPINA locus). Mutations in the locus that cause an autosomal recessive deficiency in the A1AT protein are associated with both liver and lung disease. The PiZ mutation, one of the most common deficiency alleles in people of Northern Europe descent, results in only about 10-20% of the A1AT protein being produced. This mutation is caused by a single mutation in exon 5, leading to a glutamine substitution at amino acid position 342 for a lysine where a G at position 1096 in the DNA is an A in the mutated gene sequence (reviewed in Fregonese and Stolk (2008) *Orphanet J Rare Dis* 3:16).

DNA-Binding Molecules/Domains

Described herein are compositions comprising one or more DNA-binding molecules/domains that specifically bind to a target site in any gene or locus of interest. Any DNA-binding molecules/domains can be used in the compositions and methods disclosed herein, including but not limited to a zinc finger DNA-binding domain, a TALE DNA binding domain, the DNA-binding portion (guide or sgRNA) of a CRISPR/Cas nuclease, and/or a DNA-binding domain from a meganuclease.

In certain embodiments, the base editors described herein comprise a zinc finger protein DNA-binding domain. Preferably, the zinc finger protein is non-naturally occurring in that it is engineered to bind to a target site of choice. See, for example, Beerli, et al. (2002) *Nature Biotechnol.* 20:135-141; Pabo, et al. (2001) *Ann. Rev. Biochem.* 70:313-340; Isalan, et al. (2001) *Nature Biotechnol.* 19:656-660; Segal, et al. (2001) *Curr. Opin. Biotechnol.* 12:632-637; Choo, et al. (2000) *Curr. Opin. Struct. Biol.* 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; and 7,253,273; and U.S. Patent Publication Nos. 2005/0064474; 2007/0218528; and 2005/0267061, all incorporated herein by reference in their entireties. In certain embodiments, the DNA-binding domain comprises a zinc finger protein disclosed in U.S. Patent Publication No. 2012/0060230, incorporated by reference in its entirety herein.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as International Patent Publication Nos. WO 98/37186; WO 98/53057; WO 00/27878; and WO 01/88197 and GB 2,338,237. In addition, enhancement of binding specificity for zinc finger binding domains has been described, for example, in U.S. Pat. No. 6,794,136.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein. In addition, enhancement of binding specificity for zinc finger binding domains has been described, for example, in U.S. Pat. No. 6,794,136.

Selection of target sites; ZFPs and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; and 6,200,759; and International Patent Publication Nos. WO 95/19431; WO 96/06166; WO 98/53057; WO 98/54311; WO 00/27878; WO 01/60970; WO 01/88197; WO 02/099084; WO 98/53058; WO 98/53059; WO 98/53060; WO 02/016536; and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

Usually, the ZFPs include at least three fingers. Certain of the ZFPs include four, five, six or more fingers. The ZFPs that include three fingers typically recognize a target site that includes 9 or 10 nucleotides; ZFPs that include four fingers typically recognize a target site that includes 12 to 14 nucleotides; while ZFPs having six fingers can recognize target sites that include 18 to 21 nucleotides. The ZFPs can also be fusion proteins that include one or more regulatory domains, which domains can be transcriptional activation or repression domains.

In some embodiments, the DNA-binding domain may be derived from a nuclease. For example, the recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. Nos. 5,420,032; 6,833,252; Belfort, et al. (1997) *Nucleic Acids Res.* 25:3379-3388; Dujon, et al. (1989) *Gene* 82:115-118; Perler, et al. (1994) *Nucleic Acids Res.* 22, 1125-1127; Jasin (1996) *Trends Genet.* 12:224-228; Gimble, et al. (1996) *J. Mol. Biol.* 263:163-180; Argast, et al. (1998) *J. Mol. Biol.* 280: 345-353 and the New England Biolabs catalogue. In addition, the DNA-binding specificity of homing endonucleases and meganucleases can be engineered to bind non-natural target sites. See, for example, Chevalier, et al. (2002) *Molec. Cell* 10:895-905; Epinat, et al. (2003) *Nucleic Acids Res.* 31:2952-2962; Ashworth, et al. (2006) *Nature* 441:656-659; Paques, et al. (2007) *Current Gene Therapy* 7:49-66; U.S. Patent Publication No. 2007/0117128.

In certain embodiments, the zinc finger protein used with the mutant cleavage domains described herein comprises one or more mutations (substitutions, deletions, and/or insertions) to the backbone regions (e.g., regions outside the 7-amino acid recognition helix region numbered −1 to 6), for example at one or more of positions −14, −9 and/or −5. The wild-type residue at one or more these positions may be deleted, replaced with any amino acid residue and/or include one or more additional residues. In some embodiments, the Arg (R) at position −5 is changed to a Tyr (Y), Asp (N), Glu (E), Leu (L), Gln (Q), or Ala (A). In other embodiments, the Arg (R) at position (−9) is replaced with Ser (S), Asp (N), or Glu (E). In further embodiments, the Arg (R) at position (−14) is replaced with Ser (S) or Gln (Q). In other embodiments, the fusion polypeptides can comprise mutations in the zinc finger DNA binding domain where the amino acids at the (−5), (−9) and/or (−14) positions are changed to any of the above listed amino acids in any combination.

In other embodiments, the DNA binding domain comprises an engineered domain from a Transcriptional Activator-Like (TAL) effector (TALE) similar to those derived from the plant pathogens *Xanthomonas* (see Boch, et al. (2009) *Science* 326:1509-1512 and Moscou and Bogdanove (2009) *Science* 326:1501) and *Ralstonia* (see Heuer, et al. (2007) *Applied and Environmental Microbiology* 73(13): 4379-4384); U.S. Patent Publication Nos. 2011/0301073 and 2011/0145940. The plant pathogenic bacteria of the genus *Xanthomonas* are known to cause many diseases in important crop plants. Pathogenicity of *Xanthomonas* depends on a conserved type III secretion (T3 S) system which injects more than 25 different effector proteins into the plant cell. Among these injected proteins are transcription activator-like effectors (TALE) which mimic plant transcriptional activators and manipulate the plant transcriptome (see Kay, et al. (2007) *Science* 318:648-651). These proteins contain a DNA binding domain and a transcriptional activation domain. One of the most well characterized TALEs is AvrBs3 from *Xanthomonas* campestgris pv. Vesicatoria (see Bonas, et al. (1989) *Mol Gen Genet* 218:127-136 and International Patent Publication No. WO 2010/079430). TALEs contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S., et al. (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer, et al. (2007) *Appl and Envir Micro* 73(13):4379-4384). These genes are 98.9% identical in nucleotide sequence to each other but differ by a deletion of 1,575 base pairs in the repeat domain of hpx17. However, both gene products have less than 40% sequence identity with AvrBs3 family proteins of *Xanthomonas*.

Specificity of these TAL effectors depends on the sequences found in the tandem repeats. The repeated sequence comprises approximately 102 base pairs and the repeats are typically 91-100% homologous with each other (Bonas, et al., ibid). Polymorphism of the repeats is usually located at positions 12 and 13 and there appears to be a one-to-one correspondence between the identity of the hypervariable diresidues (the repeat variable diresidue or RVD region) at positions 12 and 13 with the identity of the contiguous nucleotides in the TAL-effector's target sequence (see Moscou and Bogdanove (2009) *Science* 326: 1501 and Boch, et al. (2009) *Science* 326:1509-1512). Experimentally, the natural code for DNA recognition of these TAL-effectors has been determined such that an HD sequence at positions 12 and 13 (Repeat Variable Diresidue or RVD) leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch, et al., ibid). Engineered TAL proteins have been linked to a FokI cleavage half domain to yield a TAL effector domain nuclease fusion (TALEN), including TALENs with atypical RVDs. See, e.g., U.S. Pat. No. 8,586,526.

In some embodiments, the TALEN comprises an endonuclease (e.g., FokI) cleavage domain or cleavage half-domain. In other embodiments, the TALE-nuclease is a mega TAL. These mega TAL nucleases are fusion proteins comprising a TALE DNA binding domain and a meganuclease cleavage domain. The meganuclease cleavage domain is active as a monomer and does not require dimerization for activity. (See Boissel et al. (2013) *Nucl Acid Res:* 1-13, doi: 10.1093/nar/gkt1224).

In still further embodiments, the nuclease comprises a compact TALEN. These are single chain fusion proteins linking a TALE DNA binding domain to a TevI nuclease domain. The fusion protein can act as either a nickase localized by the TALE region, or can create a double strand break, depending upon where the TALE DNA binding domain is located with respect to the TevI nuclease domain (see Beurdeley, et al. (2013) *Nat Comm:* 1-8 DOI: 10.1038/ncomms2782). In addition, the nuclease domain may also exhibit DNA-binding functionality. Any TALENs may be used in combination with additional TALENs (e.g., one or more TALENs (cTALENs or FokI-TALENs) with one or more mega-TALEs.

In addition, as disclosed in these and other references, zinc finger domains and/or multi-fingered zinc finger proteins or TALEs may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein. In addition, enhancement of binding specificity for zinc finger binding domains has been described, for example, in U.S. Pat. No. 6,794,136.

In certain embodiments, the base editor comprises a DNA-binding domain that is part of a CRISPR/Cas nuclease system, including a single guide RNA (sgRNA) DNA binding molecule that binds to DNA. See, e.g., U.S. Pat. No. 8,697,359 and U.S. Patent Publication Nos. 2015/0056705 and 2015/0159172. The CRISPR (clustered regularly interspaced short palindromic repeats) locus, which encodes RNA components of the system, and the cas (CRISPR-associated) locus, which encodes proteins (Jansen, et al. (2002) *Mol. Microbiol.* 43:1565-1575; Makarova, et al. (2002) *Nucleic Acids Res.* 30:482-496; Makarova, et al. (2006) *Biol. Direct* 1:7; Haft, et al. (2005) *PLoS Comput. Biol.* 1:e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

In some embodiments, the DNA binding domain is part of a TtAgo system (see Swarts, et al. (2014) *Nature* 507(7491): 258-261; Swarts, et al. (2012) *PLoS* One 7(4):e35888; Sheng, et al., ibid). In eukaryotes, gene silencing is mediated by the Argonaute (Ago) family of proteins. In this paradigm, Ago is bound to small (19-31 nt) RNAs. This protein-RNA silencing complex recognizes target RNAs via Watson-Crick base pairing between the small RNA and the target and endonucleolytically cleaves the target RNA (Vogel (2014) *Science* 344:972-973). In contrast, prokaryotic Ago proteins bind to small single-stranded DNA fragments and likely function to detect and remove foreign (often viral) DNA (Yuan, et al. (2005) *Mol. Cell* 19:405; Olovnikov, et al. (2013) *Mol. Cell* 51, 594; Swarts, et al. (2014) *Nature* 507(7491):258-261; Swarts, et al. (2012) *PLoS One* 7(4): e35888). Exemplary prokaryotic Ago proteins include those from *Aquifex* aeolicus, *Rhodobacter sphaeroides*, and *Thermus thermophilus*.

One of the most well-characterized prokaryotic Ago protein is the one from *T. thermophilus* (TtAgo; Swarts, et al. (2014) *Nature* 507(7491):258-261; Swarts, et al. (2012) *PLoS* One 7(4):e35888). TtAgo associates with either 15 nt or 13-25 nt single-stranded DNA fragments with 5' phosphate groups. This "guide DNA" bound by TtAgo serves to direct the protein-DNA complex to bind a Watson-Crick complementary DNA sequence in a third-party molecule of DNA. Once the sequence information in these guide DNAs has allowed identification of the target DNA, the TtAgo-guide DNA complex cleaves the target DNA. Such a mechanism is also supported by the structure of the TtAgo-guide DNA complex while bound to its target DNA (G. Sheng, et al., ibid). Ago from *Rhodobacter sphaeroides* (RsAgo) has similar properties (Olovnikov, et al., ibid).

Exogenous guide DNAs of arbitrary DNA sequence can be loaded onto the TtAgo protein (Swarts, et al. (2014) *Nature* 507(7491):258-261; Swarts, et al. (2012) *PLoS* One 7(4):e35888). Since the specificity of TtAgo cleavage is directed by the guide DNA, a TtAgo-DNA complex formed with an exogenous, investigator-specified guide DNA will therefore direct TtAgo target DNA cleavage to a complementary investigator-specified target DNA. In this way, one may create a targeted double-strand break in DNA. Use of the TtAgo-guide DNA system (or orthologous Ago-guide DNA systems from other organisms) allows for targeted cleavage of genomic DNA within cells. Such cleavage can be either single- or double-stranded. For cleavage of mammalian genomic DNA, it would be preferable to use of a version of TtAgo codon optimized for expression in mammalian cells. Further, it might be preferable to treat cells with a TtAgo-DNA complex formed in vitro where the TtAgo protein is fused to a cell-penetrating peptide. Further, it might be preferable to use a version of the TtAgo protein that has been altered via mutagenesis to have improved activity at 37° C. Ago-RNA-mediated DNA cleavage could be used to affect a panoply of outcomes including gene knock-out, targeted gene addition, gene correction, targeted gene deletion using techniques standard in the art for exploitation of DNA breaks.

Thus, any DNA-binding molecule/domain can be used. In certain embodiments, the base editors described herein are Cas9 base editors that include a sgRNA DNA-binding domain (e.g., as a part of a Cas9 nickase) and optionally, one or more ZFP DNA-binding domains (referred to as "ZFP anchors"), which ZFP(s) can increase base editing efficiency and/or specificity. Non-limiting examples of Cas9 base editors including ZFP anchors are shown in FIG. 1B and FIG. 3.

Fusion Molecules

The DNA-editing complexes described herein can include one or more fusion molecules comprising DNA-binding domains (e.g., ZFPs or TALEs, CRISPR/Cas components such as single guide RNAs) as described herein and a heterologous (functional) domain (or functional fragment thereof) are also provided.

Common domains include, e.g., transcription factor domains (activators, repressors, co-activators, co-repressors), silencers, oncogenes (e.g., myc, jun, fos, myb, max, mad, rel, ets, bcl, myb, mos family members etc.); DNA repair enzymes and their associated factors and modifiers; helicases, double strand DNA binding proteins, DNA rearrangement enzymes and their associated factors and modifiers; chromatin associated proteins and their modifiers (e.g. kinases, acetylases and deacetylases); and DNA modifying enzymes (e.g., methyltransferases, topoisomerases, helicases, ligases, kinases, phosphatases, deaminases, polymerases, endonucleases) and their associated factors and modifiers. U.S. Patent Publication Nos. 2005/0064474; 2006/0188987; and 2007/0218528 for details regarding fusions of DNA-binding domains and nuclease cleavage domains, incorporated by reference in their entireties herein.

Fusion molecules are constructed by methods of cloning and biochemical conjugation that are well known to those of skill in the art. Fusion molecules comprise a DNA-binding domain and a functional domain (for example, a helicase and/or deaminase and/or a GUI and/or GAM). Fusion molecules also optionally comprise nuclear localization signals (such as, for example, that from the SV40 medium T-antigen) and epitope tags (such as, for example, FLAG and hemagglutinin). Fusion proteins (and nucleic acids encoding them) are designed such that the translational reading frame is preserved among the components of the fusion.

Fusions between a polypeptide component of a functional domain (or a functional fragment thereof) on the one hand, and a non-protein DNA-binding domain (e.g., antibiotic, intercalator, minor groove binder, nucleic acid) on the other, are constructed by methods of biochemical conjugation known to those of skill in the art. See, for example, the Pierce Chemical Company (Rockford, IL) Catalogue. Methods and compositions for making fusions between a minor groove binder and a polypeptide have been described. Mapp, et al. (2000) *Proc. Natl. Acad. Sci. USA* 97:3930-3935. Furthermore, single guide RNAs of the CRISPR/Cas system associate with functional domains to form active transcriptional regulators and nucleases.

In certain embodiments, the target site for the DNA-binding domain is present in an accessible region of cellular chromatin. Accessible regions can be determined as described, for example, in U.S. Pat. Nos. 7,217,509 and 7,923,542. If the target site is not present in an accessible region of cellular chromatin, one or more accessible regions can be generated as described in U.S. Pat. Nos. 7,785,792 and 8,071,370. In additional embodiments, the DNA-binding domain of a fusion molecule is capable of binding to cellular chromatin regardless of whether its target site is in an accessible region or not. For example, such DNA-binding domains are capable of binding to linker DNA and/or nucleosomal DNA. Examples of this type of "pioneer" DNA binding domain are found in certain steroid receptor and in hepatocyte nuclear factor 3 (HNF3) (Cordingley, et al. (1987) *Cell* 48:261-270; Pina, et al. (1990) *Cell* 60:719-731; and Cirillo, et al. (1998) *EMBO J.* 17:244-254).

The fusion molecule may be formulated with a pharmaceutically acceptable carrier, as is known to those of skill in the art. See, for example, Remington's Pharmaceutical Sciences, 17th ed., 1985; and U.S. Pat. Nos. 6,453,242 and 6,534,261.

The functional component(s)/domain(s) of a fusion molecule can be selected from any of a variety of different components capable of influencing the sequence of a gene once the fusion molecule binds to a target sequence via its DNA binding domain. Hence, the functional component can include, but is not limited to, various deaminases, UGI, GAM, helicases etc. In certain embodiments, the functional domain comprises one or more cytidine deaminases (e.g., an apolipoprotein B mRNA-editing complex 1 (APOBEC1) domain and/or an Activation Induced Deaminase (AID)). In other embodiments, the functional domain comprises one or more adenine deaminases (e.g., a mutated TadA (tRNA adenine deaminase (see Gaudelli, et al. (2017) *Nature* 551:464-471)). In still further embodiments, the functional domain comprises at least one uracil DNA glycosylase inhibitor (e.g. UGI) domain. In some embodiments, the base editing complex comprises a deaminase, a nickase, a UGI and/or a GAM protein. The functional domain(s) may be positioned with respect to the DNA-binding domain (and/or nickase when included in the catalytically active fusion molecule) in any way including but not limited to N-terminal (in any order when multiple functional domains are present), C-terminal (in any order when multiple functional domains are present), etc.

In some embodiments, the DNA-editing (base editing) complex further comprises a molecule to assist in opening or destabilizing a double strand DNA helix. In some embodiments, the molecule comprises an enzyme. In some embodiments, the enzyme is a helicase (for example, RecQ helicases (WRN, BLM, RecQL4 and RecQ5, (see Mo, et al. (2018) *Cancer Lett.* 413:1-10), DNA2 (Jia, et al. (2017) *DNA Repair* (Amst). 59:9-19) and any other eukaryotic helicases including for example, FANCJ, XPD, XPB, RTEL1, and PIF1 (Brosh (2013) *Nat Rev Canc* 13(8):542-558)). In some embodiments, the enzyme is a bacterial and/or a viral helicase. Exemplary viral helicases include those encoded by the Myoviridae family of viruses (for example gp41, Dda, UvsW, Gene α, and Ban); those encoded by the Podpviridae family of viruses (for example 4B); those encoded by the Siphoviridae, Baculoviridae, Herpesviridae, Polyomaviridae, Palillomaviridae and Poxviridae families (for example, G40P, p143, UL5, UL9, Tag, E1, NPH-I, NPH-II, A18R, and VETF), or any other viral helicase known in the art (see e.g. Frick and Lam (2006) *Curr Pharm Des* 12(11): 1315-1338). In some embodiments, the helicase enzyme is a bacterial enzyme. Exemplary bacterial helicases include the *P. aeruginosa* SF4 DnaB-like helicase, or the RecB and RecD helicases that are part of the bacterial RecBCD complex in bacteria such as *E coli* and *H. pylori* (Shadrick, et al. (2013) *J. Biomol Screen* 18(7):761-781). In some embodiments, the molecule comprises a CRISPR/Cas complex. In some embodiments, the CRISPR/Cas complex comprises a guide RNA. In some embodiments, the complex comprises a Cas enzyme that is catalytically defective in one of the nuclease domains. In some embodiments, the Cas enzyme is defective in its PAM recognition (Anders, et al. (2014) *Nature* 513(7519):569-573). In some embodiments, the molecule has helix-destabilizing properties. Exemplary helix-destabilizing molecules include ICP8 from herpes simplex virus type I (Boehmer and Lehman (1993) *J Virol* 67(2):711-715), Puralpha (Darbinian, et al. (2001) *J Cell Biochem* 80(4):589-95), and calf thymus DNA helix-destabilizing protein (Kohwi-Shigematsu, et al. (1978) *Proc Natl Acad Sci USA* 75(10):4689-93). In some embodiments, the molecule is a nucleic acid. In some embodiments, the nucleic acid is a DNA with homology to the region near the targeted editing. In some embodiments, the nucleic acid is an RNA with homology to the region near the targeted editing. In some embodiments, the RNA is modified. In some embodiments, the fusion molecule comprises amino acid linker sequences between one or more domains of the fusion molecule.

The DNA-editing complexes described herein can include 1, 2, 3, 4 or more fusion molecules as described herein. In certain embodiments, the DNA-editing complex comprises 2 fusion molecules: a first fusion molecule that is a catalytically active nickase (catalytically active) comprising a DNA-binding domain and nickase domain and a second catalytically inactive fusion molecule comprising a DNA-binding domain and one or more functional domains (cytidine deaminase, adenine deaminase, and/or UGI, etc.). Typically, the fusion molecules are "partners" in that the two DNA-binding domains bind to target sites such that the two fusion molecules dimerize to effect DNA editing. In other embodiments, the DNA-editing complex comprises 3 or more fusion molecules: a first fusion molecule that is a catalytically active nickase comprising a DNA-binding domain and a nickase domain; a second catalytically inactive fusion molecule comprising a DNA-binding domain (e.g., that is a partner and dimerizes with the first fusion molecule); and a third fusion molecule comprising a DNA-binding domain and one or more functional domains as described herein.

Nickase Domains

In certain embodiments, the fusion protein comprises a DNA-binding binding domain and cleavage (nuclease) domain, preferably a nickase domain. As such, gene editing can be achieved using a nuclease, for example an engineered nickase. Engineered nuclease technology is based on the engineering of naturally occurring DNA-binding proteins. For example, engineering of homing endonucleases with tailored DNA-binding specificities has been described. Chames, et al. (2005) *Nucleic Acids Res* 33(20):e178; Arnould, et al. (2006) *J. Mol. Biol.* 355:443-458. In addition, engineering of ZFPs has also been described. See, e.g., U.S. Pat. Nos. 6,534,261; 6,607,882; 6,824,978; 6,979,539; 6,933,113; 7,163,824; and 7,013,219.

In addition, ZFPs and/or TALEs have been fused to nuclease domains to create ZFNs and TALENs—a functional entity that is able to recognize its intended nucleic acid target through its engineered (ZFP or TALE) DNA binding domain and cause the DNA to be cut near the DNA binding site via the nuclease activity. See, e.g., Kim, et al. (1996) *Proc Nat'l Acad Sci USA* 93(3):1156-1160. More recently, such nucleases have been used for genome modification in a variety of organisms. See, e.g., U.S. Pat. Nos. 9,255,250; 9,200,266; 9,045,763; 9,005,973; 8,956,828; 8,945,868; 8,703,489; 8,586,526; 6,534,261; 6,599,692; 6,503,717; 6,689,558; 7,067,317; 7,262,054; 7,888,121; 7,972,854; 7,914,796; 7,951,925; 8,110,379; 8,409,861; U.S. Patent Publication Nos. 2003/0232410; 2005/0208489; 2005/0026157; 2005/0064474; 2006/0063231; 2008/0159996; 2010/0218264; 2012/0017290; 2011/0265198; 2013/0137104; 2013/0122591; 2013/0177983; 2013/0177960; and 2015/0056705.

Thus, the methods and compositions described herein are broadly applicable and may involve any nuclease of interest. Non-limiting examples of nucleases include meganucleases, TALENs and zinc finger nucleases. The nuclease may comprise heterologous DNA-binding and cleavage domains (e.g., zinc finger nucleases; meganuclease DNA-binding domains with heterologous cleavage domains) or, alternatively, the DNA-binding domain of a naturally-occurring nuclease may be altered to bind to a selected target site (e.g., a meganuclease that has been engineered to bind to site different than the cognate binding site).

In any of the nucleases described herein, the nuclease can comprise an engineered TALE DNA-binding domain and a nuclease domain (e.g., endonuclease and/or meganuclease domain), also referred to as TALENs. Methods and compositions for engineering these TALEN proteins for robust, site specific interaction with the target sequence of the user's choosing have been published (see U.S. Pat. No. 8,586,526). In some embodiments, the TALEN comprises an endonuclease (e.g., FokI) cleavage domain or cleavage half-domain. In other embodiments, the TALE-nuclease is a mega TAL. These mega TAL nucleases are fusion proteins comprising a TALE DNA binding domain and a meganuclease cleavage domain. The meganuclease cleavage domain is active as a monomer and does not require dimerization for activity. (See Boissel, et al. (2013) *Nucl AcidRes* 1-13, doi:10.1093/nar/gkt1224). In addition, the nuclease domain may also exhibit DNA-binding functionality.

In still further embodiments, the nuclease comprises a compact TALEN (cTALEN). These are single chain fusion proteins linking a TALE DNA binding domain to a TevI nuclease domain. The fusion protein can act as either a nickase localized by the TALE region, or can create a double strand break, depending upon where the TALE DNA binding domain is located with respect to the TevI nuclease domain (see Beurdeley, et al. (2013) *Nat Comm:* 1-8 DOI: 10.1038/ncomms2782). Any TALENs may be used in combination with additional TALENs (e.g., one or more TALENs (cTALENs or FokI-TALENs) with one or more mega-TALs) or other DNA cleavage enzymes.

In certain embodiments, the nuclease comprises a meganuclease (homing endonuclease) or a portion thereof that exhibits cleavage activity. Naturally-occurring meganucleases recognize 15-40 base-pair cleavage sites and are commonly grouped into four families: the LAGLIDADG family ("LAGLIDADG" disclosed as SEQ ID NO:75), the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. Nos. 5,420,032; 6,833,252; Belfort, et al. (1997) *Nucleic Acids Res.* 25:3379-3388; Dujon, et al. (1989) *Gene* 82:115-118; Perler, et al. (1994) *Nucleic Acids Res.* 22:1125-1127; Jasin (1996) *Trends Genet.* 12:224-228; Gimble, et al. (1996) *J. Mol. Biol.* 263:163-180; Argast, et al. (1998) *J. Mol. Biol.* 280: 345-353 and the New England Biolabs catalogue.

DNA-binding domains from naturally-occurring meganucleases, primarily from the LAGLIDADG family ("LAGLIDADG" disclosed as SEQ ID NO:75), have been used to promote site-specific genome modification in plants, yeast, *Drosophila*, mammalian cells and mice, but this approach has been limited to the modification of either homologous genes that conserve the meganuclease recognition sequence (Monet, et al. (1999) *Biochem. Biophysics. Res. Common* 255:88-93) or to pre-engineered genomes into which a recognition sequence has been introduced (Route, et al. (1994) *Mol. Cell. Biol.* 14:8096-106; Chilton, et al. (2003) *Plant Physiology* 133:956-65; Puchta, et al. (1996) *Proc. Natl. Acad. Sci. USA* 93:5055-60; Rong, et al. (2002) *Genes Dev.* 16:1568-81; Gouble, et al. (2006) *J. Gene Med.* 8(5):616-622). Accordingly, attempts have been made to engineer meganucleases to exhibit novel binding specificity at medically or biotechnologically relevant sites (Porteus, et al. (2005) *Nat. Biotechnol.* 23:967-73; Sussman, et al. (2004) *J. Mol. Biol.* 342:31-41; Epinat, et al. (2003) *Nucleic Acids Res.* 31:2952-62; Chevalier, et al. (2002) *Molec. Cell* 10:895-905; Epinat, et al. (2003) *Nucleic Acids Res.* 31:2952-2962; Ashworth, et al. (2006) *Nature* 441:656-659; Paques, et al. (2007) *Current Gene Therapy* 7:49-66; U.S. Patent Publication Nos. 2007/0117128; 2006/0206949; 2006/0153826; 2006/0078552; and 2004/0002092). In addition, naturally-occurring or engineered DNA-binding domains from meganucleases can be operably linked with a cleavage domain from a heterologous nuclease (e.g., FokI) and/or cleavage domains from meganucleases can be operably linked with a heterologous DNA-binding domain (e.g., ZFP or TALE).

In other embodiments, the nuclease is a zinc finger nuclease (ZFN) or TALE DNA binding domain-nuclease fusion (TALEN). ZFNs and TALENs comprise a DNA binding domain (zinc finger protein or TALE DNA binding domain) that has been engineered to bind to a target site in a gene of choice and cleavage domain or a cleavage half-domain (e.g., from a restriction and/or meganuclease as described herein).

As described in detail above, zinc finger binding domains and TALE DNA binding domains can be engineered to bind to a sequence of choice. See, for example, Beerli, et al. (2002) *Nature Biotechnol.* 20:135-141; Pabo, et al. (2001) *Ann. Rev. Biochem.* 70:313-340; Isalan, et al. (2001) *Nature Biotechnol.* 19:656-660; Segal, et al. (2001) *Curr. Opin. Biotechnol.* 12:632-637; Choo, et al. (2000) *Curr. Opin. Struct. Biol.* 10:411-416. An engineered zinc finger binding domain or TALE protein can have a novel binding specificity, compared to a naturally-occurring protein. Engineering methods include, but are not limited to, rational design and various types of selection. Rational design includes, for example, using databases comprising triplet (or quadruplet) nucleotide sequences and individual zinc finger or TALE amino acid sequences, in which each triplet or quadruplet nucleotide sequence is associated with one or more amino acid sequences of zinc fingers or TALE repeat units which bind the particular triplet or quadruplet sequence. See, for example, U.S. Pat. Nos. 6,453,242 and 6,534,261, incorporated by reference herein in their entireties.

Selection of target sites; and methods for design and construction of fusion proteins (and polynucleotides encoding same) are known to those of skill in the art and described in detail in U.S. Pat. Nos. 7,888,121 and 8,409,861, incorporated by reference in their entireties herein.

In addition, as disclosed in these and other references, zinc finger domains, TALEs and/or multi-fingered zinc finger proteins may be linked together using any suitable linker sequences, including for example, linkers of 5 or more amino acids in length. See, e.g., U.S. Pat. Nos. 6,479,626; 6,903,185; and 7,153,949 for exemplary linker sequences 6 or more amino acids in length. The proteins described herein may include any combination of suitable linkers between the individual zinc fingers of the protein. See, also, U.S. Pat. No. 8,772,453.

Thus, nucleases such as ZFNs, TALENs and/or meganucleases can comprise any DNA-binding domain and any nuclease (cleavage) domain (cleavage domain, cleavage half-domain). As noted above, the cleavage domain may be heterologous to the DNA-binding domain, for example a zinc finger or TAL-effector DNA-binding domain and a cleavage domain from a nuclease or a meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, MA; and Belfort, et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn, et al. (eds.) *Nucleases*, Cold Spring Harbor Laboratory Press, 1993).

One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-10 nucleotides or by 15-18 nucleotides. However, any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme FokI catalyzes double-stranded cleavage of DNA, at 9 nucleotides from its recognition site on one strand and 13 nucleotides from its recognition site on the other. See, for example, U.S. Pat. Nos. 5,356,802; 5,436,150; and 5,487,994; as well as Li, et al. (1992) *Proc. Natl. Acad. Sci. USA* 89:4275-4279; Li, et al. (1993) *Proc. Natl. Acad. Sci. USA* 90:2764-2768; Kim, et al. (1994a) *Proc. Natl. Acad. Sci. USA* 91:883-887; Kim, et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is FokI. This particular enzyme is active as a dimer. Bitinaite, et al. (1998) *Proc. Natl. Acad. Sci. USA* 95:10,570-10,575. Accordingly, for the purposes of the present disclosure, the portion of the FokI enzyme used in the disclosed fusion proteins is considered a cleavage half-domain. Thus, for targeted double-stranded cleavage and/or targeted replacement of cellular sequences using zinc finger-FokI fusions, two fusion proteins, each comprising a FokI cleavage half-domain, can be used to reconstitute a catalytically active cleavage domain. Alternatively, a single polypeptide molecule containing a zinc finger binding domain and two FokI cleavage half-domains can also be used. Parameters for targeted cleavage and targeted sequence alteration using zinc finger-FokI fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Patent Publication No. WO 07/014275, incorporated herein in its entirety. Additional restriction enzymes also contain separable binding and cleavage domains, and these are contemplated by the present disclosure. See, for example, Roberts, et al. (2003) *Nucleic Acids Res.* 31:418-420.

In certain embodiments, the cleavage domain is a FokI cleavage domain. The full-length FokI sequence is shown below. The cleavage domain is shown in italics and underlining (positions 384 to 579 of the full-length protein) where the holo protein sequence is described below (SEQ ID NO:5):

MVSKIRTFGWVQNPGKFENLKRVVQVFDRNSKVHNEVKNIKIPTLVKESK

IQKELVAIMNQHDLIYTYKELVGTGTSIRSEAPCDAIIQATIADQGNKKG

YIDNWSSDGFLRWAHALGFIEYINKSDSFVITDVGLAYSKSADGSAIEKE

ILIEAISSYPPAIRILTLLEDGQHLTKFDLGKNLGFSGESGFTSLPEGIL

LDTLANAMPKDKGEIRNNWEGSSDKYARMIGGWLDKLGLVKQGKKEFIIP

TLGKPDNKEFISHAFKITGEGLKVLRRAKGSTKFTRVPKRVYWEMLATNL

TDKEYVRTRRALILEILIKAGSLKIEQIQDNLKKLGFDEVIETIENDIKG

LINTGIFIEIKGRFYQLKDHILQFVIPNRGVTK*QLVKSELEEKKSELRHK*

*LKYVPHEYIELIEIARNSTQDRILEMKVMEFFMKVYGYRGKHLGGSRKPD*

*GAIYTVGSPIDYGVIVDTKAYSGGYNLPIGQADEMQRYVEENQTRNKHIN*

*PNEWWKVYPSSVTEFKFLFVSGHFKGNYKAQLTRLNHITNCNGAVLSVEE*

*LLIGGEMIKAGTLTLEEVRRKFNNGEINF*

Cleavage half domains derived from FokI may comprise a mutation in one or more of amino acid residues as shown in SEQ ID NO:5. Mutations include substitutions (of a wild-type amino acid residue for a different residue, insertions (of one or more amino acid residues) and/or deletions (of one or more amino acid residues). In certain embodiments, one or more of residues 414-426, 443-450, 467-488, 501-502, and/or 521-531 (numbered relative to SEQ ID NO:5) are mutated since these residues are located close to the DNA backbone in a molecular model of a ZFN bound to its target site described in Miller, et al. (2007) *Nat Biotechnol* 25:778-784). In certain embodiments, one or more residues at positions 416, 422, 447, 448, and/or 525 are mutated. In certain embodiments, the mutation comprises a substitution of a wild-type residue with any different residue, for example an alanine (A) residue, a cysteine (C) residue, an aspartic acid (D) residue, a glutamic acid (E) residue, a histidine (H) residue, a phenylalanine (F) residue, a glycine (G) residue, an asparagine (N) residue, a serine (S) residue or a threonine (T) residue. In other embodiments, the wild-type residue at one or more of positions 416, 418, 422, 446, 448, 476, 479, 480, 481, and/or 525 are replaced with any other residues, including but not limited to, R416D, R416E, S418E, S418D, R422H, S446D, K448A, N476D, I479Q, I479T, G480D, Q481A, Q481E, K525S, K525A, N527D, R416E+R422H, R416D+R422H, R416E+K448A, R416D+R422H, K448A+I479Q, K448A+Q481A. K448A+K525A.

In certain embodiments, the cleavage domain comprises one or more engineered cleavage half-domain (also referred to as dimerization domain mutants) that minimize or prevent homodimerization, as described, for example, in U.S. Pat. Nos. 7,914,796; 8,034,598; and 8,623,618; and U.S. Patent Publication No. 2011/0201055, the disclosures of all of which are incorporated by reference in their entireties herein. Amino acid residues at positions 446, 447, 479, 483, 484, 486, 487, 490, 491, 496, 498, 499, 500, 531, 534, 537, and 538 of FokI (numbered relative to SEQ ID NO:5) are all targets for influencing dimerization of the FokI cleavage half-domains. The mutations may include mutations to residues found in natural restriction enzymes homologous to FokI. In a preferred embodiment, the mutation at positions 416, 422, 447, 448 and/or 525 (numbered relative to SEQ ID NO:5) comprise replacement of a positively charged amino acid with an uncharged or a negatively charged amino acid. In another embodiment, the engineered cleavage half domain comprises mutations in amino acid residues 499, 496 and 486 in addition to the mutations in one or more amino acid residues 416, 422, 447, 448, or 525, all numbered relative to SEQ ID NO:5.

Any nickase domain can be used in the DNA-editing complexes described herein. Nickases comprise mutations in a catalytic domain to render a nuclease unable to make a full double strand break, but instead result in the partial cleavage, "nicking" of a double stranded DNA. In embodiments in which two or more cleavage domains are necessary to nick the target, typically at least one of the cleavage domains (e.g., cleavage half-domains) includes one more mutations to its catalytic domain, which renders the nuclease inactive (e.g., catalytically inactive half domain). Catalytically inactive cleavage domains for producing nickases include but are not limited to mutated FokI and/or dCas proteins. See, e.g., U.S. Pat. Nos. 9,522,936; 9,631,186; 9,200,266; and 8,703,489 and Guillinger, et al. (2014) *Nature Biotech.* 32(6):577-582; Cho, et al. (2014) *Genome Res.* 24(1):132-141). These catalytically inactive cleavage domain may, in combination with a catalytically active domain act as a nickase to make a single-stranded cut. Additional nickases are also known in the art, for example, McCaffery, et al. (2016) *Nucleic Acids Res.* 44(2):el 1. doi:10.1093/nar/gkv878. Epub 2015 Oct. 19.

In certain embodiments, the nickase comprises a nuclease nickase that comprises a catalytically inactive FokI cleavage domain, for example a zinc finger nuclease (ZFN) nickase or a TAL-effector domain (TALEN) nickase. Non-limiting examples of amino acids that can be mutated in the catalytic domain of FokI includes amino acid residues 450, 467 and/or 469 (as determined relative to wild-type). In certain embodiments, one or more point mutations are made in the catalytic domain of one member of the obligate heterodimer so as to inactivate the catalytic activity of the cleavage half-domain. For instance, position 450 may be mutated from D to N, position 467 may be mutated from D to A; and position 469 may be mutated from K to A. Other amino acids may be substituted at these or other positions. See, e.g., U.S. Pat. Nos. 9,522,936; 9,631,186; 8,703,489 and 9,200,266 and Guillinger, et al. (2014) *Nature Biotech.* 32(6):577-582; Cho, et al. (2014) *Genome Res.* 24(1):132-141). The catalytically inactive cleavage domain may, in combination with a catalytically active domain act as a nickase to make a single-stranded cut. Additional nickases are also known in the art, for example, McCaffery, et al. (2016) *Nucleic Acids Res.* 44(2):el 1. doi:10.1093/nar/gkv878. Epub 2015 Oct. 19. Any nuclease (e.g., ZFN or TALEN or CRISPR/Cas nuclease) can become a nickase by using cleavage domains that make a single-stranded cut in place of the cleavage domains in nucleases that make double stranded cuts.

FokI domains may also include one or more additional mutations. In certain embodiments, the compositions described herein include engineered cleavage half-domains of FokI that form obligate heterodimers as described, for example, in U.S. Pat. Nos. 7,914,796; 8,034,598; 8,962,281;

and 8,623,618; U.S. Patent Publication Nos. 2008/0131962 and 2012/0040398. Thus, in one preferred embodiment, the invention provides fusion proteins wherein the engineered cleavage half-domain comprises a polypeptide in which the wild-type Gln (Q) residue at position 486 is replaced with a Glu (E) residue, the wild-type Ile (I) residue at position 499 is replaced with a Leu (L) residue and the wild-type Asn (N) residue at position 496 is replaced with an Asp (D) or a Glu (E) residue ("ELD" or "ELE") in addition to one or more mutations at positions 416, 422, 447, 448, or 525 (numbered relative to SEQ ID NO:5). In another embodiment, the engineered cleavage half domains are derived from a wild-type FokI cleavage half domain and comprise mutations in the amino acid residues 490, 538 and 537, numbered relative to wild-type FokI (SEQ ID NO:5) in addition to the one or more mutations at amino acid residues 416, 422, 447, 448, or 525. In a preferred embodiment, the invention provides a fusion protein, wherein the engineered cleavage half-domain comprises a polypeptide in which the wild-type Glu (E) residue at position 490 is replaced with a Lys (K) residue, the wild-type Ile (I) residue at position 538 is replaced with a Lys (K) residue, and the wild-type His (H) residue at position 537 is replaced with a Lys (K) residue or an Arg (R) residue ("KKK" or "KKR") (see U.S. Pat. No. 8,962,281, incorporated by reference herein) in addition to one or more mutations at positions 416, 422, 447, 448, or 525. See, e.g., U.S. Pat. Nos. 7,914,796; 8,034,598; and 8,623,618, the disclosures of which are incorporated by reference in its entirety for all purposes. In other embodiments, the engineered cleavage half domain comprises the "Sharkey" and/ or "Sharkey mutations" (see Guo, et al. (2010)*J Mol. Biol.* 400(1):96-107).

In other embodiments, the nickases as described herein comprise engineered cleavage half domains are derived from a wild-type FokI cleavage half domain and comprise mutations in the amino acid residues 490, and 538, numbered relative to wild-type FokI or a FokI homologue in addition to the one or more mutations at amino acid residues 416, 422, 447, 448, or 525. In preferred embodiments, the invention provides a fusion protein, wherein the engineered cleavage half-domain comprises a polypeptide in which the wild-type Glu (E) residue at position 490 is replaced with a Lys (K) residue, and the wild-type Ile (I) residue at position 538 is replaced with a Lys (K) residue ("KK") in addition to one or more mutations at positions 416, 422, 447, 448, or 525. In other preferred embodiments, the description provides a fusion protein, wherein the engineered cleavage half-domain comprises a polypeptide in which the wild-type Gln (Q) residue at position 486 is replaced with an Glu (E) residue, and the wild-type Ile (I) residue at position 499 is replaced with a Leu (L) residue ("EL") (See U.S. Pat. No. 8,034,598, incorporated by reference herein) in addition to one or more mutations at positions 416, 422, 447, 448, or 525.

In some aspects, the description provides a fusion protein wherein the engineered cleavage half-domain comprises a polypeptide in which the wild-type amino acid residue at one or more of positions 387, 393, 394, 398, 400, 402, 416, 422, 427, 434, 439, 441, 447, 448, 469, 487, 495, 497, 506, 516, 525, 529, 534, 559, 569, 570, 571 in the FokI catalytic domain are mutated. In some embodiments, the one or more mutations alter the wild type amino acid from a positively charged residue to a neutral residue or a negatively charged residue. In any of these embodiments, the mutants described may also be made in a FokI domain comprising one or more additional mutations. In preferred embodiments, these additional mutations are in the dimerization domain, e.g. at positions 418, 432, 441, 481, 483, 486, 487, 490, 496, 499, 523, 527, 537, 538 and/or 559. Non-limiting examples of mutations include mutations (e.g., substitutions) of the wild-type residues of any cleavage domain (e.g., FokI or homologue of FokI) at positions 393, 394, 398, 416, 421, 422, 442, 444, 472, 473, 478, 480, 525 or 530 with any amino acid residue (e.g., K393X, K394X, R398X, R416S, D421X, R422X, K444X, S472X, G473X, S472, P478X, G480X, K525X, and A530X, where the first residue depicts wild-type and X refers to any amino acid that is substituted for the wild-type residue). In some embodiments, X is E, D, H, A, K, S, T, D or N. Other exemplary mutations include S418E, S418D, S446D, K448A, I479Q, I479T, Q481A, Q481N, Q481E, A530E and/or A530K wherein the amino acid residues are numbered relative to full length FokI wild-type cleavage domain and homologues thereof. In certain embodiments, combinations may include 416 and 422, a mutation at position 416 and K448A, K448A and I479Q, K448A and Q481A and/or K448A and a mutation at position 525. In one embodiment, the wild-residue at position 416 may be replaced with a Glu (E) residue (R416E), the wild-type residue at position 422 is replaced with a His (H) residue (R422H), and the wild-type residue at position 525 is replaced with an Ala (A) residue. The cleavage domains as described herein can further include additional mutations, including but not limited to at positions 432, 441, 483, 486, 487, 490, 496, 499, 527, 537, 538 and/or 559, for example dimerization domain mutants (e.g., ELD, KKR) and or nickase mutants (mutations to the catalytic domain). The cleavage half-domains with the mutations described herein form heterodimers as known in the art.

Nucleases may be assembled in vivo at the nucleic acid target site using so-called "split-enzyme" technology (see e.g. U.S. Patent Publication No. 2009/0068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases (e.g., ZFNs and/or TALENs) can be screened for activity prior to use, for example in a yeast-based chromosomal system as described in as described in U.S. Pat. No. 8,563,314.

In addition to or instead of ZFN or TALEN nickases, the DNA-editing complexes may comprise a CRISPR/Cas nickase. Non-limiting examples of CRISPR/Cas nickases are described in U.S. Pat. Nos. 9,840,713; 9,770,489; 9,567, 604; 8,932,814; 8,889,356; 8,697,359; 8,771,945; 8,795, 965; 8,865,406; 8,871,445; 8,889,356; 8,895,308; 8.906, 616; 8,932,814; 8,945,839; 8,945,839; 8,999,641; 10,000, 772 and the like.

The CRISPR (clustered regularly interspaced short palindromic repeats) locus, which encodes RNA components of the system, and the Cas (CRISPR-associated) locus, which encodes proteins (Jansen, et al. (2002) *Mol. Microbiol.* 43:1565-1575; Makarova, et al. (2002) *Nucleic Acids Res.* 30: 482-496; Makarova, et al. (2006) *Biol. Direct* 1:7; Haft, et al. (2005) *PLoS Comput. Biol.* 1:e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

Initially, Cas makes extensive contacts with the ribose-phosphate backbone of the guide RNA, preordering the 10-nt RNA seed sequence required for initial DNA interrogation. In addition to the preordered seed sequences, the PAM-interacting sites of the Cas protein R1333 and R1335, which are responsible for 5'-NGG-3' PAM recognition and disordered in the apo structure lacking the guide, are prepositioned prior to making contact with target DNA, indicating that sgRNA loading enables Cas to form a DNA recognition-competent structure. Once Cas binds its guide RNA, the complex is ready to search for complementary target DNA sites. Target search and recognition require both complementary base pairing between the 20-nt spacer sequence and a protospacer in the target DNA, as well as the presence of conserved PAM sequence adjacent to the target site. The PAM sequence is crucial for the discrimination between self and non-self sequences. Single-molecule experiments have demonstrated that Cas initiates the target DNA search process by probing for a proper PAM sequence before interrogating the flanking DNA for potential guide RNA complementarity. Target recognition occurs through three-dimensional collisions, in which Cas rapidly dissociates from DNA that does not contain the appropriate PAM sequence, and dwell time depends on the complementarity between guide RNA and adjacent DNA when a proper PAM is present. Once Cas has found a target site with the appropriate PAM, it triggers local DNA melting at the PAM-adjacent nucleation site, followed by RNA strand invasion to form an RNA-DNA hybrid and a displaced DNA strand (termed R-loop) from PAM-proximal to PAM-distal ends. The PAM duplex is nestled in a positively charged groove between the alpha-helical recognition (REC) lobe the nuclease (NUC) lobe containing the conserved HNH and the split RuvC nuclease domains, with the PAM-containing nontarget strand residing mainly in the C-terminal domain (CTD). The first base in the PAM sequence, denoted as N, remains base paired with its counterpart but does not interact with Cas. The conserved PAM GG dinucleotides are directly read out in the major groove by base-specific hydrogen-bonding interactions with two arginine residues (R1333 and R1335) that are located in a β-hairpin of the CTD. In addition to base-specific contacts with GG dinucleotides, Cas's CTD makes numerous hydrogen-bonding interactions with the deoxyribose-phosphate backbone of the PAM-containing nontarget DNA strand. However, no direct contact has been observed between Cas and target-strand nucleotides complementary to the PAM (Jiang and Doudna (2017) *Annual Review of Biophysics* 46:505-529). In some embodiments, the Cas disclosed in the methods and compositions of the invention is PAM agnostic. In some embodiments, positions R1333 and R1335 as disclosed above comprise mutations to alter PAM recognition (Anders, et al. (2014) *Nature* 513(7519):569-573).

In some embodiments, the CRISPR-Cpf1 system is used. The CRISPR-Cpf1 system, identified in *Francisella* spp., is a class 2 CRISPR-Cas system that mediates robust DNA interference in human cells. Although functionally conserved, Cpf1 and Cas9 differ in many aspects including in their guide RNAs and substrate specificity (see Fagerlund, et al. (2015) *Genom Bio* 16:251). A major difference between Cas9 and Cpf1 proteins is that Cpf1 does not utilize tracrRNA, and thus requires only a crRNA. The FnCpf1 crRNAs are 42-44 nucleotides long (19-nucleotide repeat and 23-25-nucleotide spacer) and contain a single stem-loop, which tolerates sequence changes that retain secondary structure. In addition, the Cpf1 crRNAs are significantly shorter than the ~100-nucleotide engineered sgRNAs required by Cas9, and the PAM requirements for FnCpf1 are 5'-TTN-3' and 5'-CTA-3' on the displaced strand. Although both Cas9 and Cpf1 make double strand breaks in the target DNA, Cas9 uses its RuvC- and HNH-like domains to make blunt-ended cuts within the seed sequence of the guide RNA, whereas Cpf1 uses a RuvC-like domain to produce staggered cuts outside of the seed. Because Cpf1 makes staggered cuts away from the critical seed region, NHEJ will not disrupt the target site, therefore ensuring that Cpf1 can continue to cut the same site until the desired HDR recombination event has taken place. Thus, in the methods and compositions described herein, it is understood that the term "'Cas" includes both Cas9 and Cfp1 proteins. Thus, as used herein, a "CRISPR/Cas system" refers both CRISPR/Cas and/or CRISPR/Cfp1 systems, including both nuclease, nickase and/or transcription factor systems.

In some embodiments, other Cas proteins may be used. Some exemplary Cas proteins include Cas9, Cpf1 (also known as Cas12a), C2c1, C2c2 (also known as Cas13a), C2c3, Cas1, Cas2, Cas4, CasX and CasY; and include engineered and natural variants thereof (Burstein, et al. (2017) *Nature* 542:237-241) for example HF1/spCas9 (Kleinstiver, et al. (2016) *Nature* 529:490-495; Cebrian-Serrano and Davies (2017) *Mamm Genome* 28(7):247-261); split Cas9 systems (Zetsche, et al. (2015) *Nat Biotechnol* 33(2):139-142), trans-spliced Cas9 based on an intein-extein system (Troung, et al. (2015) *Nucl Acid Res* 43(13):6450-8); mini-SaCas9 (Ma, et al. (2018) *ACS Synth Biol* 7(4):978-985). Thus, in the methods and compositions described herein, it is understood that the term "'Cas" includes all Cas variant proteins, both natural and engineered. Thus, as used herein, a "CRISPR/Cas system" refers to any CRISPR/Cas system, including both nuclease, nickase and/or transcription factor systems.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof such as derivative Cas proteins. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein. In some embodiments, the Cas protein is a small Cas9 ortholog for delivery via an AAV vector (Ran, et al. (2015) Nature 520(7546):186-191).

Delivery

The DNA-editing complexes (or component molecules thereof) described herein may be delivered to a target cell by any suitable means, including, for example, by injection of the protein and/or mRNA components. Delivery may be to isolated cells (which in turn may be administered to a living subject for ex vivo cell therapy) or a living subject via any suitable means. Delivery of gene editing molecules to cells and subjects are known in the art.

Suitable cells include but not limited to eukaryotic and prokaryotic cells and/or cell lines. Non-limiting examples of such cells or cell lines generated from such cells include T-cells, COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NSO, SP2/0-Ag14, HeLa, HEK293 (e.g., HEK293-F, HEK293-H, HEK293-T), and perC6 cells as well as insect cells such as Spodopterafugiperda (Sf), or fungal cells such as *Saccharomyces, Pichia* and *Schizosaccharomyces*. In certain embodiments, the cell line is a CHO-K1, MDCK or HEK293 cell line. Suitable cells also include stem cells such as, by way of example, embryonic stem cells, induced pluripotent stem cells (iPS cells), hematopoietic stem cells, neuronal stem cells and mesenchymal stem cells.

Methods of delivering proteins as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

DNA-editing complexes as described herein may also be delivered using vectors containing sequences encoding one or more of the components (e.g., fusion molecules). Additionally, additional nucleic acids (e.g., donors) also may be delivered via these vectors. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more DNA-binding protein-encoding sequences and/or additional nucleic acids as appropriate. Thus, when one or more DNA-binding proteins as described herein are introduced into the cell, and additional DNAs as appropriate, they may be carried on the same vector or on different vectors. When multiple vectors are used, each vector may comprise a sequence encoding one or multiple DNA-binding proteins and additional nucleic acids as desired. Conventional viral and non-viral based gene transfer methods can be used to introduce nucleic acids encoding engineered DNA-binding proteins in cells (e.g., mammalian cells) and target tissues and to co-introduce additional nucleotide sequences as desired. Such methods can also be used to administer nucleic acids (e.g., encoding DNA-binding proteins and/or donors) to cells in vitro. In certain embodiments, nucleic acids are administered for in vivo or ex vivo gene therapy uses. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson (1992) *Science* 256:808-813; Nabel & Felgner (1993) *TIBTECH* 11:211-217; Mitani & Caskey (1993) *TIBTECH* 11:162-166; Dillon (1993) *TIBTECH* 11:167-175; Miller (1992) *Nature* 357:455-460; Van Brunt (1988) *Biotechnology* 6(10): 1149-1154; Vigne (1995) *Restorative Neurology and Neuroscience* 8:35-36; Kremer & Perricaudet (1995) *BritishMedical Bulletin* 51(1):31-44; Haddada, et al, in Current Topics in Microbiology and Immunology Doerfler and Bohm (eds.) (1995); and Yu, et al. (1994) *Gene Therapy* 1:13-26.

Methods of non-viral delivery of nucleic acids include electroporation, lipofection, microinjection, biolistics, virosomes, liposomes, immunoliposomes, polycation or lipid:nucleic acid conjugates, naked DNA, mRNA, artificial virions, and agent-enhanced uptake of DNA. Sonoporation using, e.g., the Sonitron 2000 system (Rich-Mar) can also be used for delivery of nucleic acids. In a preferred embodiment, one or more nucleic acids are delivered as mRNA. Also preferred is the use of capped mRNAs to increase translational efficiency and/or mRNA stability. Especially preferred are ARCA (anti-reverse cap analog) caps or variants thereof. See U.S. Pat. Nos. 7,074,596 and 8,153,773, incorporated by reference herein.

Additional exemplary nucleic acid delivery systems include those provided by Amaxa Biosystems (Cologne, Germany), Maxcyte, Inc. (Rockville, Maryland), BTX Molecular Delivery Systems (Holliston, MA) and Copernicus Therapeutics Inc, (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™, Lipofectin™, and Lipofectamine™ RNAiMAX). Cationic and neutral lipids that are suitable for efficient receptor-recognition lipofection of polynucleotides include those of Felgner, International Patent Publication Nos. WO 91/17424 and WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal (1995) *Science* 270:404-410; Blaese, et al. (1995) *Cancer Gene Ther.* 2:291-297; Behr, et al. (1994) *Bioconjugate Chem.* 5:382-389; Remy, et al. (1994) *Bioconjugate Chem.* 5:647-654; Gao, et al. (1995) *Gene Therapy* 2:710-722; Ahmad, et al. (1992) *Cancer Res.* 52:4817-4820; U.S. Pat. Nos. 4,186,183; 4,217,344; 4,235,871; 4,261,975; 4,485,054; 4,501,728; 4,774,085; 4,837,028; and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid, et al. (2009) *Nature Biotechnology* 27(7):643).

The use of RNA or DNA viral based systems for the delivery of nucleic acids encoding engineered DNA-binding proteins, and/or donors (e.g. CARs or ACTRs) as desired takes advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of nucleic acids include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher, et al. (1992) *J. Virol.* 66:2731-2739; Johann, et al. (1992) *J. Virol.* 66:1635-1640; Sommerfelt, et al. (1990) *Virol.* 176: 58-59; Wilson, et al. (1989) *J. Virol.* 63:2374-2378; Miller, et al. (1991) *J. Virol.* 65:2220-2224; International Patent Publication No. WO 94/26877).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West, et al. (1987) *Virology* 160:38-47; U.S. Pat. No. 4,797,368; International Patent Publication No. WO 93/24641; Kotin (1994) *Human Gene Therapy* 5:793-801; Muzyczka (1994) *J. Clin. Invest.* 94:1351. Construction of recombinant AAV vectors are described in a number of publications, including U.S. Pat. No. 5,173,414; Tratschin, et al. (1985) *Mol. Cell. Biol.* 5:3251-3260; Tratschin, et al. (1984) *Mol. Cell. Biol.* 4:2072-2081; Hermonat & Muzyczka (1984) *PNAS USA* 81:6466-6470; and Samulski, et al. (1989) *J. Virol.* 63:03822-3828.

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar, et al. (1995) *Blood* 85:3048-305; Kohn, et al. (1995) *Nat. Med.* 1:1017-102; Malech, et al. (1997) *PNAS USA* 94(22): 12133-12138). PA317/pLASN was the first therapeutic vector used in a gene therapy trial. (Blaese, et al. (1995) *Science* 270:475-480). Transduction efficiencies of 50% or greater have been observed for MFG-S packaged vectors. (Ellem, et al. (1997) *Immunol Immunother.* 44(1): 10-20; Dranoff, et al. (1997) *Hum. Gene Ther.* 1:111-2.

Recombinant adeno-associated virus vectors (rAAV) are a promising alternative gene delivery system based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner, et al. (1998) *Lancet* 351(9117): 1702-3, Kearns, et al. (1996) *Gene Ther.* 9:748-55). Other AAV serotypes, including AAV1, AAV3, AAV4, AAV5, AAV6, AAV8, AAV8.2, AAV9 and AAVrh10 and pseudo-typed AAV such as AAV2/8, AAV2/5 and AAV2/6 can also be used in accordance with the present invention. Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector can be propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al. (1998) *Hum. Gene Ther.* 7:1083-1089). Additional examples of the use of adenovirus vectors for gene transfer in clinical trials include Rosenecker, et al. (1996) *Infection* 24(1):5-10; Sterman, et al. (1998) *Hum. Gene Ther.* 9(7):1083-1089; Welsh, et al. (1995) *Hum. Gene Ther.* 2:205-218; Alvarez, et al. (1997) *Hum. Gene Ther.* 5:597-613; Topf, et al. (1998) *Gene Ther.* 5:507-513; Sterman, et al. (1998) *Hum. Gene Ther.* 7:1083-1089.

Packaging cells are used to form virus particles that are capable of infecting a host cell. Such cells include 293 cells, which package adenovirus, and w2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han, et al. (1995) *Proc. Natl. Acad. Sci. USA* 92:9747-9751, reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Delivery methods for CRISPR/Cas systems can comprise those methods described above. For example, in animal models, in vitro transcribed Cas encoding mRNA or recombinant Cas protein can be directly injected into one-cell stage embryos using glass needles to genome-edited animals. To express Cas and guide RNAs in cells in vitro, typically plasmids that encode them are transfected into cells via lipofection or electroporation. Also, recombinant Cas protein can be complexed with in vitro transcribed guide RNA where the Cas-guide RNA ribonucleoprotein is taken up by the cells of interest (Kim, et al. (2014) *Genome Res* 24(6):1012). For therapeutic purposes, Cas and guide RNAs can be delivered by a combination of viral and non-viral techniques. For example, mRNA encoding Cas may be delivered via nanoparticle delivery while the guide RNAs and any desired transgene or repair template are delivered via AAV (Yin, et al. (2016) *Nat Biotechnol* 34(3):328).

Gene therapy vectors can be delivered in vivo by administration to an individual patient (subject), typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by re-implantation of the cells into a patient, usually after selection for cells which have incorporated the vector.

Ex vivo cell transfection for diagnostics, research, transplant or for gene therapy (e.g., via re-infusion of the transfected cells into the host organism) is well known to those of skill in the art. In a preferred embodiment, cells are isolated from the subject organism, transfected with a DNA-binding proteins nucleic acid (gene or cDNA), and re-infused back into the subject organism (e.g., patient). Various cell types suitable for ex vivo transfection are well known to those of skill in the art (see, e.g., Freshney, et al., Culture of Animal Cells, A Manual of Basic Technique (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known (see Inaba, et al. (1992) *J. Exp. Med.* 176:1693-1702).

Stem cells are isolated for transduction and differentiation using known methods. For example, stem cells are isolated from bone marrow cells by panning the bone marrow cells with antibodies which bind unwanted cells, such as CD4+ and CD8+(T cells), CD45+(panB cells), GR-1 (granulocytes), and Iad (differentiated antigen presenting cells) (see Inaba, et al. (1992) *J. Exp. Med.* 176:1693-1702).

Stem cells that have been modified may also be used in some embodiments. For example, neuronal stem cells that have been made resistant to apoptosis may be used as therapeutic compositions where the stem cells also contain the ZFP TFs of the invention. Resistance to apoptosis may come about, for example, by knocking out BAX and/or BAK using BAX- or BAK-specific ZFNs (see, U.S. Pat. No. 8,597,912) in the stem cells, or those that are disrupted in a caspase, again using caspase-6 specific ZFNs for example.

Vectors (e.g., retroviruses, adenoviruses, liposomes, etc.) containing therapeutic DNA-binding proteins (or nucleic acids encoding these proteins) can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Methods for introduction of DNA into hematopoietic stem cells are disclosed, for example, in U.S. Pat. No. 5,928,638. Vectors useful for introduction of transgenes into hematopoietic stem cells, e.g., CD34+ cells, include adenovirus Type 35.

Vectors suitable for introduction of transgenes into immune cells (e.g., T-cells) include non-integrating lentivirus vectors. See, for example, Ory, et al. (1996) *Proc. Natl. Acad. Sci. USA* 93:11382-11388; Dull, et al. (1998) *J. Virol.* 72:8463-8471; Zuffery, et al. (1998) *J. Virol.* 72:9873-9880; Follenzi, et al. (2000) *Nature Genetics* 25:217-222.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., Remington's Pharmaceutical Sciences, 17th ed., 1989).

As noted above, the disclosed methods and compositions can be used in any type of cell including, but not limited to, prokaryotic cells, fungal cells, Archaeal cells, plant cells, insect cells, animal cells, vertebrate cells, mammalian cells and human cells, including T-cells and stem cells of any type. Suitable cell lines for protein expression are known to those of skill in the art and include, but are not limited to COS, CHO (e.g., CHO-S, CHO-K1, CHO-DG44, CHO-DUXB11), VERO, MDCK, W138, V79, B14AF28-G3, BHK, HaK, NSO, SP2/0-Ag14, HeLa, HEK293 (e.g., HEK293-F, HEK293-H, HEK293-T), perC6, insect cells such as *Spodoptera fugiperda* (Sf), and fungal cells such as *Saccharomyces, Pichia* and *Schizosaccharomyces*. Progeny, variants and derivatives of these cell lines can also be used.

Applications

Use of engineered DNA base editor complexes in treatment and prevention of disease provides a significant development in medicine. The methods and compositions described herein serve to increase the specificity of these novel tools to ensure that the desired target sites will be the primary place of editing.

Exemplary genetic diseases that may be treated and/or prevented by the compositions and methods described herein include, but are not limited to, achondroplasia, achromatopsia, acid maltase deficiency, adenosine deaminase deficiency (OMIM No. 102700), adrenoleukodystrophy, aicardi syndrome, alpha-1 antitrypsin deficiency, alpha-thalassemia, androgen insensitivity syndrome, apert syndrome, arrhythmogenic right ventricular, dysplasia, ataxia telangictasia, barth syndrome, beta-thalassemia, blue rubber bleb nevus syndrome, canavan disease, chronic granulomatous diseases (CGD), cri du chat syndrome, cystic fibrosis, dercum's disease, ectodermal dysplasia, fanconi anemia, fibrodysplasia ossificans progressive, fragile X syndrome, galactosemis, Gaucher's disease, generalized gangliosidoses (e.g., GM1), hemochromatosis, the hemoglobin C mutation in the 6th codon of beta-globin (HbC), hemophilia, Huntington's disease, Hurler Syndrome, hypophosphatasia, Klinefleter syndrome, Krabbes Disease, Langer-Giedion Syndrome, leukocyte adhesion deficiency (LAD, OMIM No. 116920), leukodystrophy, long QT syndrome, Marfan syndrome, Moebius syndrome, mucopolysaccharidosis (MPS), nail patella syndrome, nephrogenic diabetes insipidius, neurofibromatosis, Neimann-Pick disease, osteogenesis imperfecta, phenylketonuria (PKU). *porphyria*, Prader-Willi syndrome, progeria, *Proteus* syndrome, retinoblastoma, Rett syndrome, Rubinstein-Taybi syndrome, Sanfilippo syndrome, severe combined immunodeficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trisomy, tuberous sclerosis, Turner's syndrome, urea cycle disorder, von Hippel-Landau disease, Waardenburg syndrome, Williams syndrome, Wilson's disease, Wiskott-Aldrich syndrome, X-linked lymphoproliferative syndrome (XLP, OMIM No. 308240).

Additional exemplary diseases that can be treated by targeted DNA base editing include acquired immunodeficiencies, lysosomal storage diseases (e.g., Gaucher's disease, GM1, Fabry disease and Tay-Sachs disease), mucopolysaccahidosis (e.g. Hunter's disease, Hurler's disease), hemoglobinopathies (e.g., sickle cell diseases, HbC, α-thalassemia, β-thalassemia) and hemophilias.

Such methods also allow for treatment of infections (viral or bacterial) in a host (e.g., by blocking expression of viral or bacterial receptors, thereby preventing infection and/or spread in a host organism) to treat genetic diseases.

Targeted base editing can also be used to treat viral infections in a host. Additionally, targeted cleavage of genes encoding receptors for viruses can be used to block expression of such receptors, thereby preventing viral infection and/or viral spread in a host organism. Targeted mutagenesis of genes encoding viral receptors (e.g., the CCR5 and CXCR4 receptors for HIV) can be used to render the receptors unable to bind to virus, thereby preventing new infection and blocking the spread of existing infections. See, U.S. Patent Publication No. 2008/0159996. Non-limiting examples of viruses or viral receptors that may be targeted include herpes simplex virus (HSV), such as HSV-1 and HSV-2, varicella zoster virus (VZV), Epstein-Barr virus (EBV) and cytomegalovirus (CMV), HHV6 and HHV7. The hepatitis family of viruses includes hepatitis A virus (HAV), hepatitis B virus (HBV), hepatitis C virus (HCV), the delta hepatitis virus (HDV), hepatitis E virus (HEV) and hepatitis G virus (HGV). Other viruses or their receptors may be targeted, including, but not limited to, Picornaviridae (e.g., polioviruses, etc.); Caliciviridae; Togaviridae (e.g., rubella virus, dengue virus, etc.); Flaviviridae; Coronaviridae; Reoviridae; Birnaviridae; Rhabodoviridae (e.g., rabies virus, etc.); Filoviridae; Paramyxoviridae (e.g., mumps virus, measles virus, respiratory syncytial virus, etc.); Orthomyxoviridae (e.g., influenza virus types A, B and C, etc.); Bunyaviridae; Arenaviridae; Retroviradae; lentiviruses (e.g., HTLV-I; HTLV-II; HIV-1 (also known as HTLV-III, LAV, ARV, hTLR, etc.) HIV-II); simian immunodeficiency virus (SIV), human papillomavirus (HPV), influenza virus and the tick-borne encephalitis viruses. See, e.g. Virology, 3rd Edition (W. K. Joklik ed. 1988); Fundamental Virology, 2nd Edition (B. N. Fields and D. M. Knipe, eds. 1991), for a description of these and other viruses. Receptors for HIV, for example, include CCR-5 and CXCR-4. As noted above, the compositions and methods described herein can be used for gene modification, gene correction, and gene disruption.

The compositions and methods described herein can also be applied to stem cell based therapies, including but not limited to editing that results in: correction of somatic cell mutations; disruption of dominant negative alleles; disruption of genes required for the entry or productive infection of pathogens into cells; enhanced tissue engineering, for example, by editing gene activity to promote the differentiation or formation of functional tissues; and/or disrupting gene activity to promote the differentiation or formation of functional tissues; blocking or inducing differentiation, for example, by editing genes that block differentiation to promote stem cells to differentiate down a specific lineage pathway Cell types for this procedure include but are not limited to, T-cells, B cells, hematopoietic stem cells, and embryonic stem cells. Additionally, induced pluripotent stem cells (iPSC) may be used which would also be generated from a patient's own somatic cells. Therefore, these stem cells or their derivatives (differentiated cell types or tissues) could be potentially engrafted into any person regardless of their origin or histocompatibility.

The compositions and methods can also be used for somatic cell therapy, thereby allowing production of stocks of cells that have been modified to enhance their biological properties. Such cells can be infused into a variety of patients, independent of the donor source of the cells and their histocompatibility to the recipient.

In addition to therapeutic applications, the DNA-editing complexes described herein can be used for crop engineering, cell line engineering and the construction of disease models. The obligate heterodimer cleavage half-domains provide a straightforward means for improving nuclease properties.

The engineered DNA-editing complexes described can also be used in gene modification protocols requiring simultaneous cleavage at multiple targets at once. Editing at two targets would require cellular expression of two DNA-editing complexes, and is preferably achieved using nickases comprising cleavage domains in each complex that do not interact (dimerize) with cleavage domains in the other complex.

EXAMPLES

Example 1: Preparation of ZFPs

ZFPs targeted to specific target sites are designed and incorporated into plasmid vectors essentially as described in Urnov, et al. (2005) *Nature* 435(7042):646-651, Perez, et al. (2008) *Nature Biotechnology* 26(7): 808-816, and International Patent Publication Nos. WO 2016/183298 and WO 2017/106528. TALEs and sgRNA to specific sites are also developed, as described in U.S. Pat. Nos. 8,586,526 and 9,873,894.

One exemplary target for base editing is the SERPINA locus which encodes Alpha-1 antitrypsin (A1AT). Mutations in the locus that cause an autosomal recessive deficiency in the A1AT protein are associated with both liver and lung disease. The PiZ mutation, one of the most common deficiency alleles in people of Northern European descent, results in only about 10-20% of the A1AT protein being produced. This mutation is caused by a single mutation in exon 5, leading to a glutamine substitution at amino acid position 342 for a lysine where a G at position 1096 in the DNA is an A in the mutated gene sequence (reviewed in Fregonese and Stolk (2008) *Orphanet J Rare Dis* 3:16.

Another exemplary target is the JAK2 V617F mutation. Editing of the V617F to form another mutation can result in a less activating JAK2. For example, the V617L, V617P and V617S mutations have been shown to be less activating than V617F (Dusa, et al. (2008) *J Biol Chem* 283(19):12941-12948).

Thus, several zinc finger proteins (ZFPs) were made that target the area near the mutations in A1AT (see FIG. 2). The design of the ZFPs are shown below in Table 1A (A1AT) and Table 1B (JAK2).

TABLE 1A

Exemplary ZFP designs for A1AT

| SBS #, Target | Design | | | | | |
|---|---|---|---|---|---|---|
| | F1 | F2 | F3 | F4 | F5 | F6 |
| SBS# 78488 atGTTTTTAGAGGC CATacccatgtcta (SEQ ID NO: 6) | TQATLGV (SEQ ID NO: 11) | DRSHLAR (SEQ ID NO: 12) | QSAHRKN (SEQ ID NO: 13) | STAALSY (SEQ ID NO: 14) | TSGSLTR (SEQ ID NO: 15) | N/A |
| SBS# 78486 atGTTTTTAGAGG CCATacccatgtct a (SEQ ID NO: 6) | SNQNLTT (SEQ ID NO: 16) | DRSHLAR (SEQ ID NO: 12) | QSAHRKN (SEQ ID NO: 13) | STAALSY (SEQ ID NO: 14) | TSGSLTR (SEQ ID NO: 15) | N/A |
| SBS# 78485 gcCATGTTTTTAGA GGCCATacccatgt (SEQ ID NO: 7) | SNQNLTT (SEQ ID NO: 16) | DRSHLAR (SEQ ID NO: 12) | QSAHRKN (SEQ ID NO: 13) | STAALSY (SEQ ID NO: 14) | TSGSLSR (SEQ ID NO: 17) | HSATLKY (SEQ ID NO: 18) |
| SBS# 78484 gcCATGTTTTTAGA GGCCATacccatgt (SEQ ID NO: 7) | SNQNLTT (SEQ ID NO: 16) | DRSHLAR (SEQ ID NO: 12) | QNAHRKT (SEQ ID NO: 19) | STAALSY (SEQ ID NO: 14) | TSGSLSR (SEQ ID NO: 17) | TSSNRAV (SEQ ID NO: 20) |
| SBS# 78483 gcCATGTTTTTAGA GGCCATacccatgt (SEQ ID NO: 7) | SNQNLTT (SEQ ID NO: 16) | DRSHLAR (SEQ ID NO: 12) | QSAHRKN (SEQ ID NO: 13) | STAALSY (SEQ ID NO: 14) | TSGSLSR (SEQ ID NO: 17) | TSSNRAV (SEQ ID NO: 20) |
| SBS# 78482 ggGCCATGttTTTA GAGGCCATacccat (SEQ ID NO: 8) | TQATLGV (SEQ ID NO: 11) | DRSHLAR (SEQ ID NO: 12) | QSAHRKN (SEQ ID NO: 13) | STAALSY (SEQ ID NO: 14) | RSDALST (SEQ ID NO: 21) | DRSTRTK (SEQ ID NO: 22) |
| SBS# 78481 ggGCCATGttTTTA GAGGCCATacccat (SEQ ID NO: 8) | SNQNLTT (SEQ ID NO: 16) | DRSHLAR (SEQ ID NO: 12) | QNAHRKT (SEQ ID NO: 19) | STAALSY (SEQ ID NO: 14) | RSDALST (SEQ ID NO: 21) | DRSTRTK (SEQ ID NO: 22) |
| SBS# 78480 ggGCCATGttTTTT AGAGGCCATaccca t(SEQ ID NO: 8) | SNQNLTT (SEQ ID NO: 16) | DRSHLAR (SEQ ID NO: 12) | QSAHRKN (SEQ ID NO: 13) | STAALSY (SEQ ID NO: 14) | RSDALST (SEQ ID NO: 21) | DRSTRTK (SEQ ID NO: 22) |
| SBS# 78477 ggGGCCATGTTTTT AGAggccataccca (SEQ ID NO: 9) | QNAHRKT (SEQ ID NO: 19) | STAALSY (SEQ ID NO: 14) | TSGSLSR (SEQ ID NO: 17) | TSSNRAV (SEQ ID NO: 20) | DSSHRTR (SEQ ID NO: 23) | N/A |
| SBS# 78476 ggGGCCATGTTTTT | QSAHRKN (SEQ ID | STAALSY (SEQ ID | TSGSLSR (SEQ ID | TSSNRAV (SEQ ID | DSSHRTR (SEQ ID | N/A |

TABLE 1A-continued

Exemplary ZFP designs for A1AT

| SBS #, Target | F1 | F2 | F3 | F4 | F5 | F6 |
|---|---|---|---|---|---|---|
| AGAggccataccca (SEQ ID NO: 9) | NO: 13) | NO: 14) | NO: 17) | NO: 20) | NO: 23) | |
| SBS# 78475 ctGGGGCCatGTTT TTAGAggccatacc (SEQ ID NO: 10) | QSAHRKN (SEQ ID NO: 13) | STAALSY (SEQ ID NO: 14) | TSGSLTR (SEQ ID NO: 15) | DRSDLSR (SEQ ID NO: 24) | RSTHLVR (SEQ ID NO: 25) | N/A |
| SBS# 78474 ctGGGGCCatGTTT TTAGAggccatacc (SEQ ID NO: 10) | QNAHRKT (SEQ ID NO: 19) | STAALSY (SEQ ID NO: 14) | TSGSLTR (SEQ ID NO: 15) | ERGTLAR (SEQ ID NO: 26) | RSDHLSR (SEQ ID NO: 27) | N/A |

TABLE 1B

Exemplary ZFP designs for JAK2

| ZFN #, Target | F1 | F2 | F3 | F4 | F5 | F6 |
|---|---|---|---|---|---|---|
| ZFP2 caAATGCTTGTGA GAAAGCTtgctca (SEQ ID NO: 81) | QSSDLSR (SEQ ID NO: 82) | LKWNLRT (SEQ ID NO: 83) | RSDNLAR (SEQ ID NO: 84) | WQSSLIV (SEQ ID NO: 85) | QSSDLSR (SEQ ID NO: 82) | QSGNRTT (SEQ ID NO: 86) |
| ZFN4 atGCTTGTGAGAA AGCTtgctcatca (SEQ ID NO: 87) | QSSDLSR (SEQ ID NO: 82) | RSDNLAR (SEQ ID NO: 84) | WQSSLIV (SEQ ID NO: 85) | QSSDLSR (SEQ ID NO: 82) | QSGNRTT (SEQ ID NO: 86) | N/A |
| ZFN6 ctTGTGAGAAAGC TtGCTCATcatac (SEQ ID NO: 88) | RSDNLAR (SEQ ID NO: 84) | WQSSLIV (SEQ ID NO: 85) | QSSDLSR (SEQ ID NO: 82) | QSGNRTT (SEQ ID NO: 86) | TNQNRIT (SEQ ID NO: 89) | RSANLTR (SEQ ID NO: 90) |
| ZFN7 gtGAGAAAGCTtG CTCATcatacttg (SEQ ID NO: 91) | AHGARWN SEQ ID NO: 92) | RSANLTR (SEQ ID NO: 90) | QSSDLSR (SEQ ID NO: 82) | TNQNRIT (SEQ ID NO: 89) | RSANLTR (SEQ ID NO: 90) | N/A |

Base editors comprising several different combinations are constructed using standard protocols. Different combinations include editors that comprise one or more deaminases, helicases, selected DNA binding domains (ZFP, TALE, sgRNA), dCas, nickase (ZFNs, TALENs, CRISPR/Cas) complexes, UGI, GAM etc. The combinations include complexes comprising the selected domains fused sequentially or wherein the combinations are supplied as separate fusion proteins. Any linker is used between the domains.

The combinations are assembled into expression constructs for transfection into cells or for use in the production of mRNAs in vitro. These mRNAs can then be introduced into the cells by methods known in the art (e.g., electroporation). Cells without the targeted mutation are used as controls.

Example 2: Adenine Base Editors

Adenine base editors were constructed using Cas9 variants with relaxed PAM requirements (SpCas9VRVRFRRD 10A; Nishimasu, et al. (2018) *Science* 361:1259-1262 or xCas9, see Hu, et al. (2018) *Nature* 556:57-63) linked to a ZFP DNA binding domain that targeted the mutated A1AT PiZ mutation on the C-terminal side of the molecule. A series of ZFP DNA binding domains (see Example 1) that were designed to bind to the adjacent DNA region were incorporated into the base editor (see FIGS. 2 and 7). The ZFP was attached to the Cas9 using a linker comprising 3 HA peptides and two nuclease localization sequences (NLS). The sequence of the linker was: GTGGPK-KKRKVYPYDVPDYAGYPYDVPDYAGSYPYDVPDY-AGSAAPAAKKKK LDFESE (SEQ ID NO:3) (see Bolukbasi, et al. (2015) *Nat Methods* 12(12):1150-1156). The Cas9 was then linked to two *E. coli* TadA adenine deaminases ("ecTadA"; Kim, et al. (2006) *Biochemistry* 45:6407-6416) on the N terminal side. In the construct, one of the TadA proteins was a wild type protein while the other was an evolved version (Gaudelli, et al. (2017) *Nature* 551:464). A serine-glycine rich linker was used twice between the Cas9 and TadA subunits and comprised the sequence: SGGSSGGSSGSETPGTSESATPESSGGSSGGS (SEQ ID NO:2). A schematic of the adenine base editor (ABE) is shown in FIG. 3A. In some instances, other types of adenine deaminases are used. For example, in some constructs, the ABE7.10 deaminase or the ABEmax adenine deaminase (Koblan, et al. (2018) *Nat Biotechnol.* 36(9):843-846) is used.

Figure 7A:
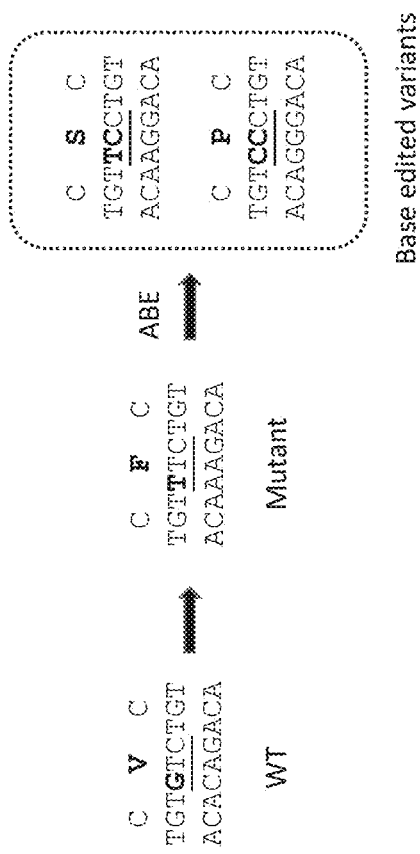
Figure 7B:
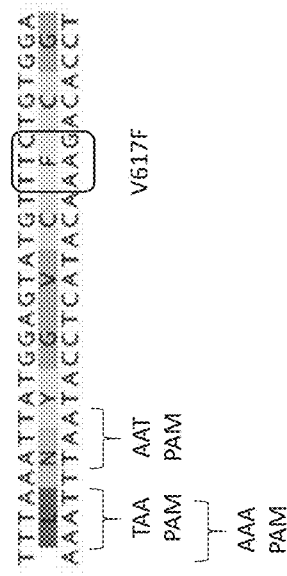
Figure 8B:
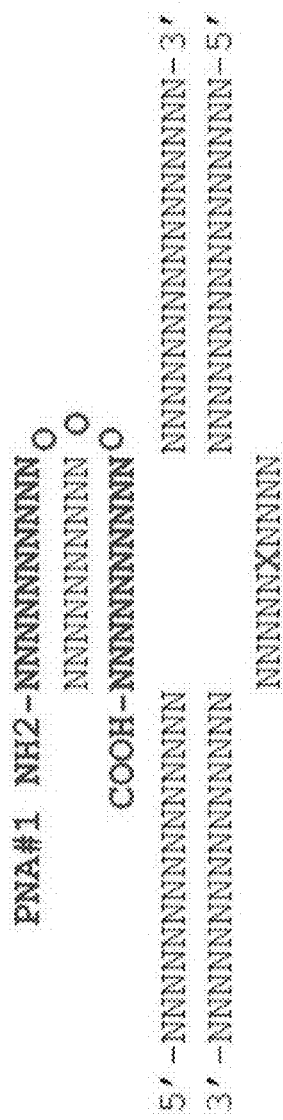
Figure 8C:
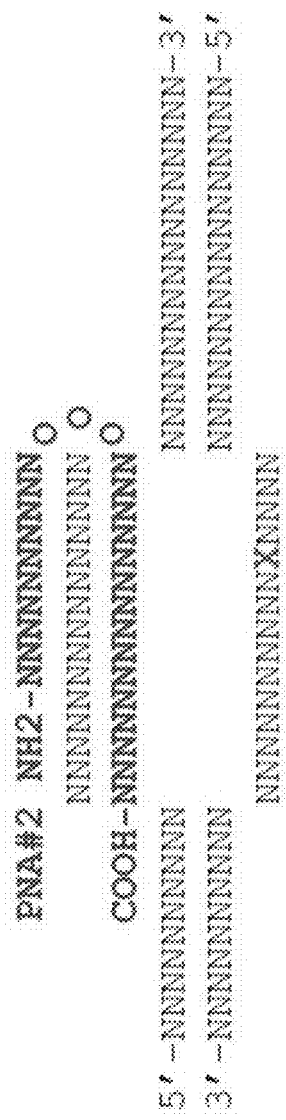
Figure 8D:
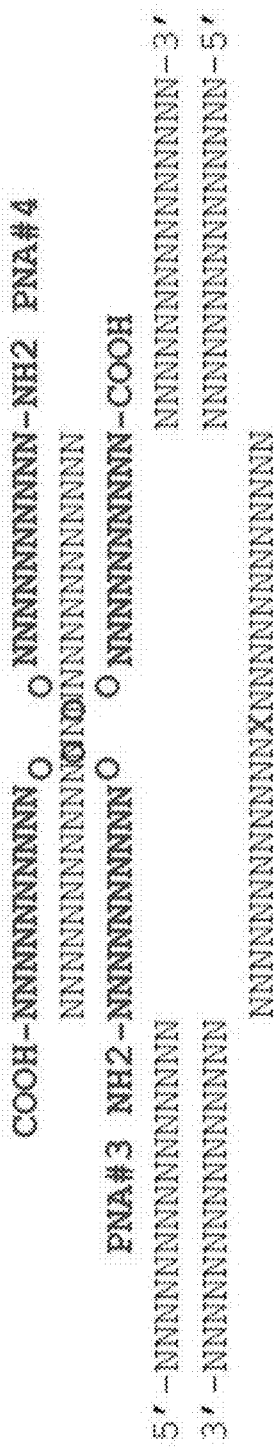
Figure 8E:
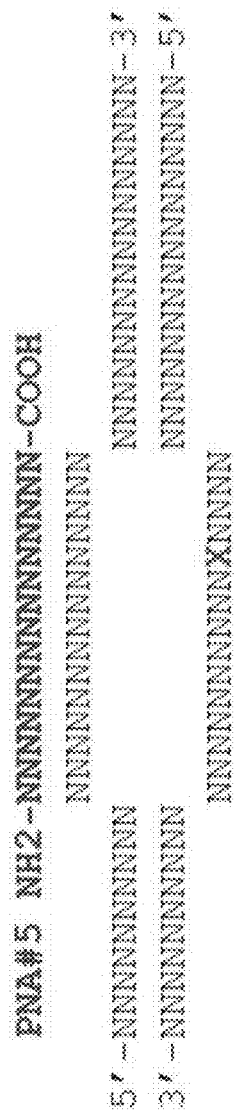

To target the JAK2 V617F mutation, Cas9NG adenine base editors targeting the JAK2 gene near the mutation site are made using the TAA or AAT or AAA PAM sites located upstream of the mutation site (see, FIGS. 7A through 7C). ZFP DNA binding domains are fused to the base editor as described above and used to edit HSC/PC. ZFP sequences are shown in Table 1B. Any linkers can be used between the fingers and/or between the ZFP and the base editor.

The results show successful editing at the target locus. FIG. 7A shows base editing to cause a change in the amino acid sequence to a serine (S) or a proline (P). Both of these variants have been shown to be less activating than the phenylalanine mutant (F) (see Dusa, et al. (2008) *J Biol Chem* 283(19): 12941-8).

Cells (e.g., K562 cells) are transfected with expression vectors (for example plasmids or viral vectors) comprising the base editors, or the cells are electroporated using the mRNAs encoding the base editors as described above. Transfected cells are harvested and the genomic DNA is isolated. On-target and off-target genomic regions of interest are amplified by PCR amplification according to the standard methods in the art. Sequences are evaluated for base editing and for the presence of indels.

Figure 4:
FIG. 4 is a schematic depicting adenine bases that lie within the editing window (SEQ ID NO:4) that are analyzed for targeting by the adenine base editor.
Figures 5A, 5B, 5C, 5D, 5E, 5F:
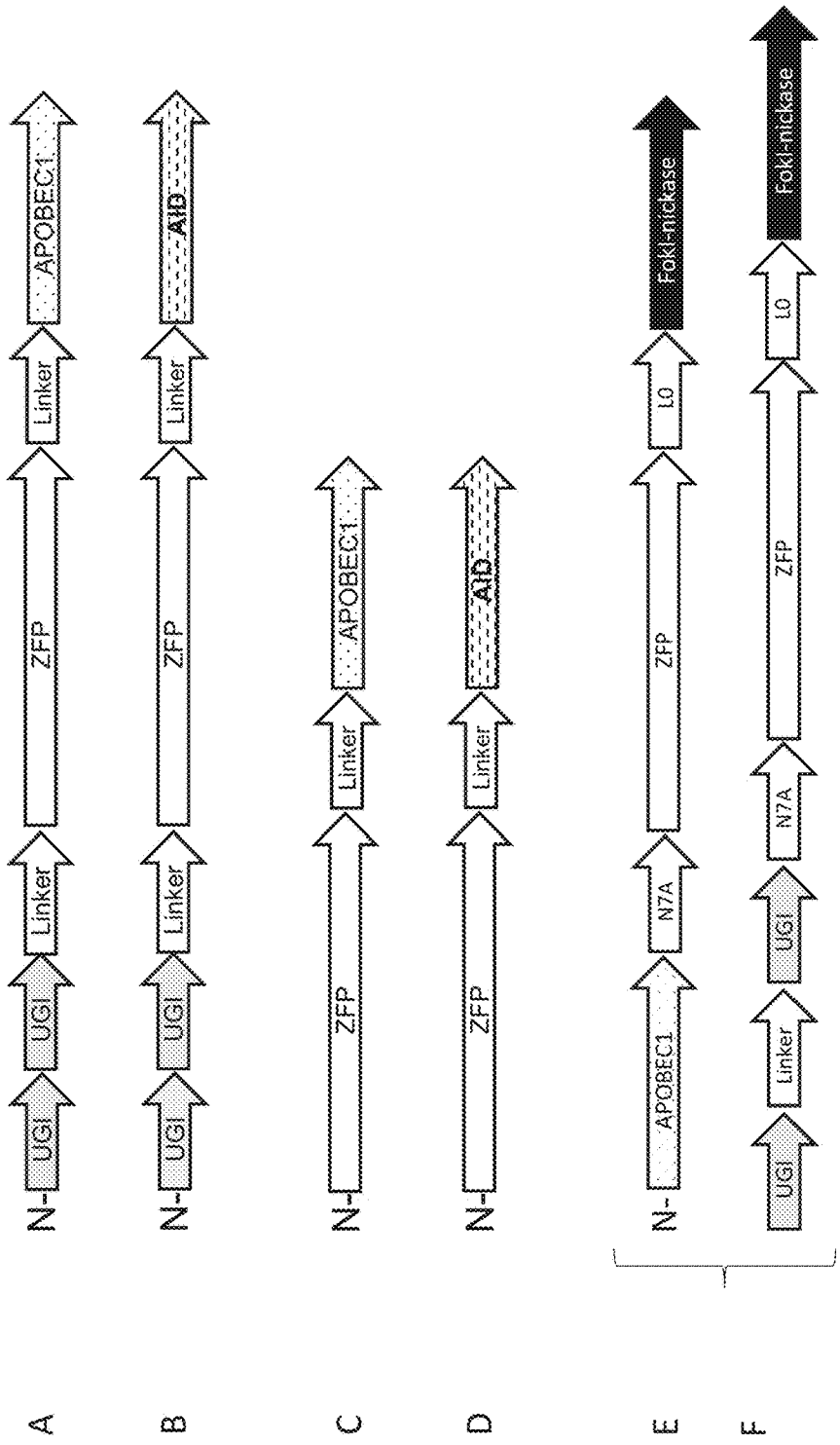
FIGS. 5A through 5F are schematics depict exemplary cytidine base editor construct.
Figures 6A, 6B:
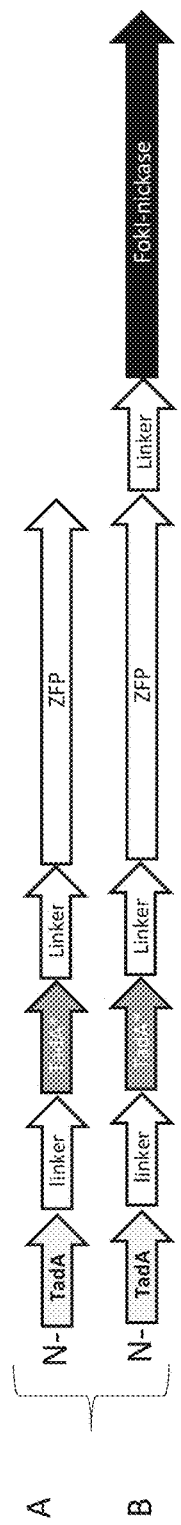
FIGS. 6A and 6B depict two exemplary adenine base editors.

The adenine base editor (ABE) was tested on the A1AT locus as described above on K562 cells where 800 ng of plasmid DNA encoding the base editor was used per 200,000 cells. Experiments were also performed in K562 cells without the Z and that A nucleotides in close proximity to the disease-causing mutations were used as a proxy to measure activity. 72 hours after transfection using an Amaxa device (according to manufacturer's protocols), cells were harvested and subject to Miseq analysis (Illumina) to analyze any editing that may have occurred. FIG. 4 illustrates the A bases that could be targeted within the editing window of the complex, where the presence of a G at these positions would indicate that the A based editing had occurred.

Three different clones of each construct comprising the variant ZFP domains were tested. The results are shown below in Table 2 (note that the terms "Cas9VRVRFRR", "Cas9VR" and "Cas9NG" are used interchangeably):

TABLE 2

Adenine base editing at A1AT locus

| | A1 % G | A5 % G | A8 % G | A10 % G | A11 % G | A12 % G | A16 % G | A20 % G |
|---|---|---|---|---|---|---|---|---|
| sgRNA_only_r1 | 0.03 | 0.12 | 0.05 | 0.11 | 0.06 | 0.22 | 0.11 | 0.03 |
| sgRNA_only_r2 | 0.08 | 0.08 | 0.07 | 0.09 | 0.07 | 0.15 | 0.14 | 0.05 |
| sgRNA_only_r3 | 0.07 | 0.07 | 0.06 | 0.09 | 0.08 | 0.06 | 0.23 | 0.04 |
| sgRNA_only_r4 | 0.05 | 0.04 | 0.08 | 0.06 | 0.06 | 0.24 | 0.17 | 0.02 |
| ABE_Cas9VR_D10A_r1 | 0.07 | 0.51 | 0.10 | 0.04 | 0.07 | 0.22 | 0.17 | 0.05 |
| ABE_Cas9VR_D10A_r2 | 0.04 | 0.45 | 0.12 | 0.06 | 0.03 | 0.20 | 0.13 | 0.04 |
| ABE_Cas9VR_D10A_r3 | 0.08 | 0.53 | 0.07 | 0.08 | 0.03 | 0.20 | 0.15 | 0.04 |
| ABE_Cas9VR_D10A_r4 | 0.04 | 0.56 | 0.13 | 0.04 | 0.02 | 0.17 | 0.14 | 0.03 |
| ABE_Cas9VR_D10A_SGMO_SBS_78474 (1) | 0.06 | 2.61 | 0.14 | 0.06 | 0.06 | 0.21 | 0.12 | 0.09 |
| ABE_Cas9VR_D10A_SGMO_SBS_78474 (2) | 0.04 | 2.83 | 0.19 | 0.19 | 0.11 | 0.28 | 0.15 | 0.05 |
| ABE_Cas9VR_D10A_SGMO_SBS_78474 (3) | NA | NA | NA | NA | NA | NA | NA | NA |
| ABE_Cas9VR_D10A_SGMO_SBS_78475 (1) | 0.05 | 0.29 | 0.06 | 0.07 | 0.02 | 0.27 | 0.17 | 0.06 |
| ABE_Cas9VR_D10A_SGMO_SBS_78475 (2) | 0.10 | 0.08 | 0.13 | 0.03 | 0.10 | 0.18 | 0.21 | 0.07 |
| ABE_Cas9VR_D10A_SGMO_SBS_78475 (3) | 0.07 | 0.41 | 0.15 | 0.06 | 0.05 | 0.19 | 0.13 | 0.10 |
| ABE_Cas9VR_D10A_SGMO_SBS_78476 (1) | 0.07 | 1.10 | 0.07 | 0.12 | 0.02 | 0.15 | 0.12 | 0.05 |
| ABE_Cas9VR_D10A_SGMO_SBS_78476 (2) | 0.05 | 1.22 | 0.15 | 0.08 | 0.05 | 0.15 | 0.19 | 0.11 |
| ABE_Cas9VR_D10A_SGMO_SBS_78476 (3) | 0.06 | 0.83 | 0.12 | 0.07 | 0.06 | 0.14 | 0.18 | 0.05 |
| ABE_Cas9VR_D10A_SGMO_SBS_78477 (1) | 0.08 | 1.50 | 0.08 | 0.04 | 0.03 | 0.19 | 0.10 | 0.03 |
| ABE_Cas9VR_D10A_SGMO_SBS_78477 (2) | 0.07 | 1.40 | 0.20 | 0.07 | 0.08 | 0.16 | 0.19 | 0.11 |
| ABE_Cas9VR_D10A_SGMO_SBS_78477 (3) | 0.06 | 1.03 | 0.11 | 0.10 | 0.06 | 0.24 | 0.17 | 0.01 |
| ABE_Cas9VR_D10A_SGMO_SBS_78480 (1) | 0.03 | 1.64 | 0.13 | 0.06 | 0.04 | 0.13 | 0.14 | 0.07 |
| ABE_Cas9VR_D10A_SGMO_SBS_78480 (2) | 0.09 | 1.61 | 0.12 | 0.04 | 0.08 | 0.26 | 0.12 | 0.03 |
| ABE_Cas9VR_D10A_SGMO_SBS_78480 (3) | 0.08 | 1.42 | 0.10 | 0.08 | 0.09 | 0.25 | 0.12 | 0.06 |
| ABE_Cas9VR_D10A_SGMO_SBS_78481 (1) | NA | NA | NA | NA | NA | NA | NA | NA |
| ABE_Cas9VR_D10A_SGMO_SBS_78481 (2) | 0.06 | 3.91 | 0.07 | 0.08 | 0.08 | 0.27 | 0.15 | 0.03 |
| ABE_Cas9VR_D10A_SGMO_SBS_78481 (3) | 0.06 | 3.05 | 0.10 | 0.12 | 0.07 | 0.27 | 0.14 | 0.06 |
| ABE_Cas9VR_D10A_SGMO_SBS_78482 (1) | 0.07 | 0.93 | 0.14 | 0.08 | 0.03 | 0.26 | 0.21 | 0.06 |
| ABE_Cas9VR_D10A_SGMO_SBS_78482 (2) | 0.05 | 1.14 | 0.12 | 0.12 | 0.06 | 0.20 | 0.21 | 0.08 |
| ABE_Cas9VR_D10A_SGMO_SBS_78482 (3) | NA | NA | NA | NA | NA | NA | NA | NA |
| ABE_Cas9VR_D10A_SGMO_SBS_78483 (1) | NA | NA | NA | NA | NA | NA | NA | NA |
| ABE_Cas9VR_D10A_SGMO_SBS_78483 (2) | 0.08 | 1.25 | 0.09 | 0.08 | 0.03 | 0.20 | 0.19 | 0.05 |
| ABE_Cas9VR_D10A_SGMO_SBS_78483 (3) | 0.09 | 0.86 | 0.14 | 0.08 | 0.09 | 0.18 | 0.17 | 0.04 |
| ABE_Cas9VR_D10A_SGMO_SBS_78484 (1) | 0.07 | 2.48 | 0.05 | 0.10 | 0.07 | 0.24 | 0.17 | 0.06 |
| ABE_Cas9VR_D10A_SGMO_SBS_78484 (2) | 0.08 | 2.47 | 0.15 | 0.06 | 0.04 | 0.22 | 0.14 | 0.04 |
| ABE_Cas9VR_D10A_SGMO_SBS_78484 (3) | 0.00 | 2.06 | 0.13 | 0.07 | 0.09 | 0.27 | 0.11 | 0.03 |
| ABE_Cas9VR_D10A_SGMO_SBS_78485 (1) | 0.08 | 1.08 | 0.06 | 0.10 | 0.04 | 0.21 | 0.15 | 0.03 |
| ABE_Cas9VR_D10A_SGMO_SBS_78485 (2) | 0.07 | 1.05 | 0.11 | 0.10 | 0.02 | 0.25 | 0.12 | 0.06 |
| ABE_Cas9VR_D10A_SGMO_SBS_78485 (3) | 0.05 | 0.61 | 0.11 | 0.05 | 0.03 | 0.16 | 0.18 | 0.04 |
| ABE_Cas9VR_D10A_SGMO_SBS_78486 (1) | NA | NA | NA | NA | NA | NA | NA | NA |
| ABE_Cas9VR_D10A_SGMO_SBS_78486 (2) | 0.09 | 2.33 | 0.20 | 0.10 | 0.07 | 0.23 | 0.18 | 0.05 |
| ABE_Cas9VR_D10A_SGMO_SBS_78486 (3) | 0.11 | 2.03 | 0.14 | 0.12 | 0.05 | 0.13 | 0.19 | 0.06 |
| ABE_Cas9VR_D10A_SGMO_SBS_78488 (1) | NA | NA | NA | NA | NA | NA | NA | NA |

TABLE 2-continued

Adenine base editing at A1AT locus

| | A1 % G | A5 % G | A8 % G | A10 % G | A11 % G | A12 % G | A16 % G | A20 % G |
|---|---|---|---|---|---|---|---|---|
| ABE_Cas9VR_D10A_SGMO_SBS_78488 (2) | 0.04 | 1.67 | 0.12 | 0.08 | 0.06 | 0.22 | 0.13 | 0.07 |
| ABE_Cas9VR_D10A_SGMO_SBS_78488 (3) | 0.10 | 1.32 | 0.08 | 0.07 | 0.09 | 0.23 | 0.18 | 0.02 |

(1), (2) and (3) represent individual clones.
NA = Clone did not pass Sanger sequencing QC and was not tested.

Rows labeled "sgRNA_only" are those comprising guide RNA only, "ABE_Cas9VR_D10A" are the complexes lacking the ZFP DNA binding domain. As can be seen from the data, targeted editing of the adenine in position A5 increased in the presence of some of the ZFP DNA binding domains as compared to the editing complex lacking the ZFP domain. The native ABE-Cas9 fusion construct without ZFP resulted in ~0.5% base editing while ABE-Cas9-ZFP fusion constructs showed at least 7-fold higher base editing efficiencies in this dataset.

In these experiments, studies were done using the xCas or the Cas9NG proteins linked to the ABEmax or the ABE7.10 adenine deaminases. The guide RNAs used were either the TGT PAM or the AGT PAM. Results showed base editing efficiencies of 5 to 10-fold or more as compared to base editors lacking the ZFP DNA binding domain (ZFP anchor).

Further experiments were carried out using alternate versions of the adenine deaminases including use of ABE 7.9 and ABE 7.8 and showed comparable results.

For base editing of the JAK2 V617F mutant, experimental conditions were the same as described above, including experiments performed in K562 cells without the V617F mutation but A nucleotides in close proximity to the disease-causing mutations were used as a proxy to measure activity. Targeted PAM sequences are shown in FIG. 7B. Studies were done using various combinations of the xCas or the Cas9NG proteins linked to ABEmax (see, e.g., FIG. 3B).

Results showed that the presence of the ZFP anchor improved editing and relaxed the PAM requirements, including showing activity at AAT and TAA PAM sequences. Notably, base editors with TAA PAM sequences are inactive at this site without the ZFP domain. See, e.g., exemplary results as shown in FIG. 7C.

Additional experiments are performed for additional disease-related point mutations and higher base editing specificity and/or activity is achieved in the presence of a ZFP anchor domain. Furthermore, depending on the targeted base to be edited, any PAM sequence can be used, including but not limited to NAN (e.g., TAA), AAT, NGG (TGG), NGT (e.g., TGT or AGT).

Example 3: Cytidine Base Editors

A cytidine base editor to convert C nucleotides to U is constructed using the apolipoprotein B mRNA editing enzyme, catalytic polypeptide-like (APOBEC) protein (Yang, et al. (2017) *J Genet Genomics* 44(9):423-437). In particular, cytidine base editors are made using a cytidine deaminase such as Apolipoprotein B mRNA editing enzyme, catalytic polypeptide 1 or APOBEC-1. The Activation-induced cytidine deaminase, also known as AICDA and AID, encoded by the AICDA gene, may also be included in cytidine deaminase base editors as described herein.

It is thought that the cellular repair response to U:G heteroduplex DNA invokes the activity of a uracil DNA glycosylase (UDG) that catalyzes the removal of U from DNA and initiates base-excision repair with reversion of the U:G pair to a C:G pair, decreasing the efficiency of base editing. Thus, cytidine base editors can have a uracil glycosylase inhibitor (UGI) fused to the editor to block endogenous UDG activity (Komor, et al. (2016) *Nature* 533 (7603):420-424). Cytidine base editors are constructed using a ZFP DNA binding domain linked to an APOBEC1 or B-cell-specific activation-induced cytidine deaminase (AID) enzyme (Kuscu, et al. (2016) *Nat Methods* 13(12):983-984). The cytidine base editors are attached to a DNA binding domain such as ZFP.

In some embodiments, the editors further comprise a UGI dimer (see, FIGS. 5A through 5F). The UGI dimer is attached to the ZFP DNA binding domain using a linker such as a L0 (LRGS, SEQ ID NO:76) or N7a (SGTPHEVGVYTL, SEQ ID NO:28, see U.S. Patent Publication No. 2017/0218349). The AID or APOBEC1 is attached to the ZFP via a linker such as L0 or a sequence such as SGGGLGST (SEQ ID NO:29, Yang, et al. (2016) *Nat Commun* DOI: 10. 1038/ncomms13330).

Cytidine base editors are also constructed without the UGI domains. Some editors are constructed to be used as a pair where one partner comprises a cytidine editor linked to a ZFP linked to a catalytically inactive FokI nickase domain. The second partner comprises the active Fok domain such that the two Fok half domains can pair and act to create a nick. The cytidine editor domain can be on either half as can a UGI dimer assembly.

Example 4: Additional Base Editors

Additional ABE and/or CBE are constructed and tested.

In particular, experiments were performed using an adenine base editor comprising (1) a Cas9 nickase, optionally operably linked to a ZFP anchor; and (2) a ZFP operably linked to an ABE domain (e.g., evolved ABE domain). See, e.g., FIG. 1B, bottom middle panel.

Results showed that these base editors were effective in targeted editing of the disease-related mutation.

In addition, experiments are performed with an ABE base editor comprising: (1) a dCas9 protein operably linked to a single guide RNA, optionally operably linked to a ZFP anchor; (2) a ZFP operably linked to an ABE domain (e.g., evolved ABE domain); and (3) a ZFN nickase. See, e.g., FIG. 1C.

Results show that base editors including a ZFN nickase increased base editing efficiency as compared to dCas9 base editors.

Example 5: Cas9-Free Base Editors

Cas9-free base editors are also constructed and evaluated. Constructs include base editors with two TadA domain are used as described above, optionally where one is wild type and one is evolved, and these may be linked to a ZFP DNA binding domain. This assembly is used alone, or may then can be linked to a catalytically inactive FokI nickase domain. When used in combination with another vector comprising an active FokI domain, the adenine base editor has nicking activity to prevent correction of the base edit. Other non-Cas base editors made are shown in FIG. 1D.

A non-Cas base editor comprising a DNA destabilizing or unwinding factor is also constructed and tested above. The DNA destabilizing factor is fused to the N- or C-terminus of a ZFP and/or ZFN nickase (see FIG. 1D) or introduced independently from the ZFP and/or nickase.

In particular, base editors are shown in FIG. 1D are generated. These base editors include a ZFP-deaminase fusion protein and a ZFN nickase. In addition, these editors include a DNA-destabilizing factor, optionally linked by its 3' end or 5' end to a ZFP or the ZFN nickase.

In particular, base editors are constructed that include one or more protein DNA-destabilizing factors as shown in Table A (e.g., helicases; factors involved in D-loop formation during DSB repair (e.g. Rad51, Rad52, RPA1, RPA2, RPA3, etc.); and/or helix-destabilizing proteins (e.g. ICP8, Puralpha or calf-thymus DNA helix-destabilizing protein), with or without one or more CRISPR proteins (e.g., non-Cas9 proteins)).

Alternatively, or in addition to, the DNA-destabilizing proteins, base editors are constructed that include one or more peptide nucleic acids (PNAs); locked nucleic acids (LNAs) and/or bridged nucleic acids (BNA). In particular, base editors comprising one or more nucleotides are constructed and tested. Base editors comprising PNAs and/or LNAs are constructed as described herein (see, also, FIG. 1D and FIG. 8).

Results show that Cas9-free base editors edit their target sites.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. One or more expression vectors for expressing a system for editing an adenine or cytosine base in DNA, the system comprising:
   a first fusion protein comprising a first inactive domain of an adenosine or cytidine deaminase and a first zinc finger protein (ZFP) DNA-binding domain,
   a second fusion protein comprising a second inactive domain of the deaminase, a second ZFP DNA-binding domain, and a catalytically active or inactive nickase domain, and
   a third fusion protein comprising a catalytically inactive or active nickase domain and a third ZFP DNA-binding domain,
   wherein the first and second inactive domains of the deaminase dimerize to form an active deaminase, and
   wherein the second and third fusion proteins form an active nickase through dimerization of the catalytically active and inactive nickase domains.

2. The one or more expression vectors of claim 1, wherein the system further comprises a uracil DNA glycosylase inhibitor (UGI).

3. The one or more expression vectors of claim 2, wherein the UGI is at the N- or C-terminal end of the fusion protein(s).

4. The one or more expression vectors of claim 1, wherein the expression vector(s) are viral vector(s), plasmid vector(s), or mRNA vector(s).

5. The one or more expression vectors of claim 4, wherein the expression vector(s) is an adeno-associated viral (AAV) vector.

6. A kit for use in editing a base in DNA, the kit comprising the one or more expression vectors of claim 1 for expressing the system for editing an adenine or cytosine base in DNA.

7. The kit of claim 6, wherein the one or more expression vectors are one or more plasmid, viral, or mRNA vectors.

8. A cell comprising the one or more expression vectors of claim 1 for expressing the system for editing an adenine or cytosine base in DNA.

* * * * *

SEQUENCE LISTING

```
<160> NUMBER OF SEQ ID NOS: 92

<210> SEQ ID NO 1
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(15)
<223> OTHER INFORMATION: a, c, t, g, unknown or other
<220> FEATURE:
<221> NAME/KEY: modified_base
<222> LOCATION: (21)..(49)
<223> OTHER INFORMATION: a, c, t, g, unknown or other

<400> SEQUENCE: 1
nnnnnnnnnn nnnnntctct nnnnnnnnnn nnnnnnnnnn nnnnnnnnn            49

<210> SEQ ID NO 2
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Ser Gly Gly Ser Ser Gly Gly Ser Ser Gly Ser Glu Thr Pro Gly Thr
1               5                   10                  15

Ser Glu Ser Ala Thr Pro Glu Ser Ser Gly Gly Ser Ser Gly Gly Ser
            20                  25                  30

<210> SEQ ID NO 3
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3
```

-continued

```
Gly Thr Gly Gly Pro Lys Lys Arg Lys Val Tyr Pro Tyr Asp Val
1               5                   10                  15

Pro Asp Tyr Ala Gly Tyr Pro Tyr Val Pro Asp Tyr Ala Gly Ser
            20                  25                  30

Tyr Pro Tyr Asp Val Pro Asp Tyr Ala Gly Ser Ala Ala Pro Ala Ala
        35                  40                  45

Lys Lys Lys Lys Leu Asp Phe Glu Ser Glu
    50                  55
```

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 4
gtgctgacca tcgacgagaa agggactgaa gct     33

<210> SEQ ID NO 5
<211> LENGTH: 579
<212> TYPE: PRT
<213> ORGANISM: Unknown
<220> FEATURE:
<223> OTHER INFORMATION: Description of Unknown: FokI
    polypeptide

<400> SEQUENCE: 5

```
Met Val Ser Lys Ile Arg Thr Phe Gly Trp Val Gln Asn Pro Gly Lys
1               5                   10                  15

Phe Glu Asn Leu Lys Arg Val Val Gln Val Phe Asp Arg Asn Ser Lys
            20                  25                  30

Val His Asn Glu Val Lys Asn Ile Lys Ile Pro Thr Leu Val Lys Glu
        35                  40                  45

Ser Lys Ile Gln Lys Glu Leu Val Ala Ile Met Asn Gln His Asp Leu
    50                  55                  60

Ile Tyr Thr Tyr Lys Glu Leu Val Gly Thr Gly Thr Ser Ile Arg Ser
65                  70                  75                  80

Glu Ala Pro Cys Asp Ala Ile Ile Gln Ala Thr Ile Ala Asp Gln Gly
                85                  90                  95

Asn Lys Lys Gly Tyr Ile Asp Asn Trp Ser Ser Asp Gly Phe Leu Arg
            100                 105                 110

Trp Ala His Ala Leu Gly Phe Ile Glu Tyr Ile Asn Lys Ser Asp Ser
        115                 120                 125

Phe Val Ile Thr Asp Val Gly Leu Ala Tyr Ser Lys Ser Ala Asp Gly
    130                 135                 140

Ser Ala Ile Glu Lys Glu Ile Leu Ile Glu Ala Ile Ser Ser Tyr Pro
145                 150                 155                 160

Pro Ala Ile Arg Ile Leu Thr Leu Leu Glu Asp Gly Gln His Leu Thr
                165                 170                 175

Lys Phe Asp Leu Gly Lys Asn Leu Gly Phe Ser Gly Glu Ser Gly Phe
            180                 185                 190

Thr Ser Leu Pro Glu Gly Ile Leu Leu Asp Thr Leu Ala Asn Ala Met
        195                 200                 205

Pro Lys Asp Lys Gly Glu Ile Arg Asn Asn Trp Glu Gly Ser Ser Asp
    210                 215                 220
```

Lys Tyr Ala Arg Met Ile Gly Gly Trp Leu Asp Lys Leu Gly Leu Val
225                 230                 235                 240

Lys Gln Gly Lys Lys Glu Phe Ile Ile Pro Thr Leu Gly Lys Pro Asp
            245                 250                 255

Asn Lys Glu Phe Ile Ser His Ala Phe Lys Ile Thr Gly Glu Gly Leu
        260                 265                 270

Lys Val Leu Arg Arg Ala Lys Gly Ser Thr Lys Phe Thr Arg Val Pro
    275                 280                 285

Lys Arg Val Tyr Trp Glu Met Leu Ala Thr Asn Leu Thr Asp Lys Glu
290                 295                 300

Tyr Val Arg Thr Arg Arg Ala Leu Ile Leu Glu Ile Leu Ile Lys Ala
305                 310                 315                 320

Gly Ser Leu Lys Ile Glu Gln Ile Gln Asp Asn Leu Lys Lys Leu Gly
            325                 330                 335

Phe Asp Glu Val Ile Glu Thr Ile Glu Asn Asp Ile Lys Gly Leu Ile
        340                 345                 350

Asn Thr Gly Ile Phe Ile Glu Ile Lys Gly Arg Phe Tyr Gln Leu Lys
    355                 360                 365

Asp His Ile Leu Gln Phe Val Ile Pro Asn Arg Gly Val Thr Lys Gln
370                 375                 380

Leu Val Lys Ser Glu Leu Glu Lys Lys Ser Glu Leu Arg His Lys
385                 390                 395                 400

Leu Lys Tyr Val Pro His Glu Tyr Ile Glu Leu Ile Glu Ile Ala Arg
            405                 410                 415

Asn Ser Thr Gln Asp Arg Ile Leu Glu Met Lys Val Met Glu Phe Phe
        420                 425                 430

Met Lys Val Tyr Gly Tyr Arg Gly Lys His Leu Gly Gly Ser Arg Lys
    435                 440                 445

Pro Asp Gly Ala Ile Tyr Thr Val Gly Ser Pro Ile Asp Tyr Gly Val
450                 455                 460

Ile Val Asp Thr Lys Ala Tyr Ser Gly Gly Tyr Asn Leu Pro Ile Gly
465                 470                 475                 480

Gln Ala Asp Glu Met Gln Arg Tyr Val Glu Glu Asn Gln Thr Arg Asn
            485                 490                 495

Lys His Ile Asn Pro Asn Glu Trp Trp Lys Val Tyr Pro Ser Ser Val
        500                 505                 510

Thr Glu Phe Lys Phe Leu Phe Val Ser Gly His Phe Lys Gly Asn Tyr
    515                 520                 525

Lys Ala Gln Leu Thr Arg Leu Asn His Ile Thr Asn Cys Asn Gly Ala
530                 535                 540

Val Leu Ser Val Glu Glu Leu Leu Ile Gly Gly Glu Met Ile Lys Ala
545                 550                 555                 560

Gly Thr Leu Thr Leu Glu Glu Val Arg Arg Lys Phe Asn Asn Gly Glu
            565                 570                 575

Ile Asn Phe

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6

```
atgtttttag aggccatacc catgtcta                                                28
```

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7

```
gccatgtttt tagaggccat acccatgt                                                28
```

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8

```
gggccatgtt tttagaggcc atacccat                                                28
```

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9

```
ggggccatgt ttttagaggc cataccca                                                28
```

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10

```
ctggggccat gttttagag gccatacc                                                 28
```

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

```
Thr Gln Ala Thr Leu Gly Val
1               5
```

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Arg Ser His Leu Ala Arg
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gln Ser Ala His Arg Lys Asn
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Thr Ala Ala Leu Ser Tyr
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Thr Ser Gly Ser Leu Thr Arg
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Asn Gln Asn Leu Thr Thr
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Thr Ser Gly Ser Leu Ser Arg
1               5

<210> SEQ ID NO 18
<211> LENGTH: 7
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 18

His Ser Ala Thr Leu Lys Tyr
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Asn Ala His Arg Lys Thr
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Thr Ser Ser Asn Arg Ala Val
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Ser Asp Ala Leu Ser Thr
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Asp Arg Ser Thr Arg Thr Lys
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Asp Ser Ser His Arg Thr Arg
1               5
```

```
<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Asp Arg Ser Asp Leu Ser Arg
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Ser Thr His Leu Val Arg
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Glu Arg Gly Thr Leu Ala Arg
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Ser Asp His Leu Ser Arg
1               5

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ser Gly Thr Pro His Glu Val Gly Val Tyr Thr Leu
1               5                   10

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29
```

Ser Gly Gly Gly Leu Gly Ser Thr
1               5

<210> SEQ ID NO 30
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30 tgtgtctgt                                                              9

<210> SEQ ID NO 31
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31 tgtttctgt                                                              9

<210> SEQ ID NO 32
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32 tgttcctgt                                                              9

<210> SEQ ID NO 33
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33 tgtccctgt                                                              9

<210> SEQ ID NO 34
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
tttaaattat ggagtatgtt tctgtgga                                        28

<210> SEQ ID NO 35
<211> LENGTH: 320
<212> TYPE: PRT
<213> ORGANISM: Bos sp.

<400> SEQUENCE: 35

Met Ser Lys Ser Glu Ser Pro Lys Glu Pro Glu Gln Leu Arg Lys Leu
1               5                   10                  15

```
Phe Ile Gly Gly Leu Ser Phe Glu Thr Thr Asp Glu Ser Leu Arg Ser
            20                  25                  30

His Phe Glu Gln Trp Gly Thr Leu Thr Asp Cys Val Val Met Arg Asp
        35                  40                  45

Pro Asn Thr Lys Arg Ser Arg Gly Phe Gly Phe Val Thr Tyr Ala Thr
    50                  55                  60

Val Glu Glu Val Asp Ala Ala Met Asn Ala Arg Pro His Lys Val Asp
65                  70                  75                  80

Gly Arg Val Val Glu Pro Lys Arg Ala Val Ser Arg Glu Asp Ser Gln
                85                  90                  95

Arg Pro Gly Ala His Leu Thr Val Lys Lys Ile Phe Val Gly Gly Ile
            100                 105                 110

Lys Glu Asp Thr Glu Glu His His Leu Arg Asp Tyr Phe Glu Gln Tyr
        115                 120                 125

Gly Lys Ile Glu Val Ile Glu Ile Met Thr Asp Arg Gly Ser Gly Lys
    130                 135                 140

Lys Arg Gly Phe Ala Phe Val Thr Phe Asp Asp His Asp Ser Val Asp
145                 150                 155                 160

Lys Ile Val Ile Gln Lys Tyr His Thr Val Asn Gly His Asn Cys Glu
                165                 170                 175

Val Arg Lys Ala Leu Ser Lys Gln Glu Met Ala Ser Ala Ser Ser Ser
            180                 185                 190

Gln Arg Gly Arg Ser Gly Ser Gly Asn Phe Gly Gly Gly Arg Gly Gly
        195                 200                 205

Gly Phe Gly Gly Asn Asp Asn Phe Gly Arg Gly Gly Asn Phe Ser Gly
    210                 215                 220

Arg Gly Gly Phe Gly Gly Ser Arg Gly Gly Gly Gly Tyr Gly Gly Ser
225                 230                 235                 240

Gly Asp Gly Tyr Asn Gly Phe Gly Asn Asp Gly Ser Asn Phe Gly Gly
                245                 250                 255

Gly Gly Ser Tyr Asn Asp Phe Gly Asn Tyr Asn Asn Gln Ser Ser Asn
            260                 265                 270

Phe Gly Pro Met Lys Gly Gly Asn Phe Gly Gly Arg Ser Ser Gly Pro
        275                 280                 285

Tyr Gly Gly Gly Gly Gln Tyr Phe Ala Lys Pro Arg Asn Gln Gly Gly
    290                 295                 300

Tyr Gly Gly Ser Ser Ser Ser Ser Ser Tyr Gly Ser Gly Arg Arg Phe
305                 310                 315                 320

<210> SEQ ID NO 36
<211> LENGTH: 587
<212> TYPE: PRT
<213> ORGANISM: Unknown
<220> FEATURE:
<223> OTHER INFORMATION: Description of Unknown:
      BPT4 sequence

<400> SEQUENCE: 36

Met Asp Ile Lys Val His Phe His Asp Phe Ser His Val Arg Ile Asp
1               5                   10                  15

Cys Glu Glu Ser Thr Phe His Glu Leu Arg Asp Phe Phe Ser Phe Glu
            20                  25                  30

Ala Asp Gly Tyr Arg Phe Asn Pro Arg Phe Arg Tyr Gly Asn Trp Asp
        35                  40                  45

Gly Arg Ile Arg Leu Leu Asp Tyr Asn Arg Leu Leu Pro Phe Gly Leu
```

-continued

```
                50                  55                  60
Val Gly Gln Ile Lys Lys Phe Cys Asp Asn Phe Gly Tyr Lys Ala Trp
65                  70                  75                  80

Ile Asp Pro Gln Ile Asn Glu Lys Glu Glu Leu Ser Arg Lys Asp Phe
                    85                  90                  95

Asp Glu Trp Leu Ser Lys Leu Glu Ile Tyr Ser Gly Asn Lys Arg Ile
                100                 105                 110

Glu Pro His Trp Tyr Gln Lys Asp Ala Val Phe Glu Gly Leu Val Asn
                115                 120                 125

Arg Arg Arg Ile Leu Asn Leu Pro Thr Ser Ala Gly Lys Ser Leu Ile
                130                 135                 140

Gln Ala Leu Leu Ala Arg Tyr Tyr Leu Glu Asn Tyr Glu Gly Lys Ile
145                 150                 155                 160

Leu Ile Ile Val Pro Thr Thr Ala Leu Thr Thr Gln Met Ala Asp Asp
                165                 170                 175

Phe Val Asp Tyr Arg Leu Phe Ser His Ala Met Ile Lys Lys Ile Gly
                180                 185                 190

Gly Gly Ala Ser Lys Asp Asp Lys Tyr Lys Asn Asp Ala Pro Val Val
                195                 200                 205

Val Gly Thr Trp Gln Thr Val Val Lys Gln Pro Lys Glu Trp Phe Ser
210                 215                 220

Gln Phe Gly Met Met Met Asn Asp Glu Cys His Leu Ala Thr Gly Lys
225                 230                 235                 240

Ser Ile Ser Ser Ile Ile Ser Gly Leu Asn Asn Cys Met Phe Lys Phe
                245                 250                 255

Gly Leu Ser Gly Ser Leu Arg Asp Gly Lys Ala Asn Ile Met Gln Tyr
                260                 265                 270

Val Gly Met Phe Gly Glu Ile Phe Lys Pro Val Thr Thr Ser Lys Leu
                275                 280                 285

Met Glu Asp Gly Gln Val Thr Glu Leu Lys Ile Asn Ser Ile Phe Leu
                290                 295                 300

Arg Tyr Pro Asp Glu Phe Thr Thr Lys Leu Lys Gly Lys Thr Tyr Gln
305                 310                 315                 320

Glu Glu Ile Lys Ile Ile Thr Gly Leu Ser Lys Arg Asn Lys Trp Ile
                325                 330                 335

Ala Lys Leu Ala Ile Lys Leu Ala Gln Lys Asp Glu Asn Ala Phe Val
                340                 345                 350

Met Phe Lys His Val Ser His Gly Lys Ala Ile Phe Asp Leu Ile Lys
                355                 360                 365

Asn Glu Tyr Asp Lys Val Tyr Tyr Val Ser Gly Glu Val Asp Thr Glu
                370                 375                 380

Thr Arg Asn Ile Met Lys Thr Leu Ala Glu Asn Gly Lys Gly Ile Ile
385                 390                 395                 400

Ile Val Ala Ser Tyr Gly Val Phe Ser Thr Gly Ile Ser Val Lys Asn
                405                 410                 415

Leu His His Val Val Leu Ala His Gly Val Lys Ser Lys Ile Ile Val
                420                 425                 430

Leu Gln Thr Ile Gly Arg Val Leu Arg Lys His Gly Ser Lys Thr Ile
                435                 440                 445

Ala Thr Val Trp Asp Leu Ile Asp Ser Ala Gly Val Lys Pro Lys Ser
450                 455                 460

Ala Asn Thr Lys Lys Lys Tyr Val His Leu Asn Tyr Leu Leu Lys His
465                 470                 475                 480
```

```
Gly Ile Asp Arg Ile Gln Arg Tyr Ala Asp Glu Lys Phe Asn Tyr Val
                485                 490                 495

Met Lys Thr Val Asn Leu Ile Ser Phe Gly Pro Leu Glu Lys Lys Met
            500                 505                 510

Leu Leu Glu Phe Lys Gln Phe Leu Tyr Glu Ala Ser Ile Asp Glu Phe
        515                 520                 525

Met Gly Lys Ile Ala Ser Cys Gln Thr Leu Glu Gly Leu Glu Glu Leu
    530                 535                 540

Glu Ala Tyr Tyr Lys Lys Arg Val Lys Glu Thr Glu Leu Lys Asp Thr
545                 550                 555                 560

Asp Asp Ile Ser Val Arg Asp Ala Leu Ala Gly Lys Arg Ala Glu Leu
                565                 570                 575

Glu Asp Ser Asp Asp Glu Val Glu Glu Ser Phe
            580                 585

<210> SEQ ID NO 37
<211> LENGTH: 715
<212> TYPE: PRT
<213> ORGANISM: Deinococcus radiodurans

<400> SEQUENCE: 37

Met Ser Ala Ala Leu Pro Ala Glu Pro Phe Arg Val Ser Gly Gly Val
1               5                   10                  15

Asn Lys Val Arg Phe Arg Ser Asp Thr Gly Phe Thr Val Met Ser Ala
            20                  25                  30

Thr Leu Arg Asn Glu Gln Gly Glu Asp Pro Asp Ala Thr Val Ile Gly
        35                  40                  45

Val Met Pro Pro Leu Asp Val Gly Asp Thr Phe Ser Ala Glu Val Leu
    50                  55                  60

Met Glu Glu His Arg Glu Tyr Gly Tyr Gln Tyr Arg Val Val Asn Met
65                  70                  75                  80

Val Leu Glu Ala Met Pro Ala Asp Leu Ser Glu Glu Gly Val Ala Ala
                85                  90                  95

Tyr Phe Glu Ala Arg Val Gly Gly Val Gly Lys Val Leu Ala Gly Arg
            100                 105                 110

Ile Ala Lys Thr Phe Gly Ala Ala Ala Phe Asp Leu Leu Glu Asp Asp
        115                 120                 125

Pro Gln Lys Phe Leu Gln Val Pro Gly Ile Thr Glu Ser Thr Leu His
    130                 135                 140

Lys Met Val Ser Ser Trp Ser Gln Gln Gly Leu Glu Arg Arg Leu Leu
145                 150                 155                 160

Ala Gly Leu Gln Gly Leu Gly Leu Thr Ile Asn Gln Ala Gln Arg Ala
                165                 170                 175

Val Lys His Phe Gly Ala Asp Ala Leu Asp Arg Leu Glu Lys Asp Leu
            180                 185                 190

Phe Thr Leu Thr Glu Val Glu Gly Ile Gly Phe Leu Thr Ala Asp Lys
        195                 200                 205

Leu Trp Gln Ala Arg Gly Gly Ala Leu Asp Asp Pro Arg Arg Leu Thr
    210                 215                 220

Ala Ala Ala Val Tyr Ala Leu Gln Leu Ala Gly Thr Gln Ala Gly His
225                 230                 235                 240

Ser Phe Leu Pro Arg Ser Arg Ala Glu Lys Gly Val Val His Tyr Thr
                245                 250                 255

Arg Val Thr Pro Gly Gln Ala Arg Leu Ala Val Glu Thr Ala Val Glu
```

```
            260                 265                 270
Leu Gly Arg Leu Ser Glu Asp Asp Ser Pro Leu Phe Ala Ala Glu Ala
            275                 280                 285

Ala Ala Thr Gly Glu Gly Arg Ile Tyr Leu Pro His Val Leu Arg Ala
            290                 295                 300

Glu Lys Lys Leu Ala Ser Leu Ile Arg Thr Leu Leu Ala Thr Pro Pro
305                 310                 315                 320

Ala Asp Gly Ala Gly Asn Asp Asp Trp Ala Val Pro Lys Lys Ala Arg
            325                 330                 335

Lys Gly Leu Ser Glu Glu Gln Ala Ser Val Leu Asp Gln Leu Ala Gly
            340                 345                 350

His Arg Leu Val Val Leu Thr Gly Pro Gly Thr Gly Lys Ser Thr
            355                 360                 365

Thr Thr Lys Ala Val Ala Asp Leu Ala Glu Ser Leu Gly Leu Glu Val
            370                 375                 380

Gly Leu Cys Ala Pro Thr Gly Lys Ala Ala Arg Arg Leu Gly Glu Val
385                 390                 395                 400

Thr Gly Arg Thr Ala Ser Thr Val His Arg Leu Leu Gly Tyr Gly Pro
            405                 410                 415

Gln Gly Phe Arg His Asn His Leu Glu Pro Ala Pro Tyr Asp Leu Leu
            420                 425                 430

Ile Val Asp Glu Val Ser Met Met Gly Asp Ala Leu Met Leu Ser Leu
            435                 440                 445

Leu Ala Ala Val Pro Pro Gly Ala Arg Val Leu Leu Val Gly Asp Thr
            450                 455                 460

Asp Gln Leu Pro Pro Val Asp Ala Gly Leu Pro Leu Leu Ala Leu Ala
465                 470                 475                 480

Gln Ala Ala Pro Thr Ile Lys Leu Thr Gln Val Tyr Arg Gln Ala Ala
            485                 490                 495

Lys Asn Pro Ile Ile Gln Ala Ala His Gly Leu Leu His Gly Glu Ala
            500                 505                 510

Pro Ala Trp Gly Asp Lys Arg Leu Asn Leu Thr Glu Ile Glu Pro Asp
            515                 520                 525

Gly Gly Ala Arg Arg Val Ala Leu Met Val Arg Glu Leu Gly Gly Pro
            530                 535                 540

Gly Ala Val Gln Val Leu Thr Pro Met Arg Lys Gly Pro Leu Gly Met
545                 550                 555                 560

Asp His Leu Asn Tyr His Leu Gln Ala Leu Phe Asn Pro Gly Glu Gly
            565                 570                 575

Gly Val Arg Ile Ala Glu Gly Glu Ala Arg Pro Gly Asp Thr Val Val
            580                 585                 590

Gln Thr Lys Asn Asp Tyr Asn Asn Glu Ile Phe Asn Gly Thr Leu Gly
            595                 600                 605

Met Val Leu Lys Ala Glu Gly Ala Arg Leu Thr Val Asp Phe Asp Gly
            610                 615                 620

Asn Val Val Glu Leu Thr Gly Ala Glu Leu Phe Asn Leu Gln Leu Gly
625                 630                 635                 640

Tyr Ala Leu Thr Val His Arg Ala Gln Gly Ser Glu Trp Gly Thr Val
            645                 650                 655

Leu Gly Val Leu His Glu Ala His Met Pro Met Leu Ser Arg Asn Leu
            660                 665                 670

Val Tyr Thr Ala Leu Thr Arg Ala Arg Asp Arg Phe Phe Ser Ala Gly
            675                 680                 685
```

```
Ser Ala Ser Ala Trp Gln Ile Ala Ala Arg Gln Arg Glu Ala Arg
    690                 695                 700

Asn Thr Ala Leu Leu Glu Arg Ile Arg Ala His
705                 710                 715

<210> SEQ ID NO 38
<211> LENGTH: 353
<212> TYPE: PRT
<213> ORGANISM: Escherichia coli

<400> SEQUENCE: 38

Met Ala Ile Asp Glu Asn Lys Gln Lys Ala Leu Ala Ala Leu Gly
1               5                   10                  15

Gln Ile Glu Lys Gln Phe Gly Lys Gly Ser Ile Met Arg Leu Gly Glu
            20                  25                  30

Asp Arg Ser Met Asp Val Glu Thr Ile Ser Thr Gly Ser Leu Ser Leu
            35                  40                  45

Asp Ile Ala Leu Gly Ala Gly Gly Leu Pro Met Gly Arg Ile Val Glu
        50                  55                  60

Ile Tyr Gly Pro Glu Ser Ser Gly Lys Thr Thr Leu Thr Leu Gln Val
65                  70                  75                  80

Ile Ala Ala Ala Gln Arg Glu Gly Lys Thr Cys Ala Phe Ile Asp Ala
                85                  90                  95

Glu His Ala Leu Asp Pro Ile Tyr Ala Arg Lys Leu Gly Val Asp Ile
                100                 105                 110

Asp Asn Leu Leu Cys Ser Gln Pro Asp Thr Gly Glu Gln Ala Leu Glu
            115                 120                 125

Ile Cys Asp Ala Leu Ala Arg Ser Gly Ala Val Asp Val Ile Val Val
        130                 135                 140

Asp Ser Val Ala Ala Leu Thr Pro Lys Ala Glu Ile Glu Gly Glu Ile
145                 150                 155                 160

Gly Asp Ser His Met Gly Leu Ala Ala Arg Met Met Ser Gln Ala Met
                165                 170                 175

Arg Lys Leu Ala Gly Asn Leu Lys Gln Ser Asn Thr Leu Leu Ile Phe
            180                 185                 190

Ile Asn Gln Ile Arg Met Lys Ile Gly Val Met Phe Gly Asn Pro Glu
        195                 200                 205

Thr Thr Thr Gly Gly Asn Ala Leu Lys Phe Tyr Ala Ser Val Arg Leu
210                 215                 220

Asp Ile Arg Arg Ile Gly Ala Val Lys Glu Gly Glu Asn Val Val Gly
225                 230                 235                 240

Ser Glu Thr Arg Val Lys Val Val Lys Asn Lys Ile Ala Ala Pro Phe
                245                 250                 255

Lys Gln Ala Glu Phe Gln Ile Leu Tyr Gly Glu Gly Ile Asn Phe Tyr
            260                 265                 270

Gly Glu Leu Val Asp Leu Gly Val Lys Glu Lys Leu Ile Glu Lys Ala
        275                 280                 285

Gly Ala Trp Tyr Ser Tyr Lys Gly Glu Lys Ile Gly Gln Gly Lys Ala
    290                 295                 300

Asn Ala Thr Ala Trp Leu Lys Asp Asn Pro Glu Thr Ala Lys Glu Ile
305                 310                 315                 320

Glu Lys Lys Val Arg Glu Leu Leu Leu Ser Asn Pro Asn Ser Thr Pro
                325                 330                 335

Asp Phe Ser Val Asp Asp Ser Glu Gly Val Ala Glu Thr Asn Glu Asp
```

Phe

<210> SEQ ID NO 39
<211> LENGTH: 1180
<212> TYPE: PRT
<213> ORGANISM: Escherichia coli

<400> SEQUENCE: 39

Met Ser Asp Val Ala Glu Thr Leu Asp Pro Leu Arg Leu Pro Leu Gln
1               5                   10                  15

Gly Glu Arg Leu Ile Glu Ala Ser Ala Gly Thr Gly Lys Thr Phe Thr
            20                  25                  30

Ile Ala Ala Leu Tyr Leu Arg Leu Leu Leu Gly Leu Gly Gly Ser Ala
        35                  40                  45

Ala Phe Pro Arg Pro Leu Thr Val Glu Glu Leu Leu Val Val Thr Phe
    50                  55                  60

Thr Glu Ala Ala Thr Ala Glu Leu Arg Gly Arg Ile Arg Ser Asn Ile
65                  70                  75                  80

His Glu Leu Arg Ile Ala Cys Leu Arg Glu Thr Thr Asp Asn Pro Leu
                85                  90                  95

Tyr Glu Arg Leu Leu Glu Glu Ile Asp Asp Lys Ala Gln Ala Ala Gln
            100                 105                 110

Trp Leu Leu Leu Ala Glu Arg Gln Met Asp Glu Ala Ala Val Phe Thr
        115                 120                 125

Ile His Gly Phe Cys Gln Arg Met Leu Asn Leu Asn Ala Phe Glu Ser
    130                 135                 140

Gly Met Leu Phe Glu Gln Gln Leu Ile Glu Asp Glu Ser Leu Leu Arg
145                 150                 155                 160

Tyr Gln Ala Cys Ala Asp Phe Trp Arg Arg His Cys Tyr Pro Leu Pro
                165                 170                 175

Arg Glu Ile Ala Gln Val Val Phe Glu Thr Trp Lys Gly Pro Gln Ala
            180                 185                 190

Leu Leu Arg Asp Ile Asn Arg Tyr Leu Gln Gly Glu Ala Pro Val Ile
        195                 200                 205

Lys Ala Pro Pro Asp Asp Glu Thr Leu Ala Ser Arg His Ala Gln
    210                 215                 220

Ile Val Ala Arg Ile Asp Thr Val Lys Gln Gln Trp Arg Asp Ala Val
225                 230                 235                 240

Gly Glu Leu Asp Ala Leu Ile Glu Ser Ser Gly Ile Asp Arg Arg Lys
                245                 250                 255

Phe Asn Arg Ser Asn Gln Ala Lys Trp Ile Asp Lys Ile Ser Ala Trp
            260                 265                 270

Ala Glu Glu Glu Thr Asn Ser Tyr Gln Leu Pro Glu Ser Leu Glu Lys
        275                 280                 285

Phe Ser Gln Arg Phe Leu Glu Asp Arg Thr Lys Ala Gly Gly Glu Thr
    290                 295                 300

Pro Arg His Pro Leu Phe Glu Ala Ile Asp Gln Leu Leu Ala Glu Pro
305                 310                 315                 320

Leu Ser Ile Arg Asp Leu Val Ile Thr Arg Ala Leu Ala Glu Ile Arg
                325                 330                 335

Glu Thr Val Ala Arg Glu Lys Arg Arg Gly Glu Leu Gly Phe Asp
            340                 345                 350

Asp Met Leu Ser Arg Leu Asp Ser Ala Leu Arg Ser Glu Ser Gly Glu

-continued

```
            355                 360                 365
Val Leu Ala Ala Ile Arg Thr Arg Phe Pro Val Ala Met Ile Asp
        370                 375                 380
Glu Phe Gln Asp Thr Asp Pro Gln Gln Tyr Arg Ile Phe Arg Arg Ile
385                 390                 395                 400
Trp His His Gln Pro Glu Thr Ala Leu Leu Leu Ile Gly Asp Pro Lys
                405                 410                 415
Gln Ala Ile Tyr Ala Phe Arg Gly Ala Asp Ile Phe Thr Tyr Met Lys
            420                 425                 430
Ala Arg Ser Glu Val His Ala His Tyr Thr Leu Asp Thr Asn Trp Arg
        435                 440                 445
Ser Ala Pro Gly Met Val Asn Ser Val Asn Lys Leu Phe Ser Gln Thr
    450                 455                 460
Asp Asp Ala Phe Met Phe Arg Glu Ile Pro Phe Ile Pro Val Lys Ser
465                 470                 475                 480
Ala Gly Lys Asn Gln Ala Leu Arg Phe Val Phe Lys Gly Glu Thr Gln
                485                 490                 495
Pro Ala Met Lys Met Trp Leu Met Glu Gly Glu Ser Cys Gly Val Gly
            500                 505                 510
Asp Tyr Gln Ser Thr Met Ala Gln Val Cys Ala Ala Gln Ile Arg Asp
        515                 520                 525
Trp Leu Gln Ala Gly Arg Gly Glu Ala Leu Leu Met Asn Gly Asp
    530                 535                 540
Asp Ala Arg Pro Val Arg Ala Ser Asp Ile Ser Val Leu Val Arg Ser
545                 550                 555                 560
Arg Gln Glu Ala Ala Gln Val Arg Asp Ala Leu Thr Leu Leu Glu Ile
                565                 570                 575
Pro Ser Val Tyr Leu Ser Asn Arg Asp Ser Val Phe Glu Thr Leu Glu
            580                 585                 590
Ala Gln Glu Met Leu Trp Leu Leu Gln Ala Val Met Thr Pro Glu Arg
        595                 600                 605
Glu Asn Thr Leu Arg Ser Ala Leu Ala Thr Ser Met Met Gly Leu Asn
    610                 615                 620
Ala Leu Asp Ile Glu Thr Leu Asn Asn Asp Glu His Ala Trp Asp Val
625                 630                 635                 640
Val Val Glu Glu Phe Asp Gly Tyr Arg Gln Ile Trp Arg Lys Arg Gly
                645                 650                 655
Val Met Pro Met Leu Arg Ala Leu Met Ser Ala Arg Asn Ile Ala Glu
            660                 665                 670
Asn Leu Leu Ala Thr Ala Gly Gly Glu Arg Arg Leu Thr Asp Ile Leu
        675                 680                 685
His Ile Ser Glu Leu Leu Gln Glu Ala Gly Thr Gln Leu Glu Ser Glu
    690                 695                 700
His Ala Leu Val Arg Trp Leu Ser Gln His Ile Leu Glu Pro Asp Ser
705                 710                 715                 720
Asn Ala Ser Ser Gln Gln Met Arg Leu Glu Ser Asp Lys His Leu Val
                725                 730                 735
Gln Ile Val Thr Ile His Lys Ser Lys Gly Leu Glu Tyr Pro Leu Val
            740                 745                 750
Trp Leu Pro Phe Ile Thr Asn Phe Arg Val Gln Glu Gln Ala Phe Tyr
        755                 760                 765
His Asp Arg His Ser Phe Glu Ala Val Leu Asp Leu Asn Ala Ala Pro
    770                 775                 780
```

-continued

Glu Ser Val Asp Leu Ala Glu Ala Glu Arg Leu Ala Glu Asp Leu Arg
785                 790                 795                 800

Leu Leu Tyr Val Ala Leu Thr Arg Ser Val Trp His Cys Ser Leu Gly
        805                 810                 815

Val Ala Pro Leu Val Arg Arg Arg Gly Asp Lys Lys Gly Asp Thr Asp
            820                 825                 830

Val His Gln Ser Ala Leu Gly Arg Leu Leu Gln Lys Gly Glu Pro Gln
            835                 840                 845

Asp Ala Ala Gly Leu Arg Thr Cys Ile Glu Ala Leu Cys Asp Asp Asp
850                 855                 860

Ile Ala Trp Gln Thr Ala Gln Thr Gly Asp Asn Gln Pro Trp Gln Val
865                 870                 875                 880

Asn Asp Val Ser Thr Ala Glu Leu Asn Ala Lys Thr Leu Gln Arg Leu
            885                 890                 895

Pro Gly Asp Asn Trp Arg Val Thr Ser Tyr Ser Gly Leu Gln Gln Arg
            900                 905                 910

Gly His Gly Ile Ala Gln Asp Leu Met Pro Arg Leu Asp Val Asp Ala
        915                 920                 925

Ala Gly Val Ala Ser Val Val Glu Glu Pro Thr Leu Thr Pro His Gln
930                 935                 940

Phe Pro Arg Gly Ala Ser Pro Gly Thr Phe Leu His Ser Leu Phe Glu
945                 950                 955                 960

Asp Leu Asp Phe Thr Gln Pro Val Asp Pro Asn Trp Val Arg Glu Lys
            965                 970                 975

Leu Glu Leu Gly Gly Phe Glu Ser Gln Trp Pro Val Leu Thr Glu
            980                 985                 990

Trp Ile Thr Ala Val Leu Gln Ala Pro Leu Asn Glu Thr Gly Val Ser
        995                 1000                1005

Leu Ser Gln Leu Ser Ala Arg Asn Lys Gln Val Glu Met Glu Phe
    1010                1015                1020

Tyr Leu Pro Ile Ser Glu Pro Leu Ile Ala Ser Gln Leu Asp Thr
    1025                1030                1035

Leu Ile Arg Gln Phe Asp Pro Leu Ser Ala Gly Cys Pro Pro Leu
    1040                1045                1050

Glu Phe Met Gln Val Arg Gly Met Leu Lys Gly Phe Ile Asp Leu
    1055                1060                1065

Val Phe Arg His Glu Gly Arg Tyr Tyr Leu Leu Asp Tyr Lys Ser
    1070                1075                1080

Asn Trp Leu Gly Glu Asp Ser Ser Ala Tyr Thr Gln Gln Ala Met
    1085                1090                1095

Ala Ala Ala Met Gln Ala His Arg Tyr Asp Leu Gln Tyr Gln Leu
    1100                1105                1110

Tyr Thr Leu Ala Leu His Arg Tyr Leu Arg His Arg Ile Ala Asp
    1115                1120                1125

Tyr Asp Tyr Glu His His Phe Gly Gly Val Ile Tyr Leu Phe Leu
    1130                1135                1140

Arg Gly Val Asp Lys Glu His Pro Gln Gln Gly Ile Tyr Thr Thr
    1145                1150                1155

Arg Pro Asn Ala Gly Leu Ile Ala Leu Met Asp Glu Met Phe Ala
    1160                1165                1170

Gly Met Thr Leu Glu Glu Ala
    1175                1180

-continued

<210> SEQ ID NO 40
<211> LENGTH: 1122
<212> TYPE: PRT
<213> ORGANISM: Escherichia coli

<400> SEQUENCE: 40

```
Met Leu Arg Val Tyr His Ser Asn Arg Leu Asp Val Leu Glu Ala Leu
1               5                   10                  15

Met Glu Phe Ile Val Glu Arg Glu Arg Leu Asp Asp Pro Phe Glu Pro
            20                  25                  30

Glu Met Ile Leu Val Gln Ser Thr Gly Met Ala Gln Trp Leu Gln Met
        35                  40                  45

Thr Leu Ser Gln Lys Phe Gly Ile Ala Ala Asn Ile Asp Phe Pro Leu
    50                  55                  60

Pro Ala Ser Phe Ile Trp Asp Met Phe Val Arg Val Leu Pro Glu Ile
65                  70                  75                  80

Pro Lys Glu Ser Ala Phe Asn Lys Gln Ser Met Ser Trp Lys Leu Met
                85                  90                  95

Thr Leu Pro Gln Leu Leu Glu Arg Glu Asp Phe Thr Leu Leu Arg
            100                 105                 110

His Tyr Leu Thr Asp Asp Ser Asp Lys Arg Lys Leu Phe Gln Leu Ser
        115                 120                 125

Ser Lys Ala Ala Asp Leu Phe Asp Gln Tyr Leu Val Tyr Arg Pro Asp
    130                 135                 140

Trp Leu Ala Gln Trp Glu Thr Gly His Leu Val Glu Gly Leu Gly Glu
145                 150                 155                 160

Ala Gln Ala Trp Gln Ala Pro Leu Trp Lys Ala Leu Val Glu Tyr Thr
                165                 170                 175

His Gln Leu Gly Gln Pro Arg Trp His Arg Ala Asn Leu Tyr Gln Arg
            180                 185                 190

Phe Ile Glu Thr Leu Glu Ser Ala Thr Thr Cys Pro Pro Gly Leu Pro
        195                 200                 205

Ser Arg Val Phe Ile Cys Gly Ile Ser Ala Leu Pro Pro Val Tyr Leu
    210                 215                 220

Gln Ala Leu Gln Ala Leu Gly Lys His Ile Glu Ile His Leu Leu Phe
225                 230                 235                 240

Thr Asn Pro Cys Arg Tyr Tyr Trp Gly Asp Ile Lys Asp Pro Ala Tyr
                245                 250                 255

Leu Ala Lys Leu Leu Thr Arg Gln Arg Arg His Ser Phe Glu Asp Arg
            260                 265                 270

Glu Leu Pro Leu Phe Arg Asp Ser Glu Asn Ala Gly Gln Leu Phe Asn
        275                 280                 285

Ser Asp Gly Glu Gln Asp Val Gly Asn Pro Leu Leu Ala Ser Trp Gly
    290                 295                 300

Lys Leu Gly Arg Asp Tyr Ile Tyr Leu Leu Ser Asp Leu Glu Ser Ser
305                 310                 315                 320

Gln Glu Leu Asp Ala Phe Val Asp Val Thr Pro Asp Asn Leu Leu His
                325                 330                 335

Asn Ile Gln Ser Asp Ile Leu Glu Leu Glu Asn Arg Ala Val Ala Gly
            340                 345                 350

Val Asn Ile Glu Glu Phe Ser Arg Ser Asp Asn Lys Arg Pro Leu Asp
        355                 360                 365

Pro Leu Asp Ser Ser Ile Thr Phe His Val Cys His Ser Pro Gln Arg
    370                 375                 380
```

```
Glu Val Glu Val Leu His Asp Arg Leu Leu Ala Met Leu Glu Glu Asp
385                 390                 395                 400

Pro Thr Leu Thr Pro Arg Asp Ile Ile Val Met Val Ala Asp Ile Asp
                405                 410                 415

Ser Tyr Ser Pro Phe Ile Gln Ala Val Phe Gly Ser Ala Pro Ala Asp
            420                 425                 430

Arg Tyr Leu Pro Tyr Ala Ile Ser Asp Arg Arg Ala Arg Gln Ser His
            435                 440                 445

Pro Val Leu Glu Ala Phe Ile Ser Leu Leu Ser Leu Pro Asp Ser Arg
        450                 455                 460

Phe Val Ser Glu Asp Val Leu Ala Leu Leu Asp Val Pro Val Leu Ala
465                 470                 475                 480

Ala Arg Phe Asp Ile Thr Glu Glu Gly Leu Arg Tyr Leu Arg Gln Trp
                485                 490                 495

Val Asn Glu Ser Gly Ile Arg Trp Gly Ile Asp Asp Asp Asn Val Arg
            500                 505                 510

Glu Leu Glu Leu Pro Ala Thr Gly Gln His Thr Trp Arg Phe Gly Leu
        515                 520                 525

Thr Arg Met Leu Leu Gly Tyr Ala Met Glu Ser Ala Gln Gly Glu Trp
    530                 535                 540

Gln Ser Val Leu Pro Tyr Asp Glu Ser Ser Gly Leu Ile Ala Glu Leu
545                 550                 555                 560

Val Gly His Leu Ala Ser Leu Leu Met Gln Leu Asn Ile Trp Arg Arg
                565                 570                 575

Gly Leu Ala Gln Glu Arg Pro Leu Glu Glu Trp Leu Pro Val Cys Arg
            580                 585                 590

Asp Met Leu Asn Ala Phe Phe Leu Pro Asp Ala Glu Thr Glu Ala Ala
        595                 600                 605

Met Thr Leu Ile Glu Gln Gln Trp Gln Ala Ile Ile Ala Glu Gly Leu
    610                 615                 620

Gly Ala Gln Tyr Gly Asp Ala Val Pro Leu Ser Leu Leu Arg Asp Glu
625                 630                 635                 640

Leu Ala Gln Arg Leu Asp Gln Glu Arg Ile Ser Gln Arg Phe Leu Ala
                645                 650                 655

Gly Pro Val Asn Ile Cys Thr Leu Met Pro Met Arg Ser Ile Pro Phe
            660                 665                 670

Lys Val Val Cys Leu Leu Gly Met Asn Asp Gly Val Tyr Pro Arg Gln
        675                 680                 685

Leu Ala Pro Leu Gly Phe Asp Leu Met Ser Gln Lys Pro Lys Arg Gly
    690                 695                 700

Asp Arg Ser Arg Arg Asp Asp Arg Tyr Leu Phe Leu Glu Ala Leu Leu
705                 710                 715                 720

Ile Ser Ala Gln Gln Lys Leu Tyr Ile Ser Tyr Ile Gly Arg Ser Ile
                725                 730                 735

Gln Asp Asn Ser Glu Arg Phe Pro Ser Val Leu Val Gln Glu Leu Ile
            740                 745                 750

Asp Tyr Ile Gly Gln Ser His Tyr Leu Pro Gly Asp Glu Ala Leu Asn
        755                 760                 765

Cys Asp Glu Ser Glu Ala Arg Val Lys Ala His Leu Thr Cys Leu His
    770                 775                 780

Thr Arg Met Pro Phe Asp Pro Gln Asn Tyr Gln Pro Gly Glu Arg Gln
785                 790                 795                 800
```

```
Ser Tyr Ala Arg Glu Trp Leu Pro Ala Ala Ser Gln Ala Gly Lys Ala
                805                 810                 815

His Ser Glu Phe Val Gln Pro Leu Pro Phe Thr Leu Pro Glu Thr Val
            820                 825                 830

Pro Leu Glu Thr Leu Gln Arg Phe Trp Ala His Pro Val Arg Ala Phe
        835                 840                 845

Phe Gln Met Arg Leu Gln Val Asn Phe Arg Thr Glu Asp Ser Glu Ile
    850                 855                 860

Pro Asp Thr Glu Pro Phe Ile Leu Glu Gly Leu Ser Arg Tyr Gln Ile
865                 870                 875                 880

Asn Gln Gln Leu Leu Asn Ala Leu Val Glu Gln Asp Ala Glu Arg
                885                 890                 895

Leu Phe Arg Arg Phe Arg Ala Ala Gly Asp Leu Pro Tyr Gly Ala Phe
            900                 905                 910

Gly Glu Ile Phe Trp Glu Thr Gln Cys Gln Glu Met Gln Gln Leu Ala
        915                 920                 925

Asp Arg Val Ile Ala Cys Arg Gln Pro Gly Gln Ser Met Glu Ile Asp
    930                 935                 940

Leu Ala Cys Asn Gly Val Gln Ile Thr Gly Trp Leu Pro Gln Val Gln
945                 950                 955                 960

Pro Asp Gly Leu Leu Arg Trp Arg Pro Ser Leu Leu Ser Val Ala Gln
                965                 970                 975

Gly Met Gln Leu Trp Leu Glu His Leu Val Tyr Cys Ala Ser Gly Gly
            980                 985                 990

Asn Gly Glu Ser Arg Leu Phe Leu Arg Lys Asp Gly Glu Trp Arg Phe
        995                 1000                1005

Pro Pro Leu Ala Ala Glu Gln Ala Leu His Tyr Leu Ser Gln Leu
        1010            1015                1020

Ile Glu Gly Tyr Arg Glu Gly Met Ser Ala Pro Leu Leu Val Leu
        1025            1030                1035

Pro Glu Ser Gly Gly Ala Trp Leu Lys Thr Cys Tyr Asp Ala Gln
        1040            1045                1050

Asn Asp Ala Met Leu Asp Asp Asp Ser Thr Leu Gln Lys Ala Arg
        1055            1060                1065

Thr Lys Phe Leu Gln Ala Tyr Glu Gly Asn Met Met Val Arg Gly
        1070            1075                1080

Glu Gly Asp Asp Ile Trp Tyr Gln Arg Leu Trp Arg Gln Leu Thr
        1085            1090                1095

Pro Glu Thr Met Glu Ala Ile Val Glu Gln Ser Gln Arg Phe Leu
        1100            1105                1110

Leu Pro Leu Phe Arg Phe Asn Gln Ser
        1115            1120
```

<210> SEQ ID NO 41
<211> LENGTH: 608
<212> TYPE: PRT
<213> ORGANISM: Escherichia coli

<400> SEQUENCE: 41

```
Met Lys Leu Gln Lys Gln Leu Glu Ala Val Glu His Lys Gln Leu
1               5                   10                  15

Arg Pro Leu Asp Val Gln Phe Ala Leu Thr Val Ala Gly Asp Glu His
                20                  25                  30

Pro Ala Val Thr Leu Ala Ala Ala Leu Leu Ser His Asp Ala Gly Glu
            35                  40                  45
```

```
Gly His Val Cys Leu Pro Leu Ser Arg Leu Glu Asn Asn Glu Ala Ser
    50                  55                  60

His Pro Leu Leu Ala Thr Cys Val Ser Glu Ile Gly Glu Leu Gln Asn
65                  70                  75                  80

Trp Glu Glu Cys Leu Leu Ala Ser Gln Ala Val Ser Arg Gly Asp Glu
                    85                  90                  95

Pro Thr Pro Met Ile Leu Cys Gly Asp Arg Leu Tyr Leu Asn Arg Met
                100                 105                 110

Trp Cys Asn Glu Arg Thr Val Ala Arg Phe Phe Asn Glu Val Asn His
            115                 120                 125

Ala Ile Glu Val Asp Glu Ala Leu Leu Ala Gln Thr Leu Asp Lys Leu
        130                 135                 140

Phe Pro Val Ser Asp Glu Ile Asn Trp Gln Lys Val Ala Ala Ala Val
145                 150                 155                 160

Ala Leu Thr Arg Arg Ile Ser Val Ile Ser Gly Gly Pro Gly Thr Gly
                165                 170                 175

Lys Thr Thr Thr Val Ala Lys Leu Leu Ala Ala Leu Ile Gln Met Ala
                180                 185                 190

Asp Gly Glu Arg Cys Arg Ile Arg Leu Ala Ala Pro Thr Gly Lys Ala
            195                 200                 205

Ala Ala Arg Leu Thr Glu Ser Leu Gly Lys Ala Leu Arg Gln Leu Pro
        210                 215                 220

Leu Thr Asp Glu Gln Lys Lys Arg Ile Pro Glu Asp Ala Ser Thr Leu
225                 230                 235                 240

His Arg Leu Leu Gly Ala Gln Pro Gly Ser Gln Arg Leu Arg His His
                245                 250                 255

Ala Gly Asn Pro Leu His Leu Asp Val Leu Val Val Asp Glu Ala Ser
                260                 265                 270

Met Ile Asp Leu Pro Met Met Ser Arg Leu Ile Asp Ala Leu Pro Asp
            275                 280                 285

His Ala Arg Val Ile Phe Leu Gly Asp Arg Asp Gln Leu Ala Ser Val
        290                 295                 300

Glu Ala Gly Ala Val Leu Gly Asp Ile Cys Ala Tyr Ala Asn Ala Gly
305                 310                 315                 320

Phe Thr Ala Glu Arg Ala Arg Gln Leu Ser Arg Leu Thr Gly Thr His
                325                 330                 335

Val Pro Ala Gly Thr Gly Thr Glu Ala Ala Ser Leu Arg Asp Ser Leu
                340                 345                 350

Cys Leu Leu Gln Lys Ser Tyr Arg Phe Gly Ser Asp Ser Gly Ile Gly
            355                 360                 365

Gln Leu Ala Ala Ala Ile Asn Arg Gly Asp Lys Thr Ala Val Lys Thr
        370                 375                 380

Val Phe Gln Gln Asp Phe Thr Asp Ile Glu Lys Arg Leu Leu Gln Ser
385                 390                 395                 400

Gly Glu Asp Tyr Ile Ala Met Leu Glu Glu Ala Leu Ala Gly Tyr Gly
                405                 410                 415

Arg Tyr Leu Asp Leu Leu Gln Ala Arg Ala Glu Pro Asp Leu Ile Ile
                420                 425                 430

Gln Ala Phe Asn Glu Tyr Gln Leu Leu Cys Ala Leu Arg Glu Gly Pro
            435                 440                 445

Phe Gly Val Ala Gly Leu Asn Glu Arg Ile Glu Gln Phe Met Gln Gln
450                 455                 460
```

```
Lys Arg Lys Ile His Arg His Pro His Ser Arg Trp Tyr Glu Gly Arg
465                 470                 475                 480

Pro Val Met Ile Ala Arg Asn Asp Ser Ala Leu Gly Leu Phe Asn Gly
            485                 490                 495

Asp Ile Gly Ile Ala Leu Asp Arg Gly Gln Gly Thr Arg Val Trp Phe
        500                 505                 510

Ala Met Pro Asp Gly Asn Ile Lys Ser Val Gln Pro Ser Arg Leu Pro
    515                 520                 525

Glu His Glu Thr Thr Trp Ala Met Thr Val His Lys Ser Gln Gly Ser
530                 535                 540

Glu Phe Asp His Ala Ala Leu Ile Leu Pro Ser Gln Arg Thr Pro Val
545                 550                 555                 560

Val Thr Arg Glu Leu Val Tyr Thr Ala Val Thr Arg Ala Arg Arg Arg
            565                 570                 575

Leu Ser Leu Tyr Ala Asp Glu Arg Ile Leu Ser Ala Ala Ile Ala Thr
        580                 585                 590

Arg Thr Glu Arg Arg Ser Gly Leu Ala Ala Leu Phe Ser Ser Arg Glu
            595                 600                 605

<210> SEQ ID NO 42
<211> LENGTH: 609
<212> TYPE: PRT
<213> ORGANISM: Escherichia coli

<400> SEQUENCE: 42

Met Ala Gln Ala Glu Val Leu Asn Leu Glu Ser Gly Ala Lys Gln Val
1               5                   10                  15

Leu Gln Glu Thr Phe Gly Tyr Gln Gln Phe Arg Pro Gly Gln Glu Glu
            20                  25                  30

Ile Ile Asp Thr Val Leu Ser Gly Arg Asp Cys Leu Val Val Met Pro
        35                  40                  45

Thr Gly Gly Gly Lys Ser Leu Cys Tyr Gln Ile Pro Ala Leu Leu Leu
    50                  55                  60

Asn Gly Leu Thr Val Val Val Ser Pro Leu Ile Ser Leu Met Lys Asp
65                  70                  75                  80

Gln Val Asp Gln Leu Gln Ala Asn Gly Val Ala Ala Ala Cys Leu Asn
                85                  90                  95

Ser Thr Gln Thr Arg Glu Gln Gln Leu Glu Val Met Thr Gly Cys Arg
            100                 105                 110

Thr Gly Gln Ile Arg Leu Leu Tyr Ile Ala Pro Glu Arg Leu Met Leu
        115                 120                 125

Asp Asn Phe Leu Glu His Leu Ala His Trp Asn Pro Val Leu Leu Ala
    130                 135                 140

Val Asp Glu Ala His Cys Ile Ser Gln Trp Gly His Asp Phe Arg Pro
145                 150                 155                 160

Glu Tyr Ala Ala Leu Gly Gln Leu Arg Gln Arg Phe Pro Thr Leu Pro
                165                 170                 175

Phe Met Ala Leu Thr Ala Thr Ala Asp Asp Thr Thr Arg Gln Asp Ile
            180                 185                 190

Val Arg Leu Leu Gly Leu Asn Asp Pro Leu Ile Gln Ile Ser Ser Phe
        195                 200                 205

Asp Arg Pro Asn Ile Arg Tyr Met Leu Met Glu Lys Phe Lys Pro Leu
    210                 215                 220

Asp Gln Leu Met Arg Tyr Val Gln Glu Gln Arg Gly Lys Ser Gly Ile
225                 230                 235                 240
```

```
Ile Tyr Cys Asn Ser Arg Ala Lys Val Glu Asp Thr Ala Ala Arg Leu
            245                 250                 255

Gln Ser Lys Gly Ile Ser Ala Ala Tyr His Ala Gly Leu Glu Asn
            260                 265                 270

Asn Val Arg Ala Asp Val Gln Glu Lys Phe Gln Arg Asp Asp Leu Gln
            275                 280                 285

Ile Val Val Ala Thr Val Ala Phe Gly Met Gly Ile Asn Lys Pro Asn
    290                 295                 300

Val Arg Phe Val Val His Phe Asp Ile Pro Arg Asn Ile Glu Ser Tyr
305                 310                 315                 320

Tyr Gln Glu Thr Gly Arg Ala Gly Arg Asp Gly Leu Pro Ala Glu Ala
                325                 330                 335

Met Leu Phe Tyr Asp Pro Ala Asp Met Ala Trp Leu Arg Arg Cys Leu
                340                 345                 350

Glu Glu Lys Pro Gln Gly Gln Leu Gln Asp Ile Glu Arg His Lys Leu
            355                 360                 365

Asn Ala Met Gly Ala Phe Ala Glu Ala Gln Thr Cys Arg Arg Leu Val
    370                 375                 380

Leu Leu Asn Tyr Phe Gly Glu Gly Arg Gln Glu Pro Cys Gly Asn Cys
385                 390                 395                 400

Asp Ile Cys Leu Asp Pro Pro Lys Gln Tyr Asp Gly Ser Thr Asp Ala
                405                 410                 415

Gln Ile Ala Leu Ser Thr Ile Gly Arg Val Asn Gln Arg Phe Gly Met
                420                 425                 430

Gly Tyr Val Val Glu Val Ile Arg Gly Ala Asn Asn Gln Arg Ile Arg
            435                 440                 445

Asp Tyr Gly His Asp Lys Leu Lys Val Tyr Gly Met Gly Arg Asp Lys
    450                 455                 460

Ser His Glu His Trp Val Ser Val Ile Arg Gln Leu Ile His Leu Gly
465                 470                 475                 480

Leu Val Thr Gln Asn Ile Ala Gln His Ser Ala Leu Gln Leu Thr Glu
                485                 490                 495

Ala Ala Arg Pro Val Leu Arg Gly Glu Ser Ser Leu Gln Leu Ala Val
                500                 505                 510

Pro Arg Ile Val Ala Leu Lys Pro Lys Ala Met Gln Lys Ser Phe Gly
            515                 520                 525

Gly Asn Tyr Asp Arg Lys Leu Phe Ala Lys Leu Arg Lys Leu Arg Lys
            530                 535                 540

Ser Ile Ala Asp Glu Ser Asn Val Pro Pro Tyr Val Val Phe Asn Asp
545                 550                 555                 560

Ala Thr Leu Ile Glu Met Ala Glu Gln Met Pro Ile Thr Ala Ser Glu
                565                 570                 575

Met Leu Ser Val Asn Gly Val Gly Met Arg Lys Leu Glu Arg Phe Gly
            580                 585                 590

Lys Pro Phe Met Ala Leu Ile Arg Ala His Val Asp Gly Asp Asp Glu
            595                 600                 605

Glu

<210> SEQ ID NO 43
<211> LENGTH: 508
<212> TYPE: PRT
<213> ORGANISM: Escherichia coli

<400> SEQUENCE: 43
```

```
Met Arg Leu Asn Pro Gly Gln Gln Ala Val Glu Phe Val Thr Gly
1               5                   10                  15

Pro Cys Leu Val Leu Ala Gly Ala Gly Ser Gly Lys Thr Arg Val Ile
            20                  25                  30

Thr Asn Lys Ile Ala His Leu Ile Arg Gly Cys Gly Tyr Gln Ala Arg
        35                  40                  45

His Ile Ala Ala Val Thr Phe Thr Asn Lys Ala Ala Arg Glu Met Lys
    50                  55                  60

Glu Arg Val Gly Gln Thr Leu Gly Arg Lys Glu Ala Arg Gly Leu Met
65                  70                  75                  80

Ile Ser Thr Phe His Thr Leu Gly Leu Asp Ile Ile Lys Arg Glu Tyr
                85                  90                  95

Ala Ala Leu Gly Met Lys Ala Asn Phe Ser Leu Phe Asp Asp Thr Asp
                100                 105                 110

Gln Leu Ala Leu Leu Lys Glu Leu Thr Glu Gly Leu Ile Glu Asp Asp
            115                 120                 125

Lys Val Leu Leu Gln Gln Leu Ile Ser Thr Ile Ser Asn Trp Lys Asn
            130                 135                 140

Asp Leu Lys Thr Pro Ala Gln Ala Ala Glu Ala Lys Gly Glu Arg
145                 150                 155                 160

Asp Arg Ile Phe Ala His Cys Tyr Gly Leu Tyr Asp Ala His Leu Lys
                165                 170                 175

Ala Cys Asn Val Leu Asp Phe Asp Asp Leu Ile Leu Leu Pro Thr Leu
                180                 185                 190

Leu Leu Gln Arg Asn Glu Glu Val Arg Glu Arg Trp Gln Asn Lys Ile
            195                 200                 205

Arg Tyr Leu Leu Val Asp Glu Tyr Gln Asp Thr Asn Thr Ser Gln Tyr
210                 215                 220

Glu Leu Val Lys Leu Leu Val Gly Ser Arg Ala Arg Phe Thr Val Val
225                 230                 235                 240

Gly Asp Asp Asp Gln Ser Ile Tyr Ser Trp Arg Gly Ala Arg Pro Gln
                245                 250                 255

Asn Leu Val Leu Leu Ser Gln Asp Phe Pro Ala Leu Lys Val Ile Lys
            260                 265                 270

Leu Glu Gln Asn Tyr Arg Ser Ser Gly Arg Ile Leu Lys Ala Ala Asn
            275                 280                 285

Ile Leu Ile Ala Asn Asn Pro His Val Phe Glu Lys Arg Leu Phe Ser
290                 295                 300

Glu Leu Gly Tyr Gly Thr Glu Leu Lys Val Leu Ser Ala Asn Asn Glu
305                 310                 315                 320

Glu His Glu Ala Glu Arg Val Thr Gly Glu Leu Ile Ala His His Phe
                325                 330                 335

Val Asn Lys Thr Gln Tyr Lys Asp Tyr Ala Ile Leu Tyr Arg Gly Asn
            340                 345                 350

His Gln Ser Arg Val Phe Glu Lys Phe Leu Met Gln Asn Arg Ile Pro
        355                 360                 365

Tyr Lys Ile Ser Gly Gly Gly Gly Gly Glu Ser Glu Glu Glu Leu
370                 375                 380

Asp Gln Val Gln Leu Met Thr Leu His Ala Ser Lys Gly Leu Glu Phe
385                 390                 395                 400

Pro Tyr Val Tyr Met Val Gly Met Glu Glu Gly Phe Leu Pro His Gln
                405                 410                 415
```

```
Ser Ser Ile Asp Glu Asp Asn Ile Asp Glu Arg Arg Leu Ala Tyr
            420                 425                 430

Val Gly Ile Thr Arg Ala Gln Lys Glu Leu Thr Phe Thr Leu Cys Lys
            435                 440                 445

Glu Arg Arg Gln Tyr Gly Glu Leu Val Arg Pro Glu Pro Ser Arg Phe
450                 455                 460

Leu Leu Glu Leu Pro Gln Asp Leu Ile Trp Gln Glu Arg Lys
465                 470                 475                 480

Val Val Ser Ala Glu Arg Met Gln Lys Gly Gln Ser His Leu Ala
                485                 490                 495

Asn Leu Lys Ala Met Met Ala Ala Lys Arg Gly Lys
            500                 505

<210> SEQ ID NO 44
<211> LENGTH: 720
<212> TYPE: PRT
<213> ORGANISM: Escherichia coli

<400> SEQUENCE: 44

Met Asp Val Ser Tyr Leu Leu Asp Ser Leu Asn Asp Lys Gln Arg Glu
1               5                   10                  15

Ala Val Ala Ala Pro Arg Ser Asn Leu Leu Val Leu Ala Gly Ala Gly
            20                  25                  30

Ser Gly Lys Thr Arg Val Leu Val His Arg Ile Ala Trp Leu Met Ser
            35                  40                  45

Val Glu Asn Cys Ser Pro Tyr Ser Ile Met Ala Val Thr Phe Thr Asn
        50                  55                  60

Lys Ala Ala Ala Glu Met Arg His Arg Ile Gly Gln Leu Met Gly Thr
65                  70                  75                  80

Ser Gln Gly Gly Met Trp Val Gly Thr Phe His Gly Leu Ala His Arg
                85                  90                  95

Leu Leu Arg Ala His His Met Asp Ala Asn Leu Pro Gln Asp Phe Gln
            100                 105                 110

Ile Leu Asp Ser Glu Asp Gln Leu Arg Leu Leu Lys Arg Leu Ile Lys
        115                 120                 125

Ala Met Asn Leu Asp Glu Lys Gln Trp Pro Pro Arg Gln Ala Met Trp
130                 135                 140

Tyr Ile Asn Ser Gln Lys Asp Glu Gly Leu Arg Pro His His Ile Gln
145                 150                 155                 160

Ser Tyr Gly Asn Pro Val Glu Gln Thr Trp Gln Lys Val Tyr Gln Ala
                165                 170                 175

Tyr Gln Glu Ala Cys Asp Arg Ala Gly Leu Val Asp Phe Ala Glu Leu
            180                 185                 190

Leu Leu Arg Ala His Glu Leu Trp Leu Asn Lys Pro His Ile Leu Gln
        195                 200                 205

His Tyr Arg Glu Arg Phe Thr Asn Ile Leu Val Asp Glu Phe Gln Asp
210                 215                 220

Thr Asn Asn Ile Gln Tyr Ala Trp Ile Arg Leu Leu Ala Gly Asp Thr
225                 230                 235                 240

Gly Lys Val Met Ile Val Gly Asp Asp Gln Ser Ile Tyr Gly Trp
                245                 250                 255

Arg Gly Ala Gln Val Glu Asn Ile Gln Arg Phe Leu Asn Asp Phe Pro
            260                 265                 270

Gly Ala Glu Thr Ile Arg Leu Glu Gln Asn Tyr Arg Ser Thr Ser Asn
        275                 280                 285
```

```
Ile Leu Ser Ala Ala Asn Ala Leu Ile Glu Asn Asn Gly Arg Leu
    290                 295                 300

Gly Lys Lys Leu Trp Thr Asp Gly Ala Asp Gly Glu Pro Ile Ser Leu
305                 310                 315                 320

Tyr Cys Ala Phe Asn Glu Leu Asp Glu Ala Arg Phe Val Val Asn Arg
                325                 330                 335

Ile Lys Thr Trp Gln Asp Asn Gly Gly Ala Leu Ala Glu Cys Ala Ile
            340                 345                 350

Leu Tyr Arg Ser Asn Ala Gln Ser Arg Val Leu Glu Glu Ala Leu Leu
                355                 360                 365

Gln Ala Ser Met Pro Tyr Arg Ile Tyr Gly Gly Met Arg Phe Phe Glu
    370                 375                 380

Arg Gln Glu Ile Lys Asp Ala Leu Ser Tyr Leu Arg Leu Ile Ala Asn
385                 390                 395                 400

Arg Asn Asp Asp Ala Ala Phe Glu Arg Val Val Asn Thr Pro Thr Arg
                405                 410                 415

Gly Ile Gly Asp Arg Thr Leu Asp Val Val Arg Gln Thr Ser Arg Asp
            420                 425                 430

Arg Gln Leu Thr Leu Trp Gln Ala Cys Arg Glu Leu Leu Gln Glu Lys
    435                 440                 445

Ala Leu Ala Gly Arg Ala Ala Ser Ala Leu Gln Arg Phe Met Glu Leu
450                 455                 460

Ile Asp Ala Leu Ala Gln Glu Thr Ala Asp Met Pro Leu His Val Gln
465                 470                 475                 480

Thr Asp Arg Val Ile Lys Asp Ser Gly Leu Arg Thr Met Tyr Glu Gln
                485                 490                 495

Glu Lys Gly Glu Lys Gly Gln Thr Arg Ile Glu Asn Leu Glu Glu Leu
            500                 505                 510

Val Thr Ala Thr Arg Gln Phe Ser Tyr Asn Glu Glu Asp Glu Asp Leu
    515                 520                 525

Met Pro Leu Gln Ala Phe Leu Ser His Ala Ala Leu Glu Ala Gly Glu
530                 535                 540

Gly Gln Ala Asp Thr Trp Gln Asp Ala Val Gln Leu Met Thr Leu His
545                 550                 555                 560

Ser Ala Lys Gly Leu Glu Phe Pro Gln Val Phe Ile Val Gly Met Glu
                565                 570                 575

Glu Gly Met Phe Pro Ser Gln Met Ser Leu Asp Glu Gly Gly Arg Leu
            580                 585                 590

Glu Glu Glu Arg Arg Leu Ala Tyr Val Gly Val Thr Arg Ala Met Gln
    595                 600                 605

Lys Leu Thr Leu Thr Tyr Ala Glu Thr Arg Arg Leu Tyr Gly Lys Glu
610                 615                 620

Val Tyr His Arg Pro Ser Arg Phe Ile Gly Glu Leu Pro Glu Glu Cys
625                 630                 635                 640

Val Glu Glu Val Arg Leu Arg Ala Thr Val Ser Arg Pro Val Ser His
                645                 650                 655

Gln Arg Met Gly Thr Pro Met Val Glu Asn Asp Ser Gly Tyr Lys Leu
            660                 665                 670

Gly Gln Arg Val Arg His Ala Lys Phe Gly Glu Gly Thr Ile Val Asn
    675                 680                 685

Met Glu Gly Ser Gly Glu His Ser Arg Leu Gln Val Ala Phe Gln Gly
    690                 695                 700
```

```
Gln Gly Ile Lys Trp Leu Val Ala Ala Tyr Ala Arg Leu Glu Ser Val
705                 710                 715                 720

<210> SEQ ID NO 45
<211> LENGTH: 968
<212> TYPE: PRT
<213> ORGANISM: Escherichia coli

<400> SEQUENCE: 45

Met Pro Phe Thr Leu Gly Gln Arg Trp Ile Ser Asp Thr Glu Ser Glu
1               5                   10                  15

Leu Gly Leu Gly Thr Val Val Ala Val Asp Ala Arg Thr Val Thr Leu
                20                  25                  30

Leu Phe Pro Ser Thr Gly Glu Asn Arg Leu Tyr Ala Arg Ser Asp Ser
            35                  40                  45

Pro Val Thr Arg Val Met Phe Asn Pro Gly Asp Thr Ile Thr Ser His
    50                  55                  60

Asp Gly Trp Gln Met Gln Val Glu Glu Val Lys Glu Glu Asn Gly Leu
65                  70                  75                  80

Leu Thr Tyr Ile Gly Thr Arg Leu Asp Thr Glu Glu Ser Gly Val Ala
                85                  90                  95

Leu Arg Glu Val Phe Leu Asp Ser Lys Leu Val Phe Ser Lys Pro Gln
            100                 105                 110

Asp Arg Leu Phe Ala Gly Gln Ile Asp Arg Met Asp Arg Phe Ala Leu
        115                 120                 125

Arg Tyr Arg Ala Arg Lys Tyr Ser Ser Glu Gln Phe Arg Met Pro Tyr
130                 135                 140

Ser Gly Leu Arg Gly Gln Arg Thr Ser Leu Ile Pro His Gln Leu Asn
145                 150                 155                 160

Ile Ala His Asp Val Gly Arg Arg His Ala Pro Arg Val Leu Leu Ala
                165                 170                 175

Asp Glu Val Gly Leu Gly Lys Thr Ile Glu Ala Gly Met Ile Leu His
            180                 185                 190

Gln Gln Leu Leu Ser Gly Ala Ala Glu Arg Val Leu Ile Ile Val Pro
        195                 200                 205

Glu Thr Leu Gln His Gln Trp Leu Val Glu Met Leu Arg Arg Phe Asn
210                 215                 220

Leu Arg Phe Ala Leu Phe Asp Asp Glu Arg Tyr Ala Glu Ala Gln His
225                 230                 235                 240

Asp Ala Tyr Asn Pro Phe Asp Thr Glu Gln Leu Val Ile Cys Ser Leu
                245                 250                 255

Asp Phe Ala Arg Arg Ser Lys Gln Arg Leu Glu His Leu Cys Glu Ala
            260                 265                 270

Glu Trp Asp Leu Leu Val Val Asp Glu Ala His His Leu Val Trp Ser
        275                 280                 285

Glu Asp Ala Pro Ser Arg Glu Tyr Gln Ala Ile Glu Gln Leu Ala Glu
290                 295                 300

His Val Pro Gly Val Leu Leu Thr Ala Thr Pro Glu Gln Leu Gly
305                 310                 315                 320

Met Glu Ser His Phe Ala Arg Leu Arg Leu Leu Asp Pro Asn Arg Phe
                325                 330                 335

His Asp Phe Ala Gln Phe Val Glu Glu Gln Lys Asn Tyr Arg Pro Val
            340                 345                 350

Ala Asp Ala Val Ala Met Leu Leu Ala Gly Asn Lys Leu Ser Asn Asp
        355                 360                 365
```

```
Glu Leu Asn Met Leu Gly Glu Met Ile Gly Glu Gln Asp Ile Glu Pro
            370                 375                 380

Leu Leu Gln Ala Ala Asn Ser Asp Ser Glu Asp Ala Gln Ser Ala Arg
385                 390                 395                 400

Gln Glu Leu Val Ser Met Leu Met Asp Arg His Gly Thr Ser Arg Val
                405                 410                 415

Leu Phe Arg Asn Thr Arg Asn Gly Val Lys Gly Phe Pro Lys Arg Glu
            420                 425                 430

Leu His Thr Ile Lys Leu Pro Leu Pro Thr Gln Tyr Gln Thr Ala Ile
            435                 440                 445

Lys Val Ser Gly Ile Met Gly Ala Arg Lys Ser Ala Glu Asp Arg Ala
        450                 455                 460

Arg Asp Met Leu Tyr Pro Glu Arg Ile Tyr Gln Glu Phe Glu Gly Asp
465                 470                 475                 480

Asn Ala Thr Trp Trp Asn Phe Asp Pro Arg Val Glu Trp Leu Met Gly
                485                 490                 495

Tyr Leu Thr Ser His Arg Ser Gln Lys Val Leu Val Ile Cys Ala Lys
            500                 505                 510

Ala Ala Thr Ala Leu Gln Leu Glu Gln Val Leu Arg Glu Arg Glu Gly
        515                 520                 525

Ile Arg Ala Ala Val Phe His Glu Gly Met Ser Ile Ile Glu Arg Asp
        530                 535                 540

Arg Ala Ala Ala Trp Phe Ala Glu Glu Asp Thr Gly Ala Gln Val Leu
545                 550                 555                 560

Leu Cys Ser Glu Ile Gly Ser Glu Gly Arg Asn Phe Gln Phe Ala Ser
                565                 570                 575

His Met Val Met Phe Asp Leu Pro Phe Asn Pro Asp Leu Leu Glu Gln
                580                 585                 590

Arg Ile Gly Arg Leu Asp Arg Ile Gly Gln Ala His Asp Ile Gln Ile
            595                 600                 605

His Val Pro Tyr Leu Glu Lys Thr Ala Gln Ser Val Leu Val Arg Trp
            610                 615                 620

Tyr His Glu Gly Leu Asp Ala Phe Glu His Thr Cys Pro Thr Gly Arg
625                 630                 635                 640

Thr Ile Tyr Asp Ser Val Tyr Asn Asp Leu Ile Asn Tyr Leu Ala Ser
                645                 650                 655

Pro Asp Gln Thr Glu Gly Phe Asp Asp Leu Ile Lys Asn Cys Arg Glu
            660                 665                 670

Gln His Glu Ala Leu Lys Ala Gln Leu Glu Gln Gly Arg Asp Arg Leu
        675                 680                 685

Leu Glu Ile His Ser Asn Gly Gly Glu Lys Ala Gln Ala Leu Ala Glu
        690                 695                 700

Ser Ile Glu Glu Gln Asp Asp Thr Asn Leu Ile Ala Phe Ala Met
705                 710                 715                 720

Asn Leu Phe Asp Ile Ile Gly Ile Asn Gln Asp Arg Gly Asp Asn
            725                 730                 735

Met Ile Val Leu Thr Pro Ser Asp His Met Leu Val Pro Asp Phe Pro
            740                 745                 750

Gly Leu Ser Glu Asp Gly Ile Thr Ile Thr Phe Asp Arg Glu Val Ala
            755                 760                 765

Leu Ala Arg Glu Asp Ala Gln Phe Ile Thr Trp Glu His Pro Leu Ile
770                 775                 780
```

Arg Asn Gly Leu Asp Leu Ile Leu Ser Gly Asp Thr Gly Ser Ser Thr
785                 790                 795                 800

Ile Ser Leu Leu Lys Asn Lys Ala Leu Pro Val Gly Thr Leu Leu Val
                805                 810                 815

Glu Leu Ile Tyr Val Val Glu Ala Gln Ala Pro Lys Gln Leu Gln Leu
            820                 825                 830

Asn Arg Phe Leu Pro Pro Thr Pro Val Arg Met Leu Leu Asp Lys Asn
        835                 840                 845

Gly Asn Asn Leu Ala Ala Gln Val Glu Phe Glu Thr Phe Asn Arg Gln
    850                 855                 860

Leu Asn Ala Val Asn Arg His Thr Gly Ser Lys Leu Val Asn Ala Val
865                 870                 875                 880

Gln Gln Asp Val His Ala Ile Leu Gln Leu Gly Glu Ala Gln Ile Glu
                885                 890                 895

Lys Ser Ala Arg Ala Leu Ile Asp Ala Ala Arg Asn Glu Ala Asp Glu
            900                 905                 910

Lys Leu Ser Ala Glu Leu Ser Arg Leu Glu Ala Leu Arg Ala Val Asn
        915                 920                 925

Pro Asn Ile Arg Asp Asp Glu Leu Thr Ala Ile Glu Ser Asn Arg Gln
    930                 935                 940

Gln Val Met Glu Ser Leu Asp Gln Ala Gly Trp Arg Leu Asp Ala Leu
945                 950                 955                 960

Arg Leu Ile Val Val Thr His Gln
                965

<210> SEQ ID NO 46
<211> LENGTH: 693
<212> TYPE: PRT
<213> ORGANISM: Escherichia coli

<400> SEQUENCE: 46

Met Lys Gly Arg Leu Leu Asp Ala Val Pro Leu Ser Ser Leu Thr Gly
1               5                   10                  15

Val Gly Ala Ala Leu Ser Asn Lys Leu Ala Lys Ile Asn Leu His Thr
            20                  25                  30

Val Gln Asp Leu Leu Leu His Leu Pro Leu Arg Tyr Glu Asp Arg Thr
        35                  40                  45

His Leu Tyr Pro Ile Gly Glu Leu Leu Pro Gly Val Tyr Ala Thr Val
    50                  55                  60

Glu Gly Glu Val Leu Asn Cys Asn Ile Ser Phe Gly Gly Arg Arg Met
65                  70                  75                  80

Met Thr Cys Gln Ile Ser Asp Gly Ser Gly Ile Leu Thr Met Arg Phe
                85                  90                  95

Phe Asn Phe Ser Ala Ala Met Lys Asn Ser Leu Ala Ala Gly Arg Arg
            100                 105                 110

Val Leu Ala Tyr Gly Glu Ala Lys Arg Gly Lys Tyr Gly Ala Glu Met
        115                 120                 125

Ile His Pro Glu Tyr Arg Val Gln Gly Asp Leu Ser Thr Pro Glu Leu
    130                 135                 140

Gln Glu Thr Leu Thr Pro Val Tyr Pro Thr Thr Glu Gly Val Lys Gln
145                 150                 155                 160

Ala Thr Leu Arg Lys Leu Thr Asp Gln Ala Leu Asp Leu Leu Asp Thr
                165                 170                 175

Cys Ala Ile Glu Glu Leu Leu Pro Pro Glu Leu Ser Gln Gly Met Met
            180                 185                 190

```
Thr Leu Pro Glu Ala Leu Arg Thr Leu His Arg Pro Pro Thr Leu
            195                 200                 205

Gln Leu Ser Asp Leu Glu Thr Gly Gln His Pro Ala Gln Arg Arg Leu
    210                 215                 220

Ile Leu Glu Glu Leu Leu Ala His Asn Leu Ser Met Leu Ala Leu Arg
225                 230                 235                 240

Ala Gly Ala Gln Arg Phe His Ala Gln Pro Leu Ser Ala Asn Asp Thr
                245                 250                 255

Leu Lys Asn Lys Leu Leu Ala Ala Leu Pro Phe Lys Pro Thr Gly Ala
            260                 265                 270

Gln Ala Arg Val Val Ala Glu Ile Glu Arg Asp Met Ala Leu Asp Val
        275                 280                 285

Pro Met Met Arg Leu Val Gln Gly Asp Val Gly Ser Gly Lys Thr Leu
        290                 295                 300

Val Ala Ala Leu Ala Ala Leu Arg Ala Ile Ala His Gly Lys Gln Val
305                 310                 315                 320

Ala Leu Met Ala Pro Thr Glu Leu Leu Ala Glu Gln His Ala Asn Asn
                325                 330                 335

Phe Arg Asn Trp Phe Ala Pro Leu Gly Ile Glu Val Gly Trp Leu Ala
            340                 345                 350

Gly Lys Gln Lys Gly Lys Ala Arg Leu Ala Gln Gln Glu Ala Ile Ala
        355                 360                 365

Ser Gly Gln Val Gln Met Ile Val Gly Thr His Ala Ile Phe Gln Glu
    370                 375                 380

Gln Val Gln Phe Asn Gly Leu Ala Leu Val Ile Asp Glu Gln His
385                 390                 395                 400

Arg Phe Gly Val His Gln Arg Leu Ala Leu Trp Glu Lys Gly Gln Gln
                405                 410                 415

Gln Gly Phe His Pro His Gln Leu Ile Met Thr Ala Thr Pro Ile Pro
            420                 425                 430

Arg Thr Leu Ala Met Thr Ala Tyr Ala Asp Leu Asp Thr Ser Val Ile
        435                 440                 445

Asp Glu Leu Pro Pro Gly Arg Thr Pro Val Thr Thr Val Ala Ile Pro
    450                 455                 460

Asp Thr Arg Arg Thr Asp Ile Ile Asp Arg Val His His Ala Cys Ile
465                 470                 475                 480

Thr Glu Gly Arg Gln Ala Tyr Trp Val Cys Thr Leu Ile Glu Glu Ser
                485                 490                 495

Glu Leu Leu Glu Ala Gln Ala Ala Glu Ala Thr Trp Glu Glu Leu Lys
            500                 505                 510

Leu Ala Leu Pro Glu Leu Asn Val Gly Leu Val His Gly Arg Met Lys
        515                 520                 525

Pro Ala Glu Lys Gln Ala Val Met Ala Ser Phe Lys Gln Gly Glu Leu
    530                 535                 540

His Leu Leu Val Ala Thr Thr Val Ile Glu Val Gly Val Asp Val Pro
545                 550                 555                 560

Asn Ala Ser Leu Met Ile Ile Glu Asn Pro Glu Arg Leu Gly Leu Ala
                565                 570                 575

Gln Leu His Gln Leu Arg Gly Arg Val Gly Arg Gly Ala Val Ala Ser
            580                 585                 590

His Cys Val Leu Leu Tyr Lys Thr Pro Leu Ser Lys Thr Ala Gln Ile
        595                 600                 605
```

```
Arg Leu Gln Val Leu Arg Asp Ser Asn Asp Gly Phe Val Ile Ala Gln
    610                 615                 620

Lys Asp Leu Glu Ile Arg Gly Pro Gly Glu Leu Leu Gly Thr Arg Gln
625                 630                 635                 640

Thr Gly Asn Ala Glu Phe Lys Val Ala Asp Leu Leu Arg Asp Gln Ala
                645                 650                 655

Met Ile Pro Glu Val Gln Arg Leu Ala Arg His Ile His Glu Arg Tyr
            660                 665                 670

Pro Gln Gln Ala Lys Ala Leu Ile Glu Arg Trp Met Pro Glu Thr Glu
                675                 680                 685

Arg Tyr Ser Asn Ala
    690

<210> SEQ ID NO 47
<211> LENGTH: 467
<212> TYPE: PRT
<213> ORGANISM: Homo sapiens

<400> SEQUENCE: 47

Met Ser Leu Ser Leu Trp Gln Gln Cys Leu Ala Arg Leu Gln Asp Glu
1               5                   10                  15

Leu Pro Ala Thr Glu Phe Ser Met Trp Ile Arg Pro Leu Gln Ala Glu
            20                  25                  30

Leu Ser Asp Asn Thr Leu Ala Leu Tyr Ala Pro Asn Arg Phe Val Leu
        35                  40                  45

Asp Trp Val Arg Asp Lys Tyr Leu Asn Asn Ile Asn Gly Leu Leu Thr
    50                  55                  60

Ser Phe Cys Gly Ala Asp Ala Pro Gln Leu Arg Phe Glu Val Gly Thr
65                  70                  75                  80

Lys Pro Val Thr Gln Thr Pro Gln Ala Ala Val Thr Ser Asn Val Ala
                85                  90                  95

Ala Pro Ala Gln Val Ala Gln Thr Gln Pro Gln Arg Ala Ala Pro Ser
            100                 105                 110

Thr Arg Ser Gly Trp Asp Asn Val Pro Ala Pro Ala Glu Pro Thr Tyr
        115                 120                 125

Arg Ser Asn Val Asn Val Lys His Thr Phe Asp Asn Phe Val Glu Gly
    130                 135                 140

Lys Ser Asn Gln Leu Ala Arg Ala Ala Arg Gln Val Ala Asp Asn
145                 150                 155                 160

Pro Gly Gly Ala Tyr Asn Pro Leu Phe Leu Tyr Gly Gly Thr Gly Leu
                165                 170                 175

Gly Lys Thr His Leu Leu His Ala Val Gly Asn Gly Ile Met Ala Arg
            180                 185                 190

Lys Pro Asn Ala Lys Val Val Tyr Met His Ser Glu Arg Phe Val Gln
        195                 200                 205

Asp Met Val Lys Ala Leu Gln Asn Asn Ala Ile Glu Glu Phe Lys Arg
    210                 215                 220

Tyr Tyr Arg Ser Val Asp Ala Leu Leu Ile Asp Asp Ile Gln Phe Phe
225                 230                 235                 240

Ala Asn Lys Glu Arg Ser Gln Glu Glu Phe Phe His Thr Phe Asn Ala
                245                 250                 255

Leu Leu Glu Gly Asn Gln Gln Ile Ile Leu Thr Ser Asp Arg Tyr Pro
            260                 265                 270

Lys Glu Ile Asn Gly Val Glu Asp Arg Leu Lys Ser Arg Phe Gly Trp
        275                 280                 285
```

```
Gly Leu Thr Val Ala Ile Glu Pro Pro Glu Leu Glu Thr Arg Val Ala
            290                 295                 300

Ile Leu Met Lys Lys Ala Asp Glu Asn Asp Ile Arg Leu Pro Gly Glu
305                 310                 315                 320

Val Ala Phe Phe Ile Ala Lys Arg Leu Arg Ser Asn Val Arg Glu Leu
                325                 330                 335

Glu Gly Ala Leu Asn Arg Val Ile Ala Asn Ala Asn Phe Thr Gly Arg
            340                 345                 350

Ala Ile Thr Ile Asp Phe Val Arg Glu Ala Leu Arg Asp Leu Leu Ala
            355                 360                 365

Leu Gln Glu Lys Leu Val Thr Ile Asp Asn Ile Gln Lys Thr Val Ala
            370                 375                 380

Glu Tyr Tyr Lys Ile Lys Val Ala Asp Leu Leu Ser Lys Arg Arg Ser
385                 390                 395                 400

Arg Ser Val Ala Arg Pro Arg Gln Met Ala Met Ala Leu Ala Lys Glu
                405                 410                 415

Leu Thr Asn His Ser Leu Pro Glu Ile Gly Asp Ala Phe Gly Gly Arg
            420                 425                 430

Asp His Thr Thr Val Leu His Ala Cys Arg Lys Ile Glu Gln Leu Arg
            435                 440                 445

Glu Glu Ser His Asp Ile Lys Glu Asp Phe Ser Asn Leu Ile Arg Thr
450                 455                 460

Leu Ser Ser
465

<210> SEQ ID NO 48
<211> LENGTH: 215
<212> TYPE: PRT
<213> ORGANISM: Homo sapiens

<400> SEQUENCE: 48

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
                20                  25                  30

Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
        50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Lys Glu Glu Glu Glu Asp Glu Glu
```

```
                180             185             190
Asp Glu Glu Asp Glu Glu Glu Asp Glu Asp Glu Asp Glu
            195                 200             205

Glu Glu Asp Asp Asp Glu
        210             215

<210> SEQ ID NO 49
<211> LENGTH: 209
<212> TYPE: PRT
<213> ORGANISM: Homo sapiens

<400> SEQUENCE: 49

Met Gly Lys Gly Asp Pro Asn Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ser Ser Val Asn Phe Ala Glu Phe Ser Lys Lys Cys Ser Glu Arg
        35                  40                  45

Trp Lys Thr Met Ser Ala Lys Glu Lys Ser Lys Phe Glu Asp Met Ala
    50                  55                  60

Lys Ser Asp Lys Ala Arg Tyr Asp Arg Glu Met Lys Asn Tyr Val Pro
65                  70                  75                  80

Pro Lys Gly Asp Lys Lys Gly Lys Lys Asp Pro Asn Ala Pro Lys
                85                  90                  95

Arg Pro Pro Ser Ala Phe Phe Leu Phe Cys Ser Glu His Arg Pro Lys
            100                 105                 110

Ile Lys Ser Glu His Pro Gly Leu Ser Ile Gly Asp Thr Ala Lys Lys
        115                 120                 125

Leu Gly Glu Met Trp Ser Glu Gln Ser Ala Lys Asp Lys Gln Pro Tyr
    130                 135                 140

Glu Gln Lys Ala Ala Lys Leu Lys Glu Lys Tyr Glu Lys Asp Ile Ala
145                 150                 155                 160

Ala Tyr Arg Ala Lys Gly Lys Ser Glu Ala Gly Lys Lys Gly Pro Gly
                165                 170                 175

Arg Pro Thr Gly Ser Lys Lys Lys Asn Glu Pro Glu Asp Glu Glu Glu
            180                 185                 190

Glu Glu Glu Glu Glu Asp Glu Asp Glu Glu Glu Asp Glu Asp Glu
        195                 200                 205

Glu

<210> SEQ ID NO 50
<211> LENGTH: 616
<212> TYPE: PRT
<213> ORGANISM: Homo sapiens

<400> SEQUENCE: 50

Met Val Gly Gln Leu Ser Glu Gly Ala Ile Ala Ile Met Gln Lys
1               5                   10                  15

Gly Asp Thr Asn Ile Lys Pro Ile Leu Gln Val Ile Asn Ile Arg Pro
            20                  25                  30

Ile Thr Thr Gly Asn Ser Pro Pro Arg Tyr Arg Leu Leu Met Ser Asp
        35                  40                  45

Gly Leu Asn Thr Leu Ser Ser Phe Met Leu Ala Thr Gln Leu Asn Pro
    50                  55                  60

Leu Val Glu Glu Glu Gln Leu Ser Ser Asn Cys Val Cys Gln Ile His
65                  70                  75                  80
```

```
Arg Phe Ile Val Asn Thr Leu Lys Asp Gly Arg Val Val Ile Leu
                 85                  90                  95

Met Glu Leu Glu Val Leu Lys Ser Ala Glu Ala Val Gly Val Lys Ile
            100                 105                 110

Gly Asn Pro Val Pro Tyr Asn Glu Gly Leu Gly Gln Pro Gln Val Ala
        115                 120                 125

Pro Pro Ala Pro Ala Ala Ser Pro Ala Ala Ser Ser Arg Pro Gln Pro
130                 135                 140

Gln Asn Gly Ser Ser Gly Met Gly Ser Thr Val Ser Lys Ala Tyr Gly
145                 150                 155                 160

Ala Ser Lys Thr Phe Gly Lys Ala Ala Gly Pro Ser Leu Ser His Thr
                165                 170                 175

Ser Gly Gly Thr Gln Ser Lys Val Val Pro Ile Ala Ser Leu Thr Pro
            180                 185                 190

Tyr Gln Ser Lys Trp Thr Ile Cys Ala Arg Val Thr Asn Lys Ser Gln
        195                 200                 205

Ile Arg Thr Trp Ser Asn Ser Arg Gly Glu Gly Lys Leu Phe Ser Leu
210                 215                 220

Glu Leu Val Asp Glu Ser Gly Glu Ile Arg Ala Thr Ala Phe Asn Glu
225                 230                 235                 240

Gln Val Asp Lys Phe Phe Pro Leu Ile Glu Val Asn Lys Val Tyr Tyr
                245                 250                 255

Phe Ser Lys Gly Thr Leu Lys Ile Ala Asn Lys Gln Phe Thr Ala Val
            260                 265                 270

Lys Asn Asp Tyr Glu Met Thr Phe Asn Asn Glu Thr Ser Val Met Pro
        275                 280                 285

Cys Glu Asp Asp His His Leu Pro Thr Val Gln Phe Asp Phe Thr Gly
290                 295                 300

Ile Asp Asp Leu Glu Asn Lys Ser Lys Asp Ser Leu Val Asp Ile Ile
305                 310                 315                 320

Gly Ile Cys Lys Ser Tyr Glu Asp Ala Thr Lys Ile Thr Val Arg Ser
                325                 330                 335

Asn Asn Arg Glu Val Ala Lys Arg Asn Ile Tyr Leu Met Asp Thr Ser
            340                 345                 350

Gly Lys Val Val Thr Ala Thr Leu Trp Gly Glu Asp Ala Asp Lys Phe
        355                 360                 365

Asp Gly Ser Arg Gln Pro Val Leu Ala Ile Lys Gly Ala Arg Val Ser
370                 375                 380

Asp Phe Gly Gly Arg Ser Leu Ser Val Leu Ser Ser Thr Ile Ile
385                 390                 395                 400

Ala Asn Pro Asp Ile Pro Glu Ala Tyr Lys Leu Arg Gly Trp Phe Asp
                405                 410                 415

Ala Glu Gly Gln Ala Leu Asp Gly Val Ser Ile Ser Asp Leu Lys Ser
            420                 425                 430

Gly Gly Val Gly Gly Ser Asn Thr Asn Trp Lys Thr Leu Tyr Glu Val
        435                 440                 445

Lys Ser Glu Asn Leu Gly Gln Gly Asp Lys Pro Asp Tyr Phe Ser Ser
450                 455                 460

Val Ala Thr Val Val Tyr Leu Arg Lys Glu Asn Cys Met Tyr Gln Ala
465                 470                 475                 480

Cys Pro Thr Gln Asp Cys Asn Lys Lys Val Ile Asp Gln Gln Asn Gly
                485                 490                 495
```

```
Leu Tyr Arg Cys Glu Lys Cys Asp Thr Glu Phe Pro Asn Phe Lys Tyr
                500                 505                 510

Arg Met Ile Leu Ser Val Asn Ile Ala Asp Phe Gln Glu Asn Gln Trp
            515                 520                 525

Val Thr Cys Phe Gln Glu Ser Ala Glu Ala Ile Leu Gly Gln Asn Ala
        530                 535                 540

Ala Tyr Leu Gly Glu Leu Lys Asp Lys Asn Glu Gln Ala Phe Glu Glu
545                 550                 555                 560

Val Phe Gln Asn Ala Asn Phe Arg Ser Phe Ile Phe Arg Val Arg Val
                565                 570                 575

Lys Val Glu Thr Tyr Asn Asp Glu Ser Arg Ile Lys Ala Thr Val Met
            580                 585                 590

Asp Val Lys Pro Val Asp Tyr Arg Glu Tyr Gly Arg Arg Leu Val Met
        595                 600                 605

Ser Ile Arg Arg Ser Ala Leu Met
    610                 615

<210> SEQ ID NO 51
<211> LENGTH: 270
<212> TYPE: PRT
<213> ORGANISM: Homo sapiens

<400> SEQUENCE: 51

Met Trp Asn Ser Gly Phe Glu Ser Tyr Gly Ser Ser Tyr Gly Gly
1               5                   10                  15

Ala Gly Gly Tyr Thr Gln Ser Pro Gly Gly Phe Gly Ser Pro Ala Pro
            20                  25                  30

Ser Gln Ala Glu Lys Lys Ser Arg Ala Arg Ala Gln His Ile Val Pro
        35                  40                  45

Cys Thr Ile Ser Gln Leu Leu Ser Ala Thr Leu Val Asp Glu Val Phe
    50                  55                  60

Arg Ile Gly Asn Val Glu Ile Ser Gln Val Thr Ile Val Gly Ile Ile
65                  70                  75                  80

Arg His Ala Glu Lys Ala Pro Thr Asn Ile Val Tyr Lys Ile Asp Asp
                85                  90                  95

Met Thr Ala Ala Pro Met Asp Val Arg Gln Trp Val Asp Thr Asp Asp
            100                 105                 110

Thr Ser Ser Glu Asn Thr Val Val Pro Pro Glu Thr Tyr Val Lys Val
        115                 120                 125

Ala Gly His Leu Arg Ser Phe Gln Asn Lys Lys Ser Leu Val Ala Phe
    130                 135                 140

Lys Ile Met Pro Leu Glu Asp Met Asn Glu Phe Thr Thr His Ile Leu
145                 150                 155                 160

Glu Val Ile Asn Ala His Met Val Leu Ser Lys Ala Asn Ser Gln Pro
                165                 170                 175

Ser Ala Gly Arg Ala Pro Ile Ser Asn Pro Gly Met Ser Glu Ala Gly
            180                 185                 190

Asn Phe Gly Gly Asn Ser Phe Met Pro Ala Asn Gly Leu Thr Val Ala
        195                 200                 205

Gln Asn Gln Val Leu Asn Leu Ile Lys Ala Cys Pro Arg Pro Glu Gly
    210                 215                 220

Leu Asn Phe Gln Asp Leu Lys Asn Gln Leu Lys His Met Ser Val Ser
225                 230                 235                 240

Ser Ile Lys Gln Ala Val Asp Phe Leu Ser Asn Glu Gly His Ile Tyr
                245                 250                 255
```

```
Ser Thr Val Asp Asp His Phe Lys Ser Thr Asp Ala Glu
        260                 265                 270

<210> SEQ ID NO 52
<211> LENGTH: 121
<212> TYPE: PRT
<213> ORGANISM: Homo sapiens

<400> SEQUENCE: 52

Met Val Asp Met Met Asp Leu Pro Arg Ser Arg Ile Asn Ala Gly Met
1               5                   10                  15

Leu Ala Gln Phe Ile Asp Lys Pro Val Cys Phe Val Gly Arg Leu Glu
            20                  25                  30

Lys Ile His Pro Thr Gly Lys Met Phe Ile Leu Ser Asp Gly Glu Gly
        35                  40                  45

Lys Asn Gly Thr Ile Glu Leu Met Glu Pro Leu Asp Glu Glu Ile Ser
    50                  55                  60

Gly Ile Val Glu Val Val Gly Arg Val Thr Ala Lys Ala Thr Ile Leu
65                  70                  75                  80

Cys Thr Ser Tyr Val Gln Phe Lys Glu Asp Ser His Pro Phe Asp Leu
                85                  90                  95

Gly Leu Tyr Asn Glu Ala Val Lys Ile Ile His Asp Phe Pro Gln Phe
            100                 105                 110

Tyr Pro Leu Gly Ile Val Gln His Asp
        115                 120

<210> SEQ ID NO 53
<211> LENGTH: 339
<212> TYPE: PRT
<213> ORGANISM: Homo sapiens

<400> SEQUENCE: 53

Met Ala Met Gln Met Gln Leu Glu Ala Asn Ala Asp Thr Ser Val Glu
1               5                   10                  15

Glu Glu Ser Phe Gly Pro Gln Pro Ile Ser Arg Leu Glu Gln Cys Gly
            20                  25                  30

Ile Asn Ala Asn Asp Val Lys Lys Leu Glu Glu Ala Gly Phe His Thr
        35                  40                  45

Val Glu Ala Val Ala Tyr Ala Pro Lys Lys Glu Leu Ile Asn Ile Lys
    50                  55                  60

Gly Ile Ser Glu Ala Lys Ala Asp Lys Ile Leu Ala Glu Ala Ala Lys
65                  70                  75                  80

Leu Val Pro Met Gly Phe Thr Thr Ala Thr Glu Phe His Gln Arg Arg
                85                  90                  95

Ser Glu Ile Ile Gln Ile Thr Thr Gly Ser Lys Glu Leu Asp Lys Leu
            100                 105                 110

Leu Gln Gly Gly Ile Glu Thr Gly Ser Ile Thr Glu Met Phe Gly Glu
        115                 120                 125

Phe Arg Thr Gly Lys Thr Gln Ile Cys His Thr Leu Ala Val Thr Cys
    130                 135                 140

Gln Leu Pro Ile Asp Arg Gly Gly Gly Glu Gly Lys Ala Met Tyr Ile
145                 150                 155                 160

Asp Thr Glu Gly Thr Phe Arg Pro Glu Arg Leu Leu Ala Val Ala Glu
                165                 170                 175

Arg Tyr Gly Leu Ser Gly Ser Asp Val Leu Asp Asn Val Ala Tyr Ala
            180                 185                 190
```

```
Arg Ala Phe Asn Thr Asp His Gln Thr Gln Leu Leu Tyr Gln Ala Ser
            195                 200                 205

Ala Met Met Val Glu Ser Arg Tyr Ala Leu Leu Ile Val Asp Ser Ala
        210                 215                 220

Thr Ala Leu Tyr Arg Thr Asp Tyr Ser Gly Arg Gly Glu Leu Ser Ala
225                 230                 235                 240

Arg Gln Met His Leu Ala Arg Phe Leu Arg Met Leu Leu Arg Leu Ala
            245                 250                 255

Asp Glu Phe Gly Val Ala Val Val Ile Thr Asn Gln Val Val Ala Gln
            260                 265                 270

Val Asp Gly Ala Ala Met Phe Ala Ala Asp Pro Lys Lys Pro Ile Gly
            275                 280                 285

Gly Asn Ile Ile Ala His Ala Ser Thr Thr Arg Leu Tyr Leu Arg Lys
            290                 295                 300

Gly Arg Gly Glu Thr Arg Ile Cys Lys Ile Tyr Asp Ser Pro Cys Leu
305                 310                 315                 320

Pro Glu Ala Glu Ala Met Phe Ala Ile Asn Ala Asp Gly Val Gly Asp
                325                 330                 335

Ala Lys Asp

<210> SEQ ID NO 54
<211> LENGTH: 418
<212> TYPE: PRT
<213> ORGANISM: Homo sapiens

<400> SEQUENCE: 54

Met Ser Gly Thr Glu Glu Ala Ile Leu Gly Gly Arg Asp Ser His Pro
1               5                   10                  15

Ala Ala Gly Gly Gly Ser Val Leu Cys Phe Gly Gln Cys Gln Tyr Thr
            20                  25                  30

Ala Glu Glu Tyr Gln Ala Ile Gln Lys Ala Leu Arg Gln Arg Leu Gly
        35                  40                  45

Pro Glu Tyr Ile Ser Ser Arg Met Ala Gly Gly Gly Gln Lys Val Cys
    50                  55                  60

Tyr Ile Glu Gly His Arg Val Ile Asn Leu Ala Asn Glu Met Phe Gly
65                  70                  75                  80

Tyr Asn Gly Trp Ala His Ser Ile Thr Gln Gln Asn Val Asp Phe Val
                85                  90                  95

Asp Leu Asn Asn Gly Lys Phe Tyr Val Gly Val Cys Ala Phe Val Arg
            100                 105                 110

Val Gln Leu Lys Asp Gly Ser Tyr His Glu Asp Val Gly Tyr Gly Val
        115                 120                 125

Ser Glu Gly Leu Lys Ser Lys Ala Leu Ser Leu Glu Lys Ala Arg Lys
    130                 135                 140

Glu Ala Val Thr Asp Gly Leu Lys Arg Ala Leu Arg Ser Phe Gly Asn
145                 150                 155                 160

Ala Leu Gly Asn Cys Ile Leu Asp Lys Asp Tyr Leu Arg Ser Leu Asn
                165                 170                 175

Lys Leu Pro Arg Gln Leu Pro Leu Glu Val Asp Leu Thr Lys Ala Lys
            180                 185                 190

Arg Gln Asp Leu Glu Pro Ser Val Glu Glu Ala Arg Tyr Asn Ser Cys
        195                 200                 205

Arg Pro Asn Met Ala Leu Gly His Pro Gln Leu Gln Gln Val Thr Ser
    210                 215                 220
```

```
Pro Ser Arg Pro Ser His Ala Val Ile Pro Ala Asp Gln Asp Cys Ser
225                 230                 235                 240

Ser Arg Ser Leu Ser Ser Ala Val Glu Ser Glu Ala Thr His Gln
        245                 250                 255

Arg Lys Leu Arg Gln Lys Gln Leu Gln Gln Gln Phe Arg Glu Arg Met
            260                 265                 270

Glu Lys Gln Gln Val Arg Val Ser Thr Pro Ser Ala Glu Lys Ser Glu
        275                 280                 285

Ala Ala Pro Pro Ala Pro Pro Val Thr His Ser Thr Pro Val Thr Val
        290                 295                 300

Ser Glu Pro Leu Leu Glu Lys Asp Phe Leu Ala Gly Val Thr Gln Glu
305                 310                 315                 320

Leu Ile Lys Thr Leu Glu Asp Asn Ser Glu Lys Trp Ala Val Thr Pro
            325                 330                 335

Asp Ala Gly Asp Gly Val Val Lys Pro Ser Ser Arg Ala Asp Pro Ala
            340                 345                 350

Gln Thr Ser Asp Thr Leu Ala Leu Asn Asn Gln Met Val Thr Gln Asn
        355                 360                 365

Arg Thr Pro His Ser Val Cys His Gln Lys Pro Gln Ala Lys Ser Gly
            370                 375                 380

Ser Trp Asp Leu Gln Thr Tyr Ser Ala Asp Gln Arg Thr Thr Gly Asn
385                 390                 395                 400

Trp Glu Ser His Arg Lys Ser Gln Asp Met Lys Lys Arg Lys Tyr Asp
                405                 410                 415

Pro Ser

<210> SEQ ID NO 55
<211> LENGTH: 1417
<212> TYPE: PRT
<213> ORGANISM: Homo sapiens

<400> SEQUENCE: 55

Met Ala Ala Val Pro Gln Asn Asn Leu Gln Glu Gln Leu Glu Arg His
1               5                   10                  15

Ser Ala Arg Thr Leu Asn Asn Lys Leu Ser Leu Ser Lys Pro Lys Phe
            20                  25                  30

Ser Gly Phe Thr Phe Lys Lys Lys Thr Ser Ser Asp Asn Asn Val Ser
        35                  40                  45

Val Thr Asn Val Ser Val Ala Lys Thr Pro Val Leu Arg Asn Lys Asp
50                  55                  60

Val Asn Val Thr Glu Asp Phe Ser Phe Ser Glu Pro Leu Pro Asn Thr
65                  70                  75                  80

Thr Asn Gln Gln Arg Val Lys Asp Phe Phe Lys Asn Ala Pro Ala Gly
            85                  90                  95

Gln Glu Thr Gln Arg Gly Gly Ser Lys Ser Leu Leu Pro Asp Phe Leu
        100                 105                 110

Gln Thr Pro Lys Glu Val Val Cys Thr Thr Gln Asn Thr Pro Thr Val
        115                 120                 125

Lys Lys Ser Arg Asp Thr Ala Leu Lys Lys Leu Glu Phe Ser Ser Ser
        130                 135                 140

Pro Asp Ser Leu Ser Thr Ile Asn Asp Trp Asp Asp Met Asp Asp Phe
145                 150                 155                 160

Asp Thr Ser Glu Thr Ser Lys Ser Phe Val Thr Pro Pro Gln Ser His
                165                 170                 175
```

```
Phe Val Arg Val Ser Thr Ala Gln Lys Ser Lys Lys Gly Lys Arg Asn
            180                 185                 190
Phe Phe Lys Ala Gln Leu Tyr Thr Thr Asn Thr Val Lys Thr Asp Leu
        195                 200                 205
Pro Pro Pro Ser Ser Glu Ser Glu Gln Ile Asp Leu Thr Glu Glu Gln
210                 215                 220
Lys Asp Asp Ser Glu Trp Leu Ser Ser Asp Val Ile Cys Ile Asp Asp
225                 230                 235                 240
Gly Pro Ile Ala Glu Val His Ile Asn Glu Asp Ala Gln Glu Ser Asp
                245                 250                 255
Ser Leu Lys Thr His Leu Glu Asp Glu Arg Asp Asn Ser Glu Lys Lys
            260                 265                 270
Lys Asn Leu Glu Glu Ala Glu Leu His Ser Thr Glu Lys Val Pro Cys
        275                 280                 285
Ile Glu Phe Asp Asp Asp Asp Tyr Asp Thr Asp Phe Val Pro Pro Ser
290                 295                 300
Pro Glu Glu Ile Ile Ser Ala Ser Ser Ser Ser Lys Cys Leu Ser
305                 310                 315                 320
Thr Leu Lys Asp Leu Asp Thr Ser Asp Arg Lys Glu Asp Val Leu Ser
            325                 330                 335
Thr Ser Lys Asp Leu Leu Ser Lys Pro Glu Lys Met Ser Met Gln Glu
            340                 345                 350
Leu Asn Pro Glu Thr Ser Thr Asp Cys Asp Ala Arg Gln Ile Ser Leu
        355                 360                 365
Gln Gln Gln Leu Ile His Val Met Glu His Ile Cys Lys Leu Ile Asp
370                 375                 380
Thr Ile Pro Asp Asp Lys Leu Lys Leu Leu Asp Cys Gly Asn Glu Leu
385                 390                 395                 400
Leu Gln Gln Arg Asn Ile Arg Arg Lys Leu Leu Thr Glu Val Asp Phe
            405                 410                 415
Asn Lys Ser Asp Ala Ser Leu Leu Gly Ser Leu Trp Arg Tyr Arg Pro
        420                 425                 430
Asp Ser Leu Asp Gly Pro Met Glu Gly Asp Ser Cys Pro Thr Gly Asn
        435                 440                 445
Ser Met Lys Glu Leu Asn Phe Ser His Leu Pro Ser Asn Ser Val Ser
450                 455                 460
Pro Gly Asp Cys Leu Leu Thr Thr Thr Leu Gly Lys Thr Gly Phe Ser
465                 470                 475                 480
Ala Thr Arg Lys Asn Leu Phe Glu Arg Pro Leu Phe Asn Thr His Leu
            485                 490                 495
Gln Lys Ser Phe Val Ser Ser Asn Trp Ala Glu Thr Pro Arg Leu Gly
        500                 505                 510
Lys Lys Asn Glu Ser Ser Tyr Phe Pro Gly Asn Val Leu Thr Ser Thr
        515                 520                 525
Ala Val Lys Asp Gln Asn Lys His Thr Ala Ser Ile Asn Asp Leu Glu
        530                 535                 540
Arg Glu Thr Gln Pro Ser Tyr Asp Ile Asp Asn Phe Asp Ile Asp Asp
545                 550                 555                 560
Phe Asp Asp Asp Asp Trp Glu Asp Ile Met His Asn Leu Ala Ala
                565                 570                 575
Ser Lys Ser Thr Ala Ala Tyr Gln Pro Ile Lys Glu Gly Arg Pro
            580                 585                 590
```

```
Ile Lys Ser Val Ser Glu Arg Leu Ser Ser Ala Lys Thr Asp Cys Leu
        595                 600                 605

Pro Val Ser Ser Thr Ala Gln Asn Ile Asn Phe Ser Glu Ser Ile Gln
    610                 615                 620

Asn Tyr Thr Asp Lys Ser Ala Gln Asn Leu Ala Ser Arg Asn Leu Lys
625                 630                 635                 640

His Glu Arg Phe Gln Ser Leu Ser Phe Pro His Thr Lys Glu Met Met
                645                 650                 655

Lys Ile Phe His Lys Lys Phe Gly Leu His Asn Phe Arg Thr Asn Gln
                660                 665                 670

Leu Glu Ala Ile Asn Ala Ala Leu Leu Gly Glu Asp Cys Phe Ile Leu
                675                 680                 685

Met Pro Thr Gly Gly Gly Lys Ser Leu Cys Tyr Gln Leu Pro Ala Cys
    690                 695                 700

Val Ser Pro Gly Val Thr Val Val Ile Ser Pro Leu Arg Ser Leu Ile
705                 710                 715                 720

Val Asp Gln Val Gln Lys Leu Thr Ser Leu Asp Ile Pro Ala Thr Tyr
                725                 730                 735

Leu Thr Gly Asp Lys Thr Asp Ser Glu Ala Thr Asn Ile Tyr Leu Gln
                740                 745                 750

Leu Ser Lys Lys Asp Pro Ile Ile Lys Leu Leu Tyr Val Thr Pro Glu
            755                 760                 765

Lys Ile Cys Ala Ser Asn Arg Leu Ile Ser Thr Leu Glu Asn Leu Tyr
            770                 775                 780

Glu Arg Lys Leu Leu Ala Arg Phe Val Ile Asp Glu Ala His Cys Val
785                 790                 795                 800

Ser Gln Trp Gly His Asp Phe Arg Gln Asp Tyr Lys Arg Met Asn Met
                805                 810                 815

Leu Arg Gln Lys Phe Pro Ser Val Pro Val Met Ala Leu Thr Ala Thr
                820                 825                 830

Ala Asn Pro Arg Val Gln Lys Asp Ile Leu Thr Gln Leu Lys Ile Leu
            835                 840                 845

Arg Pro Gln Val Phe Ser Met Ser Phe Asn Arg His Asn Leu Lys Tyr
850                 855                 860

Tyr Val Leu Pro Lys Lys Pro Lys Lys Val Ala Phe Asp Cys Leu Glu
865                 870                 875                 880

Trp Ile Arg Lys His His Pro Tyr Asp Ser Gly Ile Ile Tyr Cys Leu
                885                 890                 895

Ser Arg Arg Glu Cys Asp Thr Met Ala Asp Thr Leu Gln Arg Asp Gly
            900                 905                 910

Leu Ala Ala Leu Ala Tyr His Ala Gly Leu Ser Asp Ser Ala Arg Asp
            915                 920                 925

Glu Val Gln Gln Lys Trp Ile Asn Gln Asp Gly Cys Gln Val Ile Cys
            930                 935                 940

Ala Thr Ile Ala Phe Gly Met Gly Ile Asp Lys Pro Asp Val Arg Phe
945                 950                 955                 960

Val Ile His Ala Ser Leu Pro Lys Ser Val Glu Gly Tyr Tyr Gln Glu
                965                 970                 975

Ser Gly Arg Ala Gly Arg Asp Gly Glu Ile Ser His Cys Leu Leu Phe
            980                 985                 990

Tyr Thr Tyr His Asp Val Thr Arg  Leu Lys Arg Leu Ile  Met Met Glu
            995                 1000                1005

Lys Asp  Gly Asn His His Thr  Arg Glu Thr His Phe  Asn Asn Leu
```

-continued

```
            1010                1015                1020

Tyr Ser Met Val His Tyr Cys Glu Asn Ile Thr Glu Cys Arg Arg
        1025                1030                1035

Ile Gln Leu Leu Ala Tyr Phe Gly Glu Asn Gly Phe Asn Pro Asp
        1040                1045                1050

Phe Cys Lys Lys His Pro Asp Val Ser Cys Asp Asn Cys Cys Lys
        1055                1060                1065

Thr Lys Asp Tyr Lys Thr Arg Asp Val Thr Asp Asp Val Lys Ser
        1070                1075                1080

Ile Val Arg Phe Val Gln Glu His Ser Ser Gln Gly Met Arg
        1085                1090                1095

Asn Ile Lys His Val Gly Pro Ser Gly Arg Phe Thr Met Asn Met
        1100                1105                1110

Leu Val Asp Ile Phe Leu Gly Ser Lys Ser Ala Lys Ile Gln Ser
        1115                1120                1125

Gly Ile Phe Gly Lys Gly Ser Ala Tyr Ser Arg His Asn Ala Glu
        1130                1135                1140

Arg Leu Phe Lys Lys Leu Ile Leu Asp Lys Ile Leu Asp Glu Asp
        1145                1150                1155

Leu Tyr Ile Asn Ala Asn Asp Gln Ala Ile Ala Tyr Val Met Leu
        1160                1165                1170

Gly Asn Lys Ala Gln Thr Val Leu Asn Gly Asn Leu Lys Val Asp
        1175                1180                1185

Phe Met Glu Thr Glu Asn Ser Ser Ser Val Lys Lys Gln Lys Ala
        1190                1195                1200

Leu Val Ala Lys Val Ser Gln Arg Glu Glu Met Val Lys Lys Cys
        1205                1210                1215

Leu Gly Glu Leu Thr Glu Val Cys Lys Ser Leu Gly Lys Val Phe
        1220                1225                1230

Gly Val His Tyr Phe Asn Ile Phe Asn Thr Val Thr Leu Lys Lys
        1235                1240                1245

Leu Ala Glu Ser Leu Ser Ser Asp Pro Glu Val Leu Leu Gln Ile
        1250                1255                1260

Asp Gly Val Thr Glu Asp Lys Leu Glu Lys Tyr Gly Ala Glu Val
        1265                1270                1275

Ile Ser Val Leu Gln Lys Tyr Ser Glu Trp Thr Ser Pro Ala Glu
        1280                1285                1290

Asp Ser Ser Pro Gly Ile Ser Leu Ser Ser Ser Arg Gly Pro Gly
        1295                1300                1305

Arg Ser Ala Ala Glu Glu Leu Asp Glu Glu Ile Pro Val Ser Ser
        1310                1315                1320

His Tyr Phe Ala Ser Lys Thr Arg Asn Glu Arg Lys Arg Lys Lys
        1325                1330                1335

Met Pro Ala Ser Gln Arg Ser Lys Arg Arg Lys Thr Ala Ser Ser
        1340                1345                1350

Gly Ser Lys Ala Lys Gly Gly Ser Ala Thr Cys Arg Lys Ile Ser
        1355                1360                1365

Ser Lys Thr Lys Ser Ser Ser Ile Ile Gly Ser Ser Ser Ala Ser
        1370                1375                1380

His Thr Ser Gln Ala Thr Ser Gly Ala Asn Ser Lys Leu Gly Ile
        1385                1390                1395

Met Ala Pro Pro Lys Pro Ile Asn Arg Pro Phe Leu Lys Pro Ser
        1400                1405                1410
```

Tyr Ala Phe Ser
    1415

<210> SEQ ID NO 56
<211> LENGTH: 846
<212> TYPE: PRT
<213> ORGANISM: Homo sapiens

<400> SEQUENCE: 56

Met Gly Ile Gln Gly Leu Leu Gln Phe Ile Lys Glu Ala Ser Glu Pro
1               5                   10                  15

Ile His Val Arg Lys Tyr Lys Gly Gln Val Val Ala Val Asp Thr Tyr
            20                  25                  30

Cys Trp Leu His Lys Gly Ala Ile Ala Cys Ala Glu Lys Leu Ala Lys
        35                  40                  45

Gly Glu Pro Thr Asp Arg Tyr Val Gly Phe Cys Met Lys Phe Val Asn
    50                  55                  60

Met Leu Leu Ser His Gly Ile Lys Pro Ile Leu Val Phe Asp Gly Cys
65                  70                  75                  80

Thr Leu Pro Ser Lys Lys Glu Val Glu Arg Ser Arg Arg Glu Arg Arg
                85                  90                  95

Gln Ala Asn Leu Leu Lys Gly Lys Gln Leu Leu Arg Glu Gly Lys Val
            100                 105                 110

Ser Glu Ala Arg Glu Cys Phe Thr Arg Ser Ile Asn Ile Thr His Ala
        115                 120                 125

Met Ala His Lys Val Ile Lys Ala Ala Arg Ser Gln Gly Val Asp Cys
    130                 135                 140

Leu Val Ala Pro Tyr Glu Ala Asp Ala Gln Leu Ala Tyr Leu Asn Lys
145                 150                 155                 160

Ala Gly Ile Val Gln Ala Ile Ile Thr Glu Asp Ser Asp Leu Leu Ala
                165                 170                 175

Phe Gly Cys Lys Lys Val Ile Leu Lys Met Asp Gln Phe Gly Asn Gly
            180                 185                 190

Leu Glu Ile Asp Gln Ala Arg Leu Gly Met Cys Arg Gln Leu Gly Asp
        195                 200                 205

Val Phe Thr Glu Glu Lys Phe Arg Tyr Met Cys Ile Leu Ser Gly Cys
    210                 215                 220

Asp Tyr Leu Ser Ser Leu Arg Gly Ile Gly Leu Ala Lys Ala Cys Lys
225                 230                 235                 240

Val Leu Arg Leu Ala Asn Asn Pro Asp Ile Val Lys Val Ile Lys Lys
                245                 250                 255

Ile Gly His Tyr Leu Lys Met Asn Ile Thr Val Pro Glu Asp Tyr Ile
            260                 265                 270

Asn Gly Phe Ile Arg Ala Asn Asn Thr Phe Leu Tyr Gln Leu Val Phe
        275                 280                 285

Asp Pro Ile Lys Arg Lys Leu Ile Pro Leu Asn Ala Tyr Glu Asp Asp
    290                 295                 300

Val Asp Pro Glu Thr Leu Ser Tyr Ala Gly Gln Tyr Val Asp Asp Ser
305                 310                 315                 320

Ile Ala Leu Gln Ile Ala Leu Gly Asn Lys Asp Ile Asn Thr Phe Glu
                325                 330                 335

Gln Ile Asp Asp Tyr Asn Pro Asp Thr Ala Met Pro Ala His Ser Arg
            340                 345                 350

Ser His Ser Trp Asp Asp Lys Thr Cys Gln Lys Ser Ala Asn Val Ser

```
            355                 360                 365
Ser Ile Trp His Arg Asn Tyr Ser Pro Arg Glu Ser Gly Thr Val
370                 375                 380

Ser Asp Ala Pro Gln Leu Lys Glu Asn Pro Ser Thr Val Gly Val Glu
385                 390                 395                 400

Arg Val Ile Ser Thr Lys Gly Leu Asn Leu Pro Arg Lys Ser Ser Ile
                405                 410                 415

Val Lys Arg Pro Arg Ser Ala Glu Leu Ser Glu Asp Asp Leu Leu Ser
            420                 425                 430

Gln Tyr Ser Leu Ser Phe Thr Lys Lys Thr Lys Lys Asn Ser Ser Glu
            435                 440                 445

Gly Asn Lys Ser Leu Ser Phe Ser Glu Val Phe Val Pro Asp Leu Val
            450                 455                 460

Asn Gly Pro Thr Asn Lys Lys Ser Val Ser Thr Pro Arg Thr Arg
465                 470                 475                 480

Asn Lys Phe Ala Thr Phe Leu Gln Arg Lys Asn Glu Glu Ser Gly Ala
                485                 490                 495

Val Val Val Pro Gly Thr Arg Ser Arg Phe Phe Cys Ser Ser Asp Ser
            500                 505                 510

Thr Asp Cys Val Ser Asn Lys Val Ser Ile Gln Pro Leu Asp Glu Thr
        515                 520                 525

Ala Val Thr Asp Lys Glu Asn Asn Leu His Glu Ser Glu Tyr Gly Asp
530                 535                 540

Gln Glu Gly Lys Arg Leu Val Asp Thr Asp Val Ala Arg Asn Ser Ser
545                 550                 555                 560

Asp Asp Ile Pro Asn Asn His Ile Pro Gly Asp His Ile Pro Asp Lys
                565                 570                 575

Ala Thr Val Phe Thr Asp Glu Glu Ser Tyr Ser Phe Glu Ser Ser Lys
            580                 585                 590

Phe Thr Arg Thr Ile Ser Pro Pro Thr Leu Gly Thr Leu Arg Ser Cys
            595                 600                 605

Phe Ser Trp Ser Gly Gly Leu Gly Asp Phe Ser Arg Thr Pro Ser Pro
610                 615                 620

Ser Pro Ser Thr Ala Leu Gln Gln Phe Arg Arg Lys Ser Asp Ser Pro
625                 630                 635                 640

Thr Ser Leu Pro Glu Asn Asn Met Ser Asp Val Ser Gln Leu Lys Ser
                645                 650                 655

Glu Glu Ser Ser Asp Asp Glu Ser His Pro Leu Arg Glu Glu Ala Cys
            660                 665                 670

Ser Ser Gln Ser Gln Glu Ser Gly Glu Phe Ser Leu Gln Ser Ser Asn
            675                 680                 685

Ala Ser Lys Leu Ser Gln Cys Ser Ser Lys Asp Ser Asp Ser Glu Glu
            690                 695                 700

Ser Asp Cys Asn Ile Lys Leu Leu Asp Ser Gln Ser Asp Gln Thr Ser
705                 710                 715                 720

Lys Leu Arg Leu Ser His Phe Ser Lys Lys Asp Thr Pro Leu Arg Asn
                725                 730                 735

Lys Val Pro Gly Leu Tyr Lys Ser Ser Ser Ala Asp Ser Leu Ser Thr
            740                 745                 750

Thr Lys Ile Lys Pro Leu Gly Pro Ala Arg Ala Ser Gly Leu Ser Lys
            755                 760                 765

Lys Pro Ala Ser Ile Gln Lys Arg Lys His His Asn Ala Glu Asn Lys
770                 775                 780
```

```
Pro Gly Leu Gln Ile Lys Leu Asn Glu Leu Trp Lys Asn Phe Gly Phe
785                 790                 795                 800

Lys Lys Asp Ser Glu Lys Leu Pro Pro Cys Lys Lys Pro Leu Ser Pro
            805                 810                 815

Val Arg Asp Asn Ile Gln Leu Thr Pro Glu Ala Glu Glu Asp Ile Phe
            820                 825                 830

Asn Lys Pro Glu Cys Gly Arg Val Gln Arg Ala Ile Phe Gln
            835                 840                 845

<210> SEQ ID NO 57
<211> LENGTH: 649
<212> TYPE: PRT
<213> ORGANISM: Homo sapiens

<400> SEQUENCE: 57

Met Ala Ser Val Ser Ala Leu Thr Glu Glu Leu Asp Ser Ile Thr Ser
1               5                   10                  15

Glu Leu His Ala Val Glu Ile Gln Ile Gln Glu Leu Thr Glu Arg Gln
                20                  25                  30

Gln Glu Leu Ile Gln Lys Lys Lys Val Leu Thr Lys Lys Ile Lys Gln
            35                  40                  45

Cys Leu Glu Asp Ser Asp Ala Gly Ala Ser Asn Glu Tyr Asp Ser Ser
        50                  55                  60

Pro Ala Ala Trp Asn Lys Glu Asp Phe Pro Trp Ser Gly Lys Val Lys
65                  70                  75                  80

Asp Ile Leu Gln Asn Val Phe Lys Leu Glu Lys Phe Arg Pro Leu Gln
                85                  90                  95

Leu Glu Thr Ile Asn Val Thr Met Ala Gly Lys Glu Val Phe Leu Val
                100                 105                 110

Met Pro Thr Gly Gly Gly Lys Ser Leu Cys Tyr Gln Leu Pro Ala Leu
            115                 120                 125

Cys Ser Asp Gly Phe Thr Leu Val Ile Cys Pro Leu Ile Ser Leu Met
        130                 135                 140

Glu Asp Gln Leu Met Val Leu Lys Gln Leu Gly Ile Ser Ala Thr Met
145                 150                 155                 160

Leu Asn Ala Ser Ser Lys Glu His Val Lys Trp Val His Ala Glu
                165                 170                 175

Met Val Asn Lys Asn Ser Glu Leu Lys Leu Ile Tyr Val Thr Pro Glu
            180                 185                 190

Lys Ile Ala Lys Ser Lys Met Phe Met Ser Arg Leu Glu Lys Ala Tyr
        195                 200                 205

Glu Ala Arg Arg Phe Thr Arg Ile Ala Val Asp Glu Val His Cys Cys
    210                 215                 220

Ser Gln Trp Gly His Asp Phe Arg Pro Asp Tyr Lys Ala Leu Gly Ile
225                 230                 235                 240

Leu Lys Arg Gln Phe Pro Asn Ala Ser Leu Ile Gly Leu Thr Ala Thr
                245                 250                 255

Ala Thr Asn His Val Leu Thr Asp Ala Gln Lys Ile Leu Cys Ile Glu
            260                 265                 270

Lys Cys Phe Thr Phe Thr Ala Ser Phe Asn Arg Pro Asn Leu Tyr Tyr
        275                 280                 285

Glu Val Arg Gln Lys Pro Ser Asn Thr Glu Asp Phe Ile Glu Asp Ile
    290                 295                 300

Val Lys Leu Ile Asn Gly Arg Tyr Lys Gly Gln Ser Gly Ile Ile Tyr
```

```
            305                 310                 315                 320
Cys Phe Ser Gln Lys Asp Ser Glu Gln Val Thr Val Ser Leu Gln Asn
                325                 330                 335

Leu Gly Ile His Ala Gly Ala Tyr His Ala Asn Leu Glu Pro Glu Asp
            340                 345                 350

Lys Thr Thr Val His Arg Lys Trp Ser Ala Asn Glu Ile Gln Val Val
            355                 360                 365

Val Ala Thr Val Ala Phe Gly Met Gly Ile Asp Lys Pro Asp Val Arg
        370                 375                 380

Phe Val Ile His His Ser Met Ser Lys Ser Met Glu Asn Tyr Tyr Gln
385                 390                 395                 400

Glu Ser Gly Arg Ala Gly Arg Asp Asp Met Lys Ala Asp Cys Ile Leu
                405                 410                 415

Tyr Tyr Gly Phe Gly Asp Ile Phe Arg Ile Ser Ser Met Val Val Met
            420                 425                 430

Glu Asn Val Gly Gln Gln Lys Leu Tyr Glu Met Val Ser Tyr Cys Gln
        435                 440                 445

Asn Ile Ser Lys Cys Arg Arg Val Leu Met Ala Gln His Phe Asp Glu
450                 455                 460

Val Trp Asn Ser Glu Ala Cys Asn Lys Met Cys Asp Asn Cys Cys Lys
465                 470                 475                 480

Asp Ser Ala Phe Glu Arg Lys Asn Ile Thr Glu Tyr Cys Arg Asp Leu
                485                 490                 495

Ile Lys Ile Leu Lys Gln Ala Glu Glu Leu Asn Glu Lys Leu Thr Pro
            500                 505                 510

Leu Lys Leu Ile Asp Ser Trp Met Gly Lys Gly Ala Ala Lys Leu Arg
        515                 520                 525

Val Ala Gly Val Val Ala Pro Thr Leu Pro Arg Glu Asp Leu Glu Lys
    530                 535                 540

Ile Ile Ala His Phe Leu Ile Gln Gln Tyr Leu Lys Glu Asp Tyr Ser
545                 550                 555                 560

Phe Thr Ala Tyr Ala Thr Ile Ser Tyr Leu Lys Ile Gly Pro Lys Ala
                565                 570                 575

Asn Leu Leu Asn Asn Glu Ala His Ala Ile Thr Met Gln Val Thr Lys
            580                 585                 590

Ser Thr Gln Asn Ser Phe Arg Ala Glu Ser Ser Gln Thr Cys His Ser
        595                 600                 605

Glu Gln Gly Asp Lys Lys Met Glu Glu Lys Asn Ser Gly Asn Phe Gln
    610                 615                 620

Lys Lys Ala Ala Asn Met Leu Gln Gln Ser Gly Ser Lys Asn Thr Gly
625                 630                 635                 640

Ala Lys Lys Arg Lys Ile Asp Asp Ala
                645

<210> SEQ ID NO 58
<211> LENGTH: 760
<212> TYPE: PRT
<213> ORGANISM: Homo sapiens

<400> SEQUENCE: 58

Met Lys Leu Asn Val Asp Gly Leu Leu Val Tyr Phe Pro Tyr Asp Tyr
1               5                   10                  15

Ile Tyr Pro Glu Gln Phe Ser Tyr Met Arg Glu Leu Lys Arg Thr Leu
            20                  25                  30
```

-continued

```
Asp Ala Lys Gly His Gly Val Leu Glu Met Pro Ser Gly Thr Gly Lys
         35                  40                  45

Thr Val Ser Leu Leu Ala Leu Ile Met Ala Tyr Gln Arg Ala Tyr Pro
 50                  55                  60

Leu Glu Val Thr Lys Leu Ile Tyr Cys Ser Arg Thr Val Pro Glu Ile
65                  70                  75                  80

Glu Lys Val Ile Glu Glu Leu Arg Lys Leu Leu Asn Phe Tyr Glu Lys
                 85                  90                  95

Gln Glu Gly Glu Lys Leu Pro Phe Leu Gly Leu Ala Leu Ser Ser Arg
            100                 105                 110

Lys Asn Leu Cys Ile His Pro Glu Val Thr Pro Leu Arg Phe Gly Lys
        115                 120                 125

Asp Val Asp Gly Lys Cys His Ser Leu Thr Ala Ser Tyr Val Arg Ala
130                 135                 140

Gln Tyr Gln His Asp Thr Ser Leu Pro His Cys Arg Phe Tyr Glu Glu
145                 150                 155                 160

Phe Asp Ala His Gly Arg Glu Val Pro Leu Pro Ala Gly Ile Tyr Asn
                165                 170                 175

Leu Asp Asp Leu Lys Ala Leu Gly Arg Arg Gln Gly Trp Cys Pro Tyr
            180                 185                 190

Phe Leu Ala Arg Tyr Ser Ile Leu His Ala Asn Val Val Tyr Ser
        195                 200                 205

Tyr His Tyr Leu Leu Asp Pro Lys Ile Ala Asp Leu Val Ser Lys Glu
210                 215                 220

Leu Ala Arg Lys Ala Val Val Phe Asp Glu Ala His Asn Ile Asp
225                 230                 235                 240

Asn Val Cys Ile Asp Ser Met Ser Val Asn Leu Thr Arg Arg Thr Leu
                245                 250                 255

Asp Arg Cys Gln Gly Asn Leu Glu Thr Leu Gln Lys Thr Val Leu Arg
            260                 265                 270

Ile Lys Glu Thr Asp Glu Gln Arg Leu Arg Asp Glu Tyr Arg Arg Leu
        275                 280                 285

Val Glu Gly Leu Arg Glu Ala Ser Ala Ala Arg Glu Thr Asp Ala His
290                 295                 300

Leu Ala Asn Pro Val Leu Pro Asp Glu Val Leu Gln Glu Ala Val Pro
305                 310                 315                 320

Gly Ser Ile Arg Thr Ala Glu His Phe Leu Gly Phe Leu Arg Arg Leu
                325                 330                 335

Leu Glu Tyr Val Lys Trp Arg Leu Arg Val Gln His Val Gln Glu
            340                 345                 350

Ser Pro Pro Ala Phe Leu Ser Gly Leu Ala Gln Arg Val Cys Ile Gln
        355                 360                 365

Arg Lys Pro Leu Arg Phe Cys Ala Glu Arg Leu Arg Ser Leu Leu His
370                 375                 380

Thr Leu Glu Ile Thr Asp Leu Ala Asp Phe Ser Pro Leu Thr Leu Leu
385                 390                 395                 400

Ala Asn Phe Ala Thr Leu Val Ser Thr Tyr Ala Lys Gly Phe Thr Ile
                405                 410                 415

Ile Ile Glu Pro Phe Asp Asp Arg Thr Pro Thr Ile Ala Asn Pro Ile
            420                 425                 430

Leu His Phe Ser Cys Met Asp Ala Ser Leu Ala Ile Lys Pro Val Phe
        435                 440                 445

Glu Arg Phe Gln Ser Val Ile Ile Thr Ser Gly Thr Leu Ser Pro Leu
```

```
                450                 455                 460
Asp Ile Tyr Pro Lys Ile Leu Asp Phe His Pro Val Thr Met Ala Thr
465                 470                 475                 480

Phe Thr Met Thr Leu Ala Arg Val Cys Leu Cys Pro Met Ile Ile Gly
                485                 490                 495

Arg Gly Asn Asp Gln Val Ala Ile Ser Ser Lys Phe Glu Thr Arg Glu
            500                 505                 510

Asp Ile Ala Val Ile Arg Asn Tyr Gly Asn Leu Leu Leu Glu Met Ser
        515                 520                 525

Ala Val Val Pro Asp Gly Ile Val Ala Phe Phe Thr Ser Tyr Gln Tyr
    530                 535                 540

Met Glu Ser Thr Val Ala Ser Trp Tyr Glu Gln Gly Ile Leu Glu Asn
545                 550                 555                 560

Ile Gln Arg Asn Lys Leu Leu Phe Ile Glu Thr Gln Asp Gly Ala Glu
                565                 570                 575

Thr Ser Val Ala Leu Glu Lys Tyr Gln Glu Ala Cys Glu Asn Gly Arg
            580                 585                 590

Gly Ala Ile Leu Leu Ser Val Ala Arg Gly Lys Val Ser Glu Gly Ile
        595                 600                 605

Asp Phe Val His His Tyr Gly Arg Ala Val Ile Met Phe Gly Val Pro
    610                 615                 620

Tyr Val Tyr Thr Gln Ser Arg Ile Leu Lys Ala Arg Leu Glu Tyr Leu
625                 630                 635                 640

Arg Asp Gln Phe Gln Ile Arg Glu Asn Asp Phe Leu Thr Phe Asp Ala
                645                 650                 655

Met Arg His Ala Ala Gln Cys Val Gly Arg Ala Ile Arg Gly Lys Thr
            660                 665                 670

Asp Tyr Gly Leu Met Val Phe Ala Asp Lys Arg Phe Ala Arg Gly Asp
        675                 680                 685

Lys Arg Gly Lys Leu Pro Arg Trp Ile Gln Glu His Leu Thr Asp Ala
    690                 695                 700

Asn Leu Asn Leu Thr Val Asp Glu Gly Val Gln Val Ala Lys Tyr Phe
705                 710                 715                 720

Leu Arg Gln Met Ala Gln Pro Phe His Arg Glu Asp Gln Leu Gly Leu
                725                 730                 735

Ser Leu Leu Ser Leu Glu Gln Leu Glu Ser Glu Thr Leu Lys Arg
            740                 745                 750

Ile Glu Gln Ile Ala Gln Gln Leu
        755                 760

<210> SEQ ID NO 59
<211> LENGTH: 782
<212> TYPE: PRT
<213> ORGANISM: Homo sapiens

<400> SEQUENCE: 59

Met Gly Lys Arg Asp Arg Ala Asp Arg Asp Lys Lys Ser Arg Lys
1               5                   10                  15

Arg His Tyr Glu Asp Glu Glu Asp Glu Glu Asp Ala Pro Gly Asn
                20                  25                  30

Asp Pro Gln Glu Ala Val Pro Ser Ala Ala Gly Lys Gln Val Asp Glu
            35                  40                  45

Ser Gly Thr Lys Val Asp Glu Tyr Gly Ala Lys Asp Tyr Arg Leu Gln
        50                  55                  60
```

```
Met Pro Leu Lys Asp Asp His Thr Ser Arg Pro Leu Trp Val Ala Pro
 65                  70                  75                  80

Asp Gly His Ile Phe Leu Glu Ala Phe Ser Pro Val Tyr Lys Tyr Ala
                 85                  90                  95

Gln Asp Phe Leu Val Ala Ile Ala Glu Pro Val Cys Arg Pro Thr His
            100                 105                 110

Val His Glu Tyr Lys Leu Thr Ala Tyr Ser Leu Tyr Ala Ala Val Ser
        115                 120                 125

Val Gly Leu Gln Thr Ser Asp Ile Thr Glu Tyr Leu Arg Lys Leu Ser
    130                 135                 140

Lys Thr Gly Val Pro Asp Gly Ile Met Gln Phe Ile Lys Leu Cys Thr
145                 150                 155                 160

Val Ser Tyr Gly Lys Val Lys Leu Val Leu Lys His Asn Arg Tyr Phe
                165                 170                 175

Val Glu Ser Cys His Pro Asp Val Ile Gln His Leu Leu Gln Asp Pro
            180                 185                 190

Val Ile Arg Glu Cys Arg Leu Arg Asn Ser Glu Gly Glu Ala Thr Glu
        195                 200                 205

Leu Ile Thr Glu Thr Phe Thr Ser Lys Ser Ala Ile Ser Lys Thr Ala
    210                 215                 220

Glu Ser Ser Gly Gly Pro Ser Thr Ser Arg Val Thr Asp Pro Gln Gly
225                 230                 235                 240

Lys Ser Asp Ile Pro Met Asp Leu Phe Asp Phe Tyr Glu Gln Met Asp
                245                 250                 255

Lys Asp Glu Glu Glu Glu Glu Thr Gln Thr Val Ser Phe Glu Val
            260                 265                 270

Lys Gln Glu Met Ile Glu Glu Leu Gln Lys Arg Cys Ile His Leu Glu
        275                 280                 285

Tyr Pro Leu Leu Ala Glu Tyr Asp Phe Arg Asn Asp Ser Val Asn Pro
    290                 295                 300

Asp Ile Asn Ile Asp Leu Lys Pro Thr Ala Val Leu Arg Pro Tyr Gln
305                 310                 315                 320

Glu Lys Ser Leu Arg Lys Met Phe Gly Asn Gly Arg Ala Arg Ser Gly
                325                 330                 335

Val Ile Val Leu Pro Cys Gly Ala Gly Lys Ser Leu Val Gly Val Thr
            340                 345                 350

Ala Ala Cys Thr Val Arg Lys Arg Cys Leu Val Leu Gly Asn Ser Ala
        355                 360                 365

Val Ser Val Glu Gln Trp Lys Ala Gln Phe Lys Met Trp Ser Thr Ile
    370                 375                 380

Asp Asp Ser Gln Ile Cys Arg Phe Thr Ser Asp Ala Lys Asp Lys Pro
385                 390                 395                 400

Ile Gly Cys Ser Val Ala Ile Ser Thr Tyr Ser Met Leu Gly His Thr
                405                 410                 415

Thr Lys Arg Ser Trp Glu Ala Glu Arg Val Met Glu Trp Leu Lys Thr
            420                 425                 430

Gln Glu Trp Gly Leu Met Ile Leu Asp Glu Val His Thr Ile Pro Ala
        435                 440                 445

Lys Met Phe Arg Arg Val Leu Thr Ile Val Gln Ala His Cys Lys Leu
    450                 455                 460

Gly Leu Thr Ala Thr Leu Val Arg Glu Asp Asp Lys Ile Val Asp Leu
465                 470                 475                 480

Asn Phe Leu Ile Gly Pro Lys Leu Tyr Glu Ala Asn Trp Met Glu Leu
```

-continued

```
                485                 490                 495
Gln Asn Asn Gly Tyr Ile Ala Lys Val Gln Cys Ala Glu Val Trp Cys
            500                 505                 510

Pro Met Ser Pro Glu Phe Tyr Arg Glu Tyr Val Ala Ile Lys Thr Lys
        515                 520                 525

Lys Arg Ile Leu Leu Tyr Thr Met Asn Pro Asn Lys Phe Arg Ala Cys
    530                 535                 540

Gln Phe Leu Ile Lys Phe His Glu Arg Asn Asp Lys Ile Ile Val
545                 550                 555                 560

Phe Ala Asp Asn Val Phe Ala Leu Lys Glu Tyr Ala Ile Arg Leu Asn
                565                 570                 575

Lys Pro Tyr Ile Tyr Gly Pro Thr Ser Gln Gly Glu Arg Met Gln Ile
            580                 585                 590

Leu Gln Asn Phe Lys His Asn Pro Lys Ile Asn Thr Ile Phe Ile Ser
        595                 600                 605

Lys Val Gly Asp Thr Ser Phe Asp Leu Pro Glu Ala Asn Val Leu Ile
    610                 615                 620

Gln Ile Ser Ser His Gly Gly Ser Arg Arg Gln Glu Ala Gln Arg Leu
625                 630                 635                 640

Gly Arg Val Leu Arg Ala Lys Lys Gly Met Val Ala Glu Glu Tyr Asn
                645                 650                 655

Ala Phe Phe Tyr Ser Leu Val Ser Gln Asp Thr Gln Glu Met Ala Tyr
            660                 665                 670

Ser Thr Lys Arg Gln Arg Phe Leu Val Asp Gln Gly Tyr Ser Phe Lys
        675                 680                 685

Val Ile Thr Lys Leu Ala Gly Met Glu Glu Glu Asp Leu Ala Phe Ser
    690                 695                 700

Thr Lys Glu Glu Gln Gln Gln Leu Leu Gln Lys Val Leu Ala Ala Thr
705                 710                 715                 720

Asp Leu Asp Ala Glu Glu Glu Val Val Ala Gly Glu Phe Gly Ser Arg
                725                 730                 735

Ser Ser Gln Ala Ser Arg Arg Phe Gly Thr Met Ser Ser Met Ser Gly
            740                 745                 750

Ala Asp Asp Thr Val Tyr Met Glu Tyr His Ser Ser Arg Ser Lys Ala
        755                 760                 765

Pro Ser Lys His Val His Pro Leu Phe Lys Arg Phe Arg Lys
    770                 775                 780

<210> SEQ ID NO 60
<211> LENGTH: 1432
<212> TYPE: PRT
<213> ORGANISM: Homo sapiens

<400> SEQUENCE: 60

Met Ser Glu Lys Lys Leu Glu Thr Thr Ala Gln Gln Arg Lys Cys Pro
1               5                   10                  15

Glu Trp Met Asn Val Gln Asn Lys Arg Cys Ala Val Glu Arg Lys
            20                  25                  30

Ala Cys Val Arg Lys Ser Val Phe Glu Asp Asp Leu Pro Phe Leu Glu
        35                  40                  45

Phe Thr Gly Ser Ile Val Tyr Ser Tyr Asp Ala Ser Asp Cys Ser Phe
    50                  55                  60

Leu Ser Glu Asp Ile Ser Met Ser Leu Ser Asp Gly Asp Val Val Gly
65                  70                  75                  80
```

```
Phe Asp Met Glu Trp Pro Pro Leu Tyr Asn Arg Gly Lys Leu Gly Lys
                85                  90                  95

Val Ala Leu Ile Gln Leu Cys Val Ser Glu Ser Lys Cys Tyr Leu Phe
            100                 105                 110

His Val Ser Ser Met Ser Val Phe Pro Gln Gly Leu Lys Met Leu Leu
            115                 120                 125

Glu Asn Lys Ala Val Lys Lys Ala Gly Val Gly Ile Glu Gly Asp Gln
        130                 135                 140

Trp Lys Leu Leu Arg Asp Phe Asp Ile Lys Leu Lys Asn Phe Val Glu
145                 150                 155                 160

Leu Thr Asp Val Ala Asn Lys Lys Leu Lys Cys Thr Glu Thr Trp Ser
                165                 170                 175

Leu Asn Ser Leu Val Lys His Leu Leu Gly Lys Gln Leu Leu Lys Asp
            180                 185                 190

Lys Ser Ile Arg Cys Ser Asn Trp Ser Lys Phe Pro Leu Thr Glu Asp
            195                 200                 205

Gln Lys Leu Tyr Ala Ala Thr Asp Ala Tyr Ala Gly Phe Ile Ile Tyr
        210                 215                 220

Arg Asn Leu Glu Ile Leu Asp Asp Thr Val Gln Arg Phe Ala Ile Asn
225                 230                 235                 240

Lys Glu Glu Glu Ile Leu Leu Ser Asp Met Asn Lys Gln Leu Thr Ser
                245                 250                 255

Ile Ser Glu Glu Val Met Asp Leu Ala Lys His Leu Pro His Ala Phe
            260                 265                 270

Ser Lys Leu Glu Asn Pro Arg Arg Val Ser Ile Leu Leu Lys Asp Ile
            275                 280                 285

Ser Glu Asn Leu Tyr Ser Leu Arg Arg Met Ile Ile Gly Ser Thr Asn
        290                 295                 300

Ile Glu Thr Glu Leu Arg Pro Ser Asn Asn Leu Asn Leu Leu Ser Phe
305                 310                 315                 320

Glu Asp Ser Thr Thr Gly Gly Val Gln Gln Lys Gln Ile Arg Glu His
                325                 330                 335

Glu Val Leu Ile His Val Glu Asp Glu Thr Trp Asp Pro Thr Leu Asp
            340                 345                 350

His Leu Ala Lys His Asp Gly Glu Asp Val Leu Gly Asn Lys Val Glu
            355                 360                 365

Arg Lys Glu Asp Gly Phe Glu Asp Gly Val Glu Asp Asn Lys Leu Lys
        370                 375                 380

Glu Asn Met Glu Arg Ala Cys Leu Met Ser Leu Asp Ile Thr Glu His
385                 390                 395                 400

Glu Leu Gln Ile Leu Glu Gln Gln Ser Gln Glu Glu Tyr Leu Ser Asp
                405                 410                 415

Ile Ala Tyr Lys Ser Thr Glu His Leu Ser Pro Asn Asp Asn Glu Asn
            420                 425                 430

Asp Thr Ser Tyr Val Ile Glu Ser Asp Glu Asp Leu Glu Met Glu Met
            435                 440                 445

Leu Lys His Leu Ser Pro Asn Asp Asn Glu Asn Asp Thr Ser Tyr Val
        450                 455                 460

Ile Glu Ser Asp Glu Asp Leu Glu Met Glu Met Leu Lys Ser Leu Glu
465                 470                 475                 480

Asn Leu Asn Ser Gly Thr Val Glu Pro Thr His Ser Lys Cys Leu Lys
                485                 490                 495

Met Glu Arg Asn Leu Gly Leu Pro Thr Lys Glu Glu Glu Glu Asp Asp
```

```
              500                 505                 510
Glu Asn Glu Ala Asn Glu Gly Glu Glu Asp Asp Lys Asp Phe Leu
            515                 520                 525
Trp Pro Ala Pro Asn Glu Glu Gln Val Thr Cys Leu Lys Met Tyr Phe
530                 535                 540
Gly His Ser Ser Phe Lys Pro Val Gln Trp Lys Val Ile His Ser Val
545                 550                 555                 560
Leu Glu Glu Arg Arg Asp Asn Val Ala Val Met Ala Thr Gly Tyr Gly
                565                 570                 575
Lys Ser Leu Cys Phe Gln Tyr Pro Pro Val Tyr Val Gly Lys Ile Gly
            580                 585                 590
Leu Val Ile Ser Pro Leu Ile Ser Leu Met Glu Asp Gln Val Leu Gln
            595                 600                 605
Leu Lys Met Ser Asn Ile Pro Ala Cys Phe Leu Gly Ser Ala Gln Ser
610                 615                 620
Glu Asn Val Leu Thr Asp Ile Lys Leu Gly Lys Tyr Arg Ile Val Tyr
625                 630                 635                 640
Val Thr Pro Glu Tyr Cys Ser Gly Asn Met Gly Leu Leu Gln Gln Leu
                645                 650                 655
Glu Ala Asp Ile Gly Ile Thr Leu Ile Ala Val Asp Glu Ala His Cys
            660                 665                 670
Ile Ser Glu Trp Gly His Asp Phe Arg Asp Ser Phe Arg Lys Leu Gly
            675                 680                 685
Ser Leu Lys Thr Ala Leu Pro Met Val Pro Ile Val Ala Leu Thr Ala
            690                 695                 700
Thr Ala Ser Ser Ser Ile Arg Glu Asp Ile Val Arg Cys Leu Asn Leu
705                 710                 715                 720
Arg Asn Pro Gln Ile Thr Cys Thr Gly Phe Asp Arg Pro Asn Leu Tyr
                725                 730                 735
Leu Glu Val Arg Arg Lys Thr Gly Asn Ile Leu Gln Asp Leu Gln Pro
            740                 745                 750
Phe Leu Val Lys Thr Ser Ser His Trp Glu Phe Glu Gly Pro Thr Ile
            755                 760                 765
Ile Tyr Cys Pro Ser Arg Lys Met Thr Gln Gln Val Thr Gly Glu Leu
            770                 775                 780
Arg Lys Leu Asn Leu Ser Cys Gly Thr Tyr His Ala Gly Met Ser Phe
785                 790                 795                 800
Ser Thr Arg Lys Asp Ile His His Arg Phe Val Arg Asp Glu Ile Gln
                805                 810                 815
Cys Val Ile Ala Thr Ile Ala Phe Gly Met Gly Ile Asn Lys Ala Asp
            820                 825                 830
Ile Arg Gln Val Ile His Tyr Gly Ala Pro Lys Asp Met Glu Ser Tyr
            835                 840                 845
Tyr Gln Glu Ile Gly Arg Ala Gly Arg Asp Gly Leu Gln Ser Ser Cys
            850                 855                 860
His Val Leu Trp Ala Pro Ala Asp Ile Asn Leu Asn Arg His Leu Leu
865                 870                 875                 880
Thr Glu Ile Arg Asn Glu Lys Phe Arg Leu Tyr Lys Leu Lys Met Met
                885                 890                 895
Ala Lys Met Glu Lys Tyr Leu His Ser Ser Arg Cys Arg Arg Gln Ile
            900                 905                 910
Ile Leu Ser His Phe Glu Asp Lys Gln Val Gln Lys Ala Ser Leu Gly
            915                 920                 925
```

```
Ile Met Gly Thr Glu Lys Cys Cys Asp Asn Cys Arg Ser Arg Leu Asp
    930                 935                 940

His Cys Tyr Ser Met Asp Asp Ser Glu Asp Thr Ser Trp Asp Phe Gly
945                 950                 955                 960

Pro Gln Ala Phe Lys Leu Leu Ser Ala Val Asp Ile Leu Gly Glu Lys
                965                 970                 975

Phe Gly Ile Gly Leu Pro Ile Leu Phe Leu Arg Gly Ser Asn Ser Gln
            980                 985                 990

Arg Leu Ala Asp Gln Tyr Arg Arg His Ser Leu Phe Gly Thr Gly Lys
        995                 1000                1005

Asp Gln Thr Glu Ser Trp Trp Lys Ala Phe Ser Arg Gln Leu Ile
    1010                1015                1020

Thr Glu Gly Phe Leu Val Glu Val Ser Arg Tyr Asn Lys Phe Met
    1025                1030                1035

Lys Ile Cys Ala Leu Thr Lys Gly Arg Asn Trp Leu His Lys
    1040                1045                1050

Ala Asn Thr Glu Ser Gln Ser Leu Ile Leu Gln Ala Asn Glu Glu
    1055                1060                1065

Leu Cys Pro Lys Lys Leu Leu Pro Ser Ser Lys Thr Val Ser
    1070                1075                1080

Ser Gly Thr Lys Glu His Cys Tyr Asn Gln Val Pro Val Glu Leu
    1085                1090                1095

Ser Thr Glu Lys Lys Ser Asn Leu Glu Lys Leu Tyr Ser Tyr Lys
    1100                1105                1110

Pro Cys Asp Lys Ile Ser Ser Gly Ser Asn Ile Ser Lys Lys Ser
    1115                1120                1125

Ile Met Val Gln Ser Pro Glu Lys Ala Tyr Ser Ser Gln Pro
    1130                1135                1140

Val Ile Ser Ala Gln Glu Glu Thr Gln Ile Val Leu Tyr Gly
    1145                1150                1155

Lys Leu Val Glu Ala Arg Gln Lys His Ala Asn Lys Met Asp Val
    1160                1165                1170

Pro Pro Ala Ile Leu Ala Thr Asn Lys Ile Leu Val Asp Met Ala
    1175                1180                1185

Lys Met Arg Pro Thr Thr Val Glu Asn Val Lys Arg Ile Asp Gly
    1190                1195                1200

Val Ser Glu Gly Lys Ala Ala Met Leu Ala Pro Leu Leu Glu Val
    1205                1210                1215

Ile Lys His Phe Cys Gln Thr Asn Ser Val Gln Thr Asp Leu Phe
    1220                1225                1230

Ser Ser Thr Lys Pro Gln Glu Glu Gln Lys Thr Ser Leu Val Ala
    1235                1240                1245

Lys Asn Lys Ile Cys Thr Leu Ser Gln Ser Met Ala Ile Thr Tyr
    1250                1255                1260

Ser Leu Phe Gln Glu Lys Lys Met Pro Leu Lys Ser Ile Ala Glu
    1265                1270                1275

Ser Arg Ile Leu Pro Leu Met Thr Ile Gly Met His Leu Ser Gln
    1280                1285                1290

Ala Val Lys Ala Gly Cys Pro Leu Asp Leu Glu Arg Ala Gly Leu
    1295                1300                1305

Thr Pro Glu Val Gln Lys Ile Ile Ala Asp Val Ile Arg Asn Pro
    1310                1315                1320
```

Pro Val Asn Ser Asp Met Ser Lys Ile Ser Leu Ile Arg Met Leu
1325                1330                1335

Val Pro Glu Asn Ile Asp Thr Tyr Leu Ile His Met Ala Ile Glu
1340                1345                1350

Ile Leu Lys His Gly Pro Ser Gly Leu Gln Pro Ser Cys Asp
    1355                1360                1365

Val Asn Lys Arg Arg Cys Phe Pro Gly Ser Glu Glu Ile Cys Ser
1370                1375                1380

Ser Ser Lys Arg Ser Lys Glu Glu Val Gly Ile Asn Thr Glu Thr
    1385                1390                1395

Ser Ser Ala Glu Arg Lys Arg Arg Leu Pro Val Trp Phe Ala Lys
    1400                1405                1410

Gly Ser Asp Thr Ser Lys Lys Leu Met Asp Lys Thr Lys Arg Gly
    1415                1420                1425

Gly Leu Phe Ser
    1430

<210> SEQ ID NO 61
<211> LENGTH: 991
<212> TYPE: PRT
<213> ORGANISM: Homo sapiens

<400> SEQUENCE: 61

Met Ser Ser His His Thr Thr Phe Pro Phe Asp Pro Glu Arg Arg Val
1               5                   10                  15

Arg Ser Thr Leu Lys Lys Val Phe Gly Phe Asp Ser Phe Lys Thr Pro
                20                  25                  30

Leu Gln Glu Ser Ala Thr Met Ala Val Val Lys Gly Asn Lys Asp Val
            35                  40                  45

Phe Val Cys Met Pro Thr Gly Ala Gly Lys Ser Leu Cys Tyr Gln Leu
        50                  55                  60

Pro Ala Leu Leu Ala Lys Gly Ile Thr Ile Val Val Ser Pro Leu Ile
65                  70                  75                  80

Ala Leu Ile Gln Asp Gln Val Asp His Leu Leu Thr Leu Lys Val Arg
                85                  90                  95

Val Ser Ser Leu Asn Ser Lys Leu Ser Ala Gln Glu Arg Lys Glu Leu
            100                 105                 110

Leu Ala Asp Leu Glu Arg Glu Lys Pro Gln Thr Lys Ile Leu Tyr Ile
        115                 120                 125

Thr Pro Glu Met Ala Ala Ser Ser Ser Phe Gln Pro Thr Leu Asn Ser
    130                 135                 140

Leu Val Ser Arg His His Leu Leu Ser Tyr Leu Val Val Asp Glu Ala His
145                 150                 155                 160

Cys Val Ser Gln Trp Gly His Asp Phe Arg Pro Asp Tyr Leu Arg Leu
                165                 170                 175

Gly Ala Leu Arg Ser Arg Leu Gly His Ala Pro Cys Val Ala Leu Thr
            180                 185                 190

Ala Thr Ala Thr Pro Gln Val Gln Glu Asp Val Phe Ala Ala Leu His
        195                 200                 205

Leu Lys Lys Pro Val Ala Ile Phe Lys Thr Pro Cys Phe Arg Ala Asn
    210                 215                 220

Leu Phe Tyr Asp Val Gln Phe Lys Glu Leu Ile Ser Asp Pro Tyr Gly
225                 230                 235                 240

Asn Leu Lys Asp Phe Cys Leu Lys Ala Leu Gly Gln Glu Ala Asp Lys
                245                 250                 255

```
Gly Leu Ser Gly Cys Gly Ile Val Tyr Cys Arg Thr Arg Glu Ala Cys
            260                 265                 270

Glu Gln Leu Ala Ile Glu Leu Ser Cys Arg Gly Val Asn Ala Lys Ala
        275                 280                 285

Tyr His Ala Gly Leu Lys Ala Ser Glu Arg Thr Leu Val Gln Asn Asp
    290                 295                 300

Trp Met Glu Glu Lys Val Pro Val Ile Val Ala Thr Ile Ser Phe Gly
305                 310                 315                 320

Met Gly Val Asp Lys Ala Asn Val Arg Phe Val Ala His Trp Asn Ile
                325                 330                 335

Ala Lys Ser Met Ala Gly Tyr Tyr Gln Glu Ser Gly Arg Ala Gly Arg
            340                 345                 350

Asp Gly Lys Pro Ser Trp Cys Arg Leu Tyr Tyr Ser Arg Asn Asp Arg
        355                 360                 365

Asp Gln Val Ser Phe Leu Ile Arg Lys Glu Val Ala Lys Leu Gln Glu
    370                 375                 380

Lys Arg Gly Asn Lys Ala Ser Asp Lys Ala Thr Ile Met Ala Phe Asp
385                 390                 395                 400

Ala Leu Val Thr Phe Cys Glu Glu Leu Gly Cys Arg His Ala Ala Ile
                405                 410                 415

Ala Lys Tyr Phe Gly Asp Ala Leu Pro Ala Cys Ala Lys Gly Cys Asp
            420                 425                 430

His Cys Gln Asn Pro Thr Ala Val Arg Arg Arg Leu Glu Ala Leu Glu
        435                 440                 445

Arg Ser Ser Ser Trp Ser Lys Thr Cys Ile Gly Pro Ser Gln Gly Asn
    450                 455                 460

Gly Phe Asp Pro Glu Leu Tyr Glu Gly Gly Arg Lys Gly Tyr Gly Asp
465                 470                 475                 480

Phe Ser Arg Tyr Asp Glu Gly Ser Gly Gly Ser Gly Asp Gly Arg
                485                 490                 495

Asp Glu Ala His Lys Arg Glu Trp Asn Leu Phe Tyr Gln Lys Gln Met
            500                 505                 510

Gln Leu Arg Lys Gly Lys Asp Pro Lys Ile Glu Glu Phe Val Pro Pro
        515                 520                 525

Asp Glu Asn Cys Pro Leu Lys Glu Ala Ser Ser Arg Arg Ile Pro Arg
    530                 535                 540

Leu Thr Val Lys Ala Arg Glu His Cys Leu Arg Leu Leu Glu Glu Ala
545                 550                 555                 560

Leu Ser Ser Asn Arg Gln Ser Thr Arg Thr Ala Asp Glu Ala Asp Leu
                565                 570                 575

Arg Ala Lys Ala Val Glu Leu Glu His Glu Thr Phe Arg Asn Ala Lys
            580                 585                 590

Val Ala Asn Leu Tyr Lys Ala Ser Val Leu Lys Val Ala Asp Ile
        595                 600                 605

His Arg Ala Ser Lys Asp Gly Gln Pro Tyr Asp Met Gly Gly Ser Ala
    610                 615                 620

Lys Ser Cys Ser Ala Gln Ala Glu Pro Glu Pro Asn Glu Tyr Asp
625                 630                 635                 640

Ile Pro Pro Ala Ser His Val Tyr Ser Leu Lys Pro Lys Arg Val Gly
                645                 650                 655

Ala Gly Phe Pro Lys Gly Ser Cys Pro Phe Gln Thr Ala Thr Glu Leu
            660                 665                 670
```

-continued

```
Met Glu Thr Thr Arg Ile Arg Glu Gln Ala Pro Gln Pro Glu Arg Gly
            675                 680                 685

Gly Glu His Glu Pro Pro Ser Arg Pro Cys Gly Leu Leu Asp Glu Asp
    690                 695                 700

Gly Ser Glu Pro Leu Pro Gly Pro Arg Gly Glu Val Pro Gly Gly Ser
705                 710                 715                 720

Ala His Tyr Gly Gly Pro Ser Pro Glu Lys Lys Ala Lys Ser Ser Ser
                725                 730                 735

Gly Gly Ser Ser Leu Ala Lys Gly Arg Ala Ser Lys Lys Gln Gln Leu
            740                 745                 750

Leu Ala Thr Ala Ala His Lys Asp Ser Gln Ser Ile Ala Arg Phe Phe
        755                 760                 765

Cys Arg Arg Val Glu Ser Pro Ala Leu Leu Ala Ser Ala Pro Glu Ala
    770                 775                 780

Glu Gly Ala Cys Pro Ser Cys Glu Gly Val Gln Gly Pro Pro Met Ala
785                 790                 795                 800

Pro Glu Lys Tyr Thr Gly Glu Glu Asp Gly Ala Gly Gly His Ser Pro
                805                 810                 815

Ala Pro Pro Gln Thr Glu Glu Cys Leu Arg Glu Arg Pro Ser Thr Cys
            820                 825                 830

Pro Pro Arg Asp Gln Gly Thr Pro Glu Val Gln Pro Thr Pro Ala Lys
        835                 840                 845

Asp Thr Trp Lys Gly Lys Arg Pro Arg Ser Gln Gln Glu Asn Pro Glu
    850                 855                 860

Ser Gln Pro Gln Lys Arg Pro Arg Pro Ser Ala Lys Pro Ser Val Val
865                 870                 875                 880

Ala Glu Val Lys Gly Ser Val Ser Ala Ser Glu Gln Gly Thr Leu Asn
                885                 890                 895

Pro Thr Ala Gln Asp Pro Phe Gln Leu Ser Ala Pro Gly Val Ser Leu
            900                 905                 910

Lys Glu Ala Ala Asn Val Val Lys Cys Leu Thr Pro Phe Tyr Lys
        915                 920                 925

Glu Gly Lys Phe Ala Ser Lys Glu Leu Phe Lys Gly Phe Ala Arg His
    930                 935                 940

Leu Ser His Leu Leu Thr Gln Lys Thr Ser Pro Gly Arg Ser Val Lys
945                 950                 955                 960

Glu Glu Ala Gln Asn Leu Ile Arg His Phe Phe His Gly Arg Ala Arg
                965                 970                 975

Cys Glu Ser Glu Ala Asp Trp His Gly Leu Cys Gly Pro Gln Arg
            980                 985                 990

<210> SEQ ID NO 62
<211> LENGTH: 1208
<212> TYPE: PRT
<213> ORGANISM: Homo sapiens

<400> SEQUENCE: 62

Met Glu Arg Leu Arg Asp Val Arg Glu Arg Leu Gln Ala Trp Glu Arg
1               5                   10                  15

Ala Phe Arg Arg Gln Arg Gly Arg Pro Ser Gln Asp Asp Val Glu
            20                  25                  30

Ala Ala Pro Glu Glu Thr Arg Ala Leu Tyr Arg Glu Tyr Arg Thr Leu
        35                  40                  45

Lys Arg Thr Thr Gly Gln Ala Gly Gly Gly Leu Arg Ser Ser Glu Ser
    50                  55                  60
```

```
Leu Pro Ala Ala Ala Glu Glu Ala Pro Glu Pro Arg Cys Trp Gly Pro
 65                  70                  75                  80

His Leu Asn Arg Ala Ala Thr Lys Ser Pro Gln Ser Thr Pro Gly Arg
                 85                  90                  95

Ser Arg Gln Gly Ser Val Pro Asp Tyr Gly Gln Arg Leu Lys Ala Asn
                100                 105                 110

Leu Lys Gly Thr Leu Gln Ala Gly Pro Ala Leu Gly Arg Arg Pro Trp
                115                 120                 125

Pro Leu Gly Arg Ala Ser Ser Lys Ala Ser Thr Pro Lys Pro Pro Gly
130                 135                 140

Thr Gly Pro Val Pro Ser Phe Ala Glu Lys Val Ser Asp Glu Pro Pro
145                 150                 155                 160

Gln Leu Pro Glu Pro Gln Pro Arg Pro Gly Arg Leu Gln His Leu Gln
                165                 170                 175

Ala Ser Leu Ser Gln Arg Leu Gly Ser Leu Asp Pro Gly Trp Leu Gln
                180                 185                 190

Arg Cys His Ser Glu Val Pro Asp Phe Leu Gly Ala Pro Lys Ala Cys
            195                 200                 205

Arg Pro Asp Leu Gly Ser Glu Glu Ser Gln Leu Leu Ile Pro Gly Glu
210                 215                 220

Ser Ala Val Leu Gly Pro Gly Ala Gly Ser Gln Gly Pro Glu Ala Ser
225                 230                 235                 240

Ala Phe Gln Glu Val Ser Ile Arg Val Gly Ser Pro Gln Pro Ser Ser
                245                 250                 255

Ser Gly Gly Glu Lys Arg Arg Trp Asn Glu Glu Pro Trp Glu Ser Pro
                260                 265                 270

Ala Gln Val Gln Gln Glu Ser Ser Gln Ala Gly Pro Pro Ser Glu Gly
                275                 280                 285

Ala Gly Ala Val Ala Val Glu Glu Asp Pro Pro Gly Glu Pro Val Gln
            290                 295                 300

Ala Gln Pro Pro Gln Pro Cys Ser Ser Pro Ser Asn Pro Arg Tyr His
305                 310                 315                 320

Gly Leu Ser Pro Ser Gln Ala Arg Ala Gly Lys Ala Glu Gly Thr
                325                 330                 335

Ala Pro Leu His Ile Phe Pro Arg Leu Ala Arg His Asp Arg Gly Asn
                340                 345                 350

Tyr Val Arg Leu Asn Met Lys Gln Lys His Tyr Val Arg Gly Arg Ala
                355                 360                 365

Leu Arg Ser Arg Leu Leu Arg Lys Gln Ala Trp Lys Gln Lys Trp Arg
                370                 375                 380

Lys Lys Gly Glu Cys Phe Gly Gly Gly Ala Thr Val Thr Thr Lys
385                 390                 395                 400

Glu Ser Cys Phe Leu Asn Glu Gln Phe Asp His Trp Ala Ala Gln Cys
                405                 410                 415

Pro Arg Pro Ala Ser Glu Glu Asp Thr Asp Ala Val Gly Glu Pro
                420                 425                 430

Leu Val Pro Ser Pro Gln Pro Val Pro Glu Val Pro Ser Leu Asp Pro
                435                 440                 445

Thr Val Leu Pro Leu Tyr Ser Leu Gly Pro Ser Gly Gln Leu Ala Glu
                450                 455                 460

Thr Pro Ala Glu Val Phe Gln Ala Leu Glu Gln Leu Gly His Gln Ala
465                 470                 475                 480
```

-continued

Phe Arg Pro Gly Gln Glu Arg Ala Val Met Arg Ile Leu Ser Gly Ile
            485                 490                 495

Ser Thr Leu Leu Val Leu Pro Thr Gly Ala Gly Lys Ser Leu Cys Tyr
        500                 505                 510

Gln Leu Pro Ala Leu Leu Tyr Ser Arg Arg Ser Pro Cys Leu Thr Leu
    515                 520                 525

Val Val Ser Pro Leu Leu Ser Leu Met Asp Asp Gln Val Ser Gly Leu
530                 535                 540

Pro Pro Cys Leu Lys Ala Ala Cys Ile His Ser Gly Met Thr Arg Lys
545                 550                 555                 560

Gln Arg Glu Ser Val Leu Gln Lys Ile Arg Ala Ala Gln Val His Val
                565                 570                 575

Leu Met Leu Thr Pro Glu Ala Leu Val Gly Ala Gly Gly Leu Pro Pro
            580                 585                 590

Ala Ala Gln Leu Pro Pro Val Ala Phe Ala Cys Ile Asp Glu Ala His
        595                 600                 605

Cys Leu Ser Gln Trp Ser His Asn Phe Arg Pro Cys Tyr Leu Arg Val
    610                 615                 620

Cys Lys Val Leu Arg Glu Arg Met Gly Val His Cys Phe Leu Gly Leu
625                 630                 635                 640

Thr Ala Thr Ala Thr Arg Arg Thr Ala Ser Asp Val Ala Gln His Leu
                645                 650                 655

Ala Val Ala Glu Glu Pro Asp Leu His Gly Pro Ala Pro Val Pro Thr
            660                 665                 670

Asn Leu His Leu Ser Val Ser Met Asp Arg Asp Thr Asp Gln Ala Leu
        675                 680                 685

Leu Thr Leu Leu Gln Gly Lys Arg Phe Gln Asn Leu Asp Ser Ile Ile
    690                 695                 700

Ile Tyr Cys Asn Arg Arg Glu Asp Thr Glu Arg Ile Ala Ala Leu Leu
705                 710                 715                 720

Arg Thr Cys Leu His Ala Ala Trp Val Pro Gly Ser Gly Gly Arg Ala
                725                 730                 735

Pro Lys Thr Thr Ala Glu Ala Tyr His Ala Gly Met Cys Ser Arg Glu
            740                 745                 750

Arg Arg Arg Val Gln Arg Ala Phe Met Gln Gly Gln Leu Arg Val Val
        755                 760                 765

Val Ala Thr Val Ala Phe Gly Met Gly Leu Asp Arg Pro Asp Val Arg
    770                 775                 780

Ala Val Leu His Leu Gly Leu Pro Pro Ser Phe Glu Ser Tyr Val Gln
785                 790                 795                 800

Ala Val Gly Arg Ala Gly Arg Asp Gly Gln Pro Ala His Cys His Leu
                805                 810                 815

Phe Leu Gln Pro Gln Gly Glu Asp Leu Arg Glu Leu Arg Arg His Val
            820                 825                 830

His Ala Asp Ser Thr Asp Phe Leu Ala Val Lys Arg Leu Val Gln Arg
        835                 840                 845

Val Phe Pro Ala Cys Thr Cys Thr Cys Thr Arg Pro Pro Ser Glu Gln
    850                 855                 860

Glu Gly Ala Val Gly Gly Glu Arg Pro Val Pro Lys Tyr Pro Pro Gln
865                 870                 875                 880

Glu Ala Glu Gln Leu Ser His Gln Ala Ala Pro Gly Pro Arg Arg Val
                885                 890                 895

Cys Met Gly His Glu Arg Ala Leu Pro Ile Gln Leu Thr Val Gln Ala

```
                900           905           910
Leu Asp Met Pro Glu Ala Ile Glu Thr Leu Leu Cys Tyr Leu Glu
            915           920           925

Leu His Pro His His Trp Leu Glu Leu Leu Ala Thr Thr Tyr Thr His
            930           935           940

Cys Arg Leu Asn Cys Pro Gly Gly Pro Ala Gln Leu Gln Ala Leu Ala
945           950           955           960

His Arg Cys Pro Pro Leu Ala Val Cys Leu Ala Gln Gln Leu Pro Glu
            965           970           975

Asp Pro Gly Gln Gly Ser Ser Ser Val Glu Phe Asp Met Val Lys Leu
            980           985           990

Val Asp Ser Met Gly Trp Glu Leu Ala Ser Val Arg Arg Ala Leu Cys
            995           1000          1005

Gln Leu Gln Trp Asp His Glu Pro Arg Thr Gly Val Arg Arg Gly
            1010          1015          1020

Thr Gly Val Leu Val Glu Phe Ser Glu Leu Ala Phe His Leu Arg
            1025          1030          1035

Ser Pro Gly Asp Leu Thr Ala Glu Glu Lys Asp Gln Ile Cys Asp
            1040          1045          1050

Phe Leu Tyr Gly Arg Val Gln Ala Arg Glu Arg Gln Ala Leu Ala
            1055          1060          1065

Arg Leu Arg Arg Thr Phe Gln Ala Phe His Ser Val Ala Phe Pro
            1070          1075          1080

Ser Cys Gly Pro Cys Leu Glu Gln Gln Asp Glu Arg Ser Thr
            1085          1090          1095

Arg Leu Lys Asp Leu Leu Gly Arg Tyr Phe Glu Glu Glu Gly
            1100          1105          1110

Gln Glu Pro Gly Gly Met Glu Asp Ala Gln Gly Pro Glu Pro Gly
            1115          1120          1125

Gln Ala Arg Leu Gln Asp Trp Glu Asp Gln Val Arg Cys Asp Ile
            1130          1135          1140

Arg Gln Phe Leu Ser Leu Arg Pro Glu Glu Lys Phe Ser Ser Arg
            1145          1150          1155

Ala Val Ala Arg Ile Phe His Gly Ile Gly Ser Pro Cys Tyr Pro
            1160          1165          1170

Ala Gln Val Tyr Gly Gln Asp Arg Arg Phe Trp Arg Lys Tyr Leu
            1175          1180          1185

His Leu Ser Phe His Ala Leu Val Gly Leu Ala Thr Glu Glu Leu
            1190          1195          1200

Leu Gln Val Ala Arg
            1205

<210> SEQ ID NO 63
<211> LENGTH: 1101
<212> TYPE: PRT
<213> ORGANISM: Homo sapiens

<400> SEQUENCE: 63

Met Asp Glu Cys Gly Ser Arg Ile Arg Arg Arg Val Ser Leu Pro Lys
1               5                   10                  15

Arg Asn Arg Pro Ser Leu Gly Cys Ile Phe Gly Ala Pro Thr Ala Ala
            20                  25                  30

Glu Leu Val Pro Gly Asp Glu Gly Lys Glu Glu Glu Met Val Ala
            35                  40                  45
```

```
Glu Asn Arg Arg Arg Lys Thr Ala Gly Val Leu Pro Val Glu Val Gln
 50                  55                  60

Pro Leu Leu Leu Ser Asp Ser Pro Glu Cys Leu Val Leu Gly Gly Gly
 65                  70                  75                  80

Asp Thr Asn Pro Asp Leu Leu Arg His Met Pro Thr Asp Arg Gly Val
                 85                  90                  95

Gly Asp Gln Pro Asn Asp Ser Glu Val Asp Met Phe Gly Asp Tyr Asp
                100                 105                 110

Ser Phe Thr Glu Asn Ser Phe Ile Ala Gln Val Asp Asp Leu Glu Gln
            115                 120                 125

Lys Tyr Met Gln Leu Pro Glu His Lys Lys His Ala Thr Asp Phe Ala
        130                 135                 140

Thr Glu Asn Leu Cys Ser Glu Ser Ile Lys Asn Lys Leu Ser Ile Thr
145                 150                 155                 160

Thr Ile Gly Asn Leu Thr Glu Leu Gln Thr Asp Lys His Thr Glu Asn
                165                 170                 175

Gln Ser Gly Tyr Glu Gly Val Thr Ile Glu Pro Gly Ala Asp Leu Leu
            180                 185                 190

Tyr Asp Val Pro Ser Ser Gln Ala Ile Tyr Phe Glu Asn Leu Gln Asn
        195                 200                 205

Ser Ser Asn Asp Leu Gly Asp His Ser Met Lys Glu Arg Asp Trp Lys
    210                 215                 220

Ser Ser Ser His Asn Thr Val Asn Glu Glu Leu Pro His Asn Cys Ile
225                 230                 235                 240

Glu Gln Pro Gln Gln Asn Asp Glu Ser Ser Lys Val Arg Thr Ser
                245                 250                 255

Ser Asp Met Asn Arg Arg Lys Ser Ile Lys Asp His Leu Lys Asn Ala
        260                 265                 270

Met Thr Gly Asn Ala Lys Ala Gln Thr Pro Ile Phe Ser Arg Ser Lys
            275                 280                 285

Gln Leu Lys Asp Thr Leu Leu Ser Glu Ile Asn Val Ala Lys Lys
    290                 295                 300

Thr Val Glu Ser Ser Ser Asn Asp Leu Gly Pro Phe Tyr Ser Leu Pro
305                 310                 315                 320

Ser Lys Val Arg Asp Leu Tyr Ala Gln Phe Lys Gly Ile Glu Lys Leu
                325                 330                 335

Tyr Glu Trp Gln His Thr Cys Leu Thr Leu Asn Ser Val Gln Glu Arg
            340                 345                 350

Lys Asn Leu Ile Tyr Ser Leu Pro Thr Ser Gly Gly Lys Thr Leu Val
        355                 360                 365

Ala Glu Ile Leu Met Leu Gln Glu Leu Leu Cys Cys Arg Lys Asp Val
    370                 375                 380

Leu Met Ile Leu Pro Tyr Val Ala Ile Val Gln Glu Lys Ile Ser Gly
385                 390                 395                 400

Leu Ser Ser Phe Gly Ile Glu Leu Gly Phe Phe Val Glu Glu Tyr Ala
                405                 410                 415

Gly Ser Lys Gly Arg Phe Pro Pro Thr Lys Arg Arg Glu Lys Lys Ser
            420                 425                 430

Leu Tyr Ile Ala Thr Ile Glu Lys Gly His Ser Leu Val Asn Ser Leu
        435                 440                 445

Ile Glu Thr Gly Arg Ile Asp Ser Leu Gly Leu Val Val Val Asp Glu
    450                 455                 460

Leu His Met Ile Gly Glu Gly Ser Arg Gly Ala Thr Leu Glu Met Thr
```

```
            465                 470                 475                 480
Leu Ala Lys Ile Leu Tyr Thr Ser Lys Thr Thr Gln Ile Ile Gly Met
                    485                 490                 495

Ser Ala Thr Leu Asn Asn Val Glu Asp Leu Gln Lys Phe Leu Gln Ala
                    500                 505                 510

Glu Tyr Tyr Thr Ser Gln Phe Arg Pro Val Glu Leu Lys Glu Tyr Leu
                    515                 520                 525

Lys Ile Asn Asp Thr Ile Tyr Glu Val Asp Ser Lys Ala Glu Asn Gly
                    530                 535                 540

Met Thr Phe Ser Arg Leu Leu Asn Tyr Lys Tyr Ser Asp Thr Leu Lys
545                 550                 555                 560

Lys Met Asp Pro Asp His Leu Val Ala Leu Val Thr Glu Val Ile Pro
                    565                 570                 575

Asn Tyr Ser Cys Leu Val Phe Cys Pro Ser Lys Lys Asn Cys Glu Asn
                    580                 585                 590

Val Ala Glu Met Ile Cys Lys Phe Leu Ser Lys Glu Tyr Leu Lys His
                    595                 600                 605

Lys Glu Lys Glu Lys Cys Glu Val Ile Lys Asn Leu Lys Asn Ile Gly
                    610                 615                 620

Asn Gly Asn Leu Cys Pro Val Leu Lys Arg Thr Ile Pro Phe Gly Val
625                 630                 635                 640

Ala Tyr His His Ser Gly Leu Thr Ser Asp Glu Arg Lys Leu Leu Glu
                    645                 650                 655

Glu Ala Tyr Ser Thr Gly Val Leu Cys Leu Phe Thr Cys Thr Ser Thr
                    660                 665                 670

Leu Ala Ala Gly Val Asn Leu Pro Ala Arg Arg Val Ile Leu Arg Ala
                    675                 680                 685

Pro Tyr Val Ala Lys Glu Phe Leu Lys Arg Asn Gln Tyr Lys Gln Met
                    690                 695                 700

Ile Gly Arg Ala Gly Arg Ala Gly Ile Asp Thr Ile Gly Glu Ser Ile
705                 710                 715                 720

Leu Ile Leu Gln Glu Lys Asp Lys Gln Gln Val Leu Glu Leu Ile Thr
                    725                 730                 735

Lys Pro Leu Glu Asn Cys Tyr Ser His Leu Val Gln Glu Phe Thr Lys
                    740                 745                 750

Gly Ile Gln Thr Leu Phe Leu Ser Leu Ile Gly Leu Lys Ile Ala Thr
                    755                 760                 765

Asn Leu Asp Asp Ile Tyr His Phe Met Asn Gly Thr Phe Phe Gly Val
                    770                 775                 780

Gln Gln Lys Val Leu Leu Lys Glu Lys Ser Leu Trp Glu Ile Thr Val
785                 790                 795                 800

Glu Ser Leu Arg Tyr Leu Thr Glu Lys Gly Leu Leu Gln Lys Asp Thr
                    805                 810                 815

Ile Tyr Lys Ser Glu Glu Val Gln Tyr Asn Phe His Ile Thr Lys
                    820                 825                 830

Leu Gly Arg Ala Ser Phe Lys Gly Thr Ile Asp Leu Ala Tyr Cys Asp
                    835                 840                 845

Ile Leu Tyr Arg Asp Leu Lys Lys Gly Leu Glu Gly Leu Val Leu Glu
                    850                 855                 860

Ser Leu Leu His Leu Ile Tyr Leu Thr Thr Pro Tyr Asp Leu Val Ser
865                 870                 875                 880

Gln Cys Asn Pro Asp Trp Met Ile Tyr Phe Arg Gln Phe Ser Gln Leu
                    885                 890                 895
```

```
Ser Pro Ala Glu Gln Asn Val Ala Ala Ile Leu Gly Val Ser Glu Ser
            900                 905                 910

Phe Ile Gly Lys Lys Ala Ser Gly Gln Ala Ile Gly Lys Lys Val Asp
        915                 920                 925

Lys Asn Val Val Asn Arg Leu Tyr Leu Ser Phe Val Leu Tyr Thr Leu
    930                 935                 940

Leu Lys Glu Thr Asn Ile Trp Thr Val Ser Glu Lys Phe Asn Met Pro
945                 950                 955                 960

Arg Gly Tyr Ile Gln Asn Leu Leu Thr Gly Thr Ala Ser Phe Ser Ser
                965                 970                 975

Cys Val Leu His Phe Cys Glu Glu Leu Glu Glu Phe Trp Val Tyr Arg
            980                 985                 990

Ala Leu Leu Val Glu Leu Thr Lys Lys Leu Thr Tyr Cys Val Lys Ala
        995                 1000                1005

Glu Leu Ile Pro Leu Met Glu Val Thr Gly Val Leu Glu Gly Arg
    1010                1015                1020

Ala Lys Gln Leu Tyr Ser Ala Gly Tyr Lys Ser Leu Met His Leu
    1025                1030                1035

Ala Asn Ala Asn Pro Glu Val Leu Val Arg Thr Ile Asp His Leu
    1040                1045                1050

Ser Arg Arg Gln Ala Lys Gln Ile Val Ser Ser Ala Lys Met Leu
    1055                1060                1065

Leu His Glu Lys Ala Glu Ala Leu Gln Glu Glu Val Glu Glu Leu
    1070                1075                1080

Leu Arg Leu Pro Ser Asp Phe Pro Gly Ala Val Ala Ser Ser Thr
    1085                1090                1095

Asp Lys Ala
    1100

<210> SEQ ID NO 64
<211> LENGTH: 1196
<212> TYPE: PRT
<213> ORGANISM: Herpes simplex virus

<400> SEQUENCE: 64

Met Glu Thr Lys Pro Lys Thr Ala Thr Thr Ile Lys Val Pro Pro Gly
1               5                   10                  15

Pro Leu Gly Tyr Val Tyr Ala Arg Ala Cys Pro Ser Glu Gly Ile Glu
            20                  25                  30

Leu Leu Ala Leu Leu Ser Ala Arg Ser Gly Asp Ser Asp Val Ala Val
        35                  40                  45

Ala Pro Leu Val Val Gly Leu Thr Val Glu Ser Gly Phe Glu Ala Asn
    50                  55                  60

Val Ala Val Val Gly Ser Arg Thr Thr Gly Leu Gly Gly Thr Ala
65              70                  75                  80

Val Ser Leu Lys Leu Thr Pro Ser His Tyr Ser Ser Val Tyr Val
            85                  90                  95

Phe His Gly Gly Arg His Leu Asp Pro Ser Thr Gln Ala Pro Asn Leu
            100                 105                 110

Thr Arg Leu Cys Glu Arg Ala Arg His Phe Gly Phe Ser Asp Tyr
        115                 120                 125

Thr Pro Arg Pro Gly Asp Leu Lys His Glu Thr Thr Gly Glu Ala Leu
    130                 135                 140

Cys Glu Arg Leu Gly Leu Asp Pro Asp Arg Ala Leu Leu Tyr Leu Val
```

```
           145                 150                 155                 160
Val Thr Glu Gly Phe Lys Glu Ala Val Cys Ile Asn Asn Thr Phe Leu
                165                 170                 175

His Leu Gly Gly Ser Asp Lys Val Thr Ile Gly Gly Ala Glu Val His
                180                 185                 190

Arg Ile Pro Val Tyr Pro Leu Gln Leu Phe Met Pro Asp Phe Ser Arg
                195                 200                 205

Val Ile Ala Glu Pro Phe Asn Ala Asn His Arg Ser Ile Gly Glu Lys
                210                 215                 220

Phe Thr Tyr Pro Leu Pro Phe Phe Asn Arg Pro Leu Asn Arg Leu Leu
225                 230                 235                 240

Phe Glu Ala Val Val Gly Pro Ala Ala Val Ala Leu Arg Cys Arg Asn
                245                 250                 255

Val Asp Ala Val Ala Arg Ala Ala His Leu Ala Phe Asp Glu Asn
                260                 265                 270

His Glu Gly Ala Ala Leu Pro Ala Asp Ile Thr Phe Thr Ala Phe Glu
                275                 280                 285

Ala Ser Gln Gly Lys Thr Pro Arg Gly Gly Asp Gly Gly Gly Lys
                290                 295                 300

Gly Ala Ala Gly Gly Phe Glu Gln Arg Leu Ala Ser Val Met Ala Gly
305                 310                 315                 320

Asp Ala Ala Leu Ala Leu Glu Ser Ile Val Ser Met Ala Val Phe Asp
                325                 330                 335

Glu Pro Pro Thr Asp Ile Ser Ala Trp Pro Leu Phe Glu Gly Gln Asp
                340                 345                 350

Thr Ala Ala Arg Ala Asn Ala Val Gly Ala Tyr Leu Ala Arg Ala
                355                 360                 365

Ala Gly Leu Val Gly Ala Met Val Phe Ser Thr Asn Ser Ala Leu His
                370                 375                 380

Leu Thr Glu Val Asp Asp Ala Gly Pro Ala Asp Pro Lys Asp His Ser
385                 390                 395                 400

Lys Pro Ser Phe Tyr Arg Phe Phe Leu Val Pro Gly Thr His Val Ala
                405                 410                 415

Ala Asn Pro Gln Val Asp Arg Glu Gly His Val Pro Gly Phe Glu
                420                 425                 430

Gly Arg Pro Thr Ala Pro Leu Val Gly Thr Gln Glu Phe Ala Gly
                435                 440                 445

Glu His Leu Ala Met Leu Cys Gly Phe Ser Pro Ala Leu Leu Ala Lys
                450                 455                 460

Met Leu Phe Tyr Leu Glu Arg Cys Asp Gly Ala Val Ile Val Gly Arg
465                 470                 475                 480

Gln Glu Met Asp Val Phe Arg Tyr Val Ala Asp Ser Asn Gln Thr Asp
                485                 490                 495

Val Pro Cys Asn Leu Cys Thr Phe Asp Thr Arg His Ala Cys Val His
                500                 505                 510

Thr Thr Leu Met Arg Leu Arg Ala Arg His Pro Lys Phe Ala Ser Ala
                515                 520                 525

Ala Arg Gly Ala Ile Gly Val Phe Gly Thr Met Asn Ser Met Tyr Ser
                530                 535                 540

Asp Cys Asp Val Leu Gly Asn Tyr Ala Ala Phe Ser Ala Leu Lys Arg
545                 550                 555                 560

Ala Asp Gly Ser Glu Thr Ala Arg Thr Ile Met Gln Glu Thr Tyr Arg
                565                 570                 575
```

```
Ala Ala Thr Glu Arg Val Met Ala Glu Leu Glu Thr Leu Gln Tyr Val
            580                 585                 590

Asp Gln Ala Val Pro Thr Ala Met Gly Arg Leu Glu Thr Ile Ile Thr
            595                 600                 605

Asn Arg Glu Ala Leu His Thr Val Val Asn Asn Val Arg Gln Val Val
            610                 615                 620

Asp Arg Glu Val Glu Gln Leu Met Arg Asn Leu Val Glu Gly Arg Asn
625                 630                 635                 640

Phe Lys Phe Arg Asp Gly Leu Gly Glu Ala Asn His Ala Met Ser Leu
            645                 650                 655

Thr Leu Asp Pro Tyr Ala Cys Gly Pro Cys Pro Leu Leu Gln Leu Leu
            660                 665                 670

Gly Arg Arg Ser Asn Leu Ala Val Tyr Gln Asp Leu Ala Leu Ser Gln
            675                 680                 685

Cys His Gly Val Phe Ala Gly Gln Ser Val Glu Gly Arg Asn Phe Arg
            690                 695                 700

Asn Gln Phe Gln Pro Val Leu Arg Arg Val Met Asp Met Phe Asn
705                 710                 715                 720

Asn Gly Phe Leu Ser Ala Lys Thr Leu Thr Val Ala Leu Ser Glu Gly
            725                 730                 735

Ala Ala Ile Cys Ala Pro Ser Leu Thr Ala Gly Gln Thr Ala Pro Ala
            740                 745                 750

Glu Ser Ser Phe Glu Gly Asp Val Ala Arg Val Thr Leu Gly Phe Pro
            755                 760                 765

Lys Glu Leu Arg Val Lys Ser Arg Val Leu Phe Ala Gly Ala Ser Ala
            770                 775                 780

Asn Ala Ser Glu Ala Ala Lys Ala Arg Val Ala Ser Leu Gln Ser Ala
785                 790                 795                 800

Tyr Gln Lys Pro Asp Lys Arg Val Asp Ile Leu Leu Gly Pro Leu Gly
            805                 810                 815

Phe Leu Leu Lys Gln Phe His Ala Ala Ile Phe Pro Asn Gly Lys Pro
            820                 825                 830

Pro Gly Ser Asn Gln Pro Asn Pro Gln Trp Phe Trp Thr Ala Leu Gln
            835                 840                 845

Arg Asn Gln Leu Pro Ala Arg Leu Leu Ser Arg Glu Asp Ile Glu Thr
850                 855                 860

Ile Ala Phe Ile Lys Lys Phe Ser Leu Asp Tyr Gly Ala Ile Asn Phe
865                 870                 875                 880

Ile Asn Leu Ala Pro Asn Asn Val Ser Glu Leu Ala Met Tyr Tyr Met
            885                 890                 895

Ala Asn Gln Ile Leu Arg Tyr Cys Asp His Ser Thr Tyr Phe Ile Asn
            900                 905                 910

Thr Leu Thr Ala Ile Ile Ala Gly Ser Arg Arg Pro Pro Ser Val Gln
            915                 920                 925

Ala Ala Ala Trp Ser Ala Gln Gly Gly Ala Gly Leu Glu Ala Gly
            930                 935                 940

Ala Arg Ala Leu Met Asp Ala Val Asp Ala His Pro Gly Ala Trp Thr
945                 950                 955                 960

Ser Met Phe Ala Ser Cys Asn Leu Leu Arg Pro Val Met Ala Ala Arg
            965                 970                 975

Pro Met Val Val Leu Gly Leu Ser Ile Ser Lys Tyr Tyr Gly Met Ala
            980                 985                 990
```

```
Gly Asn Asp Arg Val Phe Gln Ala Gly Asn Trp Ala Ser Leu Met Gly
            995                1000                1005

Gly Lys Asn Ala Cys Pro Leu Leu Ile Phe Asp Arg Thr Arg Lys
        1010                1015                1020

Phe Val Leu Ala Cys Pro Arg Ala Gly Phe Val Cys Ala Ala Ser
        1025                1030                1035

Ser Leu Gly Gly Gly Ala His Glu Ser Ser Leu Cys Glu Gln Leu
        1040                1045                1050

Arg Gly Ile Ile Ser Glu Gly Gly Ala Ala Val Ala Ser Ser Val
        1055                1060                1065

Phe Val Ala Thr Val Lys Ser Leu Gly Pro Arg Thr Gln Gln Leu
        1070                1075                1080

Gln Ile Glu Asp Trp Leu Ala Leu Leu Glu Asp Glu Tyr Leu Ser
        1085                1090                1095

Glu Glu Met Met Glu Leu Thr Ala Arg Ala Leu Glu Arg Gly Asn
        1100                1105                1110

Gly Glu Trp Ser Thr Asp Ala Ala Leu Glu Val Ala His Glu Ala
        1115                1120                1125

Glu Ala Leu Val Ser Gln Leu Gly Asn Ala Gly Glu Val Phe Asn
        1130                1135                1140

Phe Gly Asp Phe Gly Cys Glu Asp Asp Asn Ala Thr Pro Phe Gly
        1145                1150                1155

Gly Pro Gly Ala Pro Gly Pro Ala Phe Ala Gly Arg Lys Arg Ala
        1160                1165                1170

Phe His Gly Asp Asp Pro Phe Gly Glu Gly Pro Pro Asp Lys Lys
        1175                1180                1185

Gly Asp Leu Thr Leu Asp Met Leu
        1190                1195

<210> SEQ ID NO 65
<211> LENGTH: 843
<212> TYPE: PRT
<213> ORGANISM: Saccharomyces cerevisiae

<400> SEQUENCE: 65

Met Thr Asp Val Glu Gly Tyr Gln Pro Lys Ser Lys Gly Lys Ile Phe
1               5                   10                  15

Pro Asp Met Gly Glu Ser Phe Phe Ser Ser Asp Glu Asp Ser Pro Ala
            20                  25                  30

Thr Asp Ala Glu Ile Asp Glu Asn Tyr Asp Asn Arg Glu Thr Ser
        35                  40                  45

Glu Gly Arg Gly Glu Arg Asp Thr Gly Ala Met Val Thr Gly Leu Lys
    50                  55                  60

Lys Pro Arg Lys Lys Thr Lys Ser Ser Arg His Thr Ala Ala Asp Ser
65                  70                  75                  80

Ser Met Asn Gln Met Asp Ala Lys Asp Lys Ala Leu Leu Gln Asp Thr
                85                  90                  95

Asn Ser Asp Ile Pro Ala Asp Phe Val Pro Asp Ser Val Ser Gly Met
            100                 105                 110

Phe Arg Ser His Asp Phe Ser Tyr Leu Arg Leu Arg Pro Asp His Ala
        115                 120                 125

Ser Arg Pro Leu Trp Ile Ser Pro Ser Asp Gly Arg Ile Ile Leu Glu
    130                 135                 140

Ser Phe Ser Pro Leu Ala Glu Gln Ala Gln Asp Phe Leu Val Thr Ile
145                 150                 155                 160
```

```
Ala Glu Pro Ile Ser Arg Pro Ser His Ile His Glu Tyr Lys Ile Thr
                165                 170                 175

Ala Tyr Ser Leu Tyr Ala Ala Val Ser Val Gly Leu Glu Thr Asp Asp
            180                 185                 190

Ile Ile Ser Val Leu Asp Arg Leu Ser Lys Val Pro Val Ala Glu Ser
        195                 200                 205

Ile Ile Asn Phe Ile Lys Gly Ala Thr Ile Ser Tyr Gly Lys Val Lys
    210                 215                 220

Leu Val Ile Lys His Asn Arg Tyr Phe Val Glu Thr Thr Gln Ala Asp
225                 230                 235                 240

Ile Leu Gln Met Leu Leu Asn Asp Ser Val Ile Gly Pro Leu Arg Ile
                245                 250                 255

Asp Ser Asp His Gln Val Gln Pro Pro Glu Asp Val Leu Gln Gln Gln
            260                 265                 270

Leu Gln Gln Thr Ala Gly Lys Pro Ala Thr Asn Val Asn Pro Asn Asp
        275                 280                 285

Val Glu Ala Val Phe Ser Ala Val Ile Gly Gly Asp Asn Glu Arg Glu
    290                 295                 300

Glu Glu Asp Asp Asp Ile Asp Ala Val His Ser Phe Glu Ile Ala Asn
305                 310                 315                 320

Glu Ser Val Glu Val Lys Lys Arg Cys Gln Glu Ile Asp Tyr Pro
                325                 330                 335

Val Leu Glu Glu Tyr Asp Phe Arg Asn Asp His Arg Asn Pro Asp Leu
            340                 345                 350

Asp Ile Asp Leu Lys Pro Ser Thr Gln Ile Arg Pro Tyr Gln Glu Lys
        355                 360                 365

Ser Leu Ser Lys Met Phe Gly Asn Gly Arg Ala Arg Ser Gly Ile Ile
    370                 375                 380

Val Leu Pro Cys Gly Ala Gly Lys Thr Leu Val Gly Ile Thr Ala Ala
385                 390                 395                 400

Cys Thr Ile Lys Lys Ser Val Ile Val Leu Cys Thr Ser Ser Val Ser
                405                 410                 415

Val Met Gln Trp Arg Gln Gln Phe Leu Gln Trp Cys Thr Leu Gln Pro
            420                 425                 430

Glu Asn Cys Ala Val Phe Thr Ser Asp Asn Lys Glu Met Phe Gln Thr
        435                 440                 445

Glu Ser Gly Leu Val Val Ser Thr Tyr Ser Met Val Ala Asn Thr Arg
    450                 455                 460

Asn Arg Ser His Asp Ser Gln Lys Val Met Asp Phe Leu Thr Gly Arg
465                 470                 475                 480

Glu Trp Gly Phe Ile Ile Leu Asp Glu Val His Val Val Pro Ala Ala
                485                 490                 495

Met Phe Arg Arg Val Val Ser Thr Ile Ala Ala His Ala Lys Leu Gly
            500                 505                 510

Leu Thr Ala Thr Leu Val Arg Glu Asp Asp Lys Ile Gly Asp Leu Asn
        515                 520                 525

Phe Leu Ile Gly Pro Lys Leu Tyr Glu Ala Asn Trp Met Glu Leu Ser
    530                 535                 540

Gln Lys Gly His Ile Ala Asn Val Gln Cys Ala Glu Val Trp Cys Pro
545                 550                 555                 560

Met Thr Ala Glu Phe Tyr Gln Glu Tyr Leu Arg Glu Thr Ala Arg Lys
                565                 570                 575
```

Arg Met Leu Leu Tyr Ile Met Asn Pro Thr Lys Phe Gln Ala Cys Gln
            580                 585                 590

Phe Leu Ile Gln Tyr His Glu Arg Arg Gly Asp Lys Ile Ile Val Phe
        595                 600                 605

Ser Asp Asn Val Tyr Ala Leu Gln Glu Tyr Ala Leu Lys Met Gly Lys
    610                 615                 620

Pro Phe Ile Tyr Gly Ser Thr Pro Gln Gln Glu Arg Met Asn Ile Leu
625                 630                 635                 640

Gln Asn Phe Gln Tyr Asn Asp Gln Ile Asn Thr Ile Phe Leu Ser Lys
                645                 650                 655

Val Gly Asp Thr Ser Ile Asp Leu Pro Glu Ala Thr Cys Leu Ile Gln
            660                 665                 670

Ile Ser Ser His Tyr Gly Ser Arg Arg Gln Glu Ala Gln Arg Leu Gly
        675                 680                 685

Arg Ile Leu Arg Ala Lys Arg Arg Asn Asp Glu Gly Phe Asn Ala Phe
    690                 695                 700

Phe Tyr Ser Leu Val Ser Lys Asp Thr Gln Glu Met Tyr Tyr Ser Thr
705                 710                 715                 720

Lys Arg Gln Ala Phe Leu Val Asp Gln Gly Tyr Ala Phe Lys Val Ile
                725                 730                 735

Thr His Leu His Gly Met Glu Asn Ile Pro Asn Leu Ala Tyr Ala Ser
            740                 745                 750

Pro Arg Glu Arg Arg Glu Leu Leu Gln Glu Val Leu Leu Lys Asn Glu
        755                 760                 765

Glu Ala Ala Gly Ile Glu Val Gly Asp Asp Ala Asp Asn Ser Val Gly
    770                 775                 780

Arg Gly Ser Asn Gly His Lys Arg Phe Lys Ser Lys Ala Val Arg Gly
785                 790                 795                 800

Glu Gly Ser Leu Ser Gly Leu Ala Gly Gly Glu Asp Met Ala Tyr Met
                805                 810                 815

Glu Tyr Ser Thr Asn Lys Asn Lys Glu Leu Lys Glu His His Pro Leu
            820                 825                 830

Ile Arg Lys Met Tyr Tyr Lys Asn Leu Lys Lys
        835                 840

<210> SEQ ID NO 66
<211> LENGTH: 778
<212> TYPE: PRT
<213> ORGANISM: Saccharomyces cerevisiae

<400> SEQUENCE: 66

Met Lys Phe Tyr Ile Asp Asp Leu Pro Val Leu Phe Pro Tyr Pro Lys
1               5                   10                  15

Ile Tyr Pro Glu Gln Tyr Asn Tyr Met Cys Asp Ile Lys Lys Thr Leu
            20                  25                  30

Asp Val Gly Gly Asn Ser Ile Leu Glu Met Pro Ser Gly Thr Gly Lys
        35                  40                  45

Thr Val Ser Leu Leu Ser Leu Thr Ile Ala Tyr Gln Met His Tyr Pro
    50                  55                  60

Glu His Arg Lys Ile Ile Tyr Cys Ser Arg Thr Met Ser Glu Ile Glu
65                  70                  75                  80

Lys Ala Leu Val Glu Leu Glu Asn Leu Met Asp Tyr Arg Thr Lys Glu
                85                  90                  95

Leu Gly Tyr Gln Glu Asp Phe Arg Gly Leu Gly Leu Thr Ser Arg Lys
            100                 105                 110

```
Asn Leu Cys Leu His Pro Glu Val Ser Lys Glu Arg Lys Gly Thr Val
            115                 120                 125

Val Asp Glu Lys Cys Arg Arg Met Thr Asn Gly Gln Ala Lys Arg Lys
        130                 135                 140

Leu Glu Glu Asp Pro Glu Ala Asn Val Glu Leu Cys Glu Tyr His Glu
145                 150                 155                 160

Asn Leu Tyr Asn Ile Glu Val Glu Asp Tyr Leu Pro Lys Gly Val Phe
                165                 170                 175

Ser Phe Glu Lys Leu Leu Lys Tyr Cys Glu Glu Lys Thr Leu Cys Pro
            180                 185                 190

Tyr Phe Ile Val Arg Arg Met Ile Ser Leu Cys Asn Ile Ile Ile Tyr
        195                 200                 205

Ser Tyr His Tyr Leu Leu Asp Pro Lys Ile Ala Glu Arg Val Ser Asn
    210                 215                 220

Glu Val Ser Lys Asp Ser Ile Val Ile Phe Asp Glu Ala His Asn Ile
225                 230                 235                 240

Asp Asn Val Cys Ile Glu Ser Leu Ser Leu Asp Leu Thr Thr Asp Ala
                245                 250                 255

Leu Arg Arg Ala Thr Arg Gly Ala Asn Ala Leu Asp Glu Arg Ile Ser
            260                 265                 270

Glu Val Arg Lys Val Asp Ser Gln Lys Leu Gln Asp Glu Tyr Glu Lys
        275                 280                 285

Leu Val Gln Gly Leu His Ser Ala Asp Ile Leu Thr Asp Gln Glu Glu
    290                 295                 300

Pro Phe Val Glu Thr Pro Val Leu Pro Gln Asp Leu Leu Thr Glu Ala
305                 310                 315                 320

Ile Pro Gly Asn Ile Arg Arg Ala Glu His Phe Val Ser Phe Leu Lys
                325                 330                 335

Arg Leu Ile Glu Tyr Leu Lys Thr Arg Met Lys Val Leu His Val Ile
            340                 345                 350

Ser Glu Thr Pro Lys Ser Phe Leu Gln His Leu Lys Gln Leu Thr Phe
        355                 360                 365

Ile Glu Arg Lys Pro Leu Arg Phe Cys Ser Glu Arg Leu Ser Leu Leu
    370                 375                 380

Val Arg Thr Leu Glu Val Thr Glu Val Glu Asp Phe Thr Ala Leu Lys
385                 390                 395                 400

Asp Ile Ala Thr Phe Ala Thr Leu Ile Ser Thr Tyr Glu Glu Gly Phe
                405                 410                 415

Leu Leu Ile Ile Glu Pro Tyr Glu Ile Glu Asn Ala Ala Val Pro Asn
            420                 425                 430

Pro Ile Met Arg Phe Thr Cys Leu Asp Ala Ser Ile Ala Ile Lys Pro
        435                 440                 445

Val Phe Glu Arg Phe Ser Ser Val Ile Ile Thr Ser Gly Thr Ile Ser
    450                 455                 460

Pro Leu Asp Met Tyr Pro Arg Met Leu Asn Phe Lys Thr Val Leu Gln
465                 470                 475                 480

Lys Ser Tyr Ala Met Thr Leu Ala Lys Lys Ser Phe Leu Pro Met Ile
                485                 490                 495

Ile Thr Lys Gly Ser Asp Gln Val Ala Ile Ser Ser Arg Phe Glu Ile
            500                 505                 510

Arg Asn Asp Pro Ser Ile Val Arg Asn Tyr Gly Ser Met Leu Val Glu
        515                 520                 525
```

Phe Ala Lys Ile Thr Pro Asp Gly Met Val Val Phe Pro Ser Tyr
530                 535                 540

Leu Tyr Met Glu Ser Ile Val Ser Met Trp Gln Thr Met Gly Ile Leu
545                 550                 555                 560

Asp Glu Val Trp Lys His Lys Leu Ile Leu Val Glu Thr Pro Asp Ala
            565                 570                 575

Gln Glu Thr Ser Leu Ala Leu Glu Thr Tyr Arg Lys Ala Cys Ser Asn
        580                 585                 590

Gly Arg Gly Ala Ile Leu Leu Ser Val Ala Arg Gly Lys Val Ser Glu
        595                 600                 605

Gly Ile Asp Phe Asp His Gln Tyr Gly Arg Thr Val Leu Met Ile Gly
610                 615                 620

Ile Pro Phe Gln Tyr Thr Glu Ser Arg Ile Leu Lys Ala Arg Leu Glu
625                 630                 635                 640

Phe Met Arg Glu Asn Tyr Arg Ile Arg Glu Asn Asp Phe Leu Ser Phe
            645                 650                 655

Asp Ala Met Arg His Ala Ala Gln Cys Leu Gly Arg Val Leu Arg Gly
        660                 665                 670

Lys Asp Asp Tyr Gly Val Met Val Leu Ala Asp Arg Arg Phe Ser Arg
        675                 680                 685

Lys Arg Ser Gln Leu Pro Lys Trp Ile Ala Gln Gly Leu Ser Asp Ala
690                 695                 700

Asp Leu Asn Leu Ser Thr Asp Met Ala Ile Ser Asn Thr Lys Gln Phe
705                 710                 715                 720

Leu Arg Thr Met Ala Gln Pro Thr Asp Pro Lys Asp Gln Glu Gly Val
            725                 730                 735

Ser Val Trp Ser Tyr Glu Asp Leu Ile Lys His Gln Asn Ser Arg Lys
        740                 745                 750

Asp Gln Gly Gly Phe Ile Glu Asn Glu Asn Lys Glu Gly Glu Gln Asp
        755                 760                 765

Glu Asp Glu Asp Glu Asp Ile Glu Met Gln
770                 775

<210> SEQ ID NO 67
<211> LENGTH: 129
<212> TYPE: PRT
<213> ORGANISM: Streptococcus pyogenes

<400> SEQUENCE: 67

Asp Val Asp Lys Leu Phe Ile Gln Leu Val Gln Thr Tyr Asn Gln Leu
1               5                   10                  15

Phe Glu Glu Asn Pro Ile Asn Ala Ser Gly Val Asp Ala Lys Ala Ile
            20                  25                  30

Leu Ser Ala Arg Leu Ser Lys Ser Arg Arg Leu Glu Asn Leu Ile Ala
        35                  40                  45

Gln Leu Pro Gly Glu Lys Lys Asn Gly Leu Phe Gly Asn Leu Ile Ala
    50                  55                  60

Leu Ser Leu Gly Leu Thr Pro Asn Phe Lys Ser Asn Phe Asp Leu Ala
65                  70                  75                  80

Glu Asp Ala Lys Leu Gln Leu Ser Lys Asp Thr Tyr Asp Asp Asp Leu
                85                  90                  95

Asp Asn Leu Leu Ala Gln Ile Gly Asp Gln Tyr Ala Asp Leu Phe Leu
            100                 105                 110

Ala Ala Lys Asn Leu Ser Asp Ala Ile Leu Leu Ser Asp Ile Leu Arg
        115                 120                 125

Val

<210> SEQ ID NO 68
<211> LENGTH: 625
<212> TYPE: PRT
<213> ORGANISM: Streptococcus pyogenes

<400> SEQUENCE: 68

```
Asp Asp Ser Phe Phe His Arg Leu Glu Glu Ser Phe Leu Val Glu Glu
1               5                   10                  15

Asp Lys Lys His Glu Arg His Pro Ile Phe Gly Asn Ile Val Asp Glu
            20                  25                  30

Val Ala Tyr His Glu Lys Tyr Pro Thr Ile Tyr His Leu Arg Lys Lys
        35                  40                  45

Leu Val Asp Ser Thr Asp Lys Ala Asp Leu Arg Leu Ile Tyr Leu Ala
    50                  55                  60

Leu Ala His Met Ile Lys Phe Arg Gly His Phe Leu Ile Glu Gly Asp
65                  70                  75                  80

Leu Asn Pro Asp Asn Ser Asp Val Asp Lys Leu Phe Ile Gln Leu Val
                85                  90                  95

Gln Thr Tyr Asn Gln Leu Phe Glu Glu Asn Pro Ile Asn Ala Ser Gly
            100                 105                 110

Val Asp Ala Lys Ala Ile Leu Ser Ala Arg Leu Ser Lys Ser Arg Arg
        115                 120                 125

Leu Glu Asn Leu Ile Ala Gln Leu Pro Gly Glu Lys Lys Asn Gly Leu
    130                 135                 140

Phe Gly Asn Leu Ile Ala Leu Ser Leu Gly Leu Thr Pro Asn Phe Lys
145                 150                 155                 160

Ser Asn Phe Asp Leu Ala Glu Asp Ala Lys Leu Gln Leu Ser Lys Asp
                165                 170                 175

Thr Tyr Asp Asp Asp Leu Asp Asn Leu Leu Ala Gln Ile Gly Asp Gln
            180                 185                 190

Tyr Ala Asp Leu Phe Leu Ala Ala Lys Asn Leu Ser Asp Ala Ile Leu
        195                 200                 205

Leu Ser Asp Ile Leu Arg Val Asn Thr Glu Ile Thr Lys Ala Pro Leu
    210                 215                 220

Ser Ala Ser Met Ile Lys Arg Tyr Asp Glu His His Gln Asp Leu Thr
225                 230                 235                 240

Leu Leu Lys Ala Leu Val Arg Gln Gln Leu Pro Glu Lys Tyr Lys Glu
                245                 250                 255

Ile Phe Phe Asp Gln Ser Lys Asn Gly Tyr Ala Gly Tyr Ile Asp Gly
            260                 265                 270

Gly Ala Ser Gln Glu Glu Phe Tyr Lys Phe Ile Lys Pro Ile Leu Glu
        275                 280                 285

Lys Met Asp Gly Thr Glu Glu Leu Leu Val Lys Leu Asn Arg Glu Asp
    290                 295                 300

Leu Leu Arg Lys Gln Arg Thr Phe Asp Asn Gly Ser Ile Pro His Gln
305                 310                 315                 320

Ile His Leu Gly Glu Leu His Ala Ile Leu Arg Arg Gln Glu Asp Phe
                325                 330                 335

Tyr Pro Phe Leu Lys Asp Asn Arg Glu Lys Ile Glu Lys Ile Leu Thr
            340                 345                 350

Phe Arg Ile Pro Tyr Tyr Val Gly Pro Leu Ala Arg Gly Asn Ser Arg
        355                 360                 365
```

```
Phe Ala Trp Met Thr Arg Lys Ser Glu Glu Thr Ile Thr Pro Trp Asn
    370                 375                 380
Phe Glu Glu Val Val Asp Lys Gly Ala Ser Ala Gln Ser Phe Ile Glu
385                 390                 395                 400
Arg Met Thr Asn Phe Asp Lys Asn Leu Pro Asn Glu Lys Val Leu Pro
                405                 410                 415
Lys His Ser Leu Leu Tyr Glu Tyr Phe Thr Val Tyr Asn Glu Leu Thr
            420                 425                 430
Lys Val Lys Tyr Val Thr Glu Gly Met Arg Lys Pro Ala Phe Leu Ser
        435                 440                 445
Gly Glu Gln Lys Lys Ala Ile Val Asp Leu Leu Phe Lys Thr Asn Arg
    450                 455                 460
Lys Val Thr Val Lys Gln Leu Lys Glu Asp Tyr Phe Lys Lys Ile Glu
465                 470                 475                 480
Cys Phe Asp Ser Val Glu Ile Ser Gly Val Glu Asp Arg Phe Asn Ala
                485                 490                 495
Ser Leu Gly Thr Tyr His Asp Leu Leu Lys Ile Ile Lys Asp Lys Asp
            500                 505                 510
Phe Leu Asp Asn Glu Glu Asn Glu Asp Ile Leu Glu Asp Ile Val Leu
        515                 520                 525
Thr Leu Thr Leu Phe Glu Asp Arg Glu Met Ile Glu Glu Arg Leu Lys
    530                 535                 540
Thr Tyr Ala His Leu Phe Asp Asp Lys Val Met Lys Gln Leu Lys Arg
545                 550                 555                 560
Arg Arg Tyr Thr Gly Trp Gly Arg Leu Ser Arg Lys Leu Ile Asn Gly
                565                 570                 575
Ile Arg Asp Lys Gln Ser Gly Lys Thr Ile Leu Asp Phe Leu Lys Ser
            580                 585                 590
Asp Gly Phe Ala Asn Arg Asn Phe Met Gln Leu Ile His Asp Asp Ser
        595                 600                 605
Leu Thr Phe Lys Glu Asp Ile Gln Lys Ala Gln Val Ser Gly Gln Gly
    610                 615                 620
Asp
625

<210> SEQ ID NO 69
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(15)
<223> OTHER INFORMATION: a, c, t, g, unknown or other
<220> FEATURE:
<221> NAME/KEY: modified_base
<222> LOCATION: (21)..(49)
<223> OTHER INFORMATION: a, c, t, g, unknown or other

<400> SEQUENCE: 69
nnnnnnnnnn nnnntctct nnnnnnnnnn nnnnnnnnnn nnnnnnnnn          49

<210> SEQ ID NO 70
<211> LENGTH: 49
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (1)..(15)
<223> OTHER INFORMATION: a, c, t, g, unknown or other
<220> FEATURE:
<221> NAME/KEY: modified_base
<222> LOCATION: (21)..(49)
<223> OTHER INFORMATION: a, c, t, g, unknown or other

<400> SEQUENCE: 70
nnnnnnnnnn nnnntctct nnnnnnnnnn nnnnnnnnnn nnnnnnnn                49

<210> SEQ ID NO 71
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(10)
<223> OTHER INFORMATION: a, c, t, g, unknown or other
<220> FEATURE:
<221> NAME/KEY: modified_base
<222> LOCATION: (16)..(25)
<223> OTHER INFORMATION: a, c, t, g, unknown or other

<400> SEQUENCE: 71
nnnnnnnnnn tctctnnnnn nnnnn                                         25

<210> SEQ ID NO 72
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(10)
<223> OTHER INFORMATION: a, c, t, g, unknown or other
<220> FEATURE:
<221> NAME/KEY: modified_base
<222> LOCATION: (16)..(25)
<223> OTHER INFORMATION: a, c, t, g, unknown or other

<400> SEQUENCE: 72
nnnnnnnnnn tctctnnnnn nnnnn                                         25

<210> SEQ ID NO 73
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(10)
<223> OTHER INFORMATION: a, c, t, g, unknown or other

<400> SEQUENCE: 73 gtrhgnnnnn                                                          10

<210> SEQ ID NO 74
<211> LENGTH: 14
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(11)
<223> OTHER INFORMATION: a, c, t, g, unknown or other

<400> SEQUENCE: 74
yyyyyyyyyy nyag                                                           14

<210> SEQ ID NO 75
<211> LENGTH: 9
<212> TYPE: PRT
<213> ORGANISM: Unknown
<220> FEATURE:
<223> OTHER INFORMATION: Description of Unknown:
      'LAGLIDADG' family motif peptide

<400> SEQUENCE: 75

Leu Ala Gly Leu Ile Asp Ala Asp Gly
1               5

<210> SEQ ID NO 76
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Leu Arg Gly Ser
1

<210> SEQ ID NO 77
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: modified_base
<222> LOCATION: (8)..(21)
<223> OTHER INFORMATION: a, c, t, g, unknown or other

<400> SEQUENCE: 77
nnnaaaannn nnnnnnnnnn ngg                                                 23

<210> SEQ ID NO 78
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
gtgctgacca tcgacgagaa agggactgaa gctgctgggg ccatgttttt agaggccat          59

<210> SEQ ID NO 79
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 79

Leu Asn Tyr Gly Val Cys Phe Cys Gly
1               5

<210> SEQ ID NO 80
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(15)
<223> OTHER INFORMATION: a, c, t, g, unknown or other
<220> FEATURE:
<221> NAME/KEY: modified_base
<222> LOCATION: (21)..(49)
<223> OTHER INFORMATION: a, c, t, g, unknown or other

<400> SEQUENCE: 80
nnnnnnnnnn nnnnntctct nnnnnnnnnn nnnnnnnnnn nnnnnnnnn                49

<210> SEQ ID NO 81
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
caaatgcttg tgagaaagct tgctca                                         26

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gln Ser Ser Asp Leu Ser Arg
1               5

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Leu Lys Trp Asn Leu Arg Thr
1               5

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 84

Arg Ser Asp Asn Leu Ala Arg
1               5

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Trp Gln Ser Ser Leu Ile Val
1               5

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gln Ser Gly Asn Arg Thr Thr
1               5

<210> SEQ ID NO 87
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
atgcttgtga gaaagcttgc tcatca                                    26

<210> SEQ ID NO 88
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
cttgtgagaa agcttgctca tcatac                                    26

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Thr Asn Gln Asn Arg Ile Thr
1               5

<210> SEQ ID NO 90
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 90

Arg Ser Ala Asn Leu Thr Arg
1               5

<210> SEQ ID NO 91
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
gtgagaaagc ttgctcatca tacttg                                          26

<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Ala His Gly Ala Arg Trp Asn
1               5
```